US012728151B2

(12) United States Patent
Rudolph et al.

(10) Patent No.: US 12,728,151 B2
(45) Date of Patent: Sep. 8, 2026

(54) TREATMENT OF CILIOPATHIES

(71) Applicant: ethris GmbH, Planegg (DE)

(72) Inventors: Carsten Rudolph, Krailling (DE); Verena Mummert, Penzberg (DE); Rebekka Kubisch-Dohmen, Neuried (DE); Christian Dohmen, Neuried (DE); Johannes Geiger, Munich (DE); Manish Aneja, Rottenburg am Neckar (DE); Ludwig Weiss, Kissing (DE); Heymut Omran, Münster (DE); Petra Pennekamp, Münster (DE); Kai Wohlgemuth, Drensteinfurt (DE); Sandra Cindric, Munich (DE); Niki Tomas Loges, Rheine (DE); Johanna Raidt, Münster (DE); Adrian Ter Steege, Bonn (DE)

(73) Assignee: Ethris GmbH, Planegg (DE)

( * ) Notice: Subject to any disclaimer, the term of this patent is extended or adjusted under 35 U.S.C. 154(b) by 1110 days.

(21) Appl. No.: 17/431,146

(22) PCT Filed: Feb. 13, 2020

(86) PCT No.: PCT/EP2020/053774

§ 371 (c)(1),
(2) Date: Aug. 13, 2021

(87) PCT Pub. No.: WO2020/165352

PCT Pub. Date: Aug. 20, 2020

(65) Prior Publication Data

US 2022/0211807 A1 Jul. 7, 2022

(30) Foreign Application Priority Data

Feb. 14, 2019 (EP) .................................... 19157210

(51) Int. Cl.

| | |
|---|---|
| ***A61K 38/17*** | (2006.01) |
| ***A61K 9/00*** | (2006.01) |
| ***A61K 31/198*** | (2006.01) |
| ***A61K 31/7105*** | (2006.01) |
| ***A61P 11/00*** | (2006.01) |

(52) U.S. Cl.

CPC ........ *A61K 38/1709* (2013.01); *A61K 31/198* (2013.01); *A61K 31/7105* (2013.01); *A61P 11/00* (2018.01); *A61K 9/0043* (2013.01); *A61K 9/0078* (2013.01)

(58) Field of Classification Search

CPC ...... A61P 11/00; A61K 9/0043; A61K 9/0078
See application file for complete search history.

(56) References Cited

U.S. PATENT DOCUMENTS

| | | | |
|---|---|---|---|
| 2011/0081296 | A1 | 4/2011 | Barr |
| 2015/0126589 | A1 | 5/2015 | Geiger |

FOREIGN PATENT DOCUMENTS

| | | | | | |
|---|---|---|---|---|---|
| RU | 2232546 | C2 | 3/2004 | | |
| WO | WO 2010/111360 | A2 | 9/2010 | | |
| WO | 2013/185069 | A1 | 12/2013 | | |
| WO | 2014/207231 | A1 | 12/2014 | | |
| WO | WO-2016075154 | A1 * | 5/2016 | ............. | A61K 35/28 |
| WO | WO 2017/198704 | A1 | 11/2017 | | |
| WO | WO 2017/205767 | A1 | 11/2017 | | |
| WO | WO 2018/203092 | A1 | 11/2018 | | |

OTHER PUBLICATIONS

Leigh et al. "Standardizing nasal nitric oxide measurement as a test for primary ciliary dyskinesia." Annals of the American Thoracic Society 10.6 (2013): 574-581. (Year: 2013).*

Cockx et al. "Chemoattractants and cytokines in primary ciliary dyskinesia and cystic fibrosis: key players in chronic respiratory diseases." Cellular & molecular immunology 15.4 (2018): 312-323. (Year: 2018).*

Guan et al. "Motile ciliary disorders in chronic airway inflammatory diseases: critical target for interventions." Current Allergy and Asthma Reports 18 (2018): 1-12. (Year: 2018).*

Suk et al. "Rapid transport of muco-inert nanoparticles in cystic fibrosis sputum treated with N-acetyl cysteine." Nanomedicine 6.2 (2011): 365-375. (Year: 2011).*

Jarzębińska et al. "A single methylene group in oligoalkylamine-based cationic polymers and lipids promotes enhanced mRNA delivery." Angewandte Chemie International Edition 55.33 (2016): 9591-9595. (Year: 2016).*

Zhang et al. "Approaches and applications in transdermal and transpulmonary gene drug delivery." Frontiers in Bioengineering and Biotechnology 12 (2025): 1519557. (Year: 2025).*

Keiser et al. "Restoring ciliary function: gene therapeutics for primary ciliary dyskinesia." Human Gene Therapy 34.17-18 (2023): 821-835. (Year: 2023).*

Elkins, M. et al., "Mechanisms and applications of hypertonic saline," Journal of the Royal Society of Medicine, 104 (I_suppl): 2-5 (2011).

Kellet, F., et al., "Nebulised 7% hypertonic saline improves lung function and quality of life in bronchiectasis," Respiratory Medicine, Elsevier, Amsterdam, NL, 105(12): 1831-1835 (2011).

(Continued)

*Primary Examiner* — Emily A Cordas
(74) *Attorney, Agent, or Firm* — Klarquist Sparkman, LLP; Susan Alper Siegel; Gregory K. Scott

(57) ABSTRACT

The present disclosure provides a pharmaceutical composition comprising a polyribonucleotide for use in treating a ciliopathy in a subject suffering of a ciliopathy, wherein the polyribonucleotide encodes a functional version of a protein a defect of which is associated with said ciliopathy, and wherein administration of said pharmaceutical composition to the respiratory system of said subject is effected when the subject shows an inflammation of the respiratory system. Further, the present disclosure relates to a method for analyzing the effect of a polyribonucleotide on ciliogenesis, wherein said polyribonucleotide encodes a protein involved in and/or required for ciliogenesis.

21 Claims, 8 Drawing Sheets

Figure 3:
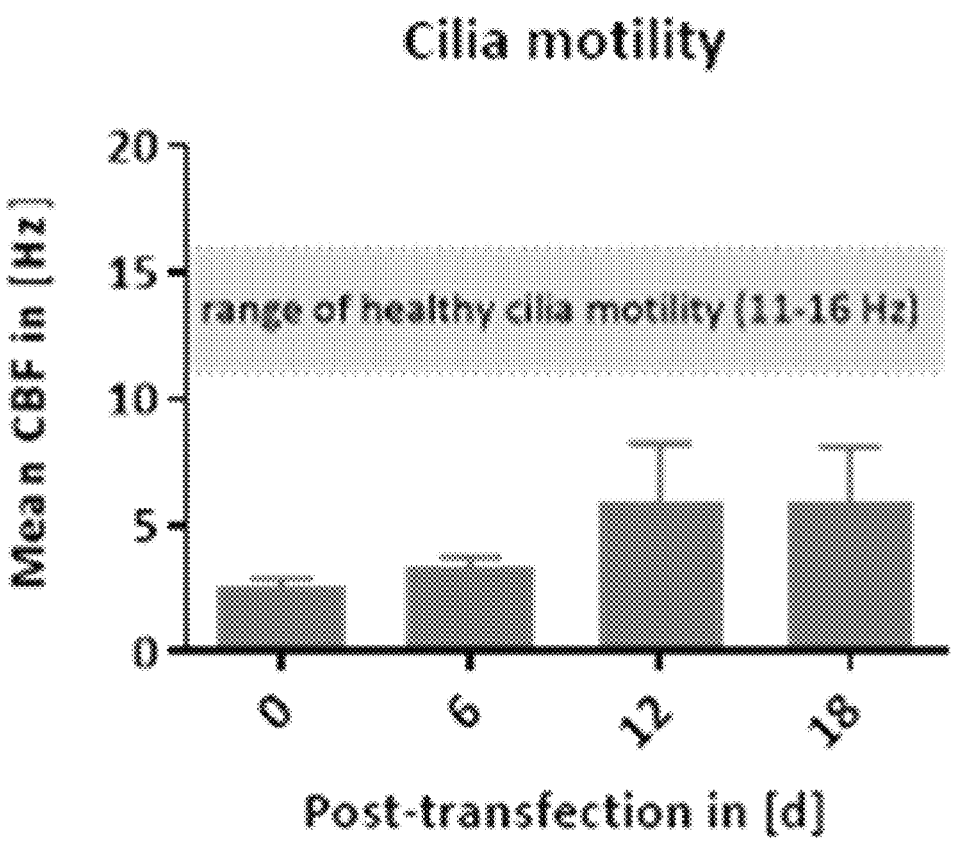

Specification includes a Sequence Listing.

(56) References Cited

OTHER PUBLICATIONS

Munchen Ludwig-Maximilians-Universitat: "Dissertation zur Erlangung des Doktorgrades der Fakultat fur Chemie und Pharmazie der", 2017, Retrieved from the Internet: URL:https://edoc.ub.uni-muenchen.de/20874/ 7/Jarzebinska_Anita.pdf, [retrieved on Oct. 18, 2023].

Stafanger, G., et al., "The clinical effect and the effect on the ciliary motility of oral N-acetylcysteine in patients with cystic fibrosis and primary ciliary dyskinesia," European Respiratory Journal, 1(2): 161-167 (1988).

Tomkiewicz, et al., "A comparison of a new mucolytic N-acetylcysteine 1-lysinate with N-acetylcysteine: Airway epithelial function and mucus changes in dog," Pulmonary Pharmacology and Therapeutics, Academis Press, GB, 8(6):259-265 (1995).

Zihlif, Nadwa, et al. "Markers of airway inflammation in primary ciliary dyskinesia studied using exhaled breath condensate." *Pediatric pulmonology* 41.6 (2006): 509-514.

Terré, Berta, et al. "GEMC1 is a critical regulator of multiciliated cell differentiation." *The EMBO journal* 35.9 (2016): 942-960.

Munye, Mustafa Mohamed. "Towards gene therapy for primary ciliary dyskinesia." Diss. UCL (University College London), p. 1-304, 2014.

Munye, Mustafa M., et al. "Novel Human Bronchial Epithelial Cell Lines for the Study of Gene Therapy Approaches To Treat Primary Ciliary Dyskinesia." *Molecular Therapy* 21, No. Suppl. 1 (2013): p. S168.

Munye, Mustafa Mohamed. "Towards gene therapy for primary ciliary dyskinesia." Cilla, Biomed Central Ltd, London UK, vol. 1, No. Suppl 1, (2012): p. P109.

McIntyre, Jeremy C., et al. "Gene therapy rescues cilia defects and restores olfactory function in a mammalian ciliopathy model." *Nature medicine* 18.9 (2012): 1423-1428.

Wheway, Gabrielle, et al. "An siRNA-based functional genomics screen for the identification of regulators of cillogenesis and ciliopathy genes." *Nature cell biology* 17.8 (2015): 1074-1087.

Horani, Amjad, et al. "Genetics and biology of primary ciliary dyskinesia." *Paediatric respiratory reviews* 18 (2015): 18-24.

Marthin, June Kehlet, et al. "Patient-specific three-dimensional explant spheroids derived from human nasal airway epithelium: a simple methodological approach for ex vivo studies of primary ciliary dyskinesia." *Cilia* 6.1 (2017): 1-9.

Kim, Joon, et al. "Functional genomic screen for modulators of cillogenesis and cilium length." *Nature* 464.7291 (2010): 1048-1051.

International Search Report issued in International Application No. PCT/EP2020/053774 dated Jul. 2, 2020.

Becker-Heck et al., "The coiled-coil domain containing protein CCDC40 is essential for motile cilia function and left-right axis formation," *Nature Genetics* 43(1):79-84, E-PUB Dec. 5, 2010.

Bengel-Ruland et al., "Cystic Fibrosis transmembrane conductance regulator-mRNA delivery: a novel alternative for cystic fibrosis gene therapy," *The Journal of Gene Medicine* 15(11-12):414-426, Nov. 2013.

Cao et al., "Invited review: human air-liquid-interface organotypic airway tissue models derived from primary tracheobronchial epithelial cells—overview and perspectives," *In Vitro Cellular & Developmental Biology—Animal* 57(2):104-132, E-PUB Nov. 11, 2020.

Dvorak et al., "Do Airway Epithelium Air-Liquid Cultures Represent the In Vivo Airwar Epithelium Transcriptome?" *American Journal of Respiratory and Molecular Cell Biology* 44(4):465-473, E-PUB Jun. 4, 2010.

FDA News Release, "FDA expands approved use of Kalydeco to treat additional mutations of cystic fibrosis," 3 pages, May 17, 2017.

Hirst et al., "Culture of Primary Ciliary Dyskinesia Epithelia Cells at Air-Liquid Interface Can Alter Ciliary Phenotype but Remains a Robust and Informative Diagnostic Aid," *PLOS One* 9(2):e89675, Feb. 25, 2014 (7 pages).

Nielsen et al., "Chronic airway disease in primary ciliary dyskinesia-spiced with geno-phenotype associations," *American Journal of Medicinal Genetics* 190(1):20-35, E-PUN Mar. 29, 2022.

Rugina et al., "Primary ciliary dyskinesia diagnosed by electron microscopy in one case of Kartagener syndrome," *Romanian Journal of Morphology & Embryology* 55(2 Suppl):697-701, 2014.

Merveille et al., "CCDC39 is required for assembly of inner dynein arms and the dynein regulatory complex and for normal ciliary motility in humans and dogs," *Nature Genetics*43(1): 72-79 (ePub Dec. 5, 2010).

Lai et al., "Gene editing of DNAH11 restores normal cilia motility in primary ciliary dyskinesia," *J Med Genet*0: 1-8 (doi:10.1136/jmedgenet-2015-103539, published online Jan. 4, 2016).

Ostrowski et al., "Cilia and Models for Studying Structure and Function," *Proc Am Thorac Soc*8:423-429 (Sep. 2011).

Waters and Beales, "Ciliopathies: an expanding disease spectrum," *Pediatr. Nephrol.*26:1039-1056 (published online Jan. 6, 2011).

* cited by examiner

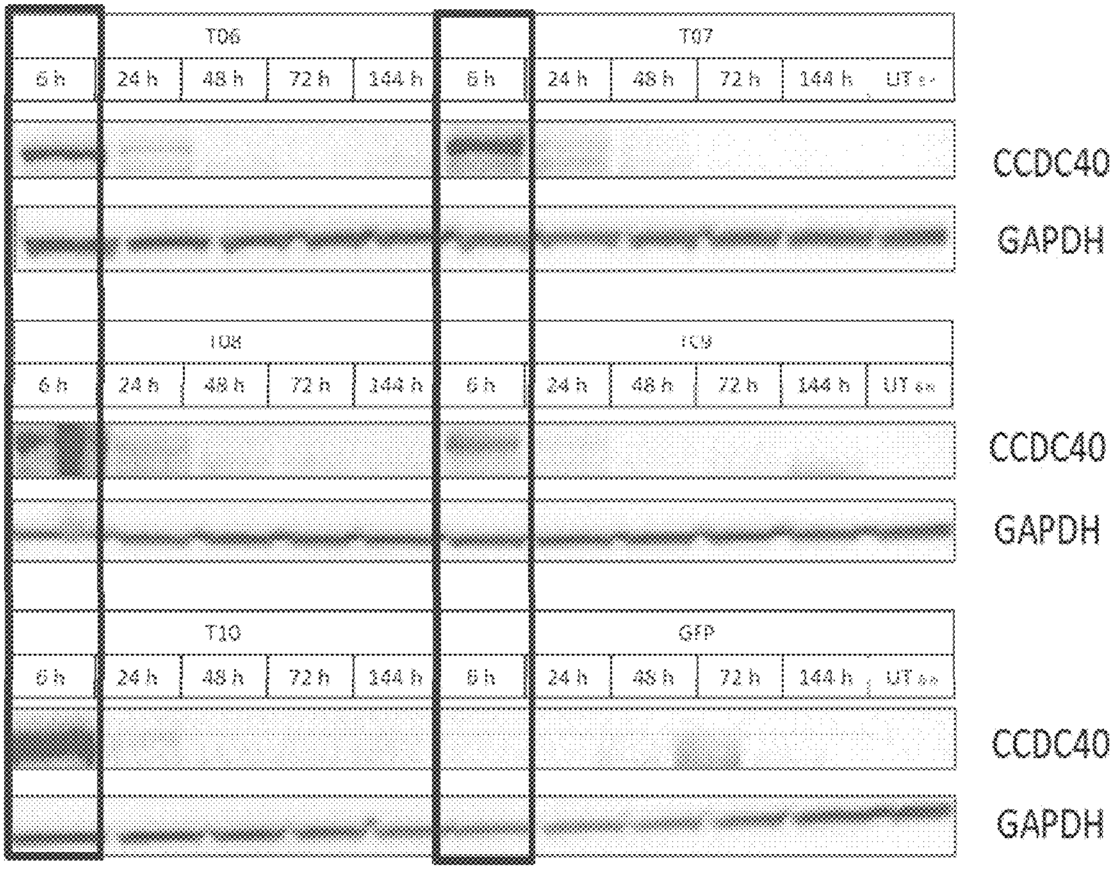
Figure 1
Figure 2
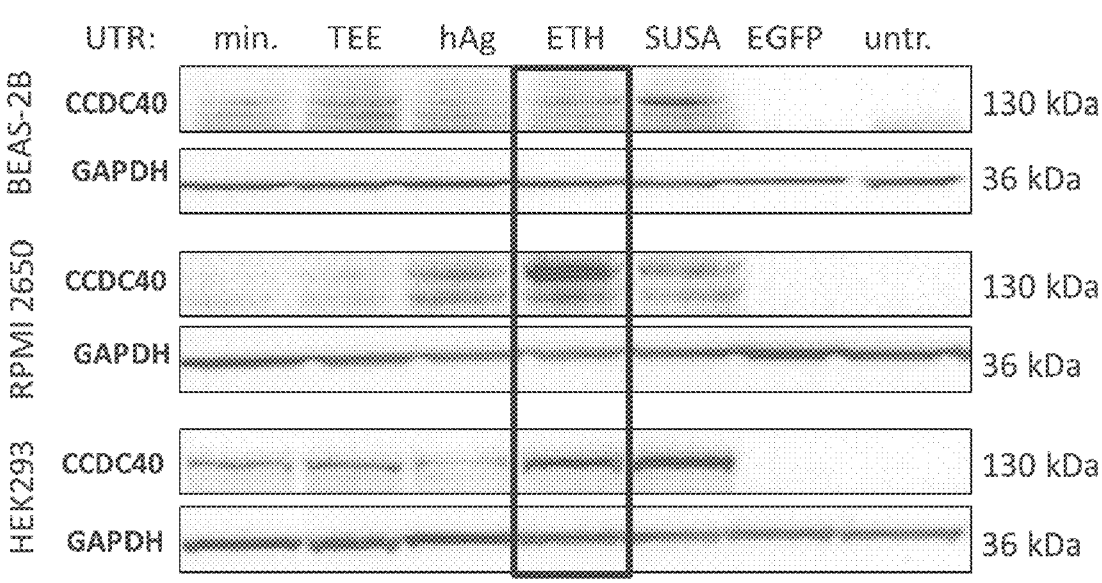

Healthy control, untreated

Patient ALI, tdTomato mRNA

Patient ALI, CCDC40 mRNA

SEQUENCE LISTING

<160> NUMBER OF SEQ ID NOS: 14

<210> SEQ ID NO 1
<211> LENGTH: 3546
<212> TYPE: RNA
<213> ORGANISM: Artificial Sequence
<220> FEATURE:
<223> OTHER INFORMATION: CCDC40 sequence with CYBA 5 and 3 UTR ETH031T09

<400> SEQUENCE: 1
gggagaccgc gccuagcagu gucccagccg gguucguguc gccgccacca uggcugaacc 60
uggcggagcc gccggaagau cccacccuga agauggcucu gccagcgagg gcgagaaaga 120
gggcaacaac gagagccaca uggugucccc cccagagaag gacgacggcc agaaaggcga 180
agaggccgug ggcucuaccg agcacccuga ggaagugacc acacaggccg aggccgccau 240
ugaagagggc gagguggaaa cagagggcga agccgcugug gaaggcgaag aggaagccgu 300
gucuuacggc gacgccgaga gcgaggaaga guacuacuac accgagacaa gcagccccga 360
gggccagauc ucugccgccg auaccaccua ccccuacuuc agcccccuc aggaacugcc 420 uggggaagag gccuacgaua gcguguccgg cgaagcuggc cugcagggcu uucagcagga 480
agccacaggc ccucccgaga gccgggaaag aagagugaca agccccgagc cuagccacgg 540
cgugcuggga ccaucugagc agaugggcca agugaccucu ggcccugcug ugggcagacu 600
gacaggcagc acagaggaac cucagggcca ggugcugccu augggagugc agcaccgguu 660
cagacugagc cacggcagcg acaucgagag cagcgaccug gaagaguucg ucagccagga 720
acccgugauc ccuccuggcg ugccagaugc ccaucccagg gaaggcgauc ugcccguguu 780
ccaggaccag auccagcagc ccucuaccga agagggggcu auggccgaga gaguggaaag 840
cgagggcucc gacgaagaag ccgaggacga gggaucucag cugguggugc uggaccccga 900
ccacccucug augugcgu uucaggccgc ccugaagaac uaccugaacc ggcagaucga 960
gaagcugaaa cuggaccugc aggaacuggu gguggccaca aagcagagca gagcccagag 1020
acaggaacug ggcgugaacc uguacgaggu gcagcagcau cuggugcauc ugcagaagcu 1080
gcuggaaaag agccacgacc ggcacgccau ggccagcucu gagcgcagac agaaagagga 1140
agaacugcag gccgccagag cccuguacac caagacaugc gccgcugcca acgaggaacg 1200
gaagaagcug gcugcccugc agaccgagau ggaaaaccug gcucugcacc uguucuacau 1260
gcagaauauc gaccaggaca ugcgggacga caucagagug augacccagg ucgugaagaa 1320
ggccgagaca gagagaaucc gggccgagau ugagaagaaa aagcaggacc uguacgugga 1380
ccagcugacc accagggccc agcagcugga agaggauauc gcccuguucg aggcccagua 1440

```
ccuggcccag gccgaagaua cccggauccu gagaaaggcc guguccgagg ccugcaccga   1500
gaucgaugcc aucagcgugg aaaagcggcg gaucaugcag cagugggcca gcagccucgu   1560
gggcaugaag cacagagaug aggcccaccg ggccgugcug gaagcucuga gaggcuguca   1620
gcaccaggcc aagagcaccg acggcgagau cgaggccuac aagaaaucca ucaugaagga   1680
agaggaaaag aacgagaaac uggccagcau ccugaacaga accgaaaccg aggccacccu   1740
gcugcagaaa cugaccaccc agugccugac caaacaggug gcccugcagu cccaguucaa   1800
caccuacaga cugacccugc aggacaccga ggacgcccug agucaggauc agcuggaaca   1860
gaugauucug accgaggaac ugcaggcuau ccggcaggcc auucaggggg agcuggaacu   1920
gcggagaaag accgacgccg ccaucagaga gaagcugcag gaacacauga ccagcaacaa   1980
gaccaccaag uacuucaacc agcugauucu gcgccugcag aaagaaaaga ccaacaugau   2040
gacacaccug agcaagauca acggcgacau ugcccagacc acccuggaca ucacccacac   2100
cagcagcaga cuggacgccc accagaaaac ccugguggaa cuggaccagg augugaagaa   2160
agugaacgag cugaucacca acagccagag cgagaucagc cggcggacca uccugaucga   2220
gagaaagcag ggccugauca acuuccugaa caaacagcug gaaagaaugg uguccgagcu   2280
gggcggcgag gaagugggac cucuggaacu ggaaaucaag cggcugagca agcugaucga   2340
cgagcacgac ggcaaggccg ugcaggcuca agugacaugg cugcggcugc agcaggaaau   2400
ggucaaagug acccaggaac aggaagaaca gcuggccucc cuggacgcca gcaagaaaga   2460
acugcacauc auggaacaga aaaagcugcg gguggaaagc aagaucgagc aggaaaaaaa   2520
agaacagaaa gaaaucgagc accacaugaa ggaccuggac aacgaccuga agaaacugaa   2580
uaugcugaug aacaagaacc gcugcuccag cgaagaacug gaacagaaca acagagugac   2640
cgagaacgag uucgugcgga gccugaaggc cagcgagcgg gaaaccauca agaugcagga   2700
caagcugaac cagcuguccg aggaaaaagc cacacugcug aaccagcugg uggaagccga   2760
gcaccagauc augcuguggg agaagaagau ccagcuggcc aaagaaaugc ggagcagcgu   2820
ggacagcgag aucggccaga ccgaaaucag agccaugaag ggcgagaucc accggaugaa   2880
agugcggcug ggacagcugc ugaaacagca ggaaaagaug auccgggcca uggaacuggc   2940
cguggccaga cgggaaaccg ugacaaccca ggcugagggc cagcggaaga uggacagaaa   3000
ggcccugacc cggaccgacu uccaccacaa gcagcuggaa cugaggcgga agauccggga   3060
cgugcggaag gccaccgaug agugcacaaa gacagugcug gaacuggaag agacacagcg   3120
gaacgugucc uccagccugc uggaaaaaca ggaaaagcug agcgugaucc aggccgacuu   3180
cgacacccug gaagcugacc ugacaagacu gggagcccug aaaagacaga accuguccga   3240
gaucguggca cugcagaccc ggcugaaaca ucugcaggcu gugaaagagg gacgcuacgu   3300
guuccuguuc agauccaagc agucucuggu gcuggaaaga cagcggcugg acaagcggcu   3360
ggcacugauu gccaccaucc uggauagagu gcgcgacgag uacccacagu uccaggaagc   3420
acugcacaag gugucccaga ugaucgccaa caagcuggaa uccccuggcc ccagcugacc   3480
ucgccccgga ccugcccucc cgccaggugc acccaccugc aauaaaugca gcgaagccgg   3540
gauucg                                                              3546
```

```
<210> SEQ ID NO 2
<211> LENGTH: 3063
<212> TYPE: RNA
<213> ORGANISM: Artificial Sequence
<220> FEATURE:
```

-continued

<223> OTHER INFORMATION: CCDC39 sequence with CYBA UTRs ETH047T04

<400> SEQUENCE: 2

```
gggagaccgc gccuagcagu gucccagccg gguucguguc gccgccacca ugagcagcga     60
guuucuggcc gaacugcacu gggaggacgg cuucgcuauu cccguggcca acgaggaaaa    120
caagcugcug gaagaucagc ugagcaagcu gaaggacgag agagccucuc ugcaggacga    180
gcugagagag uacgaggaac ggaucaacag caugaccagc cacuucaaga acgugaagca    240
agagcugagc aucacccaga gccugugcaa ggccagagag agagaaaccg agagcgagga    300
acacuucaag gcuaucgccc agcgcgagcu gggaagagug aaggaugaga uccagcggcu    360
ggaaaacgag auggccagca uccuggaaaa gaaguccgac aaagagaacg gcaucuucaa    420
ggccacacag aagcuggacg gccugaagug ccagaugaac ugggaucagc aggcccugga    480
agccuggcug gaagagucug cccacaagga uucugacgcc cugacacugc agaaguacgc    540
ccagcaggac gacaacaaga uccgggcucu gacccugcag cuggaaagac ugacccugga    600
augcaaccag aagcggaaga uccuggacaa cgagcugacc gagacaauca gcgcccagcu    660
ggaacuggau aaggccgcuc aggacuucag aaagauccac aacgagcggc aagaacugau    720
caagcagugg gagaacacca ucgagcagau gcagaaacgc gacggcgaca ucgacaacug    780
cgcccuggaa cucgcccgga ucaagcaaga gacacgcgag aaagagaacc uggucaaaga    840
gaagaucaag uuccucgagu ccgagaucgg caacaacacc gaguucgaga agcggaucag    900
cguggccgac agaaagcugc ugaagugcag aaccgccuac caggaccacg agacaagccg    960
gauucagcuc aagggcgagc uggauucucu gaaggccacc gugaacagaa ccagcagcga   1020
ucuggaagcc cugcggaaga acaucagcaa gaucaagaag gacauccacg aggaaaccgc   1080
caggcugcag aaaacaaaga accacaauga gaucauccag accaagcuga aagagaucac   1140
cgaaaagacc augagcgugg aagagaaggc cacaaaccug gaagauaugc ucaaagagga   1200
agagaaagac gucaaagagg uggacguuca acugaaccug auuaagggcg ugcuguucaa   1260
gaaggcccaa gagcugcaga ccgaaaccau gaaggaaaag gccguccugu cugagaucga   1320
gggcaccaga ucuagccuga agcaccugaa ccaucagcug cagaagcucg acuucgagac   1380
acugaagcag caagagauca uguacagcca ggauuuccac auccagcagg ucgagcggcg   1440
gaugucuaga cugaagggcg agaucaacuc cgaggaaaaa caggcccucg aggccaagau   1500
cguggaacug agaaagagcc ucgaagagaa gaagucuacc ugcggccugc uggaaaccca   1560
gauuaagaag cugcacaacg accuguacuu caucaagaaa gcccacagca agaacagcga   1620
cgagaagcag agccugauga ccaagaucaa ugagcugaac cuguucaucg aucggagcga   1680
aaaagagcug gacaaggcca agggcuucaa gcaggaccug augaucgagg acaaccugcu   1740
gaagcuggaa gugaagcgga ccagagagau gcugcacagc aaggccgagg aagugcuguc   1800
ucuggaaaag cggaagcagc agcuguacac cgccauggaa gagagaaccg aagagaucaa   1860
ggugcacaag accaugcugg cuucccagau cagauacgug gaccaagagc gcgagaacau   1920
cuccaccgag uuuagagaga gacuguccaa gaucgagaag cugaagaacc gcuacgagau   1980
ccugaccguc gugaugcugc cuccugaggg cgaagaggaa aagacccagg ccuacuacgu   2040
gaucaaggca gcccaagaaa aagaggaacu ccagagagaa ggcgacugcc uggacgccaa   2100
gauuaacaag gccgaaaaag aaaucuacgc ccucgagaac acccugcagg uccugaacag   2160
cugcaacaac aacuacaagc agagcuucaa gaaagucacc ccuagcuccg acgaguacga   2220
gcugaagauu cagcuggaag aacagaaaag agccguggac gagaaguaca gauacaagca   2280
```

```
gcggcagauc agagagcugc aagaggauau ccagagcaug gaaaacaccc uggacgugau   2340

cgagcaccug gccaacaacg ugaaagagaa gcuguccgag aaacaggccu acagcuuuca   2400

gcuguccaaa gagacagagg aacagaagcc caaacuggaa cgcgugacca agcagugcgc   2460

caagcugaca aaagagaucc ggcugcugaa agacaccaag gacgaaacca uggaagaaca   2520

agacaucaag cugcgcgaga ugaagcaguu ccacaaagug aucgacgaga ugcuggugga   2580

caucauugaa gagaacacag agauccgcau cauccugcag accuauuuuc agcagagcgg   2640

ccuggaacug ccuaccgccu cuacaaaggg cagcagacag agcagcagau ccccuagcca   2700

cacaagccug agcgccagaa gcucuagaag caccagcacc ucuaccagcc aguccagcau   2760

uaaggugcug gaacucaagu uccccgccag cucuagccuc gugggaagcc cuucuagacc   2820

uagcagcgcc ucuagcagcu ccagcaacgu gaaguccaag aaaagcucca agugaccucg   2880

ccccggaccu gcccucccgc caggugcacc caccugcaau aaaugcagcg aagccgggau   2940

ucgaaaaaaa aaaaaaaaaa aaaaaaaaaa aaaaaaaaaa aaaaaaaaaa aaaaaaaaaa   3000

aaaaaaaaaa aaaaaaaaaa aaaaaaaaaa aaaaaaaaaa aaaaaaaaaa aaaaaaaaaa   3060

aaa                                                                 3063
```

<210> SEQ ID NO 3
<211> LENGTH: 1644
<212> TYPE: RNA
<213> ORGANISM: Artificial Sequence
<220> FEATURE:
<223> OTHER INFORMATION: tdTomato

<400> SEQUENCE: 3

```
gggagaccca agcuggcuag cguuuaaacu uaagcuuggu accgcgggcc cgggauccac     60

cggucgccac caugguga gc aagggcgagg aggucaucaa agaguucaug cgcuucaagg    120

ugcgcaugga gggcuccaug aacggccacg aguucgagau cgagggcgag ggcgagggcc    180

gccccuacga gggcacccag accgccaagc ugaaggugac caagggcggc cccCugcccu    240

ucgccuggga cauccugucc ccccaguuca uguacggcuc caaggcguac gugaagcacc    300

ccgccgacau ccccgauuac aagaagcugu ccuuccccga gggcuucaag ugggagcgcg    360

ugaugaacuu cgaggacggc ggucugguga ccgugaccca ggacuccucc cugcaggacg    420

gcacgcugau cuacaaggug aagaugcgcg gcaccaacuu cccccccgac ggccccguaa    480

ugcagaagaa gaccaugggc ugggaggccu ccaccgagcg ccuguacccc cgcgacggcg    540

ugcugaaggg cgagauccac caggcccuga agcugaagga cggcggccac uaccuggugg    600

aguucaagac caucuacaug gccaagaagc ccgugcaacu gcccggcuac uacuacgugg    660

acaccaagcu ggacaucacc ucccacaacg aggacuacac caucguggaa caguacgagc    720

gcuccgaggg ccgccaccac cuguuccugg ggcauggcac cggcagcacc ggcagcggca    780

gcuccggcac cgccuccucc gaggacaaca acauggccgu caucaaagag uucaugcgcu    840

ucaaggugcg cauggagggc uccaugaacg gccacgaguu cgagaucgag ggcgagggcg    900

agggccgccc cuacgagggc acccagaccg ccaagcugaa ggugaccaag ggcggccccc    960

ugcccuucgc cugggacauc cugucccccc aguucaugua cggcuccaag gcguacguga   1020

agcaccccgc cgacaucccc gauuacaaga agcuguccuu ccccgagggc uucaaguggg   1080

agcgcgugau gaacuucgag gacggcgguc uggugaccgu gacccaggac uccucccugc   1140

aggacggcac gcugaucuac aaggugaaga ugcgcggcac caacuucccc cccgacggcc   1200
```

-continued ccguaaugca gaagaagacc augggcuggg aggccuccac cgagcgccug uacccccgcg 1260
acggcgugcu gaagggcgag auccaccagg cccugaagcu gaaggacggc ggccacuacc 1320
ugguggaguu caagaccauc uacauggcca agaagcccgu gcaacugccc ggcuacuacu 1380
acguggacac caagcuggac aucaccuccc acaacgagga cuacaccauc guggaacagu 1440
acgagcgcuc cgagggccgc caccaccugu uccuguacgg cauggacgag cuguacaagu 1500
aggcggccaa uucugcagaa aaaaaaaaaa aaaaaaaaaa aaaaaaaaaa aaaaaaaaaa 1560
aaaaaaaaaa aaaaaaaaaa aaaaaaaaaa aaaaaaaaaa aaaaaaaaaa aaaaaaaaaa 1620
aaaaaaaaaa aaaaaaaagc ggcc 1644

<210> SEQ ID NO 4
<211> LENGTH: 1327
<212> TYPE: RNA
<213> ORGANISM: Artificial Sequence
<220> FEATURE:
<223> OTHER INFORMATION: MCIDAS sequence with Ethris minimal 5 UTR and optional 3 UTR

<400> SEQUENCE: 4
gggagacgcc accaugcaag cuuguggcgg cggagcugcu ggaagaaggg ccuucgauag 60
caucugcccc aaccggaugc uugcccuucc ugguagagcc cugcugugca agccuggcaa 120
gcccgagaga aaguucgccc cuccaagaaa guucuucccc ggcuguacug gcggcagccc 180
ugugucugug uaugaggacc cuccugaugc cgagccuaca gcucugccug cucugaccac 240
aaucgaccug caggaucugg ccgauugcag cucucugcug ggaucugaug cuccuccugg 300
cggagaucug gcugccucuc agaaucacag ccaccagaca gaggccgacu ucaaccugca 360
agacuuccgg gacaccgugg acgaccugau cagcgauagc agcagcauga ugagccccac 420
ucuggccagc ggcgauuucc cauucagccc cugugacauc agcccuuucg gcccuugucu 480
gagcccucca cuggauccua gagcacugca gagcccaccu cugaggccuc cagauguucc 540
uccaccugag caguacugga aagagguggc cgaccagaac cagagagcac ugggcgacgc 600
ucugguggaa aacaaccagc ugcacgugac ccugacacag aagcaagaag agaucgccag 660
ccugaaagaa cggaaugugc agcugaaaga gcuggccucc aggacaagac accuggccag 720
ugugcuggac aagcugauga ucacccagag cagagauugc ggagccgccg cugaaccuuu 780
ucugcugaag gccaaggcca agagaagccu ggaagaacug gugucugccg ccggacagga 840
uugcgcugaa guggaugcca uccugcgcga gaucagcgag agaugugaug aggcccugca 900
gagcagggac cccaaaagac cuagacugcu gcccgagccu gccaacaccg auaccagacc 960
uggaaaucug cacggcgccu ucagaggccu gagaaccgau ugcucuagaa gcgcccugaa 1020
ccugagccac agcgaacucg aagaaggcgg cagcuucagc acccggauca gaagccacag 1080
caccaucaga acccuggccu uuccacaggg caacgccuuc acaaucagaa ccgccaacgg 1140
cggcuacaag uucagauggg ugccaagcug agcuagccac cgggcaauac gagcucaagc 1200
cagucucaaa aaaaaaaaaa aaaaaaaaaa aaaaaaaaaa aaaaaaaaaa aaaaaaaaaa 1260
aaaaaaaaaa aaaaaaaaaa aaaaaaaaaa aaaaaaaaaa aaaaaaaaaa aaaaaaaaaa 1320
aaaaaaa 1327

<210> SEQ ID NO 5
<211> LENGTH: 3446
<212> TYPE: RNA
<213> ORGANISM: Artificial Sequence
<220> FEATURE:

-continued

<223> OTHER INFORMATION: Sequence with Ethris minimal 5 UTR ETH031T06

<400> SEQUENCE: 5
gggagacgcc accauggcug aaccuggcgg agccgccgga agaucccacc cugaagaugg 60
cucugccagc gagggcgaga aagagggcaa caacgagagc cacaugg ugu cccccccaga 120
gaaggacgac ggccagaaag gcgaagaggc cgugggcucu accgagcacc cugaggaagu 180
gaccacacag gccgaggccg ccauugaaga gggcgaggug gaaacagagg gcgaagccgc 240
uguggaaggc gaagaggaag ccgugucuua cggcgacgcc gagagcgagg aagaguacua 300
cuacaccgag acaagcagcc ccgagggcca gaucucugcc gccgauacca ccuaccccua 360
cuucagcccc ccucaggaac ugccugggga agaggccuac gauagcgugu ccggcgaagc 420
uggccugcag ggcuuucagc aggaagccac aggcccuccc gagagccggg aaagaagagu 480
gacaagcccc gagccuagcc acggcgugcu gggaccaucu gagcagaugg gccaagugac 540
cucuggcccu gcugugggca gacugacagg cagcacagag gaaccucagg gccaggugcu 600
gccuauggga gugcagcacc gguucagacu gagccacggc agcgacaucg agagcagcga 660
ccuggaagag uucgucagcc aggaacccgu gaucccuccu ggcgugccag augcccaucc 720
cagggaaggc gaucugcccg uguuccagga ccagauccag cagcccucua ccgaagaggg 780
ggcuauggcc gagagagugg aaagcgaggg cuccgacgaa gaagccgagg acgagggauc 840
ucagcuggug gugcuggacc ccgaccaccc ucugauggug cgguuucagg ccgcccugaa 900
gaacuaccug aaccggcaga ucgagaagcu gaaacuggac cugcaggaac ugguggug gc 960
cacaaagcag agcagagccc agagacagga acugggcgug aaccuguacg aggugcagca 1020
gcaucuggug caucugcaga agcugcugga aaagagccac gaccggcacg ccauggccag 1080
cucugagcgc agacagaaag aggaagaacu gcaggccgcc agagcccugu acaccaagac 1140
augcgccgcu gccaacgagg aacggaagaa gcuggcugcc cugcagaccg agauggaaaa 1200
ccuggcucug caccuguucu acaugcagaa uaucgaccag gacaugcggg acgacaucag 1260
agugaugacc caggucguga agaaggccga gacagagaga auccgggccg agauugagaa 1320
gaaaaagcag gaccuguacg uggaccagcu gaccaccagg gcccagcagc uggaagagga 1380
uaucgcccug uucgaggccc aguaccuggc ccaggccgaa gauacccgga uccugagaaa 1440
ggccguguccc gaggccugca ccgagaucga ugccaucagc guggaaaagc ggcggaucau 1500
gcagcagugg gccagcagcc ucgugggcau gaagcacaga gaugaggccc accgggccgu 1560
gcuggaagcu cugagaggcu gucagcacca ggccaagagc accgacggcg agaucgaggc 1620
cuacaagaaa uccaucauga aggaagagga aaagaacgag aaacuggcca gcauccugaa 1680
cagaaccgaa accgaggcca cccugcugca gaaacugacc acccagugcc ugaccaaaca 1740
gguggcccug caguccc agu ucaacaccua cagacugacc cugcaggaca ccgaggacgc 1800
ccugagucag gaucagcugg aacagaugau ucugaccgag gaacugcagg cuauccggca 1860
ggccauucag ggggagcugg aacugcggag aaagaccgac gccgccauca gagagaagcu 1920
gcaggaacac augaccagca acaagaccac caaguacuuc aaccagcuga uucugcgccu 1980
gcagaaagaa aagaccaaca ugaugacaca ccugagcaag aucaacggcg acauugccca 2040
gaccacccug gacaucaccc acaccagcag cagacuggac gcccaccaga aaacccuggu 2100
ggaacuggac caggauguga agaaagugaa cgagcugauc accaacagcc agagcgagau 2160
cagccggcgg accauccuga ucgagagaaa gcagggccug aucaacuucc ugaacaaaca 2220
gcuggaaaga augguguccg agcugggcgg cgaggaagug ggaccucugg aacuggaaau 2280
caagcggcug agcaagcuga ucgacgagca cgacggcaag gccgugcagg cucaagugac 2340
auggcugcgg cugcagcagg aaauggucaa agugacccag gaacaggaag aacagcuggc 2400
cucccuggac gccagcaaga aagaacugca caucauggaa cagaaaaagc ugcgggugga 2460
aagcaagauc gagcaggaaa aaaaagaaca gaaagaaauc gagcaccaca ugaaggaccu 2520
ggacaacgac cugaagaaac ugaauaugcu gaugaacaag aaccgcugcu ccagcgaaga 2580
acuggaacag aacaacagag ugaccgagaa cgaguucgug cggagccuga aggccagcga 2640
gcgggaaacc aucaagaugc aggacaagcu gaaccagcug uccgaggaaa aagccacacu 2700
gcugaaccag cugguggaag ccgagcacca gaucaugcug ugggagaaga agauccagcu 2760
ggccaaagaa augcggagca gcguggacag cgagaucggc cagaccgaaa ucagagccau 2820
gaagggcgag auccaccgga ugaaagugcg gcugggacag cugcugaaac agcaggaaaa 2880
gaugauccgg gccauggaac uggccguggc cagacgggaa accgugacaa cccaggcuga 2940
gggccagcgg aagauggaca gaaaggcccu gacccggacc gacuuccacc acaagcagcu 3000
ggaacugagg cggaagaucc gggacgugcg gaaggccacc gaugagugca caaagacagu 3060
gcuggaacug gaagagacac agcggaacgu guccuccagc cugcuggaaa aacaggaaaa 3120
gcugagcgug auccaggccg acuucgacac ccuggaagcu gaccugacaa gacugggagc 3180
ccugaaaaga cagaaccugu ccgagaucgu ggcacugcag acccggcuga aacaucugca 3240
ggcugugaaa gagggacgcu acguguuccu guucagaucc aagcagucuc uggugcugga 3300
aagacagcgg cuggacaagc ggcuggcacu gauugccacc auccuggaua gagugcgcga 3360
cgaguaccca caguuccagg aagcacugca caaggugucc cagaugaucg ccaacaagcu 3420
ggaaucccu ggccccagcu gauucg 3446

<210> SEQ ID NO 6
<211> LENGTH: 3447
<212> TYPE: RNA
<213> ORGANISM: Artificial Sequence
<220> FEATURE:
<223> OTHER INFORMATION: Sequence with TISU 5 UTR ETH031T07

<400> SEQUENCE: 6
gggagacugc caagauggcu gaaccuggcg gagccgccgg aagaucccac ccugaagaug 60
gcucugccag cgagggcgag aaagagggca acaacgagag ccacauggug ucccccccag 120
agaaggacga cggccagaaa ggcgaagagg ccgugggcuc uaccgagcac ccugaggaag 180
ugaccacaca ggccgaggcc gccauugaag agggcgaggu ggaaacagag ggcgaagccg 240
cuguggaagg cgaagaggaa gccgugucuu acggcgacgc cgagagcgag gaagaguacu 300
acuacaccga gacaagcagc cccgagggcc agaucucugc cgccgauacc accuaccccu 360
acuucagccc cccucaggaa cugccugggg aagaggccua cgauagcgug uccggcgaag 420
cuggccugca gggcuuucag caggaagcca caggcccucc cgagagccgg gaaagaagag 480
ugacaagccc cgagccuagc cacggcgugc ugggaccauc ugagcagaug ggccaaguga 540
ccucuggccc ugcuguggc agacugacag gcagcacaga ggaaccucag ggccaggugc 600
ugccuauggg agugcagcac cgguucagac ugagccacgg cagcgacauc gagagcagcg 660
accuggaaga guucgucagc caggaacccg ugaucccucc uggcgugcca gaugcccauc 720
ccagggaagg cgaucugccc guguuccagg accagaucca gcagcccucu accgaagagg 780
gggcuauggc cgagagagug gaaagcgagg gcuccgacga agaagccgag gacgagggau 840

-continued

```
cucagcuggu ggugcuggac cccgaccacc cucugauggu gcgguuucag gccgcccuga    900
agaacuaccu gaaccggcag aucgagaagc ugaaacugga ccugcaggaa cugguggugg    960
ccacaaagca gagcagagcc cagagacagg aacugggcgu gaaccuguac gaggugcagc   1020
agcaucuggu gcaucugcag aagcugcugg aaaagagcca cgaccggcac gccauggcca   1080
gcucugagcg cagacagaaa gaggaagaac ugcaggccgc cagagcccug uacaccaaga   1140
caugcgccgc ugccaacgag gaacggaaga agcuggcugc ccugcagacc gagauggaaa   1200
accuggcucu gcaccuguuc uacaugcaga auaucgacca ggacaugcgg gacgacauca   1260
gagugaugac ccaggucgug aagaaggccg agacagagag aauccgggcc gagauugaga   1320
agaaaaagca ggaccuguac guggaccagc ugaccaccag ggcccagcag cuggaagagg   1380
auaucgcccu guucgaggcc caguaccugg cccaggccga agauacccgg auccugagaa   1440
aggccguguc cgaggccugc accgagaucg augccaucag cguggaaaag cggcggauca   1500
ugcagcagug ggccagcagc cucgugggca ugaagcacag agaugaggcc caccgggccg   1560
ugcuggaagc ucugagaggc ugucagcacc aggccaagag caccgacggc gagaucgagg   1620
ccuacaagaa auccaucaug aaggaagagg aaaagaacga gaaacuggcc agcauccuga   1680
acagaaccga aaccgaggcc acccugcugc agaaacugac cacccagugc cugaccaaac   1740
agguggcccu gcagucccag uucaacaccu acagacugac ccugcaggac accgaggacg   1800
cccugaguca ggaucagcug gaacagauga uucugaccga ggaacugcag gcuauccggc   1860
aggccauuca gggggagcug gaacugcgga gaaagaccga cgccgccauc agagagaagc   1920
ugcaggaaca caugaccagc aacaagacca ccaaguacuu caaccagcug auucugcgcc   1980
ugcagaaaga aaagaccaac augaugacac accugagcaa gaucaacggc gacauugccc   2040
agaccacccu ggacaucacc cacaccagca gcagacugga cgcccaccag aaaacccugg   2100
uggaacugga ccaggaugug aagaaaguga acgagcugau caccaacagc cagagcgaga   2160
ucagccggcg gaccauccug aucgagagaa agcagggccu gaucaacuuc cugaacaaac   2220
agcuggaaag aauggugucc gagcugggcg gcgaggaagu gggaccucug gaacuggaaa   2280
ucaagcggcu gagcaagcug aucgacgagc acgacggcaa ggccgugcag gcucaaguga   2340
cauggcugcg gcugcagcag gaaauggcca aagugaccca ggaacaggaa gaacagcugg   2400
ccucccugga cgccagcaag aaagaacugc acaucaugga acagaaaaag cugcgggugg   2460
aaagcaagau cgagcaggaa aaaaaagaac agaaagaaau cgagcaccac augaaggacc   2520
uggacaacga ccugaagaaa cugaauaugc ugaugaacaa gaaccgcugc uccagcgaag   2580
aacuggaaca gaacaacaga gugaccgaga acgaguucgu gcggagccug aaggccagcg   2640
agcgggaaac caucaagaug caggacaagc ugaaccagcu guccgaggaa aaagccacac   2700
ugcugaacca gcugguggaa gccgagcacc agaucaugcu gugggagaag aagauccagc   2760
uggccaaaga aaugcggagc agcguggaca gcgagaucgg ccagaccgaa aucagagcca   2820
ugaagggcga gauccaccgg augaaagugc ggcugggaca gcugcugaaa cagcaggaaa   2880
agaugauccg ggccauggaa cuggccgugg ccagacggga aaccgugaca acccaggcug   2940
agggccagcg gaagauggac agaaaggccc ugacccggac cgacuuccac cacaagcagc   3000
uggaacugag gcggaagauc cgggacgugc ggaaggccac cgaugagugc acaaagacag   3060
ugcuggaacu ggaagagaca cagcggaacg uguccuccag ccugcuggaa aaacaggaaa   3120
agcugagcgu gauccaggcc gacuucgaca cccuggaagc ugaccugaca agacugggag   3180
cccugaaaag acagaaccug uccgagaucg uggcacugca gacccggcug aaacaucugc   3240
```

```
aggcugugaa agagggacgc uacguguucc uguucagauc caagcagucu cuggugcugg   3300

aaagacagcg gcuggacaag cggcuggcac ugauugccac cauccuggau agagugcgcg   3360

acgaguaccc acaguuccag gaagcacugc acaaggugu c ccagaugauc gccaacaagc   3420

uggaaucccc uggccccagc ugauucg                                      3447


<210> SEQ ID NO 7
<211> LENGTH: 3476
<212> TYPE: RNA
<213> ORGANISM: Artificial Sequence
<220> FEATURE:
<223> OTHER INFORMATION: Sequence with hAg 5 UTR but without 3 UTR
      ETH031T08

<400> SEQUENCE: 7

gggagacucu ucuggucccc acagacucag agagaacgcc accauggcug aaccuggcgg     60

agccgccgga agaucccacc cugaagaugg cucugccagc gagggcgaga aagagggcaa    120

caacgagagc cacauggugu cccccccaga gaaggacgac ggccagaaag gcgaagaggc    180

cgugggcucu accgagcacc cugaggaagu gaccacacag gccgaggccg ccauugaaga    240

gggcgaggug gaaacagagg gcgaagccgc uguggaaggc gaagaggaag ccgugucuua    300

cggcgacgcc gagagcgagg aagaguacua cuacaccgag acaagcagcc ccgagggcca    360

gaucucugcc gccgauacca ccuaccccua cuucagcccc ccucaggaac ugccuggga    420

agaggccuac gauagcgugu ccggcgaagc uggccugcag ggcuuucagc aggaagccac    480

aggcccuccc gagagccggg aaagaagagu gacaagcccc gagccuagcc acggcgugcu    540

gggaccaucu gagcagaugg gccaagugac cucuggcccu gcugugggca gacugacagg    600

cagcacagag gaaccucagg gccaggugcu gccuauggga gugcagcacc gguucagacu    660

gagccacggc agcgacaucg agagcagcga ccuggaagag uucgucagcc aggaacccgu    720

gaucccuccu ggcgugccag augcccaucc cagggaaggc gaucugcccg uguuccagga    780

ccagauccag cagcccucua ccgaagaggg ggcuauggcc gagagagugg aaagcgaggg    840

cuccgacgaa gaagccgagg acgagggauc ucagcuggug gugcuggacc ccgaccaccc    900

ucugauggug cgguuucagg ccgcccugaa gaacuaccug aaccggcaga ucgagaagcu    960

gaaacuggac cugcaggaac ugguggugc cacaaagcag agcagagccc agagacagga   1020

acugggcgug aaccuguacg aggugcagca gcaucuggug caucugcaga agcugcugga   1080

aaagagccac gaccggcacg ccauggccag cucugagcgc agacagaaag aggaagaacu   1140

gcaggccgcc agagcccugu acaccaagac augcgccgcu gccaacgagg aacggaagaa   1200

gcuggcugcc cugcagaccg agauggaaaa ccuggcucug caccuguucu acaugcagaa   1260

uaucgaccag gacaugcggg acgacaucag agugaugacc caggucguga agaaggccga   1320

gacagagaga auccgggccg agauugagaa gaaaaagcag gaccuguacg uggaccagcu   1380

gaccaccagg gcccagcagc uggaagagga uaucgcccug uucgaggccc aguaccuggc   1440

ccaggccgaa gauacccgga uccugagaaa ggccgugucc gaggccugca ccgagaucga   1500

ugccaucagc guggaaaagc ggcggaucau gcagcagugg gccagcagcc ucgugggcau   1560

gaagcacaga gaugaggccc accgggccgu gcuggaagcu cugagaggcu gucagcacca   1620

ggccaagagc accgacggcg agaucgaggc cuacaagaaa uccaucauga aggaagagga   1680

aaagaacgag aaacuggcca gcauccugaa cagaaccgaa accgaggcca cccugcugca   1740

gaaacugacc acccagugcc ugaccaaaca gguggcccug caguccc agu ucaacaccua   1800
```

cagacugacc cugcaggaca ccgaggacgc ccugagucag gaucagcugg aacagaugau 1860
ucugaccgag gaacugcagg cuauccggca ggccauucag ggggagcugg aacugcggag 1920
aaagaccgac gccgccauca gagagaagcu gcaggaacac augaccagca acaagaccac 1980
caaguacuuc aaccagcuga uucugcgccu gcagaaagaa aagaccaaca ugaugacaca 2040
ccugagcaag aucaacggcg acauugccca gaccacccug gacaucaccc acaccagcag 2100
cagacuggac gcccaccaga aacccuggu ggaacuggac caggauguga agaaagugaa 2160
cgagcugauc accaacagcc agagcgagau cagccggcgg accauccuga ucgagagaaa 2220
gcagggccug aucaacuucc ugaacaaaca gcuggaaaga auggguccg agcugggcgg 2280 cgaggaagug ggaccucugg aacuggaaau caagcggcug agcaagcuga ucgacgagca 2340
cgacggcaag gccgugcagg cucaagugac auggcugcgg cugcagcagg aaauggucaa 2400
agugacccag gaacaggaag aacagcuggc cucccuggac gccagcaaga aagaacugca 2460
caucauggaa cagaaaaagc ugcgggugga aagcaagauc gagcaggaaa aaaaagaaca 2520
gaaagaaauc gagcaccaca ugaaggaccu ggacaacgac cugaagaaac ugaauaugcu 2580
gaugaacaag aaccgcugcu ccagcgaaga acuggaacag aacaacagag ugaccgagaa 2640
cgaguucgug cggagccuga aggccagcga gcgggaaacc aucaagaugc aggacaagcu 2700
gaaccagcug uccgaggaaa aagccacacu gcugaaccag cugguggaag ccgagcacca 2760
gaucaugcug ugggagaaga agauccagcu ggccaaagaa augcggagca gcguggacag 2820
cgagaucggc cagaccgaaa ucagagccau gaagggcgag auccaccgga ugaaagugcg 2880
gcugggacag cugcugaaac agcaggaaaa gaugauccgg gccauggaac uggccgugge 2940 cagacgggaa accgugacaa cccaggcuga gggccagcgg aagauggaca gaaaggcccu 3000
gacccggacc gacuuccacc acaagcagcu ggaacugagg cggaagaucc gggacgugcg 3060
gaaggccacc gaugagugca caaagacagu gcuggaacug gaagagacac agcggaacgu 3120
guccuccagc cugcuggaaa aacaggaaaa gcugagcgug auccaggccg acuucgacac 3180
ccuggaagcu gaccugacaa gacugggagc ccugaaaaga cagaaccugu ccgagaucgu 3240
ggcacugcag acccggcuga aacaucugca ggcugugaaa gagggacgcu acguguuccu 3300
guucagaucc aagcagucuc uggugcugga aagacagcgg cuggacaagc ggcuggcacu 3360
gauugccacc auccuggaua gagugcgcga cgaguaccca caguuccagg aagcacugca 3420
caaggugucc cagaugaucg ccaacaagcu ggaaucccu ggccccagcu gauucg 3476

<210> SEQ ID NO 8
<211> LENGTH: 3683
<212> TYPE: RNA
<213> ORGANISM: Artificial Sequence
<220> FEATURE:
<223> OTHER INFORMATION: Sequence with human CMV IE9 5 UTR and human
Growth hormone 3 UTR ETH031T10

<400> SEQUENCE: 8
gggagaccag aucgccugga gacgccaucc acgcuguuuu gaccuccaua gaagacaccg 60
ggaccgaucc agccuccgcg gccgggaacg gugcauugga acgcggauuc cccgugccaa 120
gagugacuca ccguccuuga cacggccacc auggcugaac cuggcggagc cgccggaaga 180
ucccacccug aagauggcuc ugccagcgag ggcgagaaag agggcaacaa cgagagccac 240
augguguccc ccccagagaa ggacgacggc cagaaaggcg aagaggccgu gggcucuacc 300
gagcacccug aggaagugac cacacaggcc gaggccgcca uugaagaggg cgagguggaa 360

-continued

```
acagagggcg aagccgcugu ggaaggcgaa gaggaagccg ugucuuacgg cgacgccgag    420
agcgaggaag aguacuacua caccgagaca agcagccccg agggccagau cucugccgcc    480
gauaccaccu accccuacuu cagccccccu caggaacugc cuggggaaga ggccuacgau    540
agcguguccg gcgaagcugg ccugcagggc uuucagcagg aagccacagg cccucccgag    600
agccgggaaa gaagagugac aagccccgag ccuagccacg gcgugcuggg accaucugag    660
cagaugggcc aagugaccuc uggcccugcu gugggcagac ugacaggcag cacagaggaa    720
ccucagggcc aggugcugcc uaugggagug cagcaccggu ucagacugag ccacggcagc    780
gacaucgaga gcagcgaccu ggaagaguuc gucagccagg aacccgugau cccuccuggc    840
gugccagaug cccaucccag ggaaggcgau cugcccgugu uccaggacca gauccagcag    900
cccucuaccg aagagggggc uauggccgag agaguggaaa gcgagggcuc cgacgaagaa    960
gccgaggacg agggaucuca gcugguggug cuggaccccg accacccucu gauggugcgg   1020
uuucaggccg cccugaagaa cuaccugaac cggcagaucg agaagcugaa acuggaccug   1080
caggaacugg ugguggccac aaagcagagc agagcccaga gacaggaacu gggcgugaac   1140
cuguacgagg ugcagcagca ucuggugcau cugcagaagc ugcuggaaaa gagccacgac   1200
cggcacgcca uggccagcuc ugagcgcaga cagaaagagg aagaacugca ggccgccaga   1260
gcccuguaca ccaagacaug cgccgcugcc aacgaggaac ggaagaagcu ggcugcccug   1320
cagaccgaga uggaaaaccu ggcucugcac cuguucuaca ugcagaauau cgaccaggac   1380
augcgggacg acaucagagu gaugacccag gucgugaaga aggccgagac agagagaauc   1440
cgggccgaga uugagaagaa aaagcaggac cuguacgugg accagcugac caccagggcc   1500
cagcagcugg aagaggauau cgcccuguuc gaggcccagu accuggccca ggccgaagau   1560
acccggaucc ugagaaaggc cguguccgag gccugcaccg agaucgaugc caucagcgug   1620
gaaaagcggc ggaucaugca gcagugggcc agcagccucg ugggcaugaa gcacagagau   1680
gaggcccacc gggccgugcu ggaagcucug agaggcuguc agcaccaggc caagagcacc   1740
gacggcgaga ucgaggccua caagaaaucc aucaugaagg aagaggaaaa gaacgagaaa   1800
cuggccagca uccugaacag aaccgaaacc gaggccaccc ugcugcagaa acugaccacc   1860
cagugccuga ccaaacaggu ggcccugcag ucccaguuca acaccuacag acugacccug   1920
caggacaccg aggacgcccu gagucaggau cagcuggaac agaugauucu gaccgaggaa   1980
cugcaggcua uccggcaggc cauucagggg gagcuggaac ugcggagaaa gaccgacgcc   2040
gccaucagag agaagcugca ggaacacaug accagcaaca agaccaccaa guacuucaac   2100
cagcugauuc ugcgccugca gaaagaaaag accaacauga ugacacaccu gagcaagauc   2160
aacggcgaca uugcccagac cacccuggac aucacccaca ccagcagcag acuggacgcc   2220
caccagaaaa cccuggugga acuggaccag gaugugaaga aagugaacga gcugaucacc   2280
aacagccaga gcgagaucag ccggcggacc auccugaucg agagaaagca gggccugauc   2340
aacuuccuga acaaacagcu ggaaagaaug guguccgagc ugggcggcga ggaagugggu   2400
ccucuggaac uggaaaucaa gcggcugagc aagcugaucg acgagcacga cggcaaggcc   2460
gugcaggcuc aagugacaug gcugcggcug cagcaggaaa uggucaaagu gacccaggaa   2520
caggaagaac agcuggccuc ccuggacgcc agcaagaaag aacugcacau cauggaacag   2580
aaaaagcugc ggguggaaag caagaucgag caggaaaaaa aagaacagaa agaaaucgag   2640
caccacauga aggaccugga caacgaccug aagaaacuga auaugcugau gaacaagaac   2700
```

-continued

```
cgcugcucca gcgaagaacu ggaacagaac aacagaguga ccgagaacga guucgugcgg   2760

agccugaagg ccagcgagcg ggaaaccauc aagaugcagg acaagcugaa ccagcugucc   2820

gaggaaaaag ccacacugcu gaaccagcug guggaagccg agcaccagau caugcugugg   2880

gagaagaaga uccagcuggc caaagaaaug cggagcagcg uggacagcga gaucggccag   2940

accgaaauca gagccaugaa gggcgagauc caccggauga aagugcggcu gggacagcug   3000

cugaaacagc aggaaaagau gauccgggcc auggaacugg ccguggccag acgggaaacc   3060

gugacaaccc aggcugaggg ccagcggaag auggacagaa aggcccugac ccggaccgac   3120

uuccaccaca agcagcugga acugaggcgg aagauccggg acgugcggaa ggccaccgau   3180

gagugcacaa agacagugcu ggaacuggaa gagacacagc ggaacguguc cuccagccug   3240

cuggaaaaac aggaaaagcu gagcgugauc caggccgacu ucgacacccu ggaagcugac   3300

cugacaagac ugggagcccu gaaaagacag aaccuguccg agaucguggc acugcagacc   3360

cggcugaaac aucugcaggc ugugaaagag ggacgcuacg uguuccuguu cagauccaag   3420

cagucucugg ugcuggaaag acagcggcug gacaagcggc uggcacugau ugccaccauc   3480

cuggauagag ugcgcgacga guacccacag uuccaggaag cacugcacaa ggugucccag   3540

augaucgcca acaagcugga auccccuggc cccagcugac ggguggcauc ccugugaccc   3600

cuccccagug ccucuccugg cccuggaagu ugccacucca gugcccacca gccuuguccu   3660

aauaaaauua aguugcaucu ucg                                           3683
```

<210> SEQ ID NO 9
<211> LENGTH: 4295
<212> TYPE: RNA
<213> ORGANISM: Artificial Sequence
<220> FEATURE:
<223> OTHER INFORMATION: ETH031T28 N terminal EGFP tag CCDC40

<400> SEQUENCE: 9

```
gggagacgcc accaugguga gcaagggcga ggagcuguuc accggggugg ugcccauccu     60

ggucgagcug gacggcgacg uaaacggcca caaguucagc guguccggcg agggcgaggg    120

cgaugccacc uacggcaagc ugacccugaa guucaucugc accaccggca agcugcccgu    180

gcccuggccc acccucguga ccacccugac cuacggcgug cagugcuuca gccgcuaccc    240

cgaccacaug aagcagcacg acuucuucaa guccgccaug cccgaaggcu acguccagga    300

gcgcaccauc uucuucaagg acgacggcaa cuacaagacc cgcgccgagg ugaaguucga    360

gggcgacacc cuggugaacc gcaucgagcu gaagggcauc gacuucaagg aggacggcaa    420

cauccugggg cacaagcugg aguacaacua caacagccac aacgucuaua ucauggccga    480

caagcagaag aacggcauca aggugaacuu caagauccgc cacaacaucg aggacggcag    540

cgugcagcuc gccgaccacu accagcagaa cacccccauc ggcgacggcc ccgugcugcu    600

gcccgacaac cacuaccuga gcacccaguc cgcccugagc aaagacccca acgagaagcg    660

cgaucacaug guccugcugg aguucgugac cgccgccggg aucacucucg gcauggacga    720

gcuguacaag ggcggagggg gcagcgcuga accuggcgga gccgccggaa gaucccaccc    780

ugaagauggc ucugccagcg agggcgagaa agagggcaac aacgagagcc acauggugtc    840

ccccccagag aaggacgacg gccagaaagg cgaagaggcc gugggcucua ccgagcaccc    900

ugaggaagug accacacagg ccgaggccgc cauugaagag ggcgaggugg aaacagaggg    960

cgaagccgcu guggaaggcg aagaggaagc cgugucuuac ggcgacgccg agagcgagga   1020

agaguacuac uacaccgaga caagcagccc cgagggccag aucucugccg ccgauaccac   1080
```

-continued

```
cuaccccuac uucagccccc cucaggaacu gccuggggaa gaggccuacg auagcguguc   1140
cggcgaagcu ggccugcagg gcuuucagca ggaagccaca ggcccucccg agagccggga   1200
aagaagagug acaagccccg agccuagcca cggcgugcug ggaccaucug agcagauggg   1260
ccaagugacc ucuggcccug cugugggcag acugacaggc agcacagagg aaccucaggg   1320
ccaggugcug ccuaugggag ugcagcaccg guucagacug agccacggca gcgacaucga   1380
gagcagcgac cuggaagagu ucgucagcca ggaacccgug aucccuccug gcgugccaga   1440
ugcccauccc agggaaggcg aucugcccgu guuccaggac cagauccagc agcccucuac   1500
cgaagagggg gcuauggccg agagagugga aagcgagggc uccgacgaag aagccgagga   1560
cgagggaucu cagcuggugg ugcuggaccc cgaccacccu cugauggugc gguuucaggc   1620
cgcccugaag aacuaccuga accggcagau cgagaagcug aaacuggacc ugcaggaacu   1680
gguggugccc acaaagcaga gcagagccca gagacaggaa cugggcguga accuguacga   1740
ggugcagcag caucuggugc aucugcagaa gcugcuggaa aagagccacg accggcacgc   1800
cauggccagc ucugagcgca gacagaaaga ggaagaacug caggccgcca gagcccugua   1860
caccaagaca ugcgccgcug ccaacgagga acggaagaag cuggcugccc ugcagaccga   1920
gauggaaaac cuggcucugc accuguucua caugcagaau aucgaccagg acaugcggga   1980
cgacaucaga gugaugaccc aggucgugaa gaaggccgag acagagagaa uccgggccga   2040
gauugagaag aaaaagcagg accuguacgu ggaccagcug accaccaggg cccagcagcu   2100
ggaagaggau aucgcccugu ucgaggccca guaccuggcc caggccgaag auacccggau   2160
ccugagaaag gccguguccg aggccugcac cgagaucgau gccaucagcg uggaaaagcg   2220
gcggaucaug cagcaguggg ccagcagccu cgugggcaug aagcacagag augaggccca   2280
ccgggccgug cuggaagcuc ugagaggcug ucagcaccag gccaagagca ccgacggcga   2340
gaucgaggcc uacaagaaau ccaucaugaa ggaagaggaa aagaacgaga aacuggccag   2400
cauccugaac agaaccgaaa ccgaggccac ccugcugcag aaacugacca cccagugccu   2460
gaccaaacag guggcccugc agucccaguu caacaccuac agacugaccc ugcaggacac   2520
cgaggacgcc cugagucagg aucagcugga acagaugauu cugaccgagg aacugcaggc   2580
uauccggcag gccauucagg gggagcugga acugcggaga aagaccgacg ccgccaucag   2640
agagaagcug caggaacaca ugaccagcaa caagaccacc aaguacuuca accagcugau   2700
ucugcgccug cagaaagaaa agaccaacau gaugacacac cugagcaaga ucaacggcga   2760
cauugcccag accacccugg acaucaccca caccagcagc agacuggacg cccaccagaa   2820
aacccuggug gaacuggacc aggaugugaa gaaagugaac gagcugauca ccaacagcca   2880
gagcgagauc agccggcgga ccauccugau cgagagaaag cagggccuga ucaacuuccu   2940
gaacaaacag cuggaaagaa ugguguccga gcugggcggc gaggaagugg gaccucugga   3000
acuggaaauc aagcggcuga gcaagcugau cgacgagcac gacggcaagg ccgugcaggc   3060
ucaagugaca uggcugcggc ugcagcagga aauggucaaa gugacccagg aacaggaaga   3120
acagcuggcc ucccuggacg ccagcaagaa agaacugcac aucauggaac agaaaaagcu   3180
gcggguggaa agcaagaucg agcaggaaaa aaaagaacag aaagaaaucg agcaccacau   3240
gaaggaccug gacaacgacc ugaagaaacu gaauaugcug augaacaaga accgcugcuc   3300
cagcgaagaa cuggaacaga acaacagagu gaccgagaac gaguucgugc ggagccugaa   3360
ggccagcgag cgggaaacca ucaagaugca ggacaagcug aaccagcugu ccgaggaaaa   3420
```

-continued agccacacug cugaaccagc ugguggaagc cgagcaccag aucaugcugu gggagaagaa 3480
gauccagcug gccaaagaaa ugcggagcag cguggacagc gagaucggcc agaccgaaau 3540
cagagccaug aagggcgaga uccaccggau gaaagugcgg cugggacagc ugcugaaaca 3600
gcaggaaaag augauccggg ccauggaacu ggccguggcc agacgggaaa ccgugacaac 3660
ccaggcugag ggccagcgga agauggacag aaaggcccug acccggaccg acuuccacca 3720
caagcagcug gaacugaggc ggaagauccg ggacgugcgg aaggccaccg augagugcac 3780
aaagacagug cuggaacugg aagagacaca gcggaacgug uccuccagcc ugcuggaaaa 3840
acaggaaaag cugagcguga uccaggccga cuucgacacc cuggaagcug accugacaag 3900
acugggagcc cugaaaagac agaaccuguc cgagaucgug gcacugcaga cccggcugaa 3960
acaucugcag gcugugaaag agggacgcua cguguuccug uucagaucca agcagucucu 4020
ggugcuggaa agacagcggc uggacaagcg gcuggcacug auugccacca uccuggauag 4080
agugcgcgac gaguacccac aguuccagga agcacugcac aaggRguccc agaugaucgc 4140
caacaagcug gaauccccug gccccagcug auucgaaaaa aaaaaaaaaa aaaaaaaaaa 4200
aaaaaaaaaa aaaaaaaaaa aaaaaaaaaa aaaaaaaaaa aaaaaaaaaa aaaaaaaaaa 4260
aaaaaaaaaa aaaaaaaaaa aaaaaaaaaa aaaaa 4295

<210> SEQ ID NO 10
<211> LENGTH: 4295
<212> TYPE: RNA
<213> ORGANISM: Artificial Sequence
<220> FEATURE:
<223> OTHER INFORMATION: ETH031T30 C terminal EGFP tag CCDC40

<400> SEQUENCE: 10
gggagacgcc accauggcug aaccuggcgg agccgccgga agaucccacc cugaagaugg 60
cucugccagc gagggcgaga aagagggcaa caacgagagc cacauggugu cccccccaga 120
gaaggacgac ggccagaaag gcgaagaggc cgugggcucu accgagcacc cugaggaagu 180
gaccacacag gccgaggccg ccauugaaga gggcgaggug gaaacagagg gcgaagccgc 240
uguggaaggc gaagaggaag ccgugucuua cggcgacgcc gagagcgagg aagaguacua 300
cuacaccgag acaagcagcc ccgagggcca gaucucugcc gccgauacca ccuaccccua 360
cuucagcccc ccucaggaac ugccugggga agaggccuac gauagcgugu ccggcgaagc 420
uggccugcag ggcuuucagc aggaagccac aggcccuccc gagagccggg aaagaagagu 480
gacaagcccc gagccuagcc acggcgugcu gggaccaucu gagcagaugg gccaagugac 540
cucuggcccu gcugugggca gacugacagg cagcacagag gaaccucagg gccaggugcu 600
gccuauggga gugcagcacc gguucagacu gagccacggc agcgacaucg agagcagcga 660
ccuggaagag uucgucagcc aggaacccgu gaucccuccu ggcgugccag augcccaucc 720
cagggaaggc gaucugcccg uguuccagga ccagauccag cagccucua ccgaagaggg 780 ggcuauggcc gagagagugg aaagcgaggg cuccgacgaa gaagccgagg acgagggauc 840
ucagcuggug gugcuggacc ccgaccaccc ucugauggug cgguuucagg ccgcccugaa 900
gaacuaccug aaccggcaga ucgagaagcu gaaacuggac cugcaggaac ugguggugc 960 cacaaagcag agcagagccc agagacagga acugggcgug aaccuguacg aggugcagca 1020
gcaucuggug caucugcaga agcugcugga aaagagccac gaccggcacg ccauggccag 1080
cucugagcgc agacagaaag aggaagaacu gcaggccgcc agagcccugu acaccaagac 1140
augcgccgcu gccaacgagg aacggaagaa gcuggcugcc cugcagaccg agauggaaaa 1200

-continued

```
ccuggcucug caccuguucu acaugcagaa uaucgaccag gacaugcggg acgacaucag   1260
agugaugacc caggucguga agaaggccga gacagagaga auccgggccg agauugagaa   1320
gaaaaagcag gaccuguacg uggaccagcu gaccaccagg gcccagcagc uggaagagga   1380
uaucgcccug uucgaggccc aguaccuggc ccaggccgaa gauacccgga uccugagaaa   1440
ggccgugucc gaggccugca ccgagaucga ugccaucagc guggaaaagc ggcggaucau   1500
gcagcagugg gccagcagcc ucgugggcau gaagcacaga gaugaggccc accgggccgu   1560
gcuggaagcu cugagaggcu gucagcacca ggccaagagc accgacggcg agaucgaggc   1620
cuacaagaaa uccaucauga aggaagagga aaagaacgag aaacuggcca gcauccugaa   1680
cagaaccgaa accgaggcca cccugcugca gaaacugacc acccagugcc ugaccaaaca   1740
gguggcccug cagucccagu ucaacaccua cagacugacc cugcaggaca ccgaggacgc   1800
ccugagucag gaucagcugg aacagaugau ucugaccgag gaacugcagg cuauccggca   1860
ggccauucag ggggagcugg aacugcggag aaagaccgac gccgccauca gagagaagcu   1920
gcaggaacac augaccagca acaagaccac caaguacuuc aaccagcuga uucugcgccu   1980
gcagaaagaa aagaccaaca ugaugacaca ccugagcaag aucaacggcg acauugccca   2040
gaccacccug gacaucaccc acaccagcag cagacuggac gcccaccaga aaacccuggu   2100
ggaacuggac caggauguga agaaagugaa cgagcugauc accaacagcc agagcgagau   2160
cagccggcgg accauccuga ucgagagaaa gcagggccug aucaacuucc ugaacaaaca   2220
gcuggaaaga augguguccg agcugggcgg cgaggaagug ggaccucugg aacuggaaau   2280
caagcggcug agcaagcuga ucgacgagca cgacggcaag gccgugcagg cucaagugac   2340
auggcugcgg cugcagcagg aaauggucaa agugacccag gaacaggaag aacagcuggc   2400
cucccuggac gccagcaaga aagaacugca caucauggaa cagaaaaagc ugcgggugga   2460
aagcaagauc gagcaggaaa aaaaagaaca gaaagaaauc gagcaccaca ugaaggaccu   2520
ggacaacgac cugaagaaac ugaauaugcu gaugaacaag aaccgcugcu ccagcgaaga   2580
acuggaacag aacaacagag ugaccgagaa cgaguucgug cggagccuga aggccagcga   2640
gcgggaaacc aucaagaugc aggacaagcu gaaccagcug uccgaggaaa aagccacacu   2700
gcugaaccag cugguggaag ccgagcacca gaucaugcug ugggagaaga agauccagcu   2760
ggccaaagaa augcggagca gcguggacag cgagaucggc cagaccgaaa ucagagccau   2820
gaagggcgag auccaccgga ugaaagugcg gcugggacag cugcugaaac agcaggaaaa   2880
gaugauccgg gccauggaac uggccguggc cagacgggaa accgugacaa cccaggcuga   2940
gggccagcgg aagauggaca gaaaggcccu gacccggacc gacuuccacc acaagcagcu   3000
ggaacugagg cggaagaucc gggacgugcg gaaggccacc gaugagugca caaagacagu   3060
gcuggaacug gaagagacac agcggaacgu guccuccagc cugcuggaaa aacaggaaaa   3120
gcugagcgug auccaggccg acuucgacac ccuggaagcu gaccugacaa gacugggagc   3180
ccugaaaaga cagaaccugu ccgagaucgu ggcacugcag acccggcuga aacaucugca   3240
ggcugugaaa gagggacgcu acguguuccu guucagaucc aagcagucuc uggugcugga   3300
aagacagcgg cuggacaagc ggcuggcacu gauugccacc auccuggaua gagugcgcga   3360
cgaguaccca caguuccagg aagcacugca caaggugucc cagaugaucg ccaacaagcu   3420
ggaauccccu ggccccagcg gcggaggggg cagcgugagc aagggcgagg agcuguucac   3480
cgggguggug cccauccugg ucgagcugga cggcgacgua aacggccaca aguucagcgu   3540
```

-continued

```
guccggcgag ggcgagggcg augccaccua cggcaagcug acccugaagu ucaucugcac   3600

caccggcaag cugcccgugc ccuggcccac ccucgugacc acccugaccu acggcgugca   3660

gugcuucagc cgcuaccccg accacaugaa gcagcacgac uucuucaagu ccgccaugcc   3720

cgaaggcuac guccaggagc gcaccaucuu cuucaaggac gacggcaacu acaagacccg   3780

cgccgaggug aaguucgagg gcgacacccu ggugaaccgc aucgagcuga agggcaucga   3840

cuucaaggag gacggcaaca uccuggggca caagcuggag uacaacuaca acagccacaa   3900

cgucuauauc auggccgaca agcagaagaa cggcaucaag gugaacuuca agauccgcca   3960

caacaucgag gacggcagcg ugcagcucgc cgaccacuac cagcagaaca cccccaucgg   4020

cgacggcccc gugcugcugc ccgacaacca cuaccugagc acccaguccg cccugagcaa   4080

agaccccaac gagaagcgcg aucacauggu ccugcuggag uucgugaccg ccgccgggau   4140

cacucucggc auggacgagc uguacaagug auucgaaaaa aaaaaaaaaa aaaaaaaaaa   4200

aaaaaaaaaa aaaaaaaaaa aaaaaaaaaa aaaaaaaaaa aaaaaaaaaa aaaaaaaaaa   4260

aaaaaaaaaa aaaaaaaaaa aaaaaaaaaa aaaaa                              4295
```

```
<210> SEQ ID NO 11
<211> LENGTH: 5199
<212> TYPE: RNA
<213> ORGANISM: Artificial Sequence
<220> FEATURE:
<223> OTHER INFORMATION: ETH031T26 N terminal HA Tag CCDC40 T2A peptide
      tdTomato with 5 and 3 CYBA UTRs

<400> SEQUENCE: 11

gggagaccgc gccuagcagu gucccagccg gguucguguc gccgccacca uguaccccua     60

cgacgugccc gacuacgccg gcggaggggg cagcgcugaa ccuggcggag ccgccggaag    120

aucccacccu gaagauggcu cugccagcga gggcgagaaa gagggcaaca acgagagcca    180

cauggugucc cccccagaga aggacgacgg ccagaaaggc gaagaggccg ugggcucuac    240

cgagcacccu gaggaaguga ccacacaggc cgaggccgcc auugaagagg gcgaggugga    300

aacagagggc gaagccgcug uggaaggcga agaggaagcc gugucuuacg gcgacgccga    360

gagcgaggaa gaguacuacu acaccgagac aagcagcccc gagggccaga ucucugccgc    420

cgauaccacc uaccccuacu ucagcccccc ucaggaacug ccuggggaag aggccuacga    480

uagcgugucc ggcgaagcug gccugcaggg cuuucagcag gaagccacag gcccucccga    540

gagccgggaa agaagaguga caagccccga gccuagccac ggcgugcugg gaccaucuga    600

gcagaugggc caagugaccu cuggcccugc uguugggcaga cugacaggca gcacagagga    660

accucagggc caggugcugc cuaugggagu gcagcaccgg uucagacuga gccacggcag    720

cgacaucgag agcagcgacc uggaagaguu cgucagccag gaacccguga ucccuccugg    780

cgugccagau gcccauccca gggaaggcga ucugcccgug uuccaggacc agauccagca    840

gcccucuacc gaagaggggg cuauggccga gagaguggaa agcgagggcu ccgacgaaga    900

agccgaggac gagggaucuc agcuggugu gcuggacccc gaccacccuc ugauggugcg    960

guuucaggcc gcccugaaga acuaccugaa ccggcagauc gagaagcuga aacuggaccu   1020

gcaggaacug gugguggcca caaagcagag cagagcccag agacaggaac ugggcgugaa   1080

ccuguacgag gugcagcagc aucuggugca ucugcagaag cugcuggaaa agagccacga   1140

ccggcacgcc auggccagcu cugagcgcag acagaaagag gaagaacugc aggccgccag   1200

agcccuguac accaagacau gcgccgcugc caacgaggaa cggaagaagc uggcugcccu   1260
```

-continued gcagaccgag auggaaaacc uggcucugca ccuguucuac augcagaaua ucgaccagga 1320
caugcgggac gacaucagag ugaugaccca ggucgugaag aaggccgaga cagagagaau 1380
ccgggccgag auugagaaga aaaagcagga ccuguacgug gaccagcuga ccaccagggc 1440
ccagcagcug gaagaggaua ucgcccuguu cgaggcccag uaccuggccc aggccgaaga 1500
uacccggauc cugagaaagg ccguguccga ggccugcacc gagaucgaug ccaucagcgu 1560
ggaaaagcgg cggaucaugc agcagugggc cagcagccuc gugggcauga agcacagaga 1620
ugaggcccac cgggccgugc uggaagcucu gagaggcugu cagcaccagg ccaagagcac 1680
cgacggcgag aucgaggccu acaagaaauc caucaugaag gaagaggaaa agaacgagaa 1740
acuggccagc auccugaaca gaaccgaaac cgaggccacc cugcugcaga aacugaccac 1800
ccagugccug accaaacagg uggcccugca gucccaguuc aacaccuaca gacugacccu 1860
gcaggacacc gaggacgccc ugagucagga ucagcuggaa cagaugauuc ugaccgagga 1920
acugcaggcu auccggcagg ccauucaggg ggagcuggaa cugcggagaa agaccgacgc 1980
cgccaucaga gagaagcugc aggaacacau gaccagcaac aagaccacca aguacuucaa 2040
ccagcugauu cugcgccugc agaaagaaaa gaccaacaug augacacacc ugagcaagau 2100
caacggcgac auugcccaga ccacccugga caucacccac accagcagca gacuggacgc 2160
ccaccagaaa acccuggugg aacuggacca ggaugugaag aaagugaacg agcugaucac 2220
caacagccag agcgagauca gccggcggac cauccugauc gagagaaagc agggccugau 2280
caacuuccug aacaaacagc uggaaagaau ggguguccgag cugggcggcg aggaagugggg 2340 accucuggaa cuggaaauca agcggcugag caagcugauc gacgagcacg acggcaaggc 2400
cgugcaggcu caagugacau ggcugcggcu gcagcaggaa auggucaaag ugacccagga 2460
acaggaagaa cagcuggccu cccuggacgc cagcaagaaa gaacugcaca ucauggaaca 2520
gaaaaagcug cggguggaaa gcaagaucga gcaggaaaaa aaagaacaga aagaaaucga 2580
gcaccacaug aaggaccugg acaacgaccu gaagaaacug aauaugcuga ugaacaagaa 2640
ccgcugcucc agcgaagaac uggaacagaa caacagagug accgagaacg aguucgugcg 2700
gagccugaag gccagcgagc gggaaaccau caagaugcag gacaagcuga accagcuguc 2760
cgaggaaaaa gccacacugc ugaaccagcu gguggaagcc gagcaccaga ucaugcugug 2820
ggagaagaag auccagcugg ccaaagaaau gcggagcagc guggacagcg agaucggcca 2880
gaccgaaauc agagccauga agggcgagau ccaccggaug aaagugcggc ugggacagcu 2940
gcugaaacag caggaaaaga ugauccgggc cauggaacug gccguggcca gacgggaaac 3000
cgugacaacc caggcugagg gccagcggaa gauggacaga aaggcccuga cccggaccga 3060
cuuccaccac aagcagcugg aacugaggcg gaagauccgg gacgugcgga aggccaccga 3120
ugagugcaca aagacagugc uggaacugga agagacacag cggaacgugu ccuccagccu 3180
gcuggaaaaa caggaaaagc ugagcgugau ccaggccgac uucgacaccc uggaagcuga 3240
ccugacaaga cugggagccc ugaaaagaca gaaccugucc gagaucgugg cacugcagac 3300
ccggcugaaa caucugcagg cugugaaaga gggacgcuac guguuccugu ucagauccaa 3360
gcagucucug gugcuggaaa gacagcggcu ggacaagcgg cuggcacuga uugccaccau 3420
ccuggauaga gugcgcgacg aguacccaca guuccaggaa gcacugcaca aggugucccca 3480 gaugaucgcc aacaagcugg aauccccugg ccccagcggc agcggcgagg gcagaggcag 3540
ccugcugacc ugcggcgacg uggaggagaa ccccggcccc auggugagca agggcgagga 3600
ggucaucaaa gaguucaugc gcuucaaggu gcgcauggag ggcuccauga acggccacga 3660

```
guucgagauc gagggcgagg gcgagggccg ccccuacgag ggcacccaga ccgccaagcu   3720

gaaggugacc aagggcggcc cccugcccuu cgccugggac auccuguccc cccaguucau   3780

guacggcucc aaggcguacg ugaagcaccc cgccgacauc cccgauuaca agaagcuguc   3840

cuuccccgag ggcuucaagu gggagcgcgu gaugaacuuc gaggacggcg gucuggugac   3900

cgugacccag gacuccuccc ugcaggacgg cacgcugauc uacaagguga agaugcgcgg   3960

caccaacuuc ccccccgacg gccccguaau gcagaagaag accaugggcu gggaggccuc   4020

caccgagcgc cuguaccccc gcgacggcgu gcugaagggc gagauccacc aggcccugaa   4080

gcugaaggac ggcggccacu accuggugga guucaagacc aucuacaugg ccaagaagcc   4140

cgugcaacug cccggcuacu acuacgugga caccaagcug gacaucaccu cccacaacga   4200

ggacuacacc aucguggaac aguacgagcg cuccgagggc cgccaccacc uguuccuggg   4260

gcauggcacc ggcagcaccg gcagcggcag cuccggcacc gccuccuccg aggacaacaa   4320

cauggccguc aucaaagagu ucaugcgcuu caaggugcgc auggagggcu ccaugaacgg   4380

ccacgaguuc gagaucgagg gcgagggcga gggccgcccc uacgagggca cccagaccgc   4440

caagcugaag gugaccaagg gcggcccccu gcccuucgcc ugggacaucc uguccccca   4500

guucauguac ggcuccaagg cguacgugaa gcaccccgcc gacauccccg auuacaagaa   4560

gcuguccuuc cccgagggcu ucaaguggga gcgcgugaug aacuucgagg acggcggucu   4620

ggugaccgug acccaggacu ccucccugca ggacggcacg cugaucuaca aggugaagau   4680

gcgcggcacc aacuuccccc ccgacggccc cguaaugcag aagaagacca ugggcuggga   4740

ggccuccacc gagcgccugu acccccgcga cggcgugcug aagggcgaga uccaccaggc   4800

ccugaagcug aaggacggcg gccacuaccu gguggaguuc aagaccaucu acauggccaa   4860

gaagcccgug caacugcccg gcuacuacua cguggacacc aagcuggaca ucaccuccca   4920

caacgaggac uacaccaucg uggaacagua cgagcgcucc gagggccgcc accaccuguu   4980

ccuguacggc auggacgagc uguacaagug accucgcccc ggaccugccc ucccgccagg   5040

ugcacccacc ugcaauaaau gcagcgaagc cgggauucga aaaaaaaaaa aaaaaaaaaa   5100

aaaaaaaaaa aaaaaaaaaa aaaaaaaaaa aaaaaaaaaa aaaaaaaaaa aaaaaaaaaa   5160

aaaaaaaaaa aaaaaaaaaa aaaaaaaaaa aaaaaaaaa                          5199


<210> SEQ ID NO 12
<211> LENGTH: 2963
<212> TYPE: RNA
<213> ORGANISM: Artificial Sequence
<220> FEATURE:
<223> OTHER INFORMATION: ETH047T02 CCDC39 with Ethris minimal UTR

<400> SEQUENCE: 12

gggagacgcc accaugagca gcgaguuucu ggccgaacug cacugggagg acggcuucgc     60

uauucccgug gccaacgagg aaaacaagcu gcuggaagau cagcugagca agcugaagga    120

cgagagagcc ucucugcagg acgagcugag agaguacgag gaacggauca acagcaugac    180

cagccacuuc aagaacguga agcaagagcu gagcaucacc cagagccugu gcaaggccag    240

agagagagaa accgagagcg aggaacacuu caaggcuauc gcccagcgcg agcugggaag    300

agugaaggau gagauccagc ggcuggaaaa cgagauggcc agcauccugg aaaagaaguc    360

cgacaaagag aacggcaucu ucaaggccac acagaagcug gacggccuga agugccagau    420

gaacugggau cagcaggccc uggaagccug gcuggaagag ucugcccaca aggauucuga    480
```

-continued

```
cgcccugaca cugcagaagu acgcccagca ggacgacaac aagauccggg cucugacccu    540
gcagcuggaa agacugaccc uggaaugcaa ccagaagcgg aagauccugg acaacgagcu    600
gaccgagaca aucagcgccc agcuggaacu ggauaaggcc gcucaggacu ucagaaagau    660
ccacaacgag cggcaagaac ugaucaagca gugggagaac accaucgagc agaugcagaa    720
acgcgacggc gacaucgaca acugcgcccu ggaacucgcc cggaucaagc aagagacacg    780
cgagaaagag aaccugguca aagagaagau caaguuccuc gaguccgaga ucggcaacaa    840
caccgaguuc gagaagcgga ucagcguggc cgacagaaag cugcugaagu gcagaaccgc    900
cuaccaggac cacgagacaa gccggauuca gcucaagggc gagcuggauu cucugaaggc    960
caccgugaac agaaccagca gcgaucugga agcccugcgg aagaacauca gcaagaucaa   1020
gaaggacauc cacgaggaaa ccgccaggcu gcagaaaaca aagaaccaca augagaucau   1080
ccagaccaag cugaaagaga ucaccgaaaa gaccaugagc guggaagaga aggccacaaa   1140
ccuggaagau augcucaaag aggaagagaa agacgucaaa gagguggacg uucaacugaa   1200
ccugauuaag ggcgugcugu ucaagaaggc ccaagagcug cagaccgaaa ccaugaagga   1260
aaaggccguc cugucugaga ucgagggcac cagaucuagc cugaagcacc ugaaccauca   1320
gcugcagaag cucgacuucg agacacugaa gcagcaagag aucauguaca gccaggauuu   1380
ccacauccag caggucgagc ggcggauguc uagacugaag ggcgagauca acuccgagga   1440
aaaacaggcc cucgaggcca agaucgugga acugagaaag agccucgaag agaagaaguc   1500
uaccugcggc cugcuggaaa cccagauuaa gaagcugcac aacgaccugu acuucaucaa   1560
gaaagcccac agcaagaaca gcgacgagaa gcagagccug augaccaaga ucaaugagcu   1620
gaaccuguuc aucgaucgga gcgaaaaaga gcuggacaag gccaagggcu ucaagcagga   1680
ccugaugauc gaggacaacc ugcugaagcu ggaagugaag cggaccagag agaugcugca   1740
cagcaaggcc gaggaagugc ugucucugga aaagcggaag cagcagcugu acaccgccau   1800
ggaagagaga accgaagaga ucaaggugca caagaccaug cuggcuuccc agaucagaua   1860
cguggaccaa gagcgcgaga acaucuccac cgaguuuaga gagagacugu ccaagaucga   1920
gaagcugaag aaccgcuacg agauccugac cgucgugaug cugccuccug agggcgaaga   1980
ggaaaagacc caggccuacu acgugaucaa ggcagcccaa gaaaaagagg aacuccagag   2040
agaaggcgac ugccuggacg ccaagauuaa caaggccgaa aaagaaaucu acgcccucga   2100
gaacacccug cagguccuga acagcugcaa caacaacuac aagcagagcu ucaagaaagu   2160
caccccuagc uccgacgagu acgagcugaa gauucagcug gaagaacaga aaagagccgu   2220
ggacgagaag uacagauaca agcagcggca gaucagagag cugcaagagg auauccagag   2280
cauggaaaac acccuggacg ugaucgagca ccuggccaac aacgugaaag agaagcuguc   2340
cgagaaacag gccuacagcu uucagcuguc caaagagaca gaggaacaga agcccaaacu   2400
ggaacgcgug accaagcagu gcgccaagcu gacaaaagag auccggcugc ugaaagacac   2460
caaggacgaa accauggaag aacaagacau caagcugcgc gagaugaagc aguuccacaa   2520
agugaucgac gagaugcugg uggacaucau ugaagagaac acagagaucc gcaucauccu   2580
gcagaccuau uuucagcaga gcggccugga acugccuacc gccucuacaa agggcagcag   2640
acagagcagc agaucccua gccacacaag ccugagcgcc agaagcucua gaagcaccag   2700
caccucuacc agccagucca gcauuaaggu gcuggaacuc aaguuccccg ccagcucuag   2760
ccucguggga agcccuucua gaccuagcag cgccucuagc agcuccagca acgugaaguc   2820
caagaaaagc uccaagugau ucgaaaaaaa aaaaaaaaaa aaaaaaaaaa aaaaaaaaaa   2880
```

aaaaaaaaaa aaaaaaaaaa aaaaaaaaaa aaaaaaaaaa aaaaaaaaaa aaaaaaaaaa 2940
aaaaaaaaaa aaaaaaaaaa aaa 2963

<210> SEQ ID NO 13
<211> LENGTH: 2964
<212> TYPE: RNA
<213> ORGANISM: Artificial Sequence
<220> FEATURE:
<223> OTHER INFORMATION: RNA encoding for human CCDC39 sequence and contains TISU element as 5 UTR ETH047T03

<400> SEQUENCE: 13
gggagacugc caagaugagc agcgaguuuc uggccgaacu gcacugggag gacggcuucg 60
cuauucccgu ggccaacgag gaaaacaagc ugcuggaaga ucagcugagc aagcugaagg 120
acgagagagc cucucugcag gacgagcuga gagaguacga ggaacggauc aacagcauga 180
ccagccacuu caagaacgug aagcaagagc ugagcaucac ccagagccug ugcaaggcca 240
gagagagaga aaccgagagc gaggaacacu ucaaggcuau cgcccagcgc gagcugggaa 300
gagugaagga ugagauccag cggcuggaaa acgagauggc cagcauccug gaaaagaagu 360
ccgacaaaga gaacggcauc uucaaggcca cacagaagcu ggacggccug aagugccaga 420
ugaacuggga ucagcaggcc cuggaagccu ggcuggaaga gucugcccac aaggauucug 480
acgcccugac acugcagaag uacgcccagc aggacgacaa caagauccgg gcucugaccc 540
ugcagcugga aagacugacc cuggaaugca accagaagcg gaagauccug gacaacgagc 600
ugaccgagac aaucagcgcc cagcuggaac uggauaaggc cgcucaggac uucagaaaga 660
uccacaacga gcggcaagaa cugaucaagc agugggagaa caccaucgag cagaugcaga 720
aacgcgacgg cgacaucgac aacugcgccc uggaacucgc ccggaucaag caagagacac 780
gcgagaaaga gaaccugguc aaagagaaga ucaaguuccu cgaguccgag aucggcaaca 840
acaccgaguu cgagaagcgg aucagcgugg ccgacagaaa gcugcugaag ugcagaaccg 900
ccuaccagga ccacgagaca agccggauuc agcucaaggg cgagcuggau ucucugaagg 960
ccaccgugaa cagaaccagc agcgaucugg aagcccugcg gaagaacauc agcaagauca 1020
agaaggacau ccacgaggaa accgccaggc ugcagaaaac aaagaaccac aaugagauca 1080
uccagaccaa gcugaaagag aucaccgaaa agaccaugag cguggaagag aaggccacaa 1140
accuggaaga uaugcucaaa gaggaagaga aagacgucaa agagguggac guucaacuga 1200
accugauuaa gggcgugcug uucaagaagg cccaagagcu gcagaccgaa accaugaagg 1260
aaaaggccgu ccugucugag aucgagggca ccagaucuag ccugaagcac cugaaccauc 1320
agcugcagaa gcucgacuuc gagacacuga agcagcaaga gaucauguac agccaggauu 1380
uccacaucca gcaggucgag cggcggaugu cuagacugaa gggcgagauc aacuccgagg 1440
aaaaacaggc ccucgaggcc aagaucgugg aacugagaaa gagccucgaa gagaagaagu 1500
cuaccugcgg ccugcuggaa acccagauua agaagcugca caacgaccug uacuucauca 1560
agaaagccca cagcaagaac agcgacgaga agcagagccu gaugaccaag aucaaugagc 1620
ugaaccuguu caucgaucgg agcgaaaaag agcuggacaa ggccaagggc uucaagcagg 1680
accugaugau cgaggacaac cugcugaagc uggaagugaa gcggaccaga gagaugcugc 1740
acagcaaggc cgaggaagug cugucucugg aaaagcggaa gcagcagcug uacaccgcca 1800
uggaagagag aaccgaagag aucaaggugc acaagaccau gcuggcuucc cagaucagau 1860
acguggacca agagcgcgag aacaucucca ccgaguuuag agagagacug uccaagaucg 1920
agaagcugaa gaaccgcuac gagauccuga ccgucgugau gcugccuccu gagggcgaag 1980
aggaaaagac ccaggccuac uacgugauca aggcagccca agaaaaagag gaacuccaga 2040
gagaaggcga cugccuggac gccaagauua acaaggccga aaaagaaauc uacgcccucg 2100
agaacacccu gcagguccug aacagcugca acaacaacua caagcagagc uucaagaaag 2160
ucaccccuag cuccgacgag uacgagcuga agauucagcu ggaagaacag aaaagagccg 2220
uggacgagaa guacagauac aagcagcggc agaucagaga gcugcaagag gauauccaga 2280
gcauggaaaa cacccuggac gugaucgagc accuggccaa caacgugaaa gagaagcugu 2340
ccgagaaaca ggccuacagc uuucagcugu ccaaagagac agaggaacag aagcccaaac 2400
uggaacgcgu gaccaagcag ugcgccaagc ugacaaaaga gauccggcug cugaaagaca 2460
ccaaggacga aaccauggaa gaacaagaca ucaagcugcg cgagaugaag caguuccaca 2520
aagugaucga cgagaugcug guggacauca uugaagagaa cacagagauc cgcaucaucc 2580
ugcagaccua uuuucagcag agcggccugg aacugccuac cgccucuaca aagggcagca 2640
gacagagcag cagaucccu agccacacaa gccugagcgc cagaagcucu agaagcacca 2700
gcaccucuac cagccagucc agcauuaagg ugcuggaacu caaguucccc gccagcucua 2760
gccucguggg aagcccuucu agaccuagca gcgccucuag cagcuccagc aacgugaagu 2820
ccaagaaaag cuccaaguga uucgaaaaaa aaaaaaaaaa aaaaaaaaaa aaaaaaaaaa 2880
aaaaaaaaaa aaaaaaaaaa aaaaaaaaaa aaaaaaaaaa aaaaaaaaaa aaaaaaaaaa 2940
aaaaaaaaaa aaaaaaaaaa aaaa 2964

<210> SEQ ID NO 14
<211> LENGTH: 2993
<212> TYPE: RNA
<213> ORGANISM: Artificial Sequence
<220> FEATURE:
<223> OTHER INFORMATION: ETH047T05 SP30 RNA encoding for human CCDC39
and containing random sequence of 30 nucleotides SP30 which was
used as 5 UTR

<400> SEQUENCE: 14
gggagacauu gaaauuuauc ucuuguguug uggucgcgcc accaugagca gcgaguuucu 60
ggccgaacug cacugggagg acggcuucgc uauucccgug gccaacgagg aaaacaagcu 120
gcuggaagau cagcugagca agcugaagga cgagagagcc ucucugcagg acgagcugag 180
agaguacgag gaacggauca acagcaugac cagccacuuc aagaacguga agcaagagcu 240
gagcaucacc cagagccugu gcaaggccag agagagagaa accgagagcg aggaacacuu 300
caaggcuauc gcccagcgcg agcugggaag agugaaggau gagauccagc ggcuggaaaa 360
cgagauggcc agcauccugg aaaagaaguc cgacaaagag aacggcaucu ucaaggccac 420
acagaagcug gacggccuga agugccagau gaacugggau cagcaggccc uggaagccug 480
gcuggaagag ucugcccaca aggauucuga cgcccugaca cugcagaagu acgcccagca 540
ggacgacaac aagauccggg cucugacccu gcagcuggaa agacugaccc uggaaugcaa 600
ccagaagcgg aagauccugg acaacgagcu gaccgagaca aucagcgccc agcuggaacu 660
ggauaaggcc gcucaggacu ucagaaagau ccacaacgag cggcaagaac ugaucaagca 720
gugggagaac accaucgagc agaugcagaa acgcgacggc gacaucgaca acugcgcccu 780
ggaacucgcc cggaucaagc aagagacacg cgagaaagag aaccugguca aagagaagau 840
caaguuccuc gaguccgaga ucggcaacaa caccgaguuc gagaagcgga ucagcguggc 900

-continued

```
cgacagaaag cugcugaagu gcagaaccgc cuaccaggac cacgagacaa gccggauuca    960
gcucaagggc gagcuggauu cucugaaggc caccgugaac agaaccagca gcgaucugga   1020
agcccugcgg aagaacauca gcaagaucaa gaaggacauc cacgaggaaa ccgccaggcu   1080
gcagaaaaca aagaaccaca augagaucau ccagaccaag cugaaagaga ucaccgaaaa   1140
gaccaugagc guggaagaga aggccacaaa ccuggaagau augcucaaag aggaagagaa   1200
agacgucaaa gagguggacg uucaacugaa ccugauuaag ggcgugcugu ucaagaaggc   1260
ccaagagcug cagaccgaaa ccaugaagga aaaggccguc cugucugaga ucgagggcac   1320
cagaucuagc cugaagcacc ugaaccauca gcugcagaag cucgacuucg agacacugaa   1380
gcagcaagag aucauguaca gccaggauuu ccacauccag caggucgagc ggcggauguc   1440
uagacugaag ggcgagauca acuccgagga aaaacaggcc cucgaggcca agaucgugga   1500
acugagaaag agccucgaag agaagaaguc uaccugcggc cugcuggaaa cccagauuaa   1560
gaagcugcac aacgaccugu acuucaucaa gaaagcccac agcaagaaca gcgacgagaa   1620
gcagagccug augaccaaga ucaaugagcu gaaccuguuc aucgaucgga gcgaaaaaga   1680
gcuggacaag gccaagggcu ucaagcagga ccugaugauc gaggacaacc ugcugaagcu   1740
ggaagugaag cggaccagag agaugcugca cagcaaggcc gaggaagugc ugucucugga   1800
aaagcggaag cagcagcugu acaccgccau ggaagagaga accgaagaga ucaaggugca   1860
caagaccaug cuggcuuccc agaucagaua cguggaccaa gagcgcgaga acaucuccac   1920
cgaguuuaga gagagacugu ccaagaucga gaagcugaag aaccgcuacg agauccugac   1980
cgucgugaug cugccuccug agggcgaaga ggaaaagacc caggccuacu acgugaucaa   2040
ggcagcccaa gaaaaagagg aacuccagag agaaggcgac ugccuggacg ccaagauuaa   2100
caaggccgaa aaagaaaucu acgcccucga gaacacccug cagguccuga acagcugcaa   2160
caacaacuac aagcagagcu ucaagaaagu caccccuagc uccgacgagu acgagcugaa   2220
gauucagcug gaagaacaga aaagagccgu ggacgagaag uacagauaca agcagcggca   2280
gaucagagag cugcaagagg auauccagag cauggaaaac acccuggacg ugaucgagca   2340
ccuggccaac aacgugaaag agaagcuguc cgagaaacag gccuacagcu uucagcuguc   2400
caaagagaca gaggaacaga agcccaaacu ggaacgcgug accaagcagu gcgccaagcu   2460
gacaaaagag auccggcugc ugaaagacac caaggacgaa accauggaag aacaagacau   2520
caagcugcgc gagaugaagc aguuccacaa agugaucgac gagaugcugg uggacaucau   2580
ugaagagaac acagagaucc gcaucauccu gcagaccuau uuucagcaga gcggccugga   2640
acugccuacc gccucuacaa agggcagcag acagagcagc agaucccua gccacacaag   2700
ccugagcgcc agaagcucua gaagcaccag caccucuacc agccagucca gcauuaaggu   2760
gcuggaacuc aaguuccccg ccagcucuag ccucguggga agcccuucua gaccuagcag   2820
cgccucuagc agcuccagca acgugaaguc caagaaaagc uccaagugau ucgaaaaaaa   2880
aaaaaaaaaa aaaaaaaaaa aaaaaaaaaa aaaaaaaaaa aaaaaaaaaa aaaaaaaaaa   2940
aaaaaaaaaa aaaaaaaaaa aaaaaaaaaa aaaaaaaaaa aaaaaaaaaa aaa          2993
```

TREATMENT OF CILIOPATHIES

RELATED APPLICATIONS

This application is a national stage filing under 35 U.S.C. 371 of International Application No. PCT/EP2020/053774, filed Feb. 13, 2020, which claims the benefit of EP Application Serial No. 19157210.6, filed on Feb. 14, 2019. The entire teachings of the above applications are incorporated herein by reference. International Application No. PCT/EP2020/053774 was published under PCT Article 21(2) in English.

The present invention relates to a pharmaceutical composition comprising a polyribonucleotide for use in treating a ciliopathy in a subject suffering of a ciliopathy, wherein the polyribonucleotide encodes a functional version of a protein a defect of which is associated with said ciliopathy, and wherein administration of said pharmaceutical composition to the respiratory system of said subject is effected when the subject shows an inflammation of the respiratory system. The present invention further relates to a method for analyzing the effect of a polyribonucleotide on ciliogenesis, wherein said polyribonucleotide encodes a protein involved in and/or required for ciliogenesis.

Oxygen is vital for many multicellular organisms as it is crucial for the energy supply of the cells. In mammals, oxygen comprised in the air can enter the organism via the respiratory system, which refers to the organs involved in breathing. These include for example nose, throat, larynx, trachea, bronchi, and lungs. In the latter, gas from the environment is exchanged with gas comprised in the internal blood circulatory system, which transports the oxygen from the lungs to cells in different parts of the organism. However, besides the required oxygen also other components can enter the organism via the respiratory system such as irritating agents comprised in the air including pollutants, disease causing agents and pathogens such as viruses and bacteria. Hence, defense mechanisms exist such as cough reflexes and sneezing for expelling the irritating agent from the respiratory system. For expulsion, the irritating agent is embedded in viscous mucus that is secreted by epithelial cells in the respiratory system and then transported across the epithelial surface by ciliated cells.

Ciliated cells can transport mucus and irritating agents across the epithelial surface by a synchronized beat of multiple motile cilia. Cilia are membrane-enclosed tubular structures that extend from the epithelial surface into the space of the respiratory system that is in contact with the environment. Within the cells, the axoneme of a cilium is anchored to a basal body via anchoring structures. An axoneme is a central bundle of microtubules in which nine outer doublet microtubules surround a central pair of singlet microtubules (i.e. in respiratory cilia). The outer doublet microtubules and the central pair of microtubules are connected by radial spokes. Each of the nine outer doublet microtubules consists of an A- and a B-tubulus with the doublets being circumferentially interconnected by a nexin-dynein regulatory complex. Inner dynein arm and outer dynein arm are connected to each A-tubulus. These dynein arms contain motor proteins that can walk along the microtubules, which results in bending and thus, beating of the cilium (cf. e.g. Lodish et al, 2000, Molecular Cell Biology, $4^{th}$ edition, New York: W. H. Freeman, Section 19.4). Investigations of ciliary structures using the model *Trypanosoma brucei* indicated that some of these structural components exhibit a rapid turnover, whereas skeletal components of the radial spokes, the central pair and the outer dynein arms are primarily incorporated at the distal end of the ciliary structure during development (Vincensini et al., Biol Cell, 2018, 110:1-15).

As the synchronized beating of ciliated cells is crucial for the transport of fluids across epithelial surfaces, perturbations of ciliary structures can cause serious disorders. Motility defects including a reduced amplitude and/or frequency of beating and/or asynchronicity can occur as a result of a reduction or loss of dynein arms, a disorganisation of the microtubule arrangement including mislocalization and changes in the total number of microtubules per axoneme and combinations thereof for example. As far as known, changes in these functional axonemal elements are caused by underlying genetic defects. These are mostly due to changes in the sequence of a gene that encodes an axonemal component including the ones mentioned above. As genes can be transcribed into polyribonucleotides such as mRNAs, which in turn can be translated into proteins, the DNA sequence of a gene affects the synthesis of the respective protein in view of amount and functionality. As ciliary disorders, i.e. ciliopathies, caused by sequence changes are inherited and thus, are associated with motility defects of cilia at all developmental stages including embryo or newborns, ciliopathies can have severe consequences for the organism.

A well-known example of a ciliary disorder is primary ciliary dyskinesia (PCD), a progressive disorder that is often associated with declining lung function. Thus, long-term treatments including for example chest percussions and postural drainage are required for enhancing mucus clearance with increasing frequency, and in severe cases even lung transplantation. Further, PCD patients suffer from recurrent infections in lungs and/or ears, often also from subfertility, hydrocephalus and body laterality, i.e. left-right axis, defects, as well as retinal and/or neurological problems. But despite the severity of most ciliopathies, no standardized effective strategies for treating ciliopathies like PCD exist so far. Current therapies are for example extrapolated from cystic fibrosis and have in most cases not even been validated for the specific ciliopathy to be treated, such as for example PCD. Hence, there is a need to have at hand solutions for being able to efficiently treat subjects suffering of a ciliopathy such as PCD.

The present application addresses the need for restoring ciliary function in subjects suffering of a ciliopathy, such as PCD, by providing the embodiments as recited in the claims.

In particular, the present invention relates to a pharmaceutical composition comprising a polyribonucleotide for use in treating a ciliopathy in a subject suffering of a ciliopathy, wherein the polyribonucleotide encodes a functional version of a protein a defect of which is associated with said ciliopathy, and wherein administration of said pharmaceutical composition to the respiratory system of said subject is effected when the subject shows an inflammation of the respiratory system.

The present invention is based on the finding that it is indeed possible to restore proper ciliary function by transfecting cells (which show a defect in a certain protein of a protein complex of the cilia and the defect of which leads to a loss of proper ciliary function) with polyribonucleotides which encode a functional version of said protein. However, it was also found that ciliated cells have to be transfected at an early stage during differentiation in order to achieve this effect. This leads to practical problems since the precursor cells of the epithelial cells which carry the cilia, i.e. basal cells, are not accessible for transfection via the airway system since they are located deeper down in the epithelium and are not exposed on the surface. According to the present invention, a transfection of the epithelial cells by administration of a polyribonucleotide is effected when the subject which suffers of a ciliopathy shows an inflammation of the respiratory system. During an inflammation of the respiratory system the airway epithelium shows lesions and wounds which make precursor cells of the ciliated cells accessible, i.e. the basal cells which have not yet started ciliogenesis. Transfecting these cells with a polyribonucleotide as described above which expresses a functional version of the respective protein allows to render these cells into cells which form functional cilia or at least partly functional cilia which can lead to a substantial alleviation of the respective symptoms.

In the context of the present invention, the term "ciliopathy" refers to diseases associated with and/or characterized by defects of ciliated cells. Thus, ciliopathies comprise disorders of ciliary structures, including ciliary anchoring structures, basal bodies to which ciliary structures are anchored to within a cell, and/or ciliary function. Examples of ciliopathies include PCD, Bardet-Biedl syndrome, Simpson-Golabi-Behmel syndrome (type 2), leber congenital amaurosis, nephronophthisis, cranioectodermal dysplasia (Sensenbrenner) (cf. e.g. Mitchison et al., 2017, Ultrastructural Pathology, 41(6):415-427).

The term "ciliopathy" as used herein refers to a ciliopathy which is caused by a genetic defect in the DNA of a subject, e.g. the chromosomal or the mitochondrial DNA. Such a genetic defect may be caused by a mutation and can comprise loss, addition or exchange of a sequence part. Examples are copy number variation, presence/absence variation, deletion (full or partial), insertion, miss-sense mutation, nonsense mutation, splice site variation, or a combination thereof. Such changes in the DNA can lead to changes in the availability of the encoded protein such as a loss or a reduction of the amount of protein, or to a protein with altered function.

In a preferred embodiment the term "ciliopathy" refers to a disease connected with a defect in motile cilia. One example of such a ciliopathy is primary ciliary dyskinesia (PCD). PCD is a rare disease caused by dysfunction of motile cilia. PCD is heterogeneous at the genetic, functional and ultrastructural level. PCD is associated with impaired mucus transport and clearance. Subjects suffering from PCD show recurrent nasal congestions, sinus infections, ear infections, infertility, situs abnormalities such as situs inversus totalis and heterotaxy, also referred to as "situs ambiguous", and/or hydrocephalus. On the molecular level, PCD is associated in most cases with abnormalities in the structure, function, and biogenesis of cilia of the respiratory system. Examples for such abnormalities are absent or shortened dynein arms, defective central pair complex, radial spoke or nexin links. Such abnormalities and thus, ciliary motility defects associated with PCD is caused by mutations in genes encoding the respective components, in particular by mutations in genes listed in Table 1, wherein group "A" and "B" refer to genes with pathogenic mutations estimated to account for at least 1% and less than 1% of PCD cases, respectively (cf. Zariwala et al., GENEREVIEWS®, 2007, updated 2015, Primary Ciliary Dyskinesia, editors Adam et al., Seattle (WA): University of Washington, Seattle; 1993-2018).

Hence, the polyribonucleotide comprised in the pharmaceutical composition according to the present invention is preferably a polyribonucleotide that can be translated into a functional version of a protein listed in Table 1.

More preferably, the polyribonucleotide comprised in the pharmaceutical composition according to the present invention is an mRNA that can be translated into a functional version of a protein selected from the group consisting of DNAH5, DNAH11, CCDC39, DNAI1, CCDC40, CCDC103, SPAG1, ZMYND10, ARMC4, CCDC151, DNAI2, RSPH1, CCDC114, RSPH4A, DNAAF1 (LRRC50), DNAAF2 (KTU), and LRRC6.

TABLE 1

| Gene | Locus | Protein | Group |
|---|---|---|---|
| DNAH5 | CILD3 | DNAH5 | A |
| DNAH11 | CILD7 | DNAH11 | A |
| CCDC39 | CILD14 | CCDC39 | A |
| DNAI1 | CILD1 | DNAI1 | A |
| CCDC40 | CILD15 | CCDC40 | A |
| CCDC103 | CILD17 | CCDC103 | A |
| SPAG1 | CILD28 | SPAG1 | A |
| ZMYND10 | CILD22 | ZMYND10 | A |
| ARMC4 | CILD23 | ARMC4 | A |
| CCDC151 | CILD30 | CCDC151 | A |
| DNAI2 | CILD9 | DNAI2 | A |
| RSPH1 | CILD24 | RSPH1 | A |
| CCDC114 | CILD20 | CCDC114 | A |
| RSPH4A | CILD11 | RSPH4A | A |
| DNAAF1 (LRRC50) | CILD13 | DNAAF1 (LRRC50) | A |
| DNAAF2 (KTU) | CILD10 | DNAAF2 (KTU) | A |
| LRRC6 | CILD19 | LRRC6 | A |
| C21orf59 | CILD26 | C21orf59 | B |
| CCDC65 (DRC2) | CILD27 | CCDC65 (DRC2) | B |
| CCNO | CILD29 | CCNO | B |
| DNAAF3 | CILD2 | DNAAF3 | B |
| DNAH1 | | DNAH1 | B |
| DNAH8 | | DNAH8 | B |
| DNAL1 | CILD16 | DNAL1 | B |
| DRC1 (CCDC164) | CILD21 | DRC1 (CCDC164) | B |
| DYX1C1 | CILD25 | DYX1C1 | B |
| DNAAF5 (HEATR2) | CILD18 | DNAAF5 (HEATR2) | B |
| HYDIN | CILD5 | HYDIN | B |
| MCIDAS | | MCIDAS | B |
| NME8 (TXNDC3) | CILD6 | NME8 (TXNDC3) | B |
| RSPH3 | | RSPH3 | B |
| RSPH9 | CILD12 | RSPH9 | B |

In some embodiments of any of the foregoing or other aspects and embodiments of the disclosure, the polyribonucleotide or modified polyribonucleotide comprises a primary sequence that is at least 85%, at least 90%, at least 92% or at least 95% identical (e.g., at least 95, 96, 97, 98, 99 or 100% identical) to one or more of SEQ ID NO: 1 or 5 to 11 (e.g., to the sequence set forth in SEQ ID NO: 1 or 5 to 11). In some embodiments, the polyribonucleotide is a modified polyribonucleotide having a level and/or type of modification selected from any such level and/or type set forth herein. In certain embodiments, the percent identity of a polyribonucleotide is measured only with respect to the CCDC40 coding sequence-portion of SEQ ID NO: 1 or 5 to 11 (e.g., UTRs, other non-coding sequence and GFP or epitope tags are not considered when calculating percent identity). In certain embodiments of any of the foregoing, such polyribonucleotide (or modified polyribonucleotide) encodes a functional CCDC40 protein.

In some embodiments of any of the foregoing or other aspects and embodiments of the disclosure, the polyribonucleotide or modified polyribonucleotide comprises a primary sequence that is at least 85%, at least 90%, at least 92%, or at least 95% identical (e.g., at least 95, 96, 97, 98, 99 or 100% identical) to one or more of SEQ ID NO: 2 or 12 to 14 (e.g., to the sequence set forth in SEQ ID NO: 2 or 12 to 14). In some embodiments, the polyribonucleotide is a modified polyribonucleotide having a level and/or type of modification selected from any such level and/or type set forth herein. In certain embodiments, the percent identity of a polyribonucleotide is measured only with respect to the CCDC39 coding sequence-portion of SEQ ID NO: 2 or 12 to 14 (e.g., UTRs, other non-coding sequence and GFP tags or epitope tags are not considered when calculating percent identity). In certain embodiments of any of the foregoing, such polyribonucleotide (or modified polyribonucleotide) encodes a functional CCDC39 protein.

In some embodiments of any of the foregoing or other aspects and embodiments of the disclosure, the polyribonucleotide or modified polyribonucleotide comprises a primary sequence that is at least 85%, at least 90%, at least 92%, or at least 95% identical (e.g., at least 95, 96, 97, 98, 99 or 100% identical) to SEQ ID NO: 4 (e.g., to the sequence set forth in SEQ ID NO: 4). In some embodiments, the polyribonucleotide is a modified polyribonucleotide having a level and/or type of modification selected from any such level and/or type set forth herein. In certain embodiments, the percent identity of a polyribonucleotide is measured only with respect to the MCIDAS coding sequence-portion of SEQ ID NO: 4 (e.g., UTRs, other non-coding sequence and GFP or epitope tags are not considered when calculating percent identity). In certain embodiments of any of the foregoing, such polyribonucleotide (or modified polyribonucleotide) encodes a functional MCIDAS protein.

In certain embodiments, the disclosure provides pharmaceutical compositions comprising any of the foregoing polyribonucleotides. Moreover, any such polyribonucleotides (or pharmaceutical compositions) may be used in the any of the methods described herein.

In one embodiment of the pharmaceutical composition comprising a polyribonucleotide for use in treating a ciliopathy, said ciliopathy is associated with a defect in a coiled-coil domain containing 40 (CCDC40; cf. e.g. NCBI Reference Sequences NM_017950.4 and NP_060420.2 for human mRNA and protein CCDC40 sequence, respectively) protein or with a defect in a coiled-coil domain containing 39 (CCDC39; cf. e.g. NCBI Reference Sequences NM_181426.2 and NP_852091.1 for human mRNA and protein CCDC39 sequence, respectively) protein.

CCDC40 and CCDC39 build a complex that is located between radial spokes and A-tubuli. Defect versions of the CCDC40 or CCDC39 protein can be caused by mutations in the CCDC40 gene or in the CCDC39 gene such as insertions, deletions, nonsense and splice site mutations. In particular, a deletion of position 248 and a TGT insertion between positions 2824 and 2825 in the DNA sequence encoding the CCDC40 protein appear to be quite frequent. Defect versions of CCDC40 or CCDC39 give rise to defects in structures of the axoneme such as absent or eccentric central pairs, abnormal radial spokes and nexin links, an abnormal assembly of the dynein regulatory complex, and/or a reduction of inner dynein arms. Hence, the polyribonucleotide comprised in the pharmaceutical composition according to the present invention is preferably an mRNA that can be translated into a functional version of CCDC40 and or of CCDC39. Further information on proteins involved in ciliogenesis as well as genes and molecular pathways associated with ciliopathies can be found e.g. in the review article of Reiter and Leroux (Reiter and Leroux, 2017, Nat Rev Mol Cell Biol, 18(9):533-547).

The pharmaceutical composition of the present invention is to be administered to a subject suffering from a ciliopathy. Herein a subject suffering from a ciliopathy, may also be referred to as a patient. Patients may show abnormal ciliary structure and/or function, and/or biogenesis defects that result in retention of mucus and bacteria in the respiratory tract. The diagnosis of a ciliopathy for a given subject may be based for example on clinical findings, molecular analyses and/or ciliary ultrastructural analyses of a biopsy of said subject as e.g. also reviewed in Goutaki et al. (Goutaki et al., 2016, Eur Respir J, 48(4):1081-1095).

In the context of the present invention, the term “polyribonucleotide” refers to a single-stranded sequence built up of adenosine, guanosine, cytidine, and/or uridine residues (in modified or unmodified form, see below). Herein, the term “polyribonucleotide encoding a protein” refers to a polyribonucleotide which contains a coding region which encodes a protein, i.e. which can be translated into a sequence of amino acids. Thus, in the context of the present invention the term “polyribonucleotide encoding a protein” preferably refers to an mRNA, wherein an mRNA should be understood to mean any polyribonucleotide molecule which, if it comes into the cell, is suitable for the expression of a protein or is translatable into a protein.

Herein, the term “protein” encompasses any kind of amino acid sequence, i.e. chains of two or more amino acids which are each linked via peptide bonds. The term “protein” used in this context refers to any amino acid sequence of interest. Preferably, the encoded amino acid sequence is at least 5 amino acids long, more preferably at least 10 amino acids, even more preferably at least 50, 100, 200 or 500 amino acids. Thus, the term “protein” covers short peptides as well as polypeptides. As regards the function of the encoded protein, there is no limitation except that a defect variant of the protein is associated with a ciliopathy. Herein, the term “associated with” is intended to encompass the terms “causing”, “being involved in” and/or “enhancing”.

Herein, the term “a protein the defect of which” refers to a “defect protein” or “defect version of a protein” and thus, to a version of a protein with altered function compared to a functional version of said protein. However, the term may also encompass a version of said protein with a complete or partial lack of synthesis and thus, availability in the cell. In any case, the defect of the protein version results in a version of said protein that cannot fulfill the protein’s native function.

A version of a protein that fulfils its native function is referred to as “functional protein” or “functional version of a protein” herein, and is encoded by the same DNA sequence as the respective defect protein, but without the defect causing change in the DNA sequence and thus, without a mutation in the DNA sequence.

Hence, in the context of the present invention, the “functional protein” is preferably a building block of an A-tubulus, a B-tubulus, or a nexin-dynein regulatory complex, or a radial spoke, an inner dynein arm, and/or an outer dynein arm.

Thus, the term “the polyribonucleotide encodes a functional version of a protein a defect of which is associated with said ciliopathy” preferably refers to an mRNA that encodes a functional protein, which is involved in the structural organization of a ciliar axoneme, an axoneme anchoring structure or a basal body and fulfills its native function. Thus, the polyribonucleotide according to the present invention preferably refers to an mRNA that encodes a functional protein, the presence of which in the cell of a subject suffering of a ciliopathy is needed or beneficial to moderate or prevent a manifestation of said ciliopathy that is associated with a defect of said protein as encoded by the DNA sequence of the cell or to alleviate the associated symptoms.

In addition, the polyribonucleotide employed according to the present invention may also comprise further functional regions and/or 3' or 5' non-coding regions. The 3' and/or 5' non-coding regions can be sequences which naturally flank the encoded protein or artificial sequences which contribute to the stabilization and/or regulation of said polyribonucleotide. Suitable sequences may be identified and investigated by routine experiments. Further, said polyribonucleotide can also have further functional regions and may be combined with regulatory elements and target sequences of micro-RNAs for example for spatial and temporal control the activity of the desired polyribonucleotide comprising a sequence which encodes a protein, i.e. for example with respect to specific cells or cell types and/or developmental stages or specific time frames.

The polyribonucleotide employed according to the present invention may comprise a partly or fully codon optimized sequence derived from the natural sequence to be used. Codon optimization refers to a technique which is applied to maximize protein expression by increasing the translational efficiency of the respective polyribonucleotide as in some cases codons exist that are preferentially used by some species for a given amino acid. Further, said polyribonucleotide might comprise further modifications to adjust and/or extend the duration of action. Said polyribonucleotide might also contain an m7GpppG cap, an internal ribosome entry site (IRES) and/or a polyA tail at the 3' end and/or additional sequences for promoting translation.

In some embodiments of the present invention the polyribonucleotide employed according to the present invention may contain unmodified and modified nucleotides. The term “unmodified nucleotide” used herein refers to A, C, G and U nucleotides.

The term “modified nucleotide” used herein refers to any naturally occurring or non-naturally occurring isomers of A, C, G and U nucleotides as well as to any naturally occurring or naturally occurring analogs, alternative or modified nucleotide or isomer thereof having for example chemical modifications or substituted residues. Modified nucleotides can have a base modification and/or a sugar modification. Modified nucleotides can also have phosphate group modifications, e.g., with respect to the five prime cap of an mRNA molecule. Modified nucleotides also include nucleotides that are synthesized post-transcriptionally by covalent modification of the nucleotides. Further, any suitable mixture of non-modified and modified nucleotides is possible. A non-limiting number of examples of modified nucleotides can be found in the literature (e.g. Cantara et al., Nucleic Acids Res, 2011, 39 (Issue suppl_1):D195-D201; Helm and Alfonzo, Chem Biol, 2014, 21(2):174-185; Carell et al., Angew Chem Int Ed Engl, 2012, 51(29):7110-31) and some preferable modified nucleotides are mentioned exemplarily in the following based on their respective nucleoside residue: 1-methyladenosine, 2-methylthio-N6-hydroxynorvalyl carbamoyladenosine, 2-methyladenosine, 2'-O-ribosylphosphate adenosine, N6-methyl-N6-threonylcarbamoyladenosine, N6-acetyladenosine, N6-glycinylcarbamoyladenosine, N6-isopentenyladenosine, N6-methyladenosine, N6-threonylcarbamoyladenosine, N6,N6-dimethyladenosine, N6-(cis-hydroxyisopentenyl) adenosine, N6-hydroxynorvalylcarbamoyladenosine, 1,2'-O-dimethyladenosine, N6,2'-O-dimethyladenosine, 2'-O-methyladenosine, N6, N6,2'-O-trimethyladenosine, 2-methylthio-N6-(cis-hydroxyisopentenyl) adenosine, 2-methylthio-N6-methyladenosine, 2-methylthio-N6-isopentenyladenosine, 2-methylthio-N6-threonyl carbamoyladenosine, N6-2-methylthio-N6-threonyl carbamoyladenosine, 2-methylthio-N6-(cis-hydroxyisopentenyl) adenosine, 7-methyladenosine, 2-methylthio-adenosine, 2-methoxy-adenosine, 2'-amino-2'-deoxyadenosine, 2'-azido-2'-deoxyadenosine, 2'-fluoro-2'-deoxyadenosine, 2-aminopurine, 2,6-diaminopurine, 7-deaza-adenosine, 7-deaza-8-aza-adenosine, 7-deaza-2-aminopurine, 7-deaza-8-aza-2-aminopurine, 7-deaza-2,6-diaminopurine, 7-deaza-8-aza-2,6-diaminopurine; 2-thiocytidine, 3-methylcytidine, N4-acetylcytidine, 5-formylcytidine, N4-methylcytidine, 5-methylcytidine, 5-hydroxymethylcytidine, 5-hydroxycytidine, lysidine, N4-acetyl-2'-O-methylcytidine, 5-formyl-2'-O-methylcytidine, 5,2'-O-dimethylcytidine, 2-O-methylcytidine, N4,2'-O-dimethylcytidine, N4, N4,2'-O-trimethylcytidine, isocytidine, pseudocytidine, pseudoisocytidine, 2-thio-cytidine, 2'-methyl-2'-deoxycytidine, 2'-amino-2'-deoxycytidine, 2'-fluoro-2'-deoxycytidine, 5-iodocytidine, 5-bromocytidine, 2'-azido-2'-deoxycytidine, 2'-amino-2'-deoxycytidine, 2'-fluor-2'-deoxycytidine, 5-aza-cytidine, 3-methyl-cytidine, 1-methyl-pseudoisocytidine, pyrrolo-cytidine, pyrrolo-pseudoisocytidine, 2-thio-5-methyl-cytidine, 4-thio-pseudoisocytidine, 4-thio-I-methyl-pseudoisocytidine, 4-thio-I-methyl-1-deaza-pseudoisocytidine, 1-methyl-I-deaza-pseudoisocytidine, 2-methoxy-cytidine, 2-methoxy-5-methyl-cytidine, 4-methoxy-pseudoisocytidine, 4-methoxy-I-methyl-pseudoisocytidine, zebularine, 5-aza-zebularine, 5-methyl-zebularine, 5-aza-2-thio-zebularine, 2-thio-zebularine; 1-methylguanosine, N2,7-dimethylguanosine, N2-methylguanosine, 2'-O-ribosylphosphate guanosine, 7-methylguanosine, hydroxywybutosine, 7-aminomethyl-7-deazaguanosine, 7-cyano-7-deazaguanosine, N2,N2-dimethylguanosine, N2,7,2'-O-trimethylguanosine, N2,2'-O-dimethylguanosine, 1,2'-O-dimethylguanosine, 2'-O-methylguanosine, N2,N2,2'-O-trimethylguanosine, N2, N2J-trimethylguanosine, Isoguanosine, 4-demethylwyosine, epoxyqueuosine, undermodified hydroxywybutosine, methylated undermodified hydroxywybutosine, isowyosine, peroxywybutosine, galactosyl-queuosine, mannosyl-queuosine, queuosine, archaeosine, wybutosine, methylwyosine, wyosine, 7-aminocarboxypropyldemethylwyosine, 7-aminocarboxypropylwyosine, 7-aminocarboxypropylwyosinemethylester, 7-deaza-guanosine, 7-deaza-8-aza-guanosine, 6-thio-guanosine, 6-thio-7-deaza-guanosine, 6-thio-7-deaza-8-aza-guanosine, 7-methyl-guanosine, 6-thio-7-methyl-guanosine, 7-methylinosine, 6-methoxy-guanosine, 1-methylguanosine, 8-oxo-guanosine, 7-methyl-8-oxo-guanosine, 1-methyl-6-thio-guanosine, N2-methyl-6-thio-guanosine, N2, N2-dimethyl-6-thio-guanosine, N1-methylguanosine, 2'-amino-3'-deoxyguanosine, 2'-azido-2'-deoxyguanosine, 2'-fluoro-2'-deoxyguanosine, 2-thiouridine, 3-(3-amino-3-carboxypropyl) uridine, 3-methyluridine, 4-thiouridine, 5-methyl-2-thiouridine, 5-methylaminomethyluridine, 5-carboxymethyluridine, 5-carboxymethylaminomethyluridine, 5-hydroxyuridine, 5-methyluridine, 5-taurinomethyluridine, 5-carbamoylmethyluridine, 5-(carboxyhydroxymethyl) uridine methyl ester, dihydrouridine, 5-methyldihydrouridine, 5-methylaminomethyl-2-thiouridine, 5-(carboxyhydroxymethyl) uridine, 5-(carboxyhydroxymethyl)-2'-O-methyluridine methyl ester, 5-(isopentenylaminomethyl) uridine, 5-(isopentenylaminomethyl)-2-thiouridine, 3,2'-O-dimethyluridine, 5-carboxymethylaminomethyl-2'-O-methyluridine, 5-carbamoylhydroxymethyluridine, 5-carbamoylmethyl-2'-O-methyluridine, 5-carbamoylmethyl-2-thiouridine, 5-methoxycarbonylmethyl-2'-O-methyluridine, 5-(isopentenylaminomethyl)-2'-O-methyluridine, 5,2'-O-dimethyluridine, 2'-O-methyluridine, 2'-O-methyl-2-thiorudine, 2-thio-2'-O-methyluridine, uridine 5-oxyacetic acid, 5-methoxycarbonylmethyluridine, uridine 5-oxyacetic acid methyl ester, 5-methoxyuridine, 5-aminomethyl-2-thiouridine, 5-carboxymethylaminomethyl-2-thiouridine, 5-methylaminomethyl-2-selenouridine, 5-methoxycarbonylmethyl-2-thiouridine, 5-taurinomethyl-2-thiouridine, pseudouridine, 1-methyl-3-(3-amino-3-carboxypropyl) pseudouridine, 1-methylpseudouridine, 3-methylpseudouridine, 2'-O-methylpseudouridine, 5-formyluridine, 5-aminomethyl-2-geranyluridine, 5-taurinomethyluridine, 5-iodouridine, 5-bromouridine, 2'-methyl-2'-deoxyuridine, 2'-amino-2'-deoxyuridine, 2'-azido-2'-deoxyuridine, 2'-fluoro-2'-deoxyuridine, inosine, 1-methylinosine, 1,2'-O-dimethylinosine, 2'-O-methylinosine, 5-aza-uridine, 2-thio-5-aza-uridine, 4-thio-pseudouridine, 2-thio-pseudouridine, 5-carboxymethyl-uridine, 1-carboxymethyl-pseudouridine, 5-propynyl-uridine, 1-propynyl-pseudouridine, 1-taurinomethyl-pseudouridine, 5-taurinomethyl-2-thio-uridine, 1-taurinomethyl-4-thio-uridine, 5-methyl-uridine, 1-methyl-pseudouridine, 4-thio-I-methyl-pseudouridine, 2-thio-I-methyl-pseudouridine, 1-methyl-I-deaza-pseudouridine, 2-thio-1-methyl-I-deaza-pseudouridine, dihydropseudouridine, 2-thio-dihydrouridine, 2-thio-dihydropseudouridine, 2-methoxyuridine, 2-methoxy-4-thio-uridine, 4-methoxy-pseudouridine, 4-methoxy-2-thio-pseudouridine, 1,2'-O-dimethyladenosine, 1,2'-O-dimethylguanosine, 1,2'-O-dimethylinosine, 2,8-dimethyladenosine, 2-methylthiomethylenethio-N6-isopentenyl-adenosine, 2-geranylthiouridine, 2-lysidine, 2-methylthio cyclic N6-threonylcarbamoyladenosine, 2-methylthio-N6-(cis-hydroxyisopentenyl) adenosine, 2-methylthio-N6-hydroxynorvalylcarbamoyladenosine, 2-methylthio-N6-threonylcarbamoyladenosine, 2-selenouridine, 2-thio-2'-O-methyluridine, 2'-O-methyladenosine, 2'-O-methylcytidine, 2'-O-methylguanosine, 2'-O-methylinosine, 2'-O-methylpseudouridine, 2'-O-methyluridine, 2'-O-methyluridine 5-oxyacetic acid methyl ester, 2'-O-ribosyladenosinephosphate, 2'-O-ribosylguanosinephosphate, 3,2'-O-dimethyluridine, 3-(3-amino-3-carboxypropyl)-5,6-dihydrouridine, 3-(3-amino-3-carboxypropyl) pseudouridine, 5,2'-O-dimethylcytidine, 5,2'-O-dimethyluridine, 5-(carboxyhydroxymethyl)-2'-O-methyluridine methyl ester, 55-(isopentenylaminomethyl)-2'-O-methyluridine, 5-aminomethyl-2-geranylthiouridine, 5-aminomethyl-2-selenouridine, 5-aminomethyluridine, 5-carbamoylmethyl-2'-O-methyluridine, 5-carboxyhydroxymethyluridine, 5-carboxymethyl-2-thiouridine, 5-carboxymethylaminomethyl-2-geranylthiouridine, 5-carboxymethylaminomethyl-2-selenouridine, 5-carboxymethylaminomethyl-2'-O-methyluridine, 5-cyanomethyluridine, 5-formyl-2'-O-methylcytidine, 5-methoxycarbonylmethyl-2'-O-methyluridine, 5-methylaminomethyl-2-geranylthiouridine, 7-aminocarboxypropyl-demethylwyosine, 7-methylguanosine, 8-methyladenosine, N2,2'-O-dimethylguanosine, N2,7,2'-O-trimethylguanosine, N2,7-dimethylguanosine, N2,N2,2'-O-trimethylguanosine, N2,N2,7-trimethylguanosine, N2,N2,7-trimethylguanosine, N4,2'-O-dimethylcytidine, N4, N4,2'-O-trimethylcytidine, N4, N4-dimethylcytidine, N4-acetyl-2'-O-methylcytidine, N6,2'-O-dimethyladenosine, N6, N6,2'-O-trimethyladenosine, N6-formyladenosine, N6-hydroxymethyladenosine, agmatidine, 2-methylthio cyclic N6-threonylcarbamoyladenosine, glutamyl-queuosine, guanosine added to any nucleotide, guanylylated 5' end, hydroxy-N6-threonylcarbamoyladenosine; most preferably pseudo-uridine, N1-methyl-pseudo-uridine, 2'-fluoro-2'-deoxycytidine, 5-iodocytidine, 5-methylcytidine, 2-thiouridine, 5-iodouridine and/or 5-methyl-uridine.

Furthermore, the term "modified nucleotide" comprises nucleotides containing isotopes such as deuterium. The term "isotope" refers to an element having the same number of protons but different number of neutrons resulting in different mass numbers. Thus, isotopes of hydrogen for example are not limited to deuterium, but include also tritium. Furthermore, the polyribonucleotide can also contain isotopes of other elements including for example carbon, oxygen, nitrogen and phosphor. It is also possible that modified nucleotides are deuterated or contain another isotope of hydrogen or of oxygen, carbon, nitrogen or phosphor.

The total number of modified nucleotide types in the polyribonucleotide can be 0, 1, 2, 3, or 4. Hence, in some embodiments, at least one nucleotide of one nucleotide type, e.g. at least one U nucleotide, can be a modified nucleotide. In some embodiments, at least one nucleotide of in total two nucleotide types, e.g. at least one U nucleotide and at least one C nucleotide, can be a modified nucleotide. In some embodiments, at least one nucleotide of in total three nucleotide types, e.g. at least one G nucleotide, at least one U nucleotide and at least one C nucleotide, can be a modified nucleotide. In some embodiments, at least one nucleotide of all four nucleotide types can be a modified nucleotide. In all these embodiments one or more nucleotides per nucleotide type can be modified, the percentage of said modified nucleotides of per nucleotide type being 0%, 2.5%, 5%, 7.5%, 10%, 15%, 20%, 25%, 30%, 35%, 40%, 45%, 50%, 55%, 60%, 65%, 70%, 75%, 80%, 85%, 90% or 100%. In some embodiments, the total percentage of modified nucleotides comprised in the mRNA molecules to be purified is 0%, 2.5%, 5%, 7.5%, 10%, 15%, 20%, 25%, 30%, 35%, 40%, 45%, 50%, 55%, 60%, 65%, 70%, 75%, 80%, 85%, 90% or 100%.

Hence, the polyribonucleotide can for example be characterized in that 0.5 to 50%, preferably 5 to 50% of the U nucleotides and 5 to 50% of the C nucleotides are modified. Said modified U nucleotides are preferably 5-ioduridine and said modified C nucleotides are preferably 5-iodcytidine.

In some embodiments, the polyribonucleotide can be characterized in that 15 to 25% of the U nucleotides and 3 to 15%, preferably 5 to 15% of the C nucleotides are modified, wherein said modified U nucleotides are preferably 5-methyluridine and said modified C nucleotides are preferably 5-iodcytidine.

In some embodiments, the polyribonucleotide can be characterized in that 30 to 50% of the U nucleotides and 10 to 20% of the C nucleotides are modified, wherein said modified U nucleotides are preferably 5-ioduridine and said modified C nucleotides are preferably 5-iodcytidine.

In some embodiments, the polyribonucleotide can be characterized in that 30 to 50% of the U nucleotides and 5 to 15% of the C nucleotides are modified, wherein said modified U nucleotides are preferably 5-ioduridine and said modified C nucleotides are preferably 5-iodcytidine.

In some embodiments, the polyribonucleotide can be characterized in that 0.5 to 5% of the U nucleotides and 25 to 35% of the C nucleotides are modified, wherein said modified U nucleotides are preferably 2-thiouridine and said modified C nucleotides are preferably 5-methylcytidine.

The polyribonucleotide can for example also be characterized in that 50 to 100%, preferably 100%, of the U nucleotides are modified. Said modified U nucleotides are preferably N1-methyl-pseudo-uridine.

As described above, according to the present invention, the administration of the pharmaceutical composition to the patient suffering of a ciliopathy is effected when the subject shows an inflammation of the respiratory system. In the context of the present invention, the term "inflammation" refers to cellular responses to insults including infection, trauma, and hypersensitivity. An "inflammation of the respiratory system" refers to inflammatory responses in the respiratory system, especially in, but without limitation to, nose, pharynx, larynx, trachea, bronchi and/or lung. Inflammatory responses in the respiratory system can for example be caused by irritating agents such as pathogens, toxins, pollutants, and/or allergens. During inflammation specific cell types are activated that can release for example cytokines and mediators to modify activities of other cells. These processes are. e.g., described in Iwasaki et al. (Iwasaki et al., 2017, Nat Rev Immunol, 17(1):7-20).

Thus, in one embodiment the subject suffering from a ciliopathy to which the polyribonucleotide is to be administered has been subjected, prior to treatment, to an assay in order to determine whether the subject suffers from an inflammation of the respiratory system and wherein the subject has been positively determined to have an inflammation of the respiratory system.

Preferably, the inflammation of the respiratory system is an acute inflammation. An acute inflammation can occur over seconds, minutes, hours, and days, but might not occur over longer periods. Thus, an acute inflammation is an inflammation that occurs in a time range up to 4 weeks, preferably in a time frame of less than 3 weeks. It can be determined by routine lab methods based on a locally increased blood flow, a locally increased permeability of the capillaries, and/or increased numbers of neutrophils, macrophages and/or lymphocytes. More information about markers of airway inflammation in primary ciliary dyskinesia can be found, e.g., in Zihlif et al. (Zihlif et al., 2006, Pediatr Pulmonol, 41(6):509-14).

Generally, inflammation can be classified as either acute or chronic. Acute inflammation is the response of the body to a harmful stimulus and characterized e.g. by the increased move of granulocytes to the affected tissue. The classical signs of inflammation are heat, pain, redness, swelling, and loss of function. Ciliopathies such as, PCD are an inherited disorders and as such—if untreated—a permanent, lifelong stimulus caused by a loss of function, resulting in a permanent and as such chronic kind of inflammation, typically not showing the above symptoms (beside loss of function). Further examples for diseases associated with chronic inflammation are e.g.: hay fever, periodontal disease, atherosclerosis, and osteoarthritis. Nonetheless, patients suffering from such diseases can in addition get an acute inflammation e.g. through receiving an additional harmful stimulus and as a consequence one or more of the classical symptoms like classical signs of inflammation are heat, pain, redness, swelling, and additional loss of function.

Thus, in one embodiment the subject suffering from a ciliopathy to which the polyribonucleotide is to be administered has been subjected prior to treatment to an assay in order to determine whether the subject suffers from an acute inflammation of the respiratory system and wherein the subject has been positively determined to have an acute inflammation of the respiratory system.

Alternatively or in addition, the inflammation of the respiratory system refers to an exacerbation of inflammation, preferably an acute exacerbation of inflammation. Exacerbation refers to the worsening of a disease or an increase in its symptoms. It is best investigated in the context of chronic obstructive pulmonary disease (COPD) since exacerbations result in a decrease of a patient's quality of life, accelerate the decline of lung function, and contribute substantially to disease-related costs.

In case of a clinical trial a respiratory system exacerbation could be defined as follows: "A respiratory system exacerbation is defined in a trial as either respiratory tract symptoms leading to start of systemic antibiotic treatment, irrespective of results of bacterial culture, or as a decline in forced expiratory volume in one second (FEV1) % predicted equal to or above 10 percentage points relative to the average of FEV1% predicted at screening and randomization, whether or not antibiotics are prescribed. The occurrence of exacerbations can be assessed by patient interview, physical examination and spirometry. At each trial visit, and at any extra contacts with the trial sites attributable to exacerbations, the participants can be interviewed regarding symptoms and concomitant medication since last contact with the trial site. The interview can be supplemented by a weekly patient diary on symptoms and antibiotics. A physical examination reviewing the participants' general condition, vital signs, ears, heart and lungs can be performed at all visits." (c.f. e.g. Kobbernagel et al., 2016, BMC Pulmonary Medicine, 16:104).

Hence, according to a preferred embodiment, the pharmaceutical composition comprises an mRNA for use in treating a ciliopathy in a subject suffering of a ciliopathy, wherein the mRNA encodes a functional version of a ciliary structure protein a defect of which is associated with said ciliopathy, and wherein administration of said pharmaceutical composition to the respiratory system of said subject suffering of said ciliopathy is effected when the subject suffering of a ciliopathy shows an acute inflammation, preferably an acute exacerbation, of the respiratory system.

Thus, in one embodiment the subject suffering from a ciliopathy to which the polyribonucleotide is to be administered has been subjected, prior to treatment, to an assay in order to determine whether the subject suffers from an acute inflammation, preferably an acute exacerbation, of the respiratory system and wherein the subject has been .positively determined to have a chronic inflammation, preferably an acute exacerbation, of the respiratory system.

The presence or absence of an inflammation of the respiratory system of a subject suffering of a ciliopathy can be determined by routine procedures, e.g., by analyzing a blood sample or by determining whether the patient suffers from a running nose or the like.

In the respiratory system, inflammations are generally caused by infections, in particular viral or bacterial infections. Thus, the presence or absence of an inflammation in a ciliopathy patient can, preferably, be assessed by determining the presence or absence of an infection, preferably an acute infection. Preferably, the infection is a viral and/or bacterial infection.

Acute infections are characterized by auscultation findings, purulent cough, infiltrates, hemoptysis, fever, increase in blood inflammation parameters (c-reactive protein (CRP) >200 mg/ml, blood sedimentation<100 mm/h). Chronic infections are further characterized by migrating infiltrates, antibiotic resistance, persistent general symptoms and moderately increased blood inflammation markers (CRP 50-100 mg/ml, blood sedimentation <50 mm/h) (Klinische Pneumonologie, 1. Aufl. 2014 Georg Thieme Verlag KG, ISBN 978-3-13-129751-8; Jaroszewski et al., 2012, Thorac Surg Clin, 22(3):301-24).

In the context of the present invention, the term "respiratory system" comprises organs involved in breathing such as nose, pharynx, larynx, trachea, bronchi and lungs. In particular, the respiratory system can also be referred to as respiratory tract in case of some mammals including humans, herein also referred to as subjects. Herein, the terms "respiratory system" and "respiratory tract" are used interchangeably. The respiratory tract can be divided into the upper respiratory tract and the lower respiratory tract. The upper respiratory tract includes the nose comprising nasal cavity, nasal conchae, nasal vestibulae and nasal passages; paranasal sinuses; the pharynx, and the portion of the larynx above the vocal folds (cords). The lower respiratory tract includes the portion of the larynx below the vocal folds, trachea, bronchi and bronchioles. Herein, the lungs are included in the lower respiratory tract and comprise respiratory bronchioles, alveolar ducts, alveolar sacs, and alveoli.

In the context of the present invention, the term "pharmaceutical composition" refers to a composition comprising at least a polyribonucleotide according to the present invention for administration to a subject in order to treat a ciliopathy. The polyribonucleotide is preferably included in an effective amount, i.e. an amount sufficient to induce a detectable therapeutic response in the subject to which the pharmaceutical composition is to be administered. The pharmaceutical composition of the invention can be in the form of a sterile aqueous or non-aqueous solution, suspension or emulsion or aerosol. Preferably, the pharmaceutical composition is in a form which allows administration to the respiratory system e.g. via inhalation, nebulization, via a spray or droplets, e.g. a nasal spray or nasal droplets.

This is advantageous for the patients as an administration using a spray, droplets, a nebulizer or by inhalation can easily be done by the patient, is comfortable to transport and thus, easily available for the patient without restricting any freedom of action.

In a preferred embodiment the pharmaceutical composition comprises an mRNA that can be translated into a functional version of a protein selected from the group consisting of DNAH5, DNAH11, CCDC39, DNAI1, CCDC40, CCDC103, SPAG1, ZMYND10, ARMC4, CCDC151, DNAI2, RSPH1, CCDC114, RSPH4A, DNAAF1 (LRRC50), DNAAF2 (KTU), and LRRC6, and is administered to a subject suffering from a PCD caused by a defect of said protein by using a spray, droplets, a nebulizer and/or by inhalation. More preferably the protein is CCDC40 and/or CCDC39.

The pharmaceutical composition can comprise a pharmaceutically acceptable carrier, i.e. chemical compounds, materials, ingredients, and/or compositions, which are, within the scope of sound medical judgment, suitable for use in contact with the tissues of human beings and animals without excessive toxicity, irritation, allergic response, or other problem or complication, commensurate with a reasonable benefit/risk ratio. Thus, a pharmaceutically acceptable carrier is an inactive substance formulated alongside the pharmaceutically active substance for facilitating its handling in view of dosage, adsorption, solubility or pharmacokinetic considerations. Examples of suitable pharmaceutical acceptable carriers are well known in the art and include phosphate buffered saline solutions, buffer, water, emulsions, such as oil/water emulsions, various types of wetting agents, and sterile solutions. In particularly, aqueous carriers include water, alcoholic/aqueous solutions, emulsions or suspensions, including saline and buffered media. Examples of non-aqueous solvents are propylene glycol, polyethylene glycol, vegetable oils such as olive oil, and organic esters such as ethyl oleate. Further examples of pharmaceutically acceptable carriers include but are not limited to saline, Ringer's solution and dextrose solution, citrate, phosphate, and other organic acids; salt-forming counter-ions, e.g. sodium and potassium; low molecular weight (>10 amino acid residues) polypeptides; proteins, e.g. serum albumin, or gelatine; hydrophilic polymers, e.g. polyvinylpyrrolidone; amino acids such as histidine, glutamine, lysine, asparagine, arginine, or glycine; carbohydrates including glucose, mannose, or dextrins; monosaccharides; disaccharides; other sugars, e.g. sucrose, mannitol, trehalose or sorbitol; chelating agents, e.g. EDTA; non-ionic surfactants, e.g., polyoxyethylene sorbitan monolaurate, available on the market with the commercial name Tween, propylene glycol, Pluronics or polyethylene glycol; antioxidants including methionine, ascorbic acid and tocopherol; and/or preservatives, e.g. octadecyldimethylbenzyl ammonium chloride; hexamethonium chloride; benzalkonium chloride, benzethonium chloride; phenol, butyl or benzyl alcohol; alkyl parabens, e.g. methyl or propyl paraben; catechol; resorcinol; cyclohexanol; 3-pentanol; and m-cresol). Suitable pharmaceutically acceptable carriers and their formulations are described in greater detail in Remington's Pharmaceutical Sciences, 17th ed., 1985, Mack Publishing Co. Furthermore, preservatives, stabilizers and other additives may also be present such as, for example, antimicrobials, anti-oxidants, chelating agents, and inert gases, nanosystems or liposomes, and the like.

The pharmaceutical composition of the present invention may be administered to a patient via a large range of classes of forms of administration known to the skilled person to be suitable for administration to the respiratory system, such as the use of sprays, droplets, inhalators, nebulizers and the like. Dose and duration of action depend on the function which said polyribonucleotide is to fulfil and have to be deliberately adjusted in each case. The duration of action will be as long as possible for example, if said polyribonucleotide is used, as is the case here, for the chronic therapy of a disease due to a deficient gene, i.e. changed DNA sequence. The duration may also be adjusted to a specific time window.

In one embodiment the pharmaceutical composition is administered at least once a week. This is advantageous for ensuring an efficient and persisting effect of the treatment of said PCD. Preferably the pharmaceutical composition is administered on a weekly basis for at least 2 weeks, more preferably for at least 3 weeks and even more preferably for at least 4 weeks. Alternatively, the pharmaceutical composition may be administered twice a week for at least 1 week, preferably for at least 2 weeks, more preferably for at least 3 weeks and even more preferably for at least 4 weeks. In one embodiment, if there is a need for further treatment after an initial treatment for four weeks as described above, the treatment is carried out on a weekly basis. Alternatively to the weekly administration, administration may be switched to administration once a month for a longer period of time, e.g. for at least two months, preferably for at least 3 months, more preferably for at least 4 month, even more preferably for at least 5 months and most preferably for at least 6 months.

In one preferred embodiment the pharmaceutical composition is administered to the respiratory system of the subject after the subject inhaled an appropriate solution, preferably a mucolytic agent, such as a hypertonic saline or a solution of N-acetylcysteine (NAC), or washed their nasal cavities and/or sinus with an appropriate solution, preferably a mucolytic agent, such as a hypertonic saline or N-acetylcysteine (NAC), in order to remove mucus and potentially shedded airway epithelial cells. Thus, it is preferred that the pharmaceutical composition is administered to the respiratory system of the subject after the subject inhaled an appropriate solution, preferably a mucolytic agent, such as a hypertonic saline or a solution of N-acetylcysteine (NAC), and coughed up mucus located on epithelial cells. This is especially advantageous for exposing epithelial cells before administering the pharmaceutical composition and thus, for enhancing transfection efficacy of the polyribonucleotide.

Thus, in one embodiment the subject suffering from a ciliopathy to which the polyribonucleotide is to be administered is a subject which has been subjected, prior to treatment, by inhaling an appropriate solution, preferably a mucolytic agent, such as a hypertonic saline or a solution of N-acetylcysteine (NAC), or to washing their nasal cavities and/or sinus with an appropriate solution, preferably a mucolytic agent, such as a hypertonic saline or N-acetylcysteine (NAC).

Such a step aims at physically removing mucus from the respiratory system of the subject prior to the administration of the polyribonucleotide.

In addition, such a subject is preferably a subject which has been subjected, prior to treatment, to an assay in order to determine whether the subject suffers from an inflammation, preferably an acute inflammation or exacerbation of inflammation of the respiratory system and wherein the subject has been positively determined to have an inflammation, preferably an acute inflammation or exacerbation of inflammation, of the respiratory system.

In preferred embodiments, the concentration of NAC in said solution is between 3% and 20%, preferably between 5% and 15% more preferably between 8% and 12%, most preferably it is 10%. The percentage is based on weight/weight. Preferably, a solution containing NAC also contains sodium edetate (with edetate referring to ethylendiamin tetra acetate) and/or sodium hydroxide in pharmaceutically acceptable concentrations. Preferably, the solution is an aqueous solution.

In some embodiments of the pharmaceutical composition comprising a polyribonucleotide for use in treating a ciliopathy, the pharmaceutical composition further comprises a mucolytic agent, such as N-acetylcysteine (NAC) and/or a hypertonic solution comprising sodium chloride. Both, NAC that acts as an expectorant and a hypertonic solution comprising sodium chloride are advantageous for reducing retention of viscous mucus in subjects suffering of PCD. This can reduce the risk of infections of the respiratory system, and thus, additional stress for the patient.

In preferred embodiments, the pharmaceutical composition further comprises NAC in a concentration as indicated above.

In preferred embodiments, the pharmaceutical composition further comprises a hypertonic solution comprising sodium chloride in a concentration between 2% and 8%, preferably between 3% and 7%, more preferably between 4% and 7%.

In preferred embodiments, the pharmaceutical composition further comprises NAC in a concentration between 3% and 20%, preferably between 5% and 15% more preferably between 8% and 12%, most preferably it is 10%, and/or a hypertonic solution comprising sodium chloride in a concentration between 2% and 8%, preferably between 3% and 7%, more preferably between 4% and 7%.

As stated above, in a preferred embodiment of the pharmaceutical composition according to the present invention said pharmaceutical composition comprises an mRNA that can be translated into a functional version of a protein selected from the group consisting of DNAH5, DNAH11, CCDC39, DNAI1, CCDC40, CCDC103, SPAG1, ZMYND10, ARMC4, CCDC151, DNAI2, RSPH1, CCDC114, RSPH4A, DNAAF1 (LRRC50), DNAAF2 (KTU), and LRRC6, preferably CCDC40 and/or CCDC39. Such a pharmaceutical composition is also referred to as "first pharmaceutical composition" in the following.

The multiciliate differentiation and DNA synthesis associated cell cycle (MCIDAS) protein is a transcriptional regulator protein that is specifically required for multiciliate cell differentiation which includes ciliogenesis of multiple motile cilia (cf. e.g. NCBI Reference Sequences NM_001190787.1 and NP_001177716.1 for human mRNA and protein MCIDAS sequence, respectively; or an optimized polyribonucleotide sequence as shown in SEQ ID NO: 4).

Hence, in some embodiments of the pharmaceutical composition comprising a polyribonucleotide for use in treating a ciliopathy, said pharmaceutical composition further comprises a polyribonucleotide encoding a functional version of a multiciliate differentiation and DNA synthesis associated cell cycle (MCIDAS) protein.

In some embodiments, the pharmaceutical composition is a first pharmaceutical composition as described above that is administered together with a second pharmaceutical composition comprising a polyribonucleotide encoding an MCIDAS protein.

Both pharmaceutical compositions, i.e. a first pharmaceutical composition as defined above further comprising a polyribonucleotide encoding an MCIDAS protein or a first pharmaceutical composition that is administered together with a second pharmaceutical composition comprising a polyribonucleotide encoding an MCIDAS protein, are advantageous as the administration of a pharmaceutical composition according to the present invention is especially effective in restoring ciliary cell structure and function, when the pharmaceutical composition is administered to cells before and/or during ciliogenesis. Further, both are preferably administered to a patient by using a nasal spray, and/or a nebulizer, and/or by inhalation, preferably at least once a week and/or for at least 4 weeks.

In some embodiments, the pharmaceutical composition comprises a polyribonucleotide that can be translated into a functional version of two or more proteins. This can be done e.g. using a multicistronic polyribonucleotide that is a single polyribonucleotide encoding two or more different proteins. Designing such a multicistronic polyribonucleotide using e.g. 2A peptides is well described in the literature. As an example, Liu et al. demonstrated the use of 2A peptides to generate multicistronic mRNAs (Liu et al., 2017, Scientific Reports, 7:2193). These 2A peptides can further be combined e.g. with a furin cleavage site to remove the additional amino acids (part of 2A peptide) which get appended onto the first protein in sequence as a consequence of ribosome skipping (functional feature of 2A peptide). As an example, the use of furin cleavage with 2A peptides has been described e.g. by Chng et al. (Chng et al., 2015 MAbs, 7(2):403-412). Thus, a single polyribonucleotide can be designed which encodes for two or more, preferably two therapeutic proteins (e.g. CCDC40 and MCIDAS) where the coding regions of the two therapeutic proteins are separated by a 2A peptide (as described in the above citation).

Hence, in some embodiments, the same applies as described for the embodiments above except that the pharmaceutical composition comprises a polyribonucleotide that can be translated into functional versions of two or more, preferably two proteins. Thus, in some embodiments, the pharmaceutical composition as described in the embodiments above comprises a multicistronic polyribonucleotide comprising a sequence that can be translated into a functional version of a protein selected from the group consisting of DNAH5, DNAH11, CCDC39, DNAI1, CCDC40, CCDC103, SPAG1, ZMYND10, ARMC4, CCDC151, DNAI2, RSPH1, CCDC114, RSPH4A, DNAAF1 (LRRC50), DNAAF2 (KTU), and LRRC6, preferably CCDC40 and/or CCDC39, and a sequence that can be translated into a functional version of a MCIDAS protein.

In some embodiments, the pharmaceutical composition comprises a polyribonucleotide that can be translated into a functional version of an MCIDAS protein and that comprises an optimized polyribonucleotide sequence as shown in SEQ ID NO: 4, and a polyribonucleotide that can be translated into a functional version of a CCDC40 and/or CCDC39 protein and that comprises an optimized polyribonucleotide sequence as shown in SEQ ID NO: 1 (or SEQ ID NO: 5 to 11) and/or SEQ ID NO: 2 (or SEQ ID NO: 12 to 14). Preferably, it is administered to a patient by using a nasal spray, and/or a nebulizer, and/or by inhalation, preferably at least once a week and/or for at least 4 weeks.

Alternatively or additionally to MCIDAS, GemC1, FoxJ1, and/or E2f4VP16 can be used for example. GemC1 is specifically expressed in ciliated epithelia and is a central regulator of ciliogenesis. It has been reported that ectopic expression of GemC1 was sufficient to induce early steps of multiciliogenesis in airway epithelial cells ex vivo by upregulating MCIDAS and FoxJ1, two key transcriptional regulators of multiciliogenesis (Arbi M et al., 2016, EMBO reports, 17(3):400-413). Moreover, it was reported in the same study that GemC1 can transactivate MCIDAS and FoxJ1 upstream regulatory sequences directly. E2f4VP16 refers to a form of E2f4 that contains a generic activation domain from HSV1 VP16 and can have a positive effect on the activation of the expression of key genes associated with multiciliogenesis (Kim S et al., Scientific Reports, 2018, 8:12369).

Hence, in some embodiments of the pharmaceutical composition comprising a polyribonucleotide for use in treating a ciliopathy, said pharmaceutical composition is a first pharmaceutical composition as described above and comprises further at least one of the following: a polyribonucleotide encoding a functional version of an MCIDAS protein, a polyribonucleotide encoding a functional version of a GemC1 protein, a polyribonucleotide encoding a functional version of a FoxJ1 protein, and/or a polyribonucleotide encoding a functional version of an E2f4VP16 protein.

In some embodiments of the pharmaceutical composition, a first pharmaceutical composition as described above can be administered together with a second pharmaceutical composition comprising at least one of the following: a polyribonucleotide encoding a functional version of an MCIDAS protein, a polyribonucleotide encoding a functional version of a GemC1 protein, a polyribonucleotide encoding a functional version of a FoxJ1 protein, and/or a polyribonucleotide encoding a functional version of an E2f4VP16 protein.

Both pharmaceutical compositions, i.e. a first pharmaceutical composition as defined above further comprising a polyribonucleotide encoding an MCIDAS, GemC1, FoxJ1, and/or E2f4VP16 protein or a first pharmaceutical composition that is administered together with a second pharmaceutical composition comprising a polyribonucleotide encoding an MCIDAS, GemC1, FoxJ1, and/or E2f4VP16 protein, are advantageous as the administration of a pharmaceutical composition according to the present invention is especially effective in restoring ciliatary cell structure and function, when the pharmaceutical composition is administered to cells before the cells initiate ciliogenesis or while they are in ciliogenesis. Further, both are preferably administered to a patient by using a nasal spray, and/or a nebulizer, and/or by inhalation, preferably at least once a week and/or for at least 4 weeks.

As stated above, in some embodiments, the same applies as described for the embodiments above except that the pharmaceutical composition comprises a polyribonucleotide that can be translated into functional versions of two or more, preferably two proteins. Thus, in some embodiments, the pharmaceutical composition as described in the embodiments above comprises a multicistronic polyribonucleotide.

The pharmaceutical composition may comprise compounds which facilitate transfection of cells with polyribonucleotides. Examples of such compounds are those disclosed in WO 2014/20723.

The pharmaceutical composition can further comprise one or more agent(s) or one or more reagent(s) for delivering and/or introducing the RNA into a target cell or a target tissue. In particular, it is envisaged that this/these agent(s) or reagent(s) support(s) the delivering and/or introducing the RNA into the cell or tissue. This/these agent(s) or reagent(s) may be administered together with the RNA. The RNA to be delivered/introduced may also be coupled with (e.g. covalently bound to or complexed with) or uncoupled with (for example only admixed with) this/these agent(s(or reagent(s). Respective agents or reagents are known in the art (e.g. Tavernier, J Control Release 150(3) (2011), 238-47) and are, for example, selected from the group consisting of lipids and liposomes, micelles, polymers and dendrimers, among others. Particular examples of respective agents or reagents are GL67, EDMPC, DOTAP (1,2-dioleyl-3-trimethylammonium propane), DODAP (1,2-dioleyl-3-dimethylammonium propane), DOTMA (1,2-di-O-octadecenyl-3-trimethylammonium propane), XTC (2,2-Dilinoleyl-4-dimethylaminoethyl-[1,3]-dioxolane) and MC3 (((6Z,9Z,28Z,31Z)-heptatriaconta-6,9,28,31-tetraen-19-yl 4-(dimethylamino) butanoate), ALNY-100 ((3 aR,5s,6aS)—N,N-dimethyl-2,2-di((9Z, 12Z)-octadeca-9, 12-dienyl)tetrahydro-3aH-cyclopenta[d][1,3]dioxol-5-amine)), NC98-5 (4,7, 13-tris(3-oxo-3-(undecylamino) propyl)-NI,N16-diundecyl-4,7, 10, 13-tetraazahexadecane-I, 16-diamide), C12-200, DLin-KC2-DMA, DODAP, I,2-distearyloxy-N,N-dimethyl-3-aminopropane or "DSDMA", I,2-dioleyloxy-N,N-dimethyl-3-aminopropane or "DODMA", 1,2-dilinoleyloxy-N,N-dimethyl-3-aminopropane or "DLinDMA", 1,2-dilinolenyloxy-N,N-dimethyl-3-aminopropane or "DLenDMA", N-dioleyl-N, N-dimethylammonium chloride or "DODAC", N,N-distearyl-N,N-dimethylammonium bromide or "DDAB", N-(1,2-dimyristyloxyprop-3-yl)-N,N-dimethyl-N-hydroxy ethyl ammonium bromide or "DMRIE", 3-dimethylamino-2-(cholest-5-en-3-beta-oxybutan-4-oxy)-I-(ci s,cis-9, 12-octadecadienoxy)propane or "CLinDMA", 2-[5'-(cholest-5-en-3-beta-oxy)-3'-oxapentoxy)-3-dimethy I-I-(cis,cis-9', 1-2'-octadecadienoxy)propane or "CpLinDMA", N,N-dimethyl-3,4-dioleyloxybenzylamine or "DMOBA", I,2-N,N'-dioleylcarbamyl-3-dimethylaminopropane or "DOcarbDAP", 2,3-Dilinoleoyloxy-N,N-dimethylpropylamine or "DLinDAP", I,2-N,N'-Dilinoleylcarbamyl-3-"DLincarbDAP", 1,2-Dilinoleoylcarbamyl-3-dimethylaminopropane or dimethylaminopropane or "DLinCDAP", 2,2-dilinoleyl-4-dimethylaminomethyl-[I,3]-dioxolane or "DLin-K-DMA", 2,2-dilinoleyl-4-dimethylaminoethyl-[I,3]-dioxolane or "DLin-K-XTC2-DMA", or mixtures thereof (Heyes, J Controlled Release 107 (2005), 276-287; Morrissey, Nat. Biotechnol. 23(8) (2005), 1003-1007; WO2005/121348). Further examples are DC-Chol (N,N-dimethyl-N-ethylcarboxamidocholesterol), I,4-bis(3-N-oleylamino-propyl)piperazine (Gao, Biochem. Biophys. Res. Comm. 179 (1991), 280; Wolf, et al BioTechniques 23 (1997), 139; U.S. Pat. No. 5,744,335). Further examples are LIPOFECTIN™ (DOTMA: DOPE) (Invitrogen, Carlsbad, Calif), LIPOFECTAMINE™ (DOSPA: DOPE) (Invitrogen), LIPOFECTAMINE™2000. (Invitrogen), FUGENE®, TRANSFECTAM (DOGS), and EFFECTENE®. Further examples are modified and unmodified polyacrylates, polyalkycyanoacrylates, polylactide, polylactide-polyglycolide copolymers, polycaprolactones, dextran, albumin, gelatin, alginate, collagen, chitosan, cyclodextrins, polylysin, polyarginine, oligo/polyamines and polyethylenimine.

The agents or reagents may be oligomers, polymers or lipidoids. They may comprise oligo (alkylene amine) moieties like, for example, the characteristic oligo (alkylene amine) moieties as described in PCT/EP2014/063756. In particular, the agents or reagents may be the oligomers, polymers or lipidoids as described in PCT/EP2014/063756. One main characteristic of these particular agents or reagents is that they contain a following common structural entity of formula (I):

(I)

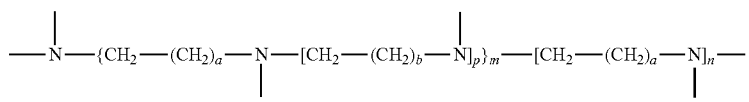

Such agents or reagents may be (a component comprising) an oligo (alkylene amine) selected from:

a) an oligomer or polymer comprising a plurality of groups of formula (II) as a side chain and/or as a terminal group:

(II)

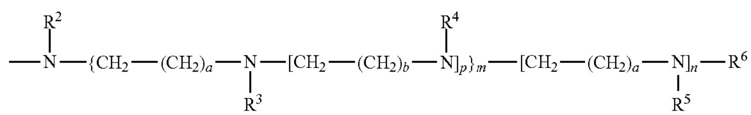

wherein the variables a, b, p, m, n and $R^2$ to $R^6$ are defined as follows, independently for each group of formula (II) in a plurality of such groups:

a is 1 and b is an integer of 2 to 4; or a is an integer of 2 to 4 and b is 1, p is 1 or 2, m is 1 or 2; n is 0 or 1 and m+n is ≥2; and $R^2$ to $R^5$ are, independently of each other, selected from hydrogen; a group $—CH_2—CH(OH)—R^7$, $—CH(R^7)—CH_2—OH$, $—CH_2—CH_2—(C{=}O)—O—R^7$, $—CH_2—CH_2—(C{=}O)—NH—R^7$ or $—CH_2—R^7$ wherein $R^7$ is selected from C3-C18 alkyl or C3-C18 alkenyl having one C—C double bond; a protecting group for an amino group; and a poly(ethylene glycol) chain;

$R^6$ is selected from hydrogen; a group-$CH_2—CH(OH)—R^7$, $—CH(R^7)—CH_2—OH$, $—CH_2—CH_2—(C{=}O)—O—R^7$, $—CH_2—CH_2—(C{=}O)—NH—R^7$ or $—CH_2—R^7$ wherein $R^7$ is selected from C3-C18 alkyl or C3-C18 alkenyl having one C═C double bond; a protecting group for an amino group; $—C(NH)—NH_2$; a poly(ethylene glycol) chain; and a receptor ligand, and wherein one or more of the nitrogen atoms indicated in formula (II) may be protonated to provide a cationic group of formula (II);

b) an oligomer or polymer comprising a plurality of groups of formula (III) as repeating units:

(III)

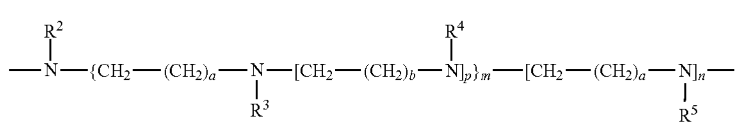

wherein the variables a, b, p, m, n and $R^2$ to $R^5$ are defined as follows, independently for each group of formula (III) in a plurality of such groups:

a is 1 and b is an integer of 2 to 4; or a is an integer of 2 to 4 and b is 1, p is 1 or 2, m is 1 or 2; n is 0 or 1 and m+n is ≥2; and $R^2$ to $R^5$ are, independently of each other, selected from hydrogen; a group-$CH_2$—CH(OH)—$R^7$, —CH($R^7$)—$CH_2$—OH, —$CH_2$—$CH_2$—(C═O)—O—$R^7$ or —$CH_2$—$CH_2$—(C═O)—NH—$R^7$ or —$CH_2$—$R^7$ wherein $R^7$ is selected from C3-C18 alkyl or C3-C18 alkenyl having one C═C double bond; a protecting group for an amino group; —C(NH)—$NH_2$; and a poly(ethylene glycol) chain;

and wherein one or more of the nitrogen atoms indicated in formula (III) may be protonated to provide a cationic group of formula (III); and c) a lipidoid having the structure of formula (IV):

(IV)

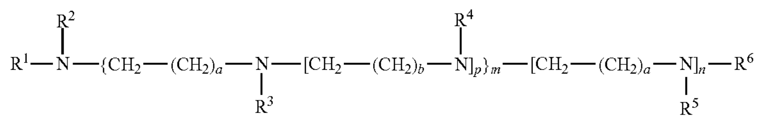

wherein the variables a, b, p, m, n and $R^1$ to $R^6$ are defined as follows:

a is 1 and b is an integer of 2 to 4; or a is an integer of 2 to 4 and b is 1, p is 1 or 2, m is 1 or 2; n is 0 or 1 and m+n is ≥2; and $R^1$ to $R^6$ are independently of each other selected from hydrogen; a group-$CH_2$—CH(OH)—$R^7$, —CH($R^7$)—$CH_2$—OH, —$CH_2$—$CH_2$—(C═O)—O—$R^7$, —$CH_2$—$CH_2$—(C═O)—NH—$R^7$ or —$CH_2$—$R^7$ wherein $R^7$ is selected from C3-C18 alkyl or C3-C18 alkenyl having one C═C double bond; a protecting group for an amino group; —C(NH)—$NH_2$; a poly (ethylene glycol) chain; and a receptor ligand; provided that at least two residues among $R^1$ to $R^6$ are a group-$CH_2$—CH(OH)—$R^7$, —CH($R^7$)—$CH_2$—OH, —$CH_2$—$CH_2$—(C═O)—O—$R^7$, —$CH_2$—$CH_2$—(C═O)—NH—$R^7$ or —$CH_2$—$R^7$ wherein $R^7$ is selected from C3-C18 alkyl or C3-C18 alkenyl having one C═C double bond;

and wherein one or more of the nitrogen atoms indicated in formula (IV) may be protonated to provide a cationic lipidoid of formula (IV).

Preferably, such agents or reagents may be (a component comprising) an oligo (alkylene amine) selected from a) and b), wherein a) is an oligomer or polymer comprising a plurality of groups of formula (IIa) as a side chain and/or as a terminal group:

$$—NR^2\{CH_2—(CH_2)_a—NR^3—CH_2—(CH_2)_b—NR^4\}_m—[CH_2—(CH_2)_a—NR^5]_n—R^6 \quad (IIa),$$

wherein a, b, m, n, and $R^2$ to $R^6$ are defined as described above, and wherein one or more of the nitrogen atoms indicated in formula (IIa) may be protonated to provide a cationic oligomer or polymer structure; and b) is an oligomer or polymer comprising a plurality of groups of formula (IIIa) as repeating units:

$$—NR^2\{CH_2—(CH_2)_a—NR^3—CH_2—(CH_2)_b—NR^4\}_m—[CH_2—(CH_2)_a—NR^5]_n— \quad (IIIa),$$

wherein a, b, m, n, and $R^2$ to $R^5$ are defined as described above, and wherein one or more of the nitrogen atoms indicated in formula (IIIa) may be protonated to provide a cationic oligomer or polymer structure.

Furthermore, such agents or reagents may be (a component comprising) an oligo (alkylene amine) selected from a lipidoid having the structure of formula (IVa):

$$R^1—NR^2\{CH_2—(CH_2)_a—NR^3—CH_2—(CH_2)_b—NR^4\}_m—[CH_2—(CH_2)_a—NR^5]_n—R^6 \quad (IVa),$$

wherein a, b, m, n, and $R^1$ to $R^6$ are defined as described above, and wherein one or more of the nitrogen atoms indicated in formula (IVa) may be protonated to provide a cationic lipidoid.

As to such agents or reagents, in formula (II), (IIa), (III), (IIIa), (IV) or (IVa) n may be 1; or m may be 1 and n may be 1.

Further, as to such agents or reagents, in formula (II), (IIa), (III), (IIIa), (IV) or (IVa) a may be 1 and b may be 2; or a may be 2 and b may be 1.

In some embodiments, the oligomer, polymer or lipidoid may be a cationic (e.g. protonated) oligomer, polymer or lipidoid.

One non-limiting example of such an oligomer, polymer or lipidoid to be employed is a cationic lipid which was prepared by mixing 100 mg N,N'-Bis(2-aminoethyl)-1,3-propanediamine (0.623 mmol) with 575.07 mg 1,2-Epoxydodecane (3.12 mmol, (N-1) eq. where N is 2× amount of primary amine plus 1× amount secondary amine per oligo (alkylene amine)) and mixed for 96 h at 80° C. under constant shaking. Such an oligomer, polymer or lipidoid is also referred to as lipidoid "C12-(2-3-2)".

An agent or reagent, in particular a polymer, to be employed may be a copolymer, in particular a statistical copolymer. Such a copolymer may be a copolymer which contains a statistical/random arrangement of alkylene amine repeating units of alternating length (e.g. in contrast to a less preferred polymer which contains analogous arrangements of alkylene amine repeating units of non-alternating length). The copolymer may be a cationic (e.g. protonated) copolymer. Copolymers to be employed are known in the art and are, for example, described in EP 14 19 9439.2, WO 01/00708, EP-A1 1 198 489 and CA-A1 2,377,207.

In particular, the copolymer may be a statistical copolymer comprising a plurality of repeating units (a) independently selected from repeating units of the following formulae (a1) and (a2):

$$—CH_2—CH_2—NH— \quad (a1)$$

(a2)

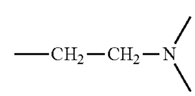

, and a plurality of repeating units (b) independently selected from repeating units of the following formulae (b1) to (b4):

(b1)

$$-CH_2-CH_2-CH_2-NH-$$

(b2)

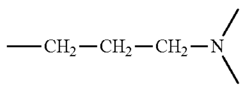

(b3)

$$-CH_2-CH_2-CH_2-CH_2-NH-$$

(b4)

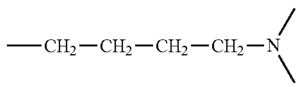

wherein the molar ratio of the sum of the repeating units (a) to the sum of the repeating units (b) lies within the range of 0.7/1.0 to 1.0/0.7, and wherein one or more of the nitrogen atoms of the repeating units (a) and/or (b) contained in the copolymer may be protonated to provide a cationic copolymer.

The copolymer may be a statistical copolymer, wherein any repeating units (a) and any repeating units (b) are statistically distributed in the copolymer macromolecule. It is typically obtained from the copolymerization of a mixture of monomers yielding, during the polymerization reaction, the repeating units (a) with monomers yielding, during the polymerization reaction, the repeating units (b). Preferably, the copolymer is a random copolymer wherein any repeating units (a) and any repeating units (b) are randomly distributed in the polymer macromolecule.

Such a copolymer can be a linear, branched or dendritic copolymer. As will be understood by the skilled reader, a repeating unit of the formula (a1), (b1) or (b3) with two valencies (i.e. open bonds to neighboring units) leads to a propagation of the copolymer structure in a linear manner. Thus, a linear copolymer may comprise repeating units of formula (a1) and one or more types of the repeating units of formulae (b1) and (b3), but no repeating units of formula (a2), (b2) or (b4). As will be further understood, the presence of a repeating unit of formula (a2), (b2) or (b4) with three valencies provides a branching point in the copolymer structure. Thus, a branched copolymer comprises one or more types of the repeating units of formulae (a2), (b2) and (b4), and may further comprise one or more types of the repeating units of formulae (a1), (b1) and (b3).

Such a copolymer may comprise a plurality of repeating units (a) independently selected from repeating units of formulae (a1) and (a2) defined above, and a plurality of repeating units (b) independently selected from repeating units of formulae (b1) to (b4) defined above. Preferred are copolymers comprising a plurality of repeating units (a) independently selected from repeating units of formulae (a1) and (a2) defined above, and a plurality of repeating units (b) independently selected from repeating units of formulae (b1) and (b2) defined above.

Preferably, such a copolymer is a branched copolymer comprising one or more types of repeating units selected from repeating units (a2), (b2) and (b4), and which optionally further comprises one or more types of the repeating units of formulae (a1), (b1) and (b3), and in particular a copolymer which comprises repeating units of the formula (a2) and one or more type of the repeating units of formulae (b2) and (b4), and which optionally further comprises one or more types of the repeating units of formulae (a1), (b1) and (b3). In line with the above, a more preferred copolymer is thus a branched copolymer which comprises repeating units of the formula (a2) and repeating units of formula (b2), and which optionally further comprises one or more types of the repeating units of formulae (a1) and (b1).

In the copolymers, the total number of the repeating units (a) and repeating units (b) is typically 20 or more, preferably 50 or more and more preferably 100 or more.

Typically, the total number of the repeating units (a) and repeating units (b) is 10,000 or less, preferably 5,000 or less, more preferably 1,000 or less.

Furthermore, it is preferred for the copolymers that the repeating units (a) and (b) account for 80 mol % or more, more preferably 90 mol % or more of all repeating units in the copolymer. Further preferred are copolymers wherein repeating units (a) selected from (a1) and (a2) and repeating units (b) selected from (b1) and (b2) account for 80 mol % or more, more preferably 90 mol % or more of all repeating units in the copolymer. It is most preferred that all of the repeating units in the copolymer are repeating units (a) or (b), in particular that all of the repeating units in the copolymer are repeating units (a) selected from (a1) and (a2) or repeating units (b) selected from (b1) and (b2).

The weight average molecular weight of the copolymer, as measured e.g. via size exclusion chromatography relative to linear poly(ethylene oxide) standards, generally ranges from 1,000 to 500,000 Da, preferably from 2,500 to 250,000 Da and more preferably 5,000-50,000 less.

The terminal groups of such a copolymer typically comprise one or more types of groups (c) independently selected from groups of the formulae (c1) to (c3) below, preferably from groups of the formulae (c1) and (c2) below:

$$-CH_2-CH_2-NH_2 \quad (c1)$$

$$-CH_2-CH_2-CH_2-NH_2 \quad (c2)$$

$$-CH_2-CH_2-CH_2-CH_2-NH_2 \quad (c3).$$

Preferably, the terminal groups in the copolymer consist of one or more types of groups (c) independently selected from groups of the formulae (c1) to (c3) below, preferably from groups of the formulae (c1) and (c2). As will be understood by the skilled person, the number of terminal groups depends on the structure of the copolymer. While a linear copolymer has only two terminals, larger numbers of terminal groups are contained in a branched, in particular in a dendritic copolymer. As will be further understood, also one or more of the nitrogen atoms of the terminal groups (c) contained in the copolymer may be protonated to provide a cationic copolymer.

In the copolymer, the molar ratio of the sum of the repeating units (a) to the sum of the repeating units (b) lies within the range of 0.7/1.0 to 1.0/0.7, and preferably within the range of 0.8/1.0 to 1.0/0.8. This molar ratio can be determined, e.g., via NMR. It will thus be understood that the ratio is usually determined for a plurality of macromolecules of the copolymer, and typically indicates the overall ratio of the sum of repeating units (a) to the sum of repeating units (b) in the plurality of macromolecules.

As indicated above, one or more of the nitrogen atoms of the copolymer may be protonated to result in a copolymer in a cationic form, typically an oligocationic or polycationic form. It will be understood that the primary, secondary, or tertiary amino groups in the repeating units (a) or (b) or in the terminal groups (c) can act as proton acceptors, especially in water and aqueous solutions, including physiological fluids. Thus, such copolymers typically have an overall positive charge in an aqueous solution at a pH of below 7.5. An aqueous solution, as referred to herein, is a solution wherein the solvent comprises 50% (vol./vol.) or more, preferably 80 or 90% or more, and most preferably 100% of water. Also, if the compositions are in contact with a physiological fluid having a pH of below 7.5, including e.g. blood and lung fluid, they typically contain repeating units (a) and (b) wherein the nitrogen atoms are protonated. The $pK_a$ values of the copolymers used in the compositions can be determined by acid-base titration using an automated $pK_a$ titrator. The net charge at a given pH value can then be calculated e.g. from the Henderson-Hasselbach equation. Any charge may be shared across several of the basic centres and cannot necessarily be attributed to a single point. Typically, in solutions at physiological pH, the copolymers used in the compositions comprise repeating units with amino groups in protonated state and repeating units with amino groups in unprotonated state.

However, as will be understood by the skilled reader, the copolymers as well as the compositions may also be provided as a dry salt form which contains the copolymer in a cationic form.

As will be further understood, counterions (anions) for the positive charges of protonated amino groups in compositions comprising the copolymer and nucleic acid, in particular RNA, preferably single-stranded RNA such as mRNA, are typically provided by anionic moieties contained in the nucleic acid. If the positively charged groups are present in excess compared to the anionic moieties in the nucleic acid, positive charges may be balanced by other anions, in particular those typically encountered in physiological fluids, such as $Cl^-$ or $HCO_3^-$.

In line with the above, a preferred copolymer is a random copolymer, wherein 80 mol % or more of all repeating units, more preferably all repeating units, are formed by a plurality of repeating units (a) independently selected from repeating units of the following formulae (a1) and (a2):

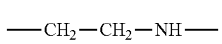
(a1)

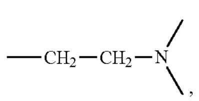
(a2)

and a plurality of repeating units (b) independently selected from repeating units of the following formulae (b1) and (b2):

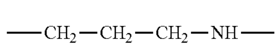
(b1)

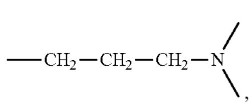
(b2)

wherein the molar ratio of the sum of the repeating units (a) to the sum of the repeating units (b) lies within the range of 0.7/1.0 to 1.0/0.7, more preferably within the range of 0.8/1.0 to 1.0/0.8;

wherein the terminal groups of the copolymer are formed by groups (c) independently selected from groups of the formulae (c1) and (c2):

$$—CH_2—CH_2—NH_2 \quad (c1)$$

$$—CH_2—CH_2—CH_2—NH_2 \quad (c2);\ \text{and}$$

wherein one or more of the nitrogen atoms of the repeating units (a) and/or (b) and/or of the terminal groups (c) contained in the copolymer may be protonated to provide a cationic copolymer. It is further preferred that the copolymer is a branched copolymer, comprising units (a2) and (b2), optionally together with units (a1) and/or (b1).

The copolymers can be conveniently prepared with procedures analogous to those known for the preparation of polyalkyleneimines, such as branched or linear polyethyleneimine (PEI). It will be understood that the monomers used for the production of the copolymers will have to be adjusted accordingly. Herein, it has been found that the monomers can be conveniently reacted in a quantitative manner, such that the ratio of the units (a) and (b) in the copolymer can be adjusted by adjusting the monomer ratio accordingly in the monomer mixture subjected to polymerization. While polyethyleneimine can be prepared e.g. via ring-opening polymerization of aziridine, the copolymers can be prepared via ring opening polymerization of a monomer mixture comprising or consisting of aziridine, azetidine and, where applicable pyrrolidine, or, in preferred embodiments, of aziridine and azetidine. It will be understood that the expression "where applicable" refers to the presence or absence of repeating units (b3) and (b4) or terminal groups (c3) which would be formed by the pyrrolidine. The ring opening polymerization of the non-substituted cyclic amines usually leads to branched copolymers. Linear copolymers can be prepared, e.g., via polymerization of suitable N-substituted aziridines, N-substituted azetidines and N-substituted pyrrolidines, or N-substituted aziridines and N-substituted azetidines, which may be followed e.g. by a hydrolytic cleavage of N-substituents attached to the resulting polyalkyleneimine chain, e.g. in analogy to the procedure published in Katrien F. Weyts, Eric J. Goethals, New synthesis of linear polyethyleneimine, Polymer Bulletin, 1988, 19(1):13-19. Dendrimers can be synthesized e.g. according to the method described in Yemul et al, Colloid and Polymer Science, 2008, 286(6-7):747-752, Synthesis and characterization of poly(ethylenimine) denrimers.

For the preparation of a dendrimer (or dendritic copolymer), synthetic strategies can be analogously applied which are known for the production of polyethyleneimine or polypropyleneamine dendrimers. Polypropylenimine dendrimers can be synthesized from acrylonitrile building blocks using a repetitive sequence of a Michael addition to a primary amine, followed by a heterogeneously catalyzed hydrogenation (Newkome and Shreiner Poly(amidoamine), polypropylenimine, and related dendrimers and dendrons possessing different 1→2 branching motifs: An overview of the divergent procedures. Polymer 49 (2008) 1-173; De Brabander-Van Den Berg et al. Large-scale production of polypropylenimine dendrimers, Macromolecular Symposia (1994) 77 (1) 51-62). Polyethylenimine dendrimers can be produced using a repetitive sequence of a Michael addition of a vinyl bromide building block to a primary amine followed by a conversion of alkylbromide to amine using a Gabriel amine synthesis method (Yemul & Imae, Synthesis and characterization of poly(ethyleneimine) dendrimers, Colloid Polym Sci (2008) 286:747-752). Hence the person skilled in the art will be able to produce not only dendrimers with strictly alternating layers of e.g. propylenimine and ethylenimine can be produced. Similarly dendrimer generations with layers comprising or consisting of random compositions of repeating units of formula (a2), (b2) and (b4) and preferably repeating units (a2) and (b2) can be generated.

The ring opening polymerization of aziridine and azetidine, or of aziridine, azetidine and pyrrolidine, can be carried out in solution, e.g. in water. The total monomer concentration is not particularly limited, typical concentrations range from 10% wt/wt to 80% wt/wt, preferably 30% wt/wt to 60% wt/wt. Typically, the polymerization is initiated by protons, such that it is preferred to add a Brønsted acid, in particular a mineral acid such as sulphuric acid to the reaction system. Small amounts of acid are generally sufficient, such as 0.001 to 0.01 equivalents, based on the total concentration of monomers. The reaction proceeds at convenient rates e.g. in the temperature range of 50 to 150° C., in particular 90 to 140° C. In these ranges, higher molecular weight copolymers are usually at higher temperatures, and lower molecular weight copolymers at lower temperatures.

In principle, a lipidoid is a preferred agent or reagent to be employed, in particular as compared to an oligomer and, more particular particular, to a polymer.

Further examples of the one or more agent(s) or one or more reagent(s) for delivering and/or introducing the RNA into a target cell or a target tissue are the liposomal transfection reagents (LTR'S) and magnetic particles (MPs) as described herein elsewhere.

One particular mode for delivering and/or introducing the RNA into target cells or target tissue is transfection. Hence, the RNA to be employed can be envisaged to be transfected (into (target) cells or tissue), to be delivered/administered via transfection and/or to be prepared for transfection. Means and methods for transfecting RNA are well known in the art and are, for example, described in Tavernier (loc. cit.), Yamamoto (Eur J Pharm Biopharm. 71(3) (2009), 484-9) and Kormann (Nat Biotechnol. 29(2) (2011), 154-7). Particular modes of transfection are lipofection, magnetofection or magnetolipofection.

Hence, the RNA to be employed may be prepared for lipofection, prepared to be transfected by lipofection, delivered/introduced via lipofection and/or administered via lipofection.

Thus, the pharmaceutical composition may (further) comprise at least one lipid or liposomal transfection reagent or enhancer (LTR; liposomal transfection reagent). The RNA to be employed may be comprised in, complexed with and/or delivered by the LTR. In particular, the RNA to be employed may be comprised in and/or delivered by (respective) lipofection complexes comprising the RNA and the LTR. The pharmaceutical composition may (further) comprise the lipofection complexes.

LTRs are known in the art and are, for example, distributed by OzBiosciences, Marseille, France. LTRs to be employed may be selected from the group consisting of the above-described agents or reagents for delivering and/or introducing the RNA into a target cell or a target tissue. For example, such LTRs may be lipids or lipidoids, preferably cationic lipids or cationic lipidoids, like the lipidoids as disclosed in PCT/EP2014/063756 (e.g. C12-(2-3-2), the lipids as disclosed in EP2285772 (e.g. Dogtor) and the lipopolyamines as disclosed in EP1003711 (e. g. DREAMFECT™ and DREAMFECT GOLD™). A particular LTR may be selected from the group consisting of (i) C12-(2-3-2);
(ii) DREAMFECT™, preferably DREAMFECT GOLD™ (DF™/DF-GOLD™; OzBiosciences, Marseille, France);
(iii) Dogtor (OzBiosciences, Marseille, France); and
(iv) LIPOFECTAMINE™ like, for example, LIPOFECTAMINE™2000 (Invitrogene, CA, USA).

In principle, Dogtor is a preferred, DREAMFECT™ is a more preferred and DF-GOLD™ and C12-(2-3-2) are even more preferred LTR(s).

LTRs like Dogtor are, for example, described in EP2285772. LTRs like DF™ or DF-GOLD™ are, for example, described in EP1003711. In principle, the oligomers, polymers or lipidoids as disclosed in PCT/EP2014/063756, the particular cationic lipids as disclosed in EP2285772 and the particular lipopolyamines as disclosed in EP1003711 are preferred LTRs. LTRs like C12-(2-3-2) and DF-GOLD™ are most preferred.

Non-limiting examples of lipofection complexes are DF-GOLD™/RNA lipoplexes and C12-(2-3-2)/RNA lipoplexes.

C12-(2-3-2) is a particularly preferred LTR having the structure shown in formula (V) (cf. Jarzębińska et al., Angew Chem Int Ed Engl., 2016; 55(33):9591-5):

formula (V)

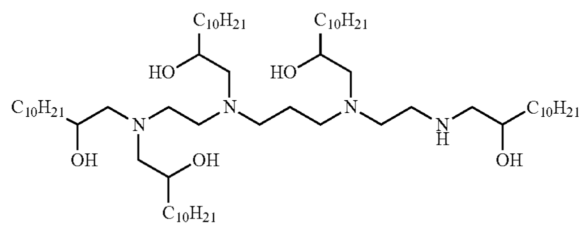

C12-(2-3-2)

C12-(2-3-2) is preferably prepared as described e.g. in WO 2016/075154 A1, EP 3013964, and Jarzębińska et al. (Angew Chem Int Ed Engl., 2016; 55(33):9591-5). The cationic lipidoid can be prepared by mixing N1-(2-aminoethyl)-N3-(2-((3,4-dimethoxybenzyl)amino)ethyl)propane-1,3-diamine (8.9 g, 1 eq., 28.67 mmol) with 1,2-Epoxydodecane (42.27, 8 eq., 229.4 mmol) and mixed for 24 h at 80° C. under constant shaking followed by purification and removal of the 3,4-dimethoxybenzyl protection group.

Different isomers, of C12-(2-3-2) can be used such as a racemate, an S-isomer, and/or an R-isomer. Preferably, C12-(2-3-2) is used as pure R-isomer and has the structure shown in formula (VI). For obtaining pure R-isomers of C12-(2-3-2) it can be prepared as described above for C12-(2-3-2) using the R-isomer of 1,2-Epxoydodecane for synthesis.

formula (VI)

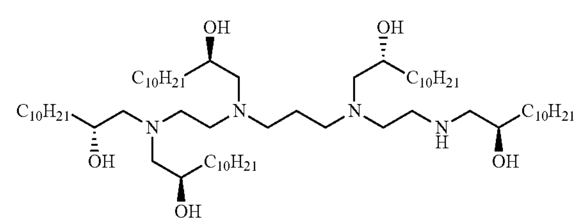

Hence, in preferred embodiments the pharmaceutical composition comprises a polyribonucleotide for use in treating a ciliopathy and further comprises a lipidoid having the structure shown in formula (V), preferably as shown in formula (VI).

A further particularly preferred LTR is a cationic lipidoid having formula (VII), herein also referred to as "dL_P" which can be synthesized via reaction of N,N'-Bis(2-aminoethyl)-1,3-propanediamine with N-Dodecylacrylamide using boric acid as catalyst. For the reaction, the mixture can be stirred at 100° C. under microwave irradiations.

Hence, in further preferred embodiments the pharmaceutical composition comprises a polyribonucleotide for use in treating a ciliopathy and further comprises a lipidoid having having the structure shown in formula (VII).

formula (VII)

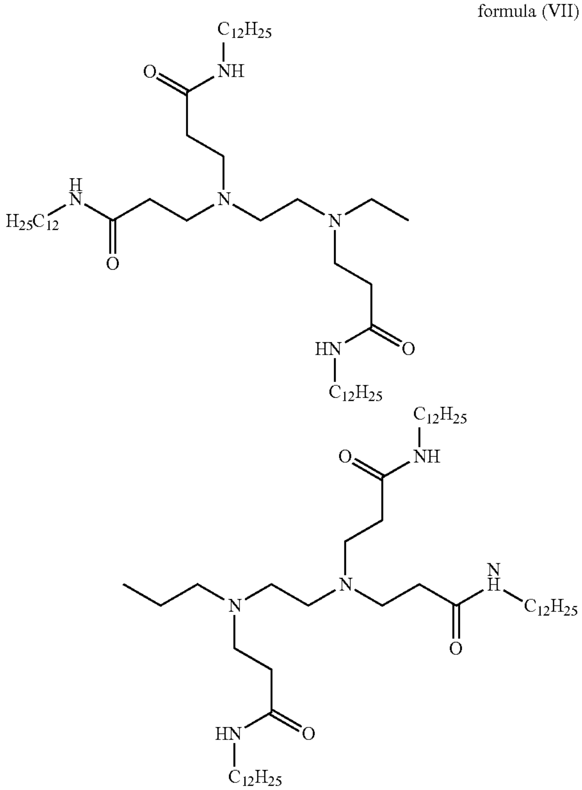

Furthermore, the pharmaceutical composition comprises a cationic lipidoid having formula (V), (VI) and/or (VII), preferably dL_P and/or C12-(2-3-2), more preferably dL_P and/or the R-isomer of C12-(2-3-2), comprised in a formulation as described in the following. In particular, the herein described agents and reagents for delivering and/or introducing the RNA into a target cell or a target tissue and the herein described LTRs may be combined with one or more (e.g. two, three or four) further lipid(s) (like, for example, cholesterol, DPPC, DOPE and/or PEG-lipids (e.g. DMPE-PEG, DMG-PEG2000)). These further lipids may support the desired function of the agents/reagents and LTRs (support and/or increase the delivering and/or introducing of RNA into the cell or tissue and improve transfection efficiency, respectively) and function as respective "helper lipids". Particular examples of such "helper lipids" are cholesterol, DPPC, DOPE and/or PEG-lipids (e.g. DMPE-PEG, DMG-PEG (e.g. DMG-PEG2000). The further lipids (e.g. "helper lipids") may also be part(s) of the herein disclosed complexes/particles. The skilled person is readily in the position to prepare complexes/particles in accordance with the invention. Examples of further lipids (e.g. "helper lipids") are also known in the art. The skilled person is readily in the position to choose suitable further lipids (e.g. "helper lipids") and ratios of the agents/reagents/LTRs and the further lipids (e.g. "helper lipids"). Such ratios may be molar ratios of 1-4:1-5, 3-4:4-6, about 4:about 5, about 4:about 5.3 of agents/reagents/LTRs: further lipid(s) (the more narrow ranges are preferred). For example, the agents/reagents/LTRs may be combined with three further lipids, like DPPC, cholesterol, and DMG-PEG2000, at a molar ratio of 8:5.3:4.4:0.9, respectively, or, more particular, 8:5.29:4.41:0.88, respectively.

Preferably, dL_P and/or C12-(2-3-2), more preferably dL_P and/or the R-isomer of C12-(2-3-2), is generated as described above and used with helper lipids DPPC and cholesterol and PEG-lipid DMG-PEG2000 at the molar ratios 8:5.29:4.41:0.88 for formulating lipoid particles.

A composition in which the R-isomer of C12-(2-3-2) (formula VI) is formulated with the lipids DPPC and cholesterol and PEG-lipid DMG-PEG2000 at the molar ratios 8:5.29:4.41:0.88 is also referred herein as "LF92". A composition in which the dL_P (formula VII) is formulated with the lipids DPPC and cholesterol and PEG-lipid DMG-PEG2000 at the molar ratios 8:5.29:4.41:0.88 is also referred herein as "LF111".

As also exemplarily described e.g. in WO 2016/075154 A1, EP 3013964, and Zhang et al. (TERMIS, 2019, Tissue Engineering: Part A, Vol. 25, Numbers 1 and 2), dL_P and/or C12-(2-3-2) can be used as a non-viral vector, to make a stable lipoplex with mRNA molecules, based on electrostatic interaction between the positive amino groups of lipidoid and negative phosphate groups of mRNA molecules (Anderson, Human Gene Therapy 14, 2003, 191-202). To stabilized the lipoplex structure and reduce the leakage, dL_P and/or C12-(2-3-2), more preferably dL_P and/or the R-isomer of C12-(2-3-2), can be supplied with two helper lipids entitled 1,2-dipalmitoyl-sn-glycero-3-phosphocholine (DPPC) and cholesterol (Anderson, Drug Delivery 11, 2004, 33-39; Liang, Journal of Colliod and Interface Science 278, 2004, 53-62). At the end, 1,2-Dimyristoyl-sn-glycerol, methoxypolyethylene Glycol (DMG-PEG) 2 kD (DMG-PEG2000) is to be added to the lipid mix to provide a PEGylated liposome. It is already well known that PEGylation improves the physico-chemical characteristic of liposome formulation by increasing water solubility, protecting from enzymatic degradation, and limiting immunogenic and antigenic reactions (Milla, Current Drug Metabolism 13, 2012, 105-119). Final N/P ratios for entire ethanoic lipid mixture are to be 8:5.29:4.41:0.88 standing for molar ratios of amino group of dL_P and/or C12-(2-3-2)/DPPC/cholesterol/DMG-PEG2000, respectively, to one phosphate group of mRNA molecule.

Hence, in preferred embodiments the pharmaceutical composition comprises a polyribonucleotide for use in treating a ciliopathy further comprises dL_P and/or C12-(2-3-2), preferably dL_P and/or the R-isomer of C12-(2-3-2), formulated with DPPC, cholesterol, and DMG-PEG2000.

Moreover, in particularly preferred embodiments the pharmaceutical composition comprises a polyribonucleotide for use in treating a ciliopathy further comprises dL_P and/or C12-(2-3-2), preferably dL_P and/or the R-isomer of C12-(2-3-2), formulated with DPPC, cholesterol, and DMG-PEG2000 with final N/P ratios for entire ethanoic lipid mixture of 8:5.29:4.41:0.88 for molar ratios of amino group of dL_P and/or C12-(2-3-2)/DPPC/cholesterol/DMG-PEG2000, respectively, to one phosphate group of mRNA molecule.

R-isomers of C12-(2-3-2) formulated with DPPC, cholesterol, and DMG-PEG2000 as stated above are also referred to as LF92 formulation.

Hence, in particularly preferred embodiments of the pharmaceutical composition comprising a polyribonucleotide for use in treating a ciliopathy, said pharmaceutical composition further comprises an LF92 formulation.

dL_P formulated with DPPC, cholesterol, and DMG-PEG2000 as stated above are also referred to as LF111 formulation.

Hence, in particularly preferred embodiments of the pharmaceutical composition comprising a polyribonucleotide for use in treating a ciliopathy, said pharmaceutical composition further comprises an LF111 formulation.

In a preferred embodiment of the pharmaceutical composition comprising a polyribonucleotide for use in treating a ciliopathy, said pharmaceutical composition further comprises an LF92 and/or LF111 formulation. LF92 and/or LF111 refers to a carrier formulation that is used for cell transfection. This is advantageous as the use of LF92 and/or LF111 is associated with high transfection efficiencies and thus, ensures that the polyribonucleotide encoding a functional version of a protein a defect of which is associated with the ciliopathy can efficiently enter a cell, preferably an undifferentiated ciliary cell or basal cell, and thus restore ciliated cell function in the subject suffering of PCD.

In a particularly preferred embodiment, the pharmaceutical composition comprises an LF92 and/or LF111 formulation, at least one of the following: an mRNA that can be translated into a functional version of a MCIDAS protein, an mRNA that can be translated into a functional version of a GemC1 protein, an mRNA that can be translated into a functional version of a FoxJ1 protein, an mRNA that can be translated into a functional version of a E2f4VP16 protein; and an mRNA that can be translated into a functional version of CCDC40 and/or CCDC39. Preferably, such a composition is administered to a patient by using a spray, droplets and/or a nebulizer, and/or by inhalation, preferably at least once a week and/or for at least 4 weeks. Hence, in some embodiments, the same applies as described for the embodiments above except that the pharmaceutical composition comprises a polyribonucleotide that can be translated into functional versions of two or more, preferably two proteins. Thus, in some embodiments, the pharmaceutical composition as described in the embodiments above comprises a multicistronic polyribonucleotide.

The present invention also relates to a method of treating a ciliopathy in a subject suffering of a ciliopathy, comprising the administration of a pharmaceutical composition comprising a polyribonucleotide wherein the polyribonucleotide encodes a functional version of a protein a defect of which is associated with said ciliopathy, and wherein said pharmaceutical composition is administered to the respiratory system of said subject and is effected when the subject shows an inflammation of the respiratory system. As regards the possible embodiments and preferred embodiments of the pharmaceutical composition and its ways and time of administration, the same applies as has been set forth herein above in connection with the pharmaceutical composition according to the present invention.

The present invention also relates to a pharmaceutical composition comprising a polyribonucleotide encoding a protein a defect of which is associated with a ciliopathy and N-acetylcysteine (NAC), a hypertonic solution comprising sodium chloride, and/or an LF92 and/or LF111 formulation.

As regards the pharmaceutical composition and its components, the same applies as described above in connection with the pharmaceutical composition comprising a polyribonucleotide for use in treating a ciliopathy in a subject suffering of a ciliopathy. Moreover, also the other features of such a pharmaceutical composition can be as described above.

Hence, in a preferred embodiment, the pharmaceutical composition can further comprise an mRNA that can be translated into a functional version of MCIDAS.

The present disclosure also relates to a polyribonucleotide encoding human CCDC40 as shown in any of SEQ ID NO: 1 or 5 to 11.

In some embodiments of any of the foregoing or other aspects and embodiments of the disclosure, the polyribonucleotide or modified polyribonucleotide encodes human CCDC40 (e.g., functional human CCDC40) and comprises a primary sequence that is at least 85%, at least 90%, at least 92%, or at least 95% identical (e.g., at least 95, 96, 97, 98, 99 or 100% identical) to one or more of SEQ ID NO: 1 or 5 to 11 (e.g., to the sequence set forth in SEQ ID NO: 1 or 5 to 11).

In certain embodiments, said polyribonucleotide contains at its 5' end a part of the T7 promoter, Ethris' minimal 5' untranslated region (UTR), a CYBA 5' UTR, a Kozak element followed by a codon optimized sequence encoding a functional version of a human CCDC40 protein, a CYBA 3' UTR, and a poly(A) tail (cf. e.g. SEQ ID NO: 1). In certain embodiments, said polyribonucleotide contains at its 5' end a part of the T7 promoter, Ethris' minimal 5' untranslated region (UTR), a Kozak element followed by a codon optimized sequence encoding a functional version of a human CCDC40 protein, and a poly(A) tail (cf. e.g. SEQ ID NO: 5).

In certain embodiments, said polyribonucleotide contains at its 5' end a part of the T7 promoter, Ethris' minimal 5' untranslated region (UTR), an additional U nucleotide, a TISU element followed by a codon optimized sequence encoding a functional version of a human CCDC40 protein, and a poly(A) tail (cf. e.g. SEQ ID NO: 6).

In certain embodiments, said polyribonucleotide contains at its 5' end a part of the T7 promoter, Ethris' minimal 5' untranslated region (UTR), a hAg 5' UTR, a Kozak element followed by a codon optimized sequence encoding a functional version of a human CCDC40 protein, and a poly(A) tail (cf. e.g. SEQ ID NO: 7).

In certain embodiments, said polyribonucleotide contains at its 5' end a part of the T7 promoter, Ethris' minimal 5' untranslated region (UTR), a human CMV IE9 5' UTR, a Kozak element followed by a codon optimized sequence encoding a functional version of a human CCDC40 protein, a human Growth hormone 3' UTR, and a poly(A) tail (cf. e.g. SEQ ID NO: 8).

In certain embodiments, said polyribonucleotide contains at its 5' end a part of the T7 promoter, Ethris' minimal 5' untranslated region (UTR), a Kozak element, an EGFP encoding sequence, a G4S spacer followed by a codon optimized sequence encoding a functional version of a human CCDC40 protein, and a poly(A) tail (cf. e.g. SEQ ID NO: 9).

In certain embodiments, said polyribonucleotide contains at its 5' end a part of the T7 promoter, Ethris' minimal 5' untranslated region (UTR), a Kozak element followed by a codon optimized sequence encoding a functional version of a human CCDC40 protein, a G4S spacer, an EGFP encoding sequence, and a poly(A) tail (cf. e.g. SEQ ID NO: 10).

In certain embodiments, said polyribonucleotide contains at its 5' end a part of the T7 promoter, Ethris' minimal 5' untranslated region (UTR), a CYBA 5' UTR, a Kozak element followed by a HA tag, a G4S spacer, a codon optimized sequence encoding a functional version of a human CCDC40 protein, a T2A peptide, a sequence encoding tdTomato, a CYBA 3' UTR, and a poly(A) tail (cf. e.g. SEQ ID NO: 11).

In some embodiments, the polyribonucleotide is a modified polyribonucleotide having a level and/or type of modification selected from any such level and/or type set forth herein.

In certain embodiments, the percent identity of a polyribonucleotide is measured only with respect to the CCDC40 coding sequence-portion of SEQ ID NO: 1 or 5 to 11 (e.g., UTRs, other non-coding sequence and GFP or epitope tags are not considered when calculating percent identity, and the polyribonucleotide may or may not contain such regions).

In certain embodiments of any of the foregoing, such polyribonucleotide (or modified polyribonucleotide) encodes a functional CCDC40 protein.

The present disclosure also relates to a polyribonucleotide encoding human CCDC39 as shown in any of SEQ ID NO: 2 or 12 to 14.

In some embodiments of any of the foregoing or other aspects and embodiments of the disclosure, the polyribonucleotide or modified polyribonucleotide encodes human CCDC39 and comprises a primary sequence that is at least 85%, at least 90%, at least 92% or at least 95% identical (e.g., at least 95, 96, 97, 98, 99 or 100% identical) to one or more of SEQ ID NO: 2 or 12 to 14 (e.g., to the sequence set forth in SEQ ID NO: 2 or 12 to 14).

In certain embodiments, said polyribonucleotide contains at its 5' end a part of the T7 promoter, Ethris' minimal 5' UTR, a CYBA 5' UTR, a Kozak element followed by a codon optimized sequence encoding a functional version of a human CCDC39 protein, a CYBA 3' UTR, and a poly(A) tail (cf. e.g. SEQ ID NO: 2).

In certain embodiments, said polyribonucleotide contains at its 5' end a part of the T7 promoter, Ethris' minimal 5' UTR, a Kozak element followed by a codon optimized sequence encoding a functional version of a human CCDC39 protein, and a poly(A) tail (cf. e.g. SEQ ID NO: 12).

In certain embodiments, said polyribonucleotide contains at its 5' end a part of the T7 promoter, Ethris' minimal 5' UTR, an additional U nucleotide, a TISU element followed by a codon optimized sequence encoding a functional version of a human CCDC39 protein, and a poly(A) tail (cf. e.g. SEQ ID NO: 13).

In certain embodiments, said polyribonucleotide contains at its 5' end a part of the T7 promoter, Ethris' minimal 5' UTR, a SP30 as 5' UTR (i.e. a random sequence of 30 nucleotides), a Kozak element followed by a codon optimized sequence encoding a functional version of a human CCDC39 protein, and a poly(A) tail (cf. e.g. SEQ ID NO: 14).

In some embodiments, the polyribonucleotide is a modified polyribonucleotide having a level and/or type of modification selected from any such level and/or type set forth herein.

In certain embodiments, the percent identity of a polyribonucleotide is measured only with respect to the CCDC39 coding sequence-portion of SEQ ID NO: 2 or 12 to 14 (e.g., UTRs, other non-coding sequence and GFP or epitope tags are not considered when calculating percent identity, and the polyribonucleotide may or may not contain such regions).

In certain embodiments of any of the foregoing, such polyribonucleotide (or modified polyribonucleotide) encodes a functional CCDC39 protein.

The present disclosure also relates to a polyribonucleotide encoding human MCIDAS as shown in SEQ ID NO: 4. In some embodiments of any of the foregoing or other aspects and embodiments of the disclosure, the polyribonucleotide or modified polyribonucleotide encodes human MCIDAS and comprises a primary sequence that is at least 85%, at least 90%, at least 92% or at least 95% identical (e.g., at least 95, 96, 97, 98, 99 or 100% identical) to SEQ ID NO: 4 (e.g., to the sequence set forth in SEQ ID NO: 4). In certain embodiments, said polyribonucleotide contains at its 5' end a part of the T7 promoter, Ethris' minimal 5' UTR, a Kozak element followed by a codon optimized sequence encoding a functional version of a human MCIDAS protein, an optional 3' UTR that also functions as reverse primer binding site for PCR based template production as well as a poly(A) tail. In some embodiments, the polyribonucleotide is a modified polyribonucleotide having a level and/or type of modification selected from any such level and/or type set forth herein. In certain embodiments, the percent identity of a polyribonucleotide is measured only with respect to the MCIDAS coding sequence-portion of SEQ ID NO: 4 (e.g., UTRs, other non-coding sequence and GFP or epitope tags are not considered when calculating percent identity, and the polyribonucleotide may or may not contain such regions). In certain embodiments of any of the foregoing, such polyribonucleotide (or modified polyribonucleotide) encodes a functional MCIDAS protein.

For purposes of determining percentage identity of a first sequence relative to a second sequence, an analog (e.g., methylcytidine) matches cytidine, etc. In certain embodiments, the term “primary sequence” may be used to refer to a polynucleotide sequence without regard to whether or the level of modification, such that a primary sequence identical to CUCUCUA would include that sequence regardless of whether any or all of the recited nucleotides are modified (e.g., analogs of any more or more of C, U and A may be present and would be considered the same primary sequence). In certain embodiments, percent identity is only determined by reference to the portion of a given listed sequence corresponding to the coding sequence for, for example, CCDC40 or CCDC39. While in other embodiments, the percent identity is determined by reference to both the coding sequence and one or more non-coding sequences. In certain embodiments, the percent identity is determinated across the entire length of a listed sequence (e.g., by reference to the entire length of a sequence listed in the sequence listing herein).

The present invention furthermore relates to a method for analyzing the effect of a polyribonucleotide on ciliogenesis, wherein said polyribonucleotide encodes a protein involved in and/or required for ciliogenesis, said method comprising the steps of:

(a) obtaining a nose brush of a subject having a ciliopathy, said nose brush comprising undifferentiated basal cells and differentiated ciliated cells,
(b) culturing the cells obtained from step (a) as a submerse cell culture for obtaining undifferentiated basal cells and dedifferentiated ciliated cells,
(c) culturing undifferentiated basal cells and dedifferentiated ciliated cells obtained from step (b) as an air liquid interface cell culture and performing an air lift,
(d) transfecting cells obtained from step (c) with a polyribonucleotide encoding a protein involved in and/or required for ciliogenesis, (e) culturing the transfected cells obtained from step (d) for obtaining differentiated ciliated cells, and (f) determining the effect of said polyribonucleotide on ciliogenesis using a lactate dehydrogenase measurement, a NUCGREEN™ assay, a high speed video microscopy, a ciliary beat frequency measurement, a mucociliary clearance assay, and/or immunofluorescence staining.

For obtaining cells of the respiratory epithelium of a patient, a nose brush is advantageous as it is easy to handle and the procedure fast and painless for the patient. Cells obtained from a nose brush comprise undifferentiated basal cells and differentiated ciliated cells that can be cultured as a submerse cell culture. By culturing the cells as submerse cell culture undifferentiated basal cells and dedifferentiated ciliated cells can be obtained as the submerse conditions induce a dedifferentiation of epithelial cells. The thus obtained dedifferentiated ciliated cells as well as the undifferentiated basal cells of the nose brush are then to be cultured as an air liquid interface (ALI) cell culture.

An air liquid interface cell culture of step (c) refers to a cell culture that is characterized in that the basal surface of the cells is in contact with a liquid culture medium, whereas the apical surface is exposed to air. Cells can be seeded for example onto a permeable membrane of a cell culture insert, which is initially supplied with culture medium to both the apical and basal compartments. This can also be referred to as “submerse cell culture”. Once confluence is reached, the cells are then subjected to an “air-lift” step, where the medium is supplied only to the basal chamber. This mimics the conditions found in, for example, the respiratory system and induces cell differentiation including ciliogenesis in undifferentiated ciliary cells. Thus, cells mimicking the epithelium of the respiratory system including, for example, basal and ciliated cells can be obtained for further investigation in vitro.

The obtained epithelium mimicking cells can then be transfected with a polyribo-nucleotide encoding a protein involved in and/or required for ciliogenesis. Thus, said polyribonucleotide is introduced into the cells which can be done artificially by viral infection or means other than viral infection to express the exogenous polyribonucleotide in the cells. The transfected cells are then cultured for obtaining differentiated ciliated cells from basal and undifferentiated ciliated cells. Thus, the effect of a polyribonucleotide such as an mRNA on ciliogenesis can be determined in vitro while preserving an environment of the cells that mimics the epithelium of the respiratory system as it can be found for example in a subject.

The effect of a polyribonucleotide on ciliogenesis can be determined by various methods known to a person skilled in the art. These methods include for example a lactate dehydrogenase measurement, a NUCGREEN™ assay, a high speed video microscopy, a ciliary beat frequency measurement, a mucociliary clearance assay, and/or immunofluorescence staining. Thus, a lactate dehydrogenase measurement (LDH) can be performed to determine the amount of LDH released in the environment surrounding the cells. The respective assay can be a colorimetric assay, wherein the amount of released LDH is measured with an enzymatic reaction which converts for example iodonitrotetrazolium or a tetrazolium salt into a red color formazan. Thus, the assay can be easily read out by spectroscopy.

Alternatively or additionally, a NUCGREEN™ assay can be performed. NUCGREEN™ is a permanent green fluorescing nucleic acid stain upon binding to nucleic acids and can be used to investigate toxicity-related effects of transfection for example. Alternatively or additionally, immunofluorescence staining of the protein encoded by the transfected polyribonucleotide can be performed to determine its amount and cellular localization including co-localization with other proteins. For determining the amount of the expressed protein, it is also possible to use Western Blot technology.

Furthermore, ciliary structural defects or lack of cilia can be detected for example using specialised microscopy. Screening tests include measurement of nasal nitric oxide production rate, ciliary motility by high speed video microscopy of nasal cells, or in vivo tests including a saccharin test for example. More specific diagnosis requires for example examination of cilia by immunofluorescence and transmission electron microscopy.

Alternatively or additionally, ciliary beat frequency measurement can be applied to investigate beat frequency, number of beating cilia and ciliated cells, and beating synchronicity using high speed video microscopy. The same applies to mucociliary clearance assays that can be performed to determine the rate of mucus clearance which is affected by ciliary function.

As regards the polyribonucleotide to be employed in the described method, the same applies as described above in connection with the pharmaceutical composition of the present invention for use in treating a ciliopathy. Moreover, also the other features of such a polyribonucleotide can be as described above.

Furthermore, the polyribonucleotide might contain a sequence encoding a marker. Examples include tdTomato (as comprised e.g. in SEQ ID NO: 3), green fluorescent protein (GFP), and enhanced GFP (eGFP) as described in the appended examples together with respective detection methods. This is especially advantageous for validating a successful transfection of a cell with the polyribonucleotide.

In some embodiments of the method for analyzing the effect of a polyribonucleotide on ciliogenesis, the cells are transfected within 0 to 12 days, preferably within 0 to 11 days, more preferably within 0 to 6 days, even more preferably 0 to 4 days and most preferably 0 to 48 hours after the air lift is performed in step (c). This is advantageous as the air lift step induces ciliogenesis of basal and undifferentiated ciliary cells.

In some embodiments of the method for analyzing the effect of a polyribonucleotide on ciliogenesis, the cells are transfected with a polyribonucleotide, preferably an mRNA, encoding a protein involved in and/or required for ciliogenesis using a lipidoid having the structure shown in formula (V), (VI), and/or (VII).

In some embodiments of the method for analyzing the effect of a polyribonucleotide on ciliogenesis, the cells are cultured in steps (b) to (e) using Medium G. The composition of Medium G is typically as shown in Table 2).

TABLE 2

| Substance | Volume | Final concentration |
|---|---|---|
| DMEM/Ham's F12 | 100 mL | |
| ULTROSER ™ G | 2 mL | 2% |
| Fetal Clone II | 2 mL | 2% |
| Insulin | 100 μL | 2.5 μg/mL |
| Bovine Brain Extract | 250 μL | 22.5 μg/mL |
| Transferrin | 100 μL | 2.5 μg/mL |
| Hydrocortisone | 20 μL | 20 nM |
| 3,3',5-Triiodo-L-thyronine | 3.33 μL | 500 nM |
| Epinephrine | 10 μL | 1.5 μM |
| Retinoic Acid | 10 μL | 10 nM |

TABLE 2-continued

| Substance | Volume | Final concentration |
|---|---|---|
| Phosphorylethanolamine | 5 μL | 250 nM |
| Ethanolamine | 100 μL | 250 nM |
| DAPT | 10 μL | 1 μM |

In some embodiments of the method for analyzing the effect of a polyribonucleotide on ciliogenesis, the cells are cultured in steps (b) to (e) using one of the media shown in Table 3. The media shown in Table 3 are some commercially available media on the market that can be used to grow ALI culture.

TABLE 3

| Supplier | Growth Phase | Differentiation Phase |
|---|---|---|
| LONZA | ALI-G | ALI-D |
| StemCell | ALI-Ex | ALI-M |
| Epithelix | MUCILAIR ™ | MUCILAIR ™ |
| PELOBiotech | Pelo | Pelo |

In some embodiments of the method for analyzing the effect of a polyribonucleotide on ciliogenesis, the nose brush further comprises fibroblasts and wherein growth of said fibroblasts is inhibited in steps (b) to (e). This is advantageous as fibroblasts grow faster compared to basal and undifferentiated ciliary cells and can thus hamper the investigation of the effect of a polyribonucleotide on ciliogenesis as described above.

Before transferring the cells into the flask of the stationary phase, fibroblasts can be separated from the rest of the cells due to a short incubation time of 1-2 h. During that time, fibroblasts can settle down and adhere to the cell flask. All other cells remain in the media as suspension cells and can be easily transferred afterwards to the "stationary phase flask".

The method according to the present invention preferably results in the identification of a polyribonucleotide that has a positive effect on ciliogenesis and that can be used to restore ciliary cell structure in function and thus, in a pharmaceutical composition according to the second aspect and its use in treating a ciliopathy in a subject suffering of a ciliopathy according to the first aspect of the invention. Thus, as regards features of the polyribonucleotide, the same applies as described above in connection with the pharmaceutical composition of the present invention for the use in treating a ciliopathy. Moreover, also the other features of such a polyribonucleotide can be as described above.

FIG. 1: Translation efficiency of CCDC40 mRNA. 2/1.4/0.3/0.2/0.05×10^6 HEK293 cells were seeded in 6-well plates. 24 h after seeding cells were transfected with different CCDC40 constructs (ETH031T06-T10, 2.5 μg/9.5 $cm^2$) using LIPOFECTAMINE™ 2000. Cells lysis was performed 6, 24, 48, 72 and 144 h after transfection. 50 μg of total protein lysate were analyzed with SDS-PAGE and Western Blot. CCDC40 was detected using Anti-CCDC40 Antibody (HPA022974) from Atlas Antibodies (1:2000). GAPDH served as a loading control. GFP served as a transfection control.

FIG. 2: Translation efficiency of CCDC40 mRNA constructs in BEAS-2B, RPMI2650, and HEK293 cells: 2×10^6 HEK293, 7.5×10^5 BEAS-2B and 5×10^5 RPMI 2650 cells were seeded in 6-well plates. 24 h after seeding cells were transfected with different CCDC40 constructs (2.5 μg/9.5 $cm^2$) using LIPOFECTAMINE™2000. Cells lysis was performed 6 h after transfection. Protein lysates were analyzed with SDS-PAGE and Western Blot (HEK293: 50 μg, RPMI 2650:20 μg, BEAS-2B: 30 μg of total lysate). CCDC40 was detected using Anti-CCDC40 Antibody (HPA022974) from Atlas Antibodies (1:2000).

FIG. 3: High speed video microscopy (HSVM) results after LF92/CCDC40 transfection. Patient derived ALI cultures were transfected every other day with 3 μg LF92/CCDC40. Prior transfection and every 24 h after transfection, videos (20 per insert) were taken and CFB (ciliary beat frequency) was calculated using the SAVA (Sisson-Ammons video analysis) Software. Allover 16 transfections (1 month) were performed. Measurement was done at 37° C. using the 40× magnification. Calculated are the mean values of the ciliary beat frequency measurements (Whole Field Analysis, WFA).

Figure 4:
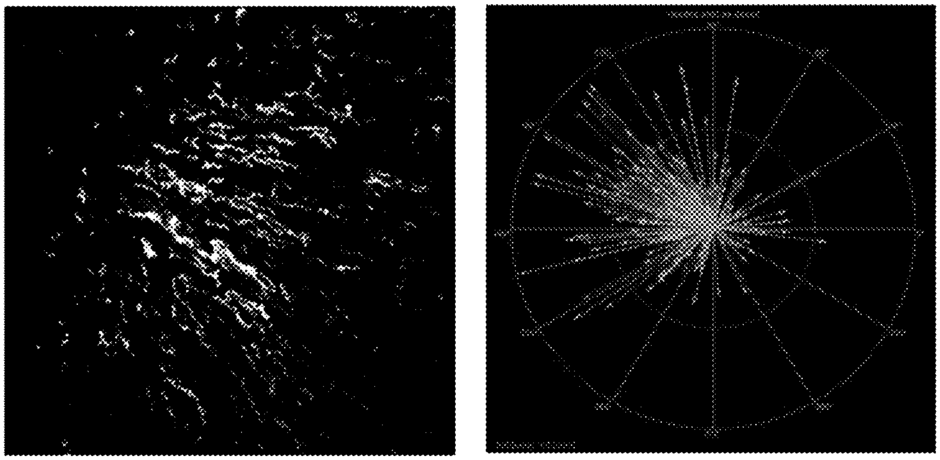

FIG. 4: Mucociliary clearance (MCC) shown as Z-Projection and Polargraph. CCDC40 patient ALI culture was transfected with CCDC40 mRNA/LF92 at a concentration of 3 μg/insert, 18 d upon air-lift. ALI cultures were maintained in Medium G during the experiment. Transfections (TFs) were performed once a week for 4 weeks (=4×TF). Mucociliary Clearance (MCC) was measured using 0.5 μm fluorescent beads at 20× magnification. 30 s videos of different areas were taken and analyzed with the Polargraph software from NIKON®one week after the last TF. One exemplary picture is shown.

Figure 5:
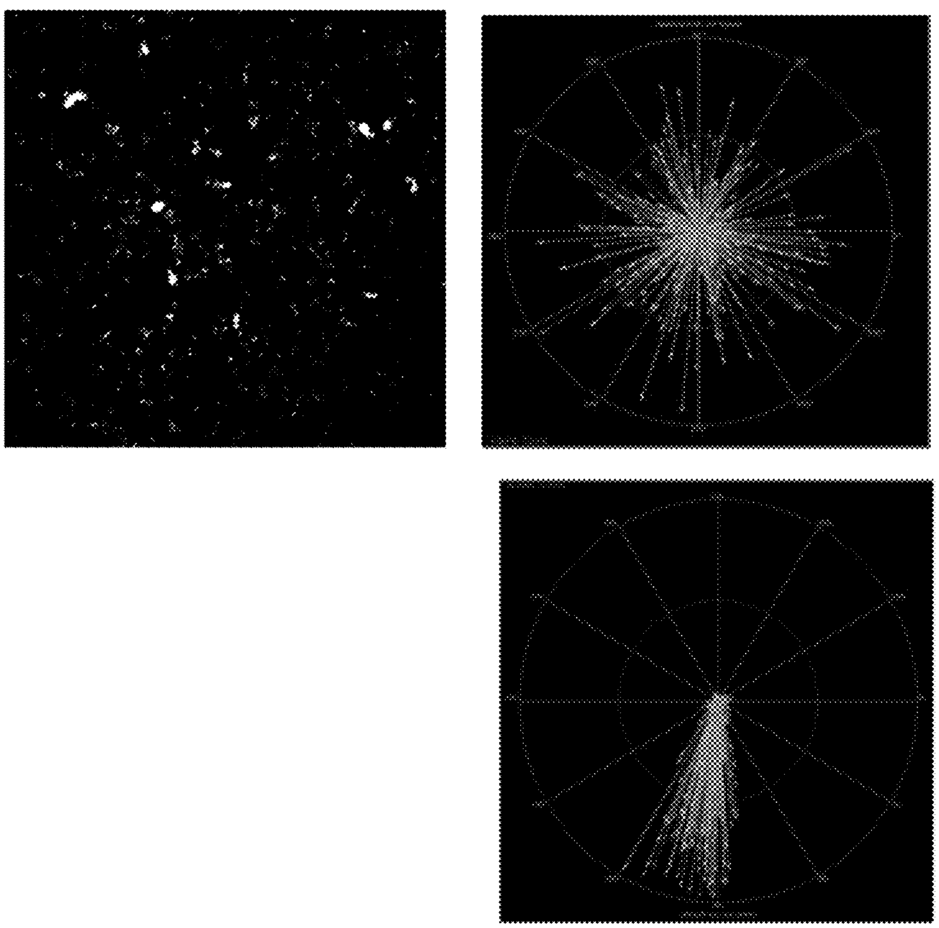

FIG. 5: Mucociliary clearance (MCC) shown as Z-Projection (upper left) and Polargraph (upper right) for a tdTomato and Polargraph of a healthy (lower right) control. Upper row: Cells from patient with CCDC40 mutation in ALI culture were transfected with tdTomato mRNA/LF111 at a concentration of 3 μg/insert, 18 d upon air-lift. ALI cultures were maintained in Medium G during the experiment. Transfections (TFs) were performed once a week for 4 weeks (=4×TF). Mucociliary Clearance (MCC) was measured using 0.5 μm fluorescent beads at 30× magnification. 20 s videos of different areas were taken and analyzed with the Polargraph software from NIKON®one week after the last TF. One exemplary video was shown. Lower right: Particle tracking of healthy WT ALI culture. MCC was measured using 0.5 μm fluorescent beads at 20× magnification. 20 s videos of different areas were taken and analyzed with the Polargraph software from NIKON®one week after the last TF. One exemplary picture and two analyzed ROIs are shown.

Figure 6:
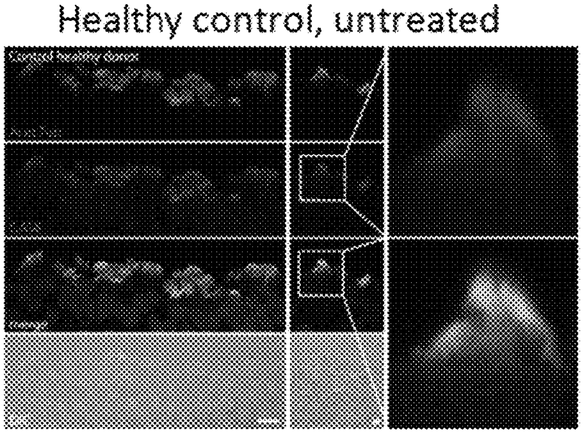
Figure 6:
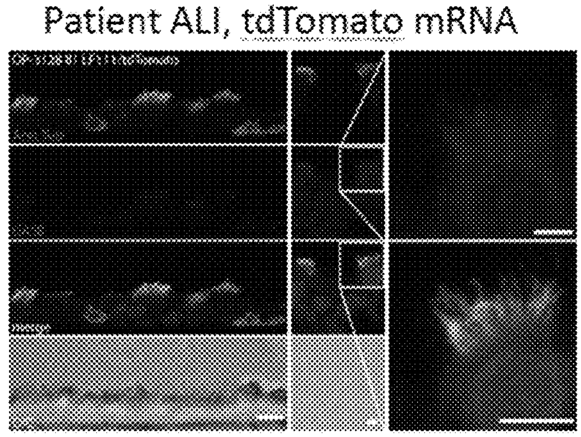
Figure 6:
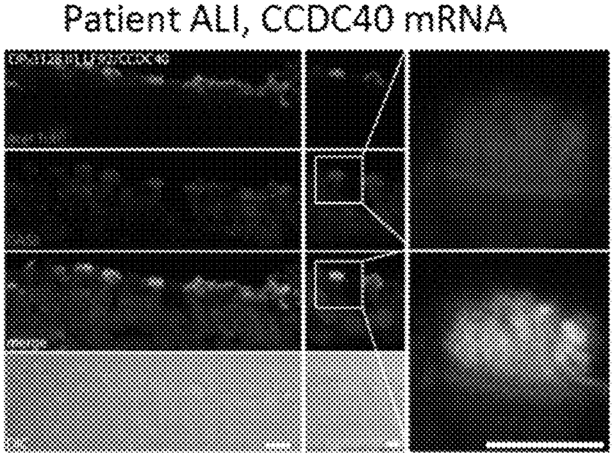

FIG. 6: Cells from patient with CCDC40 mutation in ALI culture were transfected either with tdTomato mRNA/LF111 or with CCDC40 mRNA/LF92 at a dose of 3 μg/insert, 18 d upon air-lift. ALI cultures were maintained in Medium G during the experiment. Transfections (TFs) were performed once a week for 4 weeks (=4×TF). As a control, WT ALI from healthy nose brushes were used. Samples for cryo-embedding were prepared one week after the last TF. CCDC40 mRNA and tdTomato mRNA treated ALI membranes were cut at 20 μm and stained with anti-GAS8, anti-acetylated Tubulin and DAPI. Pictures were taken with the confocal microscope. One exemplary image is shown. Scale bar represents 10 μm.

Figure 7:
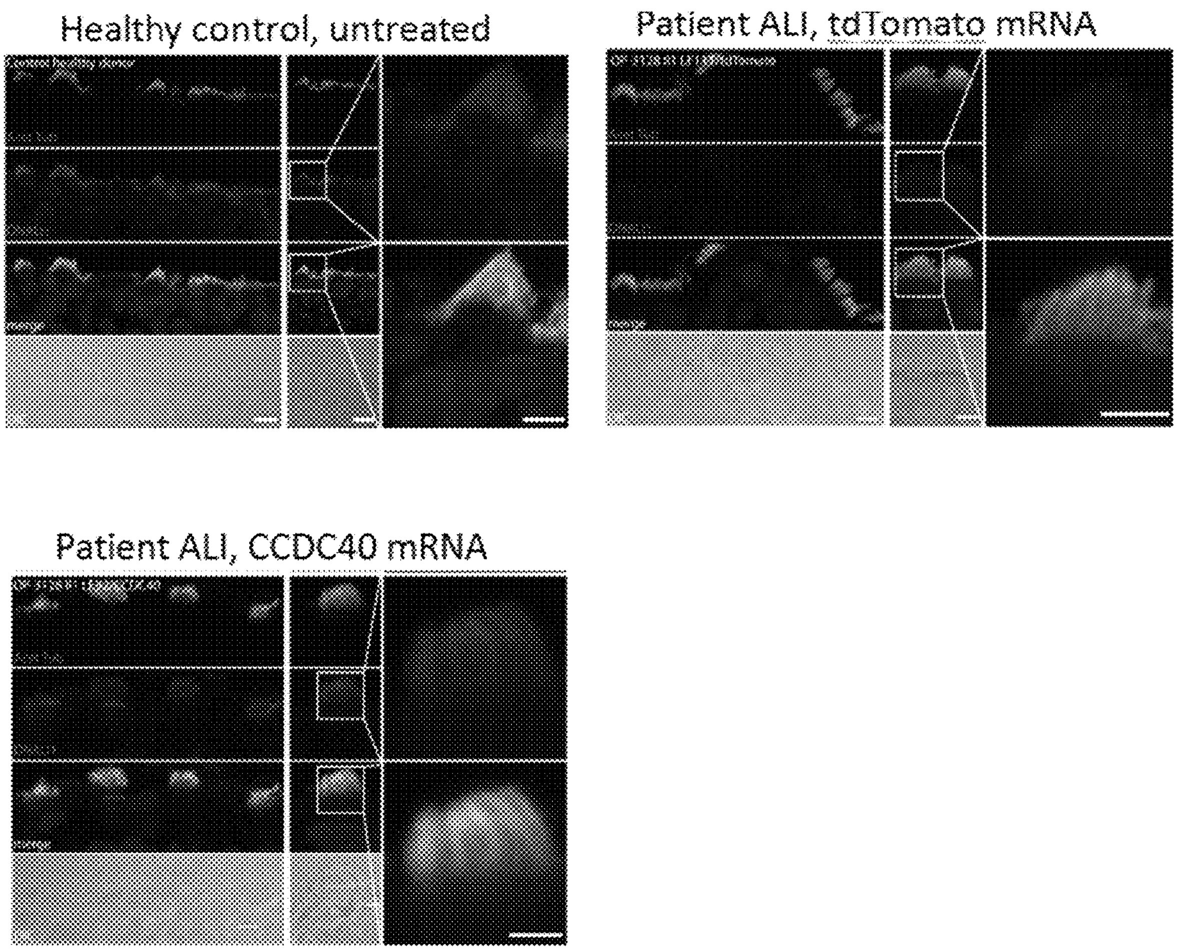

FIG. 7: Cells from patient with CCDC40 mutation in ALI culture were transfected either with tdTomato mRNA/LF111 or with CCDC40 mRNA/LF92 at a dose of 3 μg/insert, 18 d upon air-lift. ALI cultures were maintained in Medium G during the experiment. Transfections (TFs) were performed once a week for 4 weeks (=4×TF). As a control, ALI from healthy controls were used. Samples for cryo-embedding were prepared one week after the last TF. CCDC40 mRNA and tdTomato mRNA treated ALI membranes were cut at 20 μm and stained with anti-DNALI1, anti-acetylated Tubulin and DAPI. Pictures were taken with the confocal microscope. One exemplary image is shown. Scale bar represents 10 μm.

Figure 8:
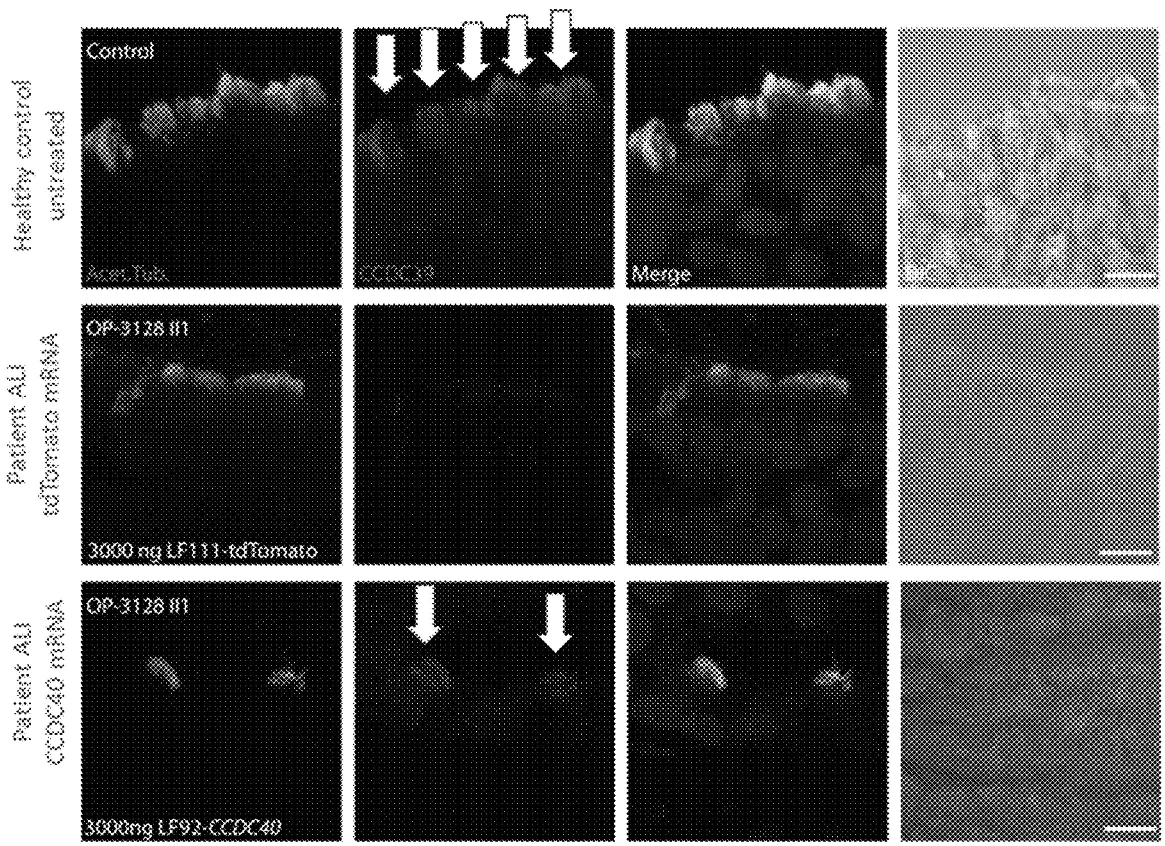

FIG. 8: Cells from patient with CCDC40 mutation in ALI culture were transfected either with tdTomato mRNA/LF111 or with CCDC40 mRNA/LF92 at a dose of 3 μg/insert, 18 d upon air-lift. ALI cultures were maintained in Medium G during the experiment. Transfections (TFs) were performed once a week for 4 weeks (=4×TF). As a control, ALI from healthy controls were used. Samples for cryo-embedding were prepared one week after the last TF. CCDC40 mRNA and tdTomato mRNA treated ALI membranes were cut at 20 μm and stained with anti-CCDC39 (1:200), anti-acetylated Tubulin (1:10.000) and DAPI. Pictures were taken with the confocal microscope. One exemplary image is shown. Magnification 40×.

Figure 9:
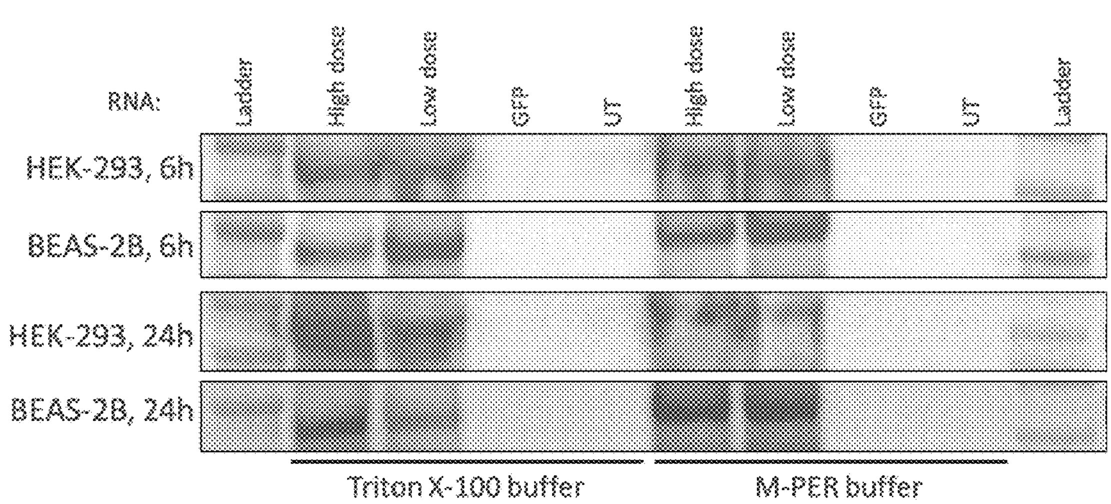
Figure 10:
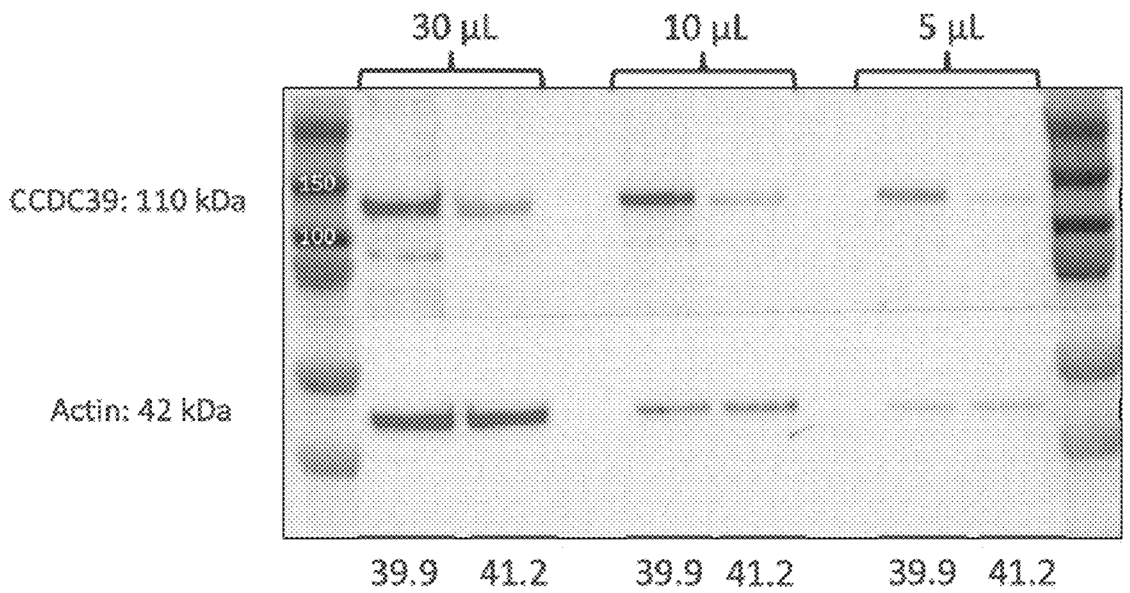

FIG. 9: CCDC39 protein (110 kDa) expression in HEK-293 & BEAS-2B, 6 h & 24 h after transfection. 1.4×10ˆ5 HEK-293 cells and 3.5×10ˆ5 BEAS-2B cells were seeded in 6-well plates and transfected with CCDC39-RNA (ETH047T02, minimal 5'UTR, LIPOFECTAMINE™ MESSENGERMAX™; Ratio 1:1.5). After 6 h and 24 h cells were lysed with M-PER and with TRITON® X-100 buffer. 50 μg of protein lysate were used for Western blot analysis. As a control, lysate of untransfected (UT) and EGFP transfected cells were used. High dose=0.5 μg/cm$^2$, low dose=0.25 μg/cm$^2$.

FIG. 10:

CCDC39 protein (110 kDa) expression in untreated ALI cultures. Two inserts were extracted using the axonemal extraction protocol. 30, 10 and 5 μL of protein lysate were used for Western blot analysis. Active Area: Insert 39.9=71.25%, Insert 41.2=59.88%

FIG. 11:

CCDC39 protein (110 kDa) expression in 16HBE14o- after treatment with proteasome inhibitor. 6.0×10ˆ5 16HBE14o- cells were seeded in 6-well plates and transfected with CCDC39-RNA (LIPOFECTAMINE™ MESSENGERMAX™ Ratio 1:1.5). After 6 h cells were lysed with M-PER buffer. 20 μg of protein lysate were used for Western blot analysis. As a control, lysate of untransfected (UT) and EGFP transfected cells were used. High dose=0.5 μg/cm$^2$, low dose=0.25 μg/cm$^2$. RNA: ETH047T02: minimal 5'UTR, ETH047T03: TISU, ETH047T04: CYBA, ETH047T05: SP30.

Figure 12:
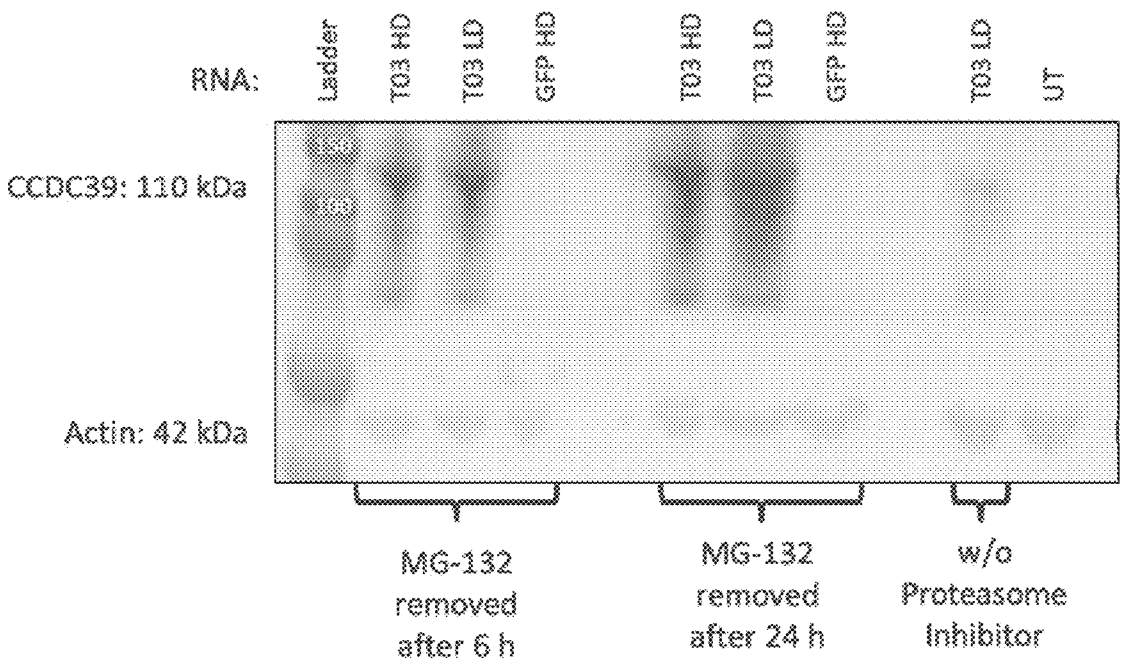

FIG. 12: CCDC39 protein (110 kDa) expression in 16HBE14o- after treatment with proteasome inhibitor. 6.0×10ˆ5 16HBE14o- cells were seeded in 6-well plates and transfected with CCDC39-RNA (ETH047T03, TISU 5'UTR, LIPOFECTAMINE™ MESSENGERMAX™; Ratio 1:1.5). After 24 h cells were lysed with M-PER buffer. 20 μg of protein lysate were used for Western blot analysis. As a control, lysate of untransfected (UT) and EGFP transfected cells were used. High dose=0.5 g/cm$^2$, low dose=0.25 μg/cm$^2$.

Other aspects and advantages of the invention will be described in the following examples, which are given for purposes of illustration and not by way of limitation. Each publication, patent, patent application or other document cited in this application is hereby incorporated by reference in its entirety.

EXAMPLES

Methods and materials are described herein for use in the present disclosure; other, suitable methods and materials known in the art can also be used. The materials, methods, and examples are illustrative only and not intended to be limiting.

I. Material and Methods

Materials, Devices, Software, and Test System Used

Materials are listed in Table 4.

TABLE 4

| Substance/Consumable/Chemical | Supplier | Cat # |
|---|---|---|
| DPBS (w/o Mg2+/Ca2+) | Thermo Fisher Scientific | 14190-169 |
| LHC-9 medium | Thermo Fisher Scientific | 12677019 |
| DMEM (1×) - GLUTAMAX ™ Supplement | Thermo Fisher Scientific | 21885 |
| BEAS-2B | ATCC | CRL 9609 |
| HEK 293 | DSMZ | ACC305 |
| Trypsin inhibitor | Thermo Fisher Scientific | R007100 |
| RPMI 2650 | DSMZ | ACC207) |
| Fibronectin | Merck Millipore | FC010 |
| Collagen | Corning Incorporated | 354236 |
| PIERCE ™ Bovine Serum Albumin | Thermo Fisher Scientific | 23209 |
| DPBS (with Mg2+/Ca2+), for air-brush | Thermo Fisher Scientific | 14040133 |
| LIPOFECTAMINE ™ 2000 | Thermo Fisher Scientific | 11668027 |
| CORNING ® Cell Scrapers | Corning Incorporated | CORN3010 |
| Protease inhibitor COMPLETE ™ | Sigma Aldrich | 11873580001 |
| PIERCE ™ BCA Protein Assay Kit | Thermo Fisher Scientific | 23225 |
| BOLT ™ LDS Sample Buffer (4x) | Thermo Fisher Scientific | B0007 |
| BOLT ™ Sample Reducing Agent (10x) | Thermo Fisher Scientific | B0009 |
| PRECISION PLUS PROTEIN ™ Dual Color Standards | BIO-RAD | 161-0374 |
| TRANS-BLOT ® TURBO ™ Transfer Pack Mini 0.2 μm PVDF | BIO-RAD | 1704156 |
| LUMINATA ™ Crescendo Western HRP Substrate | Merck Millipore | WBLUR0500 |
| GAPDH (D16H11)XP ® Rabbit mAb | Cell Signaling | 5174 |
| Anti-CCDC40 antibody | Sigma Aldrich | HPA022974 |
| Goat anti-rabbit IgG-HRP | Santa Cruz | sc-2004 |
| CELLETTA ™ brush cell collector | Engelbrecht Medizin-und Labortechnik | 9100060 |

TABLE 4-continued

| Substance/Consumable/Chemical | Supplier | Cat # |
|---|---|---|
| ULTROSER ™ G | Pall Life Sciences | 15950 |
| Gelatine | Caelo | 01704140 |
| NaCl | Carl Roth | 0601.1 |
| TRIS | Carl Roth | AE15.3 |
| TRIS/HCl | Carl Roth | A9090.3 |
| EDTA | Carl Roth | X986.1 |
| NaOH (32%) | Carl Roth | T196.1 |
| FBS (submerse culture) | Thermo Fisher Scientific | 10500-064 |
| Penicillin-Streptomycin | Thermo Fisher Scientific | 15140-122 |
| Collagen I, rat tail | Gibco | A1048301 |
| Acetic acid 100% | Carl Roth | 3738.1 |
| CORNING ® Transwell | Costar | 3470 |
| Trypsin/EDTA 1× | Sigma Aldrich | 13924 |
| Collagenase type 4 | Worthington Biochemical Company | LS004188 |
| Antibiotics/Antimycotics 100× | Thermo Scientific | 15240 |
| PNEUMACULT ™ ALI medium | STEMCELL Technologies | 5001 |
| Sucrose (CAS# 57-50-1) | Sigma Aldrich | S1888 |
| Lactate Dehydrogenase Cytotoxicity Assay Kit | Pierce Biotechnology | 88954 |
| NUCGREEN ™ Dead 488 READYPROBES ® Reagent | Life Technologies | R37109 |
| NaCl 0.9% MINI-PLASCO ® connect (Isotonic Saline Solution) | BBraun | 9511711 |
| FBS (ALI culture) | Thermo Fisher Scientific | A3160801 |
| Shandon CRYOMATRIX ™ Frozen Embedding Medium | Thermo Fisher Scientific | 6769006 |
| SUPERFROST ULTRA PLUSSLIDES ® | Thermo Fisher Scientific | J1800AMNZ |
| Paraformaldehyde | Sigma Aldrich | P6148 |
| Goat serum | Abcam | Ab7481 |
| BSA IgG free protease free | Jackson Immunoresearch | 001-000-161 |
| Skim milk (Blotting grade) | Carl Roth | T145.2 |
| Hoechst33342 | Thermo Fisher Scientific | H3570 |
| monoclonal anti-acetylated alpha-tubulin antibody | Sigma Aldrich | T6793 |
| polyclonal anti-CCDC40 antibody | Proteintech | 25049-1-AP |
| polyclonal anti-CCDC39 antibody | Atlas antibodies | HPA035364 |
| ALEXA FLUOR ™ 546 antibody | Thermo Fisher Scientific | A11035 |
| ALEXA FLUOR ™ 488 antibody | Thermo Fisher Scientific | A11029 |
| Insulin | Sigma Aldrich | I9278 |
| Bovine Brain Extract | Lonza | CC-4098 |
| Transferrin | Sigma Aldrich | T8158 |
| Hydrocortisone | Sigma Aldrich | H4001 |
| 3,3',5-Triiodo-L-thyronine sodium sal | Sigma Aldrich | T6397 |
| Epinephrine | Sigma Aldrich | E4642 |
| Retinoic Acid | Sigma Aldrich | R2625 |
| Phosphorylethanolamine | Sigma Aldrich | P0503 |
| Ethanolamine | Sigma Aldrich | E0135 |
| DAPT | Tocris | 2634 |
| PBS(w/o Mg2+/Ca2+) | Thermo Fisher Scientific | 14190-94 |
| 10x PBS (with Mg2+/Ca2+) | Thermo Fisher Scientific | AM9625 |
| TRITON ® X 100 (ALI culture) | Sigma Aldrich | T8787 |
| TRITON ® X-100 (submerse culture) | Sigma Aldrich | T9284 |
| DMEM/Ham's F-12 1:1 | Invitrogen | 11039 |
| ULTROSER ™ G | Pall Life Sciences | 15950-017 |
| Circular plasmid | Ethris | |
| BstBI | New England BioLabs | |
| Chloroform | Sigma Aldrich | 288306 |
| Ethanol | Sigma Aldrich | 34852-M |
| ARCA cap analogue | Jena Biosciences | |
| Cytidine-5'-triphosphate | Jena Biosciences | |
| 5-Iodocytidine-5'-triphosphate | Jena Biosciences | |
| Uridine-5'-triphosphate | Jena Biosciences | |
| 5-Iodouridine-5'-triphosphate | Jena Biosciences | |
| Cytidine-5'-triphosphate | Jena Biosciences | |
| 5-Iodocytidine-5'-triphosphate | Jena Biosciences | |
| Uridine-5'-triphosphate | Jena Biosciences | |
| 5-Methyl-uridine-5'-triphosphate | Jena Biosciences | |
| DNaseI | Thermo Fisher Scientific | |
| Ammonium acetate | Sigma | |
| Quick dephosphorylation Kit | New England BioLabs | |
| Poly(A) polymerase | New England BioLabs | |
| β-Mercaptoethanol | Sigma-Aldrich | M3148 |
| 6-Well Plate | Omnilab | CORN3506 |
| BCA Protein Assay Kit | Thermo Fisher Scientific | 23225 |
| BOLT ™ Antioxidant | Thermo Fisher Scientific | BT0005 |

TABLE 4-continued

| Substance/Consumable/Chemical | Supplier | Cat # |
|---|---|---|
| BOLT ™ 4-12% SDS-PAGE gel | Thermo Fisher Scientific | NW04120BOX |
| BOLT ™ MES SDS Running buffer (20×) | Thermo Fisher Scientific | B0002 |
| COMPLETE ™, EDTA-free Protease Inhibitor Cocktail | Sigma-Aldrich | 11873580001 |
| DNase I Solution (2500 U/mL) | Thermo Fisher Scientific | 90083 |
| DPBS | Life Technologies | 14040133 |
| DTT | Sigma Aldrich | 646563 |
| EDTA | Carl Roth | 8040.3 |
| Heat inactivated FBS | Thermo Fisher Scientific | 10500064 |
| HEPES | Carl Roth | HN78.2 |
| LHC-9 Medium | Thermo Fisher Scientific | 12680013 |
| LUMINATA ™ Classico Western HRP substrate | Merck Millipore | WBLUC0500 |
| MEM GLUTAMAX ™ | Thermo Fisher Scientific | 41090028 |
| M-PER ™ buffer | Thermo Fisher Scientific | 78501 |
| MgSO4 | Carl Roth | T888.1 |
| Pen/Strep | Thermo Fisher Scientific | 15140122 |
| SDS 10% | Thermo Fisher Scientific | 24730020 |
| Sodium deoxycholate | Sigma-Aldrich | D6750-10G |
| SUPERSIGNAL ™ West Festo | Thermo Fisher Scientific | 34095 |
| T175 Flasks | Corning/Omnilab | CORN431080 |
| T75 Flasks | Corning/Omnilab | CORN430641 |
| TRANS-BLOT ® TURBO ™ Mini PVDF Transfer Packs | Bio-Rad | 1704156 |
| TRITON ® X-100 | Sigma-Aldrich | T9284-100ML |
| TRYPSIN-EDTA (0.05%) | Thermo Fisher Scientific | 25300054 |
| LIPOFECTAMINE ™ MESSENGERMAX ™ Transfection Reagent | Thermo Fisher Scientific | LMRNA003 |
| Aqua bidest. | Kerndl | 22501 |
| ALI membranes | Sigma-Aldrich | CLS3470 |
| LUMINATIA ™ Forte Western HRP substrate | Merck Millipore | WBLUF0500 |
| MMRB (cf. Table 18) | | |
| Liquid nitrogen | | |
| WFI | B Braun | 3703444 |
| T7 RNA Polymerase | Thermo Fisher Scientific | |
| Inorganic Pyrophosphatase | Thermo Fisher Scientific | |
| RNAse Inhibitor | Thermo Fisher Scientific | |
| HCL | Roth | 4625.2 |
| T175 Flasks (CORN431080) | Corning/Omnilab | |
| T75 Flasks (CORN430641) | Corning/Omnilab | |

Devices are listed in Table 5.

TABLE 5

| Device | Supplier |
|---|---|
| TECAN INFINITE ® 200 PRO plate reader | Tecan |
| THERMOMIXER ® C | Eppendorf |
| PowerPAC ™ 300 | BIO-RAD |
| TRANS-BLOT ® TURBO ™ Transfer System | BIO-RAD |
| CHEMIDOC ™ XRS System | BIO-RAD |
| TriStar2 Multimode Reader LB 942 | Berthold Technologies, Bad Wildbad, Germany |
| High-speed video microscopy | Ammons Engineering, Mt Morris, MI, USA |
| NIKON ® Eclipse Ti-S | NIKON ®MEA53300 |
| ELWD 40x S Plan Fluor o | NIKON ®, MEA48430 |
| Minitube SC300 heating system | Minitube International AG |
| Superfrost Ultra Plus slides | Thermo Fisher Scientific |
| 100 MWCO cut of filter | Sartorius |
| Cryostat Microm HM560 | Microm |
| CHEMIDOC ™ | Bio-Rad |
| COUNTESS ™ Cell Counting Device (C10281) | Thermo Fisher Scientific |
| Fluorescence microscope (DMi8) | Leica |
| Mini Gel Tank | Thermo Fisher Scientific |
| TRANS-BLOT ® TURBO ™ Transfer System | Bio-Rad |
| Lysing Matrix A Tubes | MP Biomedicals |

TABLE 5-continued

| Device | Supplier |
|---|---|
| MP FASTPREP-24 ™ (HOM-1) | MP Biomedicals |
| 96-well black microplates (655090) | Greiner |

Software is listed in Table 6.

TABLE 6

| Software | Provider |
|---|---|
| MAGELLAN ™ - Data Analysis Software | Tecan |
| IMAGE LAB ™ | BIO-RAD |
| Sisson-Ammons Video Analysis (SAVA software) | Ammons Engineering, Mt Morris, MI, USA |
| Megaplus camera model ES 310 turbo | Redlake Inc., USA |
| NIS-Elements Basic Research | NIKON ® |
| NIKON ® NIS Elemets AR Software | NIKON ® |

The test system is listed in Table 7.

TABLE 7

| Test System | Species | Strain |
|---|---|---|
| HEK 293 | human primary embryonal kidney | DSMZ no.: ACC305 |
| RPMI 2650 | anaplastic squamous cell carcinoma | DSMZ no.: ACC207 |

TABLE 7-continued

| Test System | Species | Strain |
|---|---|---|
| BEAS-2B | bronchial epithelium | ATCC no.: CRL 9609 |

1. Submerse Cell Culture

1. Culturing

Cell lines were cultivated in a cell incubator under humidified atmosphere at 37° C. and 5% $CO_2$ content. All reagents and solutions were heated to 37° C. in a water bath before usage.

Confluent cells (about 90%) were first washed with 20 mL DPBS (w/o $Mg^{2+}/Ca^{2+}$) to remove dead cells. To detach the cells 2 mL of Trypsin/EDTA solution (0.05%) was added per flask. Cells were then incubated at 37° C. until detachment of cells occurs. 8 mL of the respective medium was used to stop the Trypsin. Because LHC-9 medium was almost serum-free at least an equal volume of Trypsin inhibitor was added to the detached BEAS-2B cells to inactivate trypsinisation. The cell solution had to be centrifuged afterwards for 5 minutes (min) at 1100 revolutions per minute (rpm) to remove the trypsin inhibitor again. The pellet was then resolved in medium. For passaging, the cells were split in different ratios according to the next use.

HEK 293 (DSMZ No.: ACC305)

This established cell line was from a human primary embryonal kidney transformed by adenovirus type 5 (AD 5). It was cultured in Dulbecco's Modified Eagle Medium (DMEM)-GLUTAMAX™ Supplement with 10% heat inactivated (h.i.) fetal calf serum (FBS) and 1% penicillin/streptomycin (P/S). This cell line was split two times a week.

RPMI 2650 (DSMZ No.: ACC207)

This cell line had its origin from the pleural effusion of a 52-year-old man with anaplastic squamous cell carcinoma of the nasal septum. It was chosen because of the epitheloid ciliated morphology and the similarity to the bronchiolar epithelium. It was also cultured in Dulbecco's Modified Eagle Medium (DMEM)-GLUTAMAX™Supplement with 10% heat inactivated (h.i.) fetal calf serum (FBS)+1% penicillin/streptomycin (P/S)+1× Non-essential-amino-acid solution (NEAA). This cell line was split 1-2 times a week.

BEAS-2B (ATCC No.: CRL 9609)

BEAS-2B cells were derived from normal bronchial epithelium obtained from autopsy of non-cancerous individuals. Cells were then infected with a replication-defective SV40/adenovirus 12 hybrid and cloned. The used culture medium was LHC-9 with modification w/o additives. They were also split 1-2 times a week depending on the confluence.

The flasks used for BEAS-2B cells were coated with a mixture of 0.01 mg/ml fibronectin, 0.03 mg/mL collagen and 0.01 mg/mL bovine serum albumin dissolved in LHC-9. The mixture was added at a ratio of 0.2 mL per $cm^2$ surface area. Afterwards, incubation at 37° C. for at least 6 h was necessary. Prior to the addition of cells, the flasks were washed three times with Dulbecco's phosphate-buffered saline (DPBS) without $Mg^{2+}/Ca^{2+}$.

2. In Vitro Transcription

To generate templates for in vitro transcription, circular plasmids were linearized by restriction digestion with BstBI and further purified by chloroform ethanol precipitation.

mRNA was produced using a standard in vitro transcription mix (including indicated modified triphosphate nucleotides) containing T7 RNA polymerase, inorganic pyrophosphatase, and RNase inhibitor. Co-transcriptional capping was achieved by addition of an ARCA cap analogue. For in vitro transcription of chemically modified RNA, 7.5% of Cytidine-5'-Triphosphate were replaced by 5-Iodocytidine-5'-Triphosphate and 30% Uridine-5'-Triphosphate were replaced by 5-Iodouridine-5'-Triphosphate (Jena Biosciences), respectively (cf. e.g SEQ ID NO: 1). In another chemically modified RNA production setup 3% of Cytidine-5'-Triphosphate were replaced by 5-Iodocytidine-5'-Triphosphate and 15% Uridine-5'-Triphosphate were replaced by 5-Methyl-Uridine-5'-Triphosphate (Jena Biosciences), respectively (cf. e.g SEQ ID NO: 2). Residual template DNA was digested using DNaseI. Subsequently mRNA was purified by ammonium acetate precipitation followed by a washing step using 70% ethanol.

Dephosphorylation of residual uncapped mRNA was carried out using a Quick dephosphorylation Kit followed by purification via ammonium acetate precipitation followed by a washing step using 70% ethanol and ultrafiltration using a 100 MWCO cut of filter.

mRNA was further polyadenylated by using a poly(A) polymerase. Again mRNA was purified by ammonium acetate precipitation followed by a washing step using 70% ethanol and ultrafiltration using a 100 MWCO cut of filter. Poly(A) length was determined by capillary gel electrophoresis to be between 100 and 250 nucleotides.

In particular, the CCDC40 mRNA constructs investigated in this experiment comprised an 5' ARCA cap and PPA and were the following: with Ethris' minimal UTR (ETH031T06; T06; SEQ ID NO: 5), with TISU 5' UTR but without 3' UTR (ETH031T07; T07; SEQ ID NO: 6), with hAg 5' UTR but without 3' UTR (ETH031T08; T08; SEQ ID NO: 7), with CYBA 5' and 3' UTR (ETH031T0; T09; SEQ ID NO: 1), and with 5' UTR from human CMV IE9 and 3' UTR from human Growth hormone (ETH031T0; T10; SEQ ID NO: 8).

3. Transfection

To provide at least 90% confluency, cells were seeded in 6-well plates 24 h before transfection. Cell counts differed according to the time point of read-out and cell type (compare Table 8).

TABLE 8

| | cells/well × $10^6$ | | |
|---|---|---|---|
| Time | HEK 293 | RPMI 2650 | BEAS-2B |
| 6 h | 2 | 0.6 | 0.75 |
| 24 h | 1.4 | 0.4 | 0.5 |
| 48 h | 1 | 0.3 | — |
| 72 h | 0.75 | 0.2 | — |
| 144 h | 0.125 | 0.05 | — |

Transfection was performed using different CCDC40 mRNA constructs as well as mRNA encoding for enhanced green fluorescent protein (eGFP) as a transfection control. Transfection was performed using LIPOFECTAMINE™2000 Prior to the transfection culture medium was exchanged to provide optimal conditions for the cells. The lipoplex reaction required an mRNA/WFI mix as well as a LIPOFECTAMINE™2000/medium mix. 125 μL of each mix was used with volume ratio of 1:2 from mRNA to LIPOFECTAMINE™2000 as the mRNAs showed a stock concentration of 1 μg/μl. Different mRNA concentrations were used and the mix was adjusted accordingly (see Table 9 for an exemplary pipetting scheme).

TABLE 9

| μg RNA/well | RNA in μL | +WFI in μL | LIPOFECTAMINE ™ 2000 in μL | +serumfree medium in μL |
|---|---|---|---|---|
| 5 | 5 | 120 | 10 | 115 |
| 2.5 | 2.5 | 122.5 | 5 | 120 |
| 1 | 1 | 124 | 2 | 123 |

After preparing both mixes the mRNA/WFI Mix was added to the LIPOFECTAMINE™ 2000/Medium Mix and the solution incubated for ≥5 min before adding it dropwise to the seeded cells. To obtain a better viability of the cells, an additional medium change was performed 4 h after transfection.

4. CCDC40 Western Blot a. Sampling for Western Blot

For cell lysis the culture medium from transfection was removed and the cells were washed with DPBS (without $Mg^{2+}/Ca^{2+}$) and then scraped off using CORNING®Cell Scrapers. The cells were lysed with 100 μL of a Lysis-Buffer solution [10×TRITON® X-100 lysis buffer (250 mM Tris-HCl, 1% TRITON® X-100, pH: 7.8) was adjusted to 1× in WFI and complemented with protease inhibitorCOMPLETE™] before samples were frozen at −20° C.

Total protein concentration was determined using PIERCE™BCA Protein Assay Kit (BCA assay). The assay was performed according to the manufacturers' protocol. Briefly, a 1:50 BCA Working Reagent (WR) dilution was prepared. 5 μL of each sample were transferred to a 96-well plate (flat bottom, transparent) and 200 μL WR were added per well. The last step was an incubation at 37° C. for 30 min. Results were measured on a Tecan INFINITE®200 PRO plate reader using MAGELLAN™-Data Analysis Software.

b. Preparation of NET-Gelatine

TABLE 10

| Substance | Final concentration |
|---|---|
| TRIS/HCl, pH 7.5 | 0.2M |
| EDTA, pH 8.0 | 0.05M |
| TRITON ® X-100 | 0.5% (v/v) |
| NaCl | 1.16M |
| Gelatine | 25 g/L |

c. SDS-PAGE and Western Blot

To perform sodium dodecyl sulfate-polyacrylamide gel electrophoresis (SDS-PAGE) the lysates were mixed with 5 μL Bolt LDS Sample Buffer (4×) and 2 μL Bolt Sample Reducing Agent (10×) and then heated to 70° C. for 10 min and 350 rpm in the THERMOMIXER®C. To enable comparison between the samples on one gel, the same amount of total protein was loaded. 7 μL of the marker (PRECISION PLUS PROTEIN™Dual Color Standards) were filled into the first pocket of each gel, to enable the accurate protein size estimation afterwards. The gel tank was then connected to the power supply (Power PAC 300) for 30 min at 1 A. Subsequently the cassette was opened with a spatula and the gel was then moved to the blotting station.

The Transfer System (TRANS-BLOT® TURBO™Transfer System, 30 min, 25 V, 1 A) and suitable membranes (TRANS-BLOT® TURBO™Transfer Pack Mini 0.2 μm PVDF) were used for blotting according to the manufacturer's instructions. By scrolling a roller over the "sandwich", any bubbles which could interfere the protein transfer were eliminated. To block free binding sites, the membrane was put into an NET-gelatine and shaken for 60 min on a plate shaker. The gel was cut at the 75 kD band to detect CCDC40 and Glycerinaldehyd-3-phosphat-Dehydrogenase (GAPDH) at the same time. Antibodies were diluted with NET-gelatine (Anti-CCDC40 1:2000 in 6 mL, GAPDH 1:10000 in 10 mL NET-gelatine) and the membranes were incubated with their corresponding antibody on a plate shaker over night at 4° C. GAPDH functions as a loading control. A list of employed antibodies was shown in Table 11. The next day the membrane was washed three times with NET-gelatine for 10 min to remove antibodies that were non-specifically bound or residual. The secondary antibody Goat anti-rabbit IgG-HRP was diluted 1:10,000 with NET-gelatine. After a 60 min incubation on a plate shaker at room temperature (RT), the membranes were washed again three times for 10 min with NET-gelatine. The horseradish peroxidase HRP conjugated secondary antibody could be detected via a molecular imager (CHEMIDOC™ XRS System). Therefore, 5 mL of LUMINATA™ Crescendo Western HRP Substrate was added on the gel and incubated for 5 min. The last picture that was not yet overexposed and the colorimetric picture were then merged and illustrated with the IMAGE LAB-™Software. In addition, the band intensities were determined with IMAGE LAB™ afterwards.

TABLE 11

| Name | Manufacturer | Usage |
|---|---|---|
| GAPDH (D16H11)XP ® Rabbit mAb | Cell Signalling | Primary antibody |
| Anti-CCDC40 | SIGMA-ALDRICH | Primary antibody |
| Goat anti-rabbit IgG-HRP | SCBT | Secondary antibody |

II. ALI Culture

1. Sampling of Human Respiratory Epithelial Cells (hREC)

a. Nasal Brushing

RPMI medium was heated to room temperature and the brush was wet with sterile isotonic saline solution. A CELLETTA™ brush cell collector with protective tip was applied. After asking the patient to clean his nose, he had to sit in a chair with the head against a wall to hold the head. The brush was rubbed a few times rapidly against the medial and superior side of the inferior nasal meatus using rotatory and linear movements. When taking the brush out it was immediately put in a collecting tube (15 mL cornicle) with 5 ml pre-warmed RPMI medium. The brush was vigorously shaken within the tube for at least 40 times to detach the cells from the brush.

b. Stationary Culture

The tube was spun at 900 rpm for 5 min at room temperature. After discarding the supernatant, the pellet was resolved in UG medium [DMEM/Ham's F-12 1:1 with 5 mL sterile 100× antibiotics/mycotics and 10 mL sterile ULTROSER™ G]. 5 mL medium were used for a T25 and 25 mL for a T75 flask.

Having transferred the cells to the cell culture flask, the cells were incubated at 37° C. in a humidified incubator with 5% $CO_2$ over night. Cells should get attached after 20-24 h. UG medium was replaced 3 times a week (Monday, Wednesday and Friday).

2. Generation and Transfection of ALI Culture a. Coating of Transwell Inserts (0.33 $cm^2$)

Following plates were employed for ALI culture: Corning Transwell with clear polyester-membrane (0.4 μm pores, 6.5 mm diameter of inserts, 24-well plates). Rat-tail collagen was diluted 1:5 in acetic acid and 250 μL were loaded on the apical side of each insert. After incubating the plates over night at room temperature, the remaining liquid was aspirated with a pasteur pipette and then the plate left to dry with an open lid for at least 5 min (sterile). Finally, inserts were washed twice with DPBS (w/o $Ca^{2+}/Mg^{2+}$) and then dried over night at room temperature (sterile). Inserts were stored at 4° C. for up to one month.

b. Cell Expansion of hREC as Submerse Culture (Stationary Culture)

Cells were fed every 2 to 3 days (Monday, Wednesday and Friday) with 15 mL pre-warmed UG medium. Care had to be taken not to add new medium directly onto the collagen layer to prevent damage of the collagen layer and detachment of the cells. As soon as cells were 80% confluent or collagen layer began to detach, cells were transferred to ALI filters (approximately after 3 weeks in submerse culture).

c. Preparation of Medium G

Different ALI media were tested, but the self-made Medium G was preferred. This medium was prepared for one week but needed to be stored at 4° C. Batches were frozen in aliquots based on upcoming experiment size. Table 2 shows the composition of Medium G.

d. Seeding and Air-Lift of hREC (ALI Culture)

1. Aspirate UG medium, wash once with wash medium [DMEM/Ham's F-12 1:1 with 1× sterile antibiotics/antimycotics (AA)] or DPBS (w/o $Ca^{2+}/Mg^{2+}$)
2. In case of coated flasks with self-made rat-tail collagen:
   a. Dissolve collagen layer by adding 9 mL collagenase (1×) and incubate for 45 to 60 min at 37° C.
   b. Transfer cells into a 15 mL cornicle tube and centrifuge at 1000 rpm, room temperature for 5 min
   c. Wash cells with wash buffer (1000 rpm, room temperature, for 5 min)
   d. Add 2 mL Trypsin EDTA (1×) and pipette gently up and down to separate the cells, incubate cells at 37° C. and shake the cornicle until the cell clusters disintegrate (approximately 5 minutes)

In case of coated flasks with collagen purchased from gibco:
   a. Add 3 ml Trypsin EDTA (1×) to the cell culture flask until the cells detach (approximately 5 min)
3. Stop trypsin by adding 0.5 mL FBS and 5 mL wash medium
4. Transfer cells into a 15 ml falcon and wash cells twice with wash medium (1000 rpm, room temperature, for 5 min)
5. Resuspend pellet in appropriate amount of ALI medium (1-2 mL, depends on pellet size) and count the cells using cell counter
6. Add 250 μL of the cell suspension (400,000 cells/mL) into each collagen coated transwell with 500 μL ALI medium in the basolateral side
7. Incubate cells at 37° C. in a humidified, 5% $CO_2$ incubator over night Day 3-5: ALI-Growth 8. Check inserts under the microscope consistently
9. Feed cells with ALI medium every day until 80-100% confluence (3-4 days)

ALI-Differentiation

10. Airlift cells when 80-100% confluency is reached
    a. Aspirate ALI medium from both, the apical and basolateral side
    b. Add 500 μL fresh ALI medium to the basolateral compartment
    c. Incubate cells at 37° C. in a humidified, 5% $CO_2$ incubator
11. Wash cells with preheated wash medium (apical) once a week and feed cells with ALI medium every 2-3 days (or Monday-Wednesday-Friday)

e. Transfection of hREC

The formulations (LF111-mRNA) were diluted in 2% sucrose to a final concentration of 3 μg/insert (=9 μg/$cm^2$). To remove mucus, the inserts were washed with 200 μL DPBS (w/o $Ca^{2+}/Mg^{2+}$) on the apical side and incubated for 20 min at 37° C. (Epithelix ALI) or 200 μL DPBS (w/o $Ca^{2+}/Mg^{2+}$) on the apical side and incubated for 5 min at room temperature (hREC, UKM) prior transfection. Afterwards DPBS (w/o $Ca^{2+}/Mg^{2+}$) from the apical surface was removed by gentle aspiration without damaging the epithelium. Directly after the mucus wash, the cells were washed again with WFI (100 μL) to remove traces of DPBS (w/o $Ca^{2+}/Mg^{2+}$). 25 μL of the formulation was added on the apical side of the insert to allow cellular uptake. Removal of carrier was performed after 6 h of incubation, cells were washed once with 200 μL DPBS (w/o $Ca^{2+}/Mg^{2+}$) and culture was maintained as ALI without liquid on the apical side.

3. Read-Out Assays

Various read-out assays are employed. LDH measurement and NUCGREEN™ assay were used to investigate toxicity-related effects of transfection. Ciliary beat frequency measurements (CBF) were needed to examine the manner of ciliary beating with regard to beat frequency and percentage of ciliated area. If ciliary beating leads to a directed flow it can be studied using the Mucociliary Clearance (MCC) Assay. Immunofluorescence (IF) stainings for CCDC40, its heterodimer partner CCDC39 and the cilia marker acetylated alpha-tubulin were utilized to detect if, after treatment, CCDC40 protein or its partner CCDC39 can be detected in the cilia. In addition, proteins of the dynein regulator complex (DRC) like GAS8 and DNALI1 were stained. The DRC is anchored by CCDC40/CCDC39 and only present if CCDC40/CCDC39 are correctly integrated into the cilia axoneme.

a. LDH Measurement

The LDH concentration is measured using the PIERCE™ Lactate Dehydrogenase Cytotoxicity Assay Kit. The procedure is performed as described in the manufacturer's protocol. The ALI cultures were incubated on the apical side with 100 μL DPBS (with $Mg^{2+}/Ca^{2+}$) for 30 min at 37° C. and 5% $CO_2$. 50 μL of the LDH reaction mix and 50 μL of the incubation medium were mixed utilizing a 96-well format and incubated protected from light at room temperature for 30 min adding 50 μL stop solution. The absorbance of the formazan was measured at 490 nm and 680 nm using a microplate reader (TriStar2 Multimode Reader LB 942). The 680 nm value was subtracted from the 490 nm for background normalization. A double determination for each insert was carried out.

b. Ciliary Beat Frequency (CBF) Measurement

Ciliary beat frequency (CBF) analyses of hRECs were performed by high-speed video microscopy and Sisson-Ammons Video Analysis. Videos (125 fps, 640×480 pixel resolution) were recorded using a Megaplus camera model ES 310 turbo attached to an inverted phase-contrast microscope equipped with an ELWD 40× S Plan Fluor objective under physiological conditions, by maintaining the temperature at 36° C. by a Minitube SC300 heating system.

c. Mucociliary Clearance Assay (MCC, Fluorescence Beads)

ALI medium and DPBS (w/o $Ca^{2+}/Mg^{2+}$) were pre-warmed to room temperature and the plate of the microscope was heated to 37° C. ALI inserts were transferred to a new plate and washed apically twice with pre-warmed ALI medium (alternative DPBS w/o $Ca^{2+}/Mg^{2+}$). 100 μL ALI medium was added to the apical compartment before recording 20 videos per insert (40× magnification, Ph2) to get an overall impression of the insert (SAVA software). Red fluorescent particles with a diameter of 0.5 μm were diluted 1:1000 in DPBS (w/o $Ca^{2+}/Mg^{2+}$) and vortexed for at least 1 min. 10 μL of the particle dilution were added to 100 μL of ALI medium, vortexed and 110 μL added to the apical compartment. While handling the beads, it was important to vortex before each step to prevent agglutination. Moreover, work with dimmed light was necessary to avoid bleaching.

The flow of the fluorescent particles was recorded with the NIS-Elements Basic Research software. Movement was recorded over 20-30 s using a 20× magnifcation (Ph1) while exciting the particles with a 488 nm laser. The exposure time had to be adjusted to the number of recorded frames per second (fps). For 7.5 fps the exposure time was set to 100 ms and for 15 fps to 50 ms. The exact observation area was analyzed with SAVA (20× magnifcation, Ph1) to visualize ciliary movement and 3D structures of the cell layer.

For evaluation and data analysis, NIKON®NIS Elemets AR Software, NIS PLUG-IN <ADVANCED 2D TRACKING> <AR> (see above NIS Elements AR Tracking Modul) is employed.

d. IF of ALI Culture

Embedding of ALI Culture

Prior membrane preparation, the ALI insert was washed twice with DPBS (w/o $Mg^{2+}/Ca^{2+}$, 200 μL, 1 min, room temperature) to remove the mucus. The following membrane preparation as carried out according to the following protocol (see below).

The transwell filter membrane was cut out using a scalpel or a syringe before transferring the membrane into a petri dish with 3 mL DPBS ($Ca^{2+}/Mg^{2+}$). The membrane was cut into equal pieces (4-6) and cryomolds were prepared with Shandon CRYOMATRIX™ Frozen Embedding Medium (intermediate size). Membrane pieces were put into the CRYOMATRIX™ and arranged in parallel to each other before cryomolds were incubated on dry ice until the CRYOMATRIX™hardens. Cryomolds were stored at −80° C. for at least 2 h before cutting at cryostat.

Cutting of ALI Membranes

ALI membranes embedded in Shandon CRYOMATRIX™ were cut using the cryostat Microm HM560. Therefore, the cryostat was pre-cooled (2-3 h prior cutting) to −20° C. (table at −21° C. and chamber at −25° C.). The ALI membrane containing cryomolds was transferred from −80° C. to −20° C. for at least 1 h. Cutting of the membrane was performed at 20 μm, depending on the handling conditions of the membrane. The membrane slices were transferred to SUPERFROST® Ultra Plus slides, dried for at least 1 h at room temperature and stored at −80° C. over night or until use at −80° C.

Staining Procedure

For applied antibodies, see Table 12.

Day 1:

1. Wash with 1×DPBS ($Ca^{2+}/Mg^{2+}$) for 5 min at room temperature
2. Fixation: 4% PFA/1×DPBS ($Ca^{2+}/Mg^{2+}$) for 15 min at room temperature
3. Wash 3×DPBS ($Ca^{2+}/Mg^{2+}$) (2× quick, 1×5 min)
4. Permeabilization:
   a. 0.5% TRITON® X-100 für 5 min or
   b. 0.2% TRITON® X-100 für 10 min (depends on the used antibody)
5. Wash 3×DPBS ($Ca^{2+}/Mg^{2+}$) (2× quick, 1×5 min) at room temperature
6. Blocking: 5% normal goat serum+2% BSA in DPBS ($Ca^{2+}/Mg^{2+}$) or 5% skim milk in DPBS ($Ca^{2+}/Mg^{2+}$) →2 h at room temperature
7. 1$^{st}$ antibody: 200 μl over night at 4° C.

Day 2:

8. Wash for 45 min with DPBS ($Ca^{2+}/Mg^{2+}$) (3×15 min)
9. 2$^{nd}$ antibody: 200 μl for 1 h at room temperature
10. Hoechst33342 1:1000 in DPBS ($Ca^{2+}/Mg^{2+}$) for 10 min at room temperature in the dark
11. Wash 6×5 min with DPBS ($Ca^{2+}/Mg^{2+}$)
12. Mount cover slips with DAKO® antifade

TABLE 12

| Name | Species | Dilution | Reactivity | Cat. No. |
|---|---|---|---|---|
| monoclonal anti-acetylated alpha-tubulin | mouse IgG2b, clone 6-11B-1 | 1:10000 | human | T6793 |
| polyclonal anti-CCDC40 | rabbit IgG | 1:200 | human | 25049-1-AP |
| polyclonal anti-CCDC39 | rabbit, affinity purified | 1:300 | human | HPA035364 |
| polyclonal anti-GAS8 | rabbit IgG | 1:200 | Human | HPA041311 |
| polyclonal anti-DNALI1 | rabbit, affinity isolated | 1:200 | human | HPA028305 |
| Alexa Fluor 546 | goat anti-rabbit IgG (H + L) | 1:1000 | human | A11035 |

TABLE 12-continued

| Name | Species | Dilution | Reactivity | Cat. No. |
|---|---|---|---|---|
| Alexa Fluor 488 | goat anti-mouse IgG (H + L) | 1:1000 | human | A11029 |
| DAPI | — | 1:000 | — | 62249 |

e. Air-Brush on ALI Culture

An air-brush model was employed to generate differentiating ALI culture. The protocol was established after Crespin et al. 2011 (Approaches to Study Differentiation and Repair of Human Airway Epithelial Cells).

Cells were shortly washed on the apical side with pre-warmed DPBS ($Mg^{2+}/Ca^{2+}$). The compressor connected to the air-brush was set to 1 $kg/cm^2$ by running the air-brush and turning the small wheel. The air-brush might need to run for some time to stay at a constant value. Then the small reservoir on top of the air-brush was filled with DPBS ($Mg^{2+}/Ca^{2+}$) and the insert put to a new plate without basal medium. The air-brush was started by pressing to the first pressure point and waiting until the pressure on the compressor stays constant. Than the air-brush was put vertically on top of the insert and the lever of the air-brush was pressed very little beyond the first pressure point [disperses the DPBS ($Mg^{2+}/Ca^{2+}$) from the reservoir] for 2 s. Following, the apical side of the insert was shortly washed with pre-warmed DPBS ($Mg^{2+}/Ca^{2+}$) and the insert was put into fresh medium applicable for ALI differentiation. The wound was checked by microscopic observation. If it was too small (less than ⅓ of insert area) or the cells in the wound only slightly detached, the procedure was repeated. Cultures were incubated in a humidified atmosphere at 37° C., 5% $CO_2$ and cultured as ALI.

III. Tagged CCDC40 mRNAs

The mRNAs under study are shown in Table 13.

TABLE 13

| RNA-ID | ORF | 5' UTR | 3' UTR | Modified NTP I [%] | Modified NTP I [Name] | Modified NTP II [%] | Modified NTP II [Name] |
|---|---|---|---|---|---|---|---|
| ETH031T28 (SEQ ID NO: 9) | eGFP-hCCDC40 | minimal | no | 15 | 5-Methyl-UTP | 3 | 5-Iodo-CTP |
| ETH031T30 (SEQ ID NO: 10) | hCCDC40-eGFP | minimal | no | 15 | 5-Methyl-UTP | 3 | 5-Iodo-CTP |
| ETH031T26 (SEQ ID NO: 11) | HA-CCDC40-T2A-tdTomato | CYBA | CYBA | 15 | 5-Methyl-UTP | 3 | 5-Iodo-CTP |

a. Cell Culture

HEK-293 cells are cultivated in MEM GLUTAMAX™, 10% FBS, 100 U/ml P/S (=cultivation medium) at 37° C., 5% $CO_2$.

Before seeding, cells are washed with DPBS and detached using Trypsin. After trypsinisation, trypsin is deactivated using cultivation medium containing FBS. Therefore, an equal or greater volume of culture medium is used. After centrifugation for 5 min at 1100×g and resuspension in normal growth media, cells are counted using a COUNTESS™ Cell Counting Device.

b. In Vitro Transcription

To generate templates for in vitro transcription, circular plasmids were linearized by restriction digestion with BstBI and further purified by chloroform ethanol precipitation.

mRNA was produced using a standard in vitro transcription mix containing T7 RNA polymerase, inorganic pyrophosphatase, and RNase inhibitor. Co-transcriptional capping was achieved by addition of an ARCA cap analogue. For in vitro transcription of chemically modified RNA, 7.5% of cytidine-5'-triphosphate were replaced by 5-iodocytidine-5'-triphosphate and 30% uridine-5'-triphosphate were replaced by 5-iodouridine-5'-triphosphate, respectively. In another SNIM® RNA production setup 3% of cytidine-5'-triphosphate was replaced by 5-iodocytidine-5'-triphosphate and 15% uridine-5'-triphosphate was replaced by 5-methyl-uridine-5'-triphosphate, respectively. Residual template DNA was digested using DNaseI. Subsequently mRNA was purified by ammonium acetate precipitation followed by a washing step using 70% ethanol.

Dephosphorylation of residual uncapped mRNA was carried out using a Quick dephosphorylation Kit followed by purification via ammonium acetate precipitation followed by a washing step using 70% ethanol and ultrafiltration using a 100 MWCO cut of filter.

mRNA was further polyadenylated by using a poly(A) polymerase. Again mRNA was purified by ammonium acetate precipitation followed by a washing step using 70% ethanol and ultrafiltration using a 100 MWCO cut of filter. Poly(A) length was determined by capillary gel electrophoresis to be between 100 and 250 nucleotides.

c. Seeding, Transfection and Readout

Cells were seeded in 96-well black microplates (25,000 cells per well) 24 h before treatment. 24 h after seeding fresh medium was added to each well (100 μL). mRNA was transfected using LIPOFECTAMINE™ MESSENGERMAX™ in a RNA to LIPOFECTAMINE™ ratio of 1:1.5 (w/v). 250 ng/96-well (≙ 758 $ng/cm^2$) eGFP-CCDC40 (ETH031T28 or ETH031T30) or HA-CCDC40-T2A-tdTomato (ETH031T26) mRNA was employed. All RNAs were having a stock concentration of 1 mg/mL. For lipoplex formation mRNA was diluted in aqua bidest. LIPOFECTAMINE™ MESSENGERMAX™ was diluted in SFM (serum-free medium) and was mixed by pipetting. After incubation of 10 min at RT, the RNA solution was added to the LIPOFECTAMINE™ MESSENGERMAX™ solution, mixed and incubated for another 5 min at RT. Afterwards, the mix was diluted two-fold in SFM before adding the Lipoplex solution to the wells. In Table 14 an example for one RNA was calculated.

TABLE 14

| ng RNA/ well | RNA [μL] | H2O [μL] | MM [μL] | SFM [μL] | Total volume added to cells [μL] |
|---|---|---|---|---|---|
| 250 | 4.5 | 108 | 6.76 | 105.76 | 25 |

6 h and 24 h post transfection, transfection efficiency was examined by fluorescence microscopy, pictures were taken at 10× magnification.

IV. CCDC39

The mRNA (ETH047T02; SEQ ID NO: 12) under study encoded hCCDC39 and comprised Ethris minimal UTR. In total, 15% of uridine-5'-triphosphates were replaced by 5-methyl-uridine-5'-triphosphates, and in total 3% of cytidine-5'-triphosphates by 5-iodo-cytidine-5'-triphosphates. Antibodies used are shown in Table 15.

TABLE 15

| Type | Antibody Number | Antibody Name | Supplier | Cat. No |
|---|---|---|---|---|
| First | 207 | CCDC39 | atlas antibodies | HPA035364 |
| First | 219 | Actin | abcam | ab8227 |
| Second | Goat Anti-Rabbit IgG H&L (HRP) | Abcam | ab205718 | Goat Anti-Rabbit IgG H&L (HRP) |

1. CCDC39 Transfection and Western Blot in Submerse Cell Culture a. Cell Culture

BEAS-2B cells were cultivated in LHC-9 media in coated flasks. For details see I 1 above. Experiments were performed in uncoated plates.

HEK-293 cells were cultivated in MEM GLUTAMAX-™media, supplemented with heat inactivated FBS and penicillin/streptomycin (P/S).

Before seeding, cells were washed with DPBS and detached using Trypsin. After trypsinisation, trypsin was deactivated using either a trypsin inhibitor for BEAS-2B or cultivation medium containing FBS for HEK-293. Therefore, an equal or greater volume of trypsin inhibitor/culture medium was used. After centrifugation for 5 min at 1100×g and resuspension in normal growth media, cells were counted using a COUNTESS™ Cell Counting Device. Considering a seeding volume of 2 mL and a 6-well plate format, $5.0\times10^5$ seeded BEAS-2B cells and $1.4\times10^6$ seeded HEK-293 cells were obtained.

b. Transfection

Cells were seeded in their respective density 24 h before treatment. 24 h after seeding 2 mL of fresh medium was added to each well. mRNA was transfected using LIPOFECTAMINE™ MESSENGERMAX™ in a RNA to Lipofectamine ratio of 1:1.5 (w/v). All RNAs were having a stock concentration of 1 mg/mL. For lipoplex formation mRNA was diluted in acqua bidest. LIPOFECTAMINE™ MESSENGERMAX™ was diluted in SFM and was mixed by pipetting. After incubation of 10 min at RT, the RNA solution was added to the LIPOFECTAMINE™ MESSENGERMAX™ solution, mixed and incubated for another 5 min at RT. Afterwards, the Lipoplex solution was added to the wells. In Table 16 an example for transfection is calculated for one 6-well plate.

TABLE 16

| | ng/well | RNA [μL] | H2O [μL] | MM [μL] | SFM [μL] | Total volume added to cells [μL] |
|---|---|---|---|---|---|---|
| High dose | 5000 | 5.0 | 120 | 7.5 | 117.5 | 250 |
| Lowe dose | 2500 | 2.5 | 122.5 | 3.75 | 121.25 | 250 |

c. Cell Lysis

To obtain optimal cell lysis, two different lysis buffers were compared, a TRITON® X-100 buffer and the commercially available lysis buffer M-PER™, both of them complemented with protease inhibitorCOMPLETE™, EDTA-free, and 40 μL/mL DNase I Solution (in a mixture of 23:1:1). Therefore, cells were seeded in a 6-well plate and treated for 6 h and 24 h. After treatment, cells were harvested. Therefore, plates were washed once using 1 mL DPBS. To remove the cells from the plate another 1 mL of DPBS was added and cells were scraped from plates and moved to EPPENDORF® tubes. To remove DPBS, cells were centrifuged at 6250×g for 2 min at 4° C. Cell lysis was performed by adding 200 μL of the respective buffer. To ensure complete lysis the cells were incubated on ice for 30 min. After lysis, BCA Assay was performed to determine the total protein concentration using a BCA Protein Assay Kit according to the manufacturer's instructions with the following changes:

200 μL working reagent were added to 5 μL cell lysate

Samples and standard were measured in triplicate.

Before incubation of samples at 37° C. for 30 minutes, the plate was shaken for 30 seconds at 450 rpm d. Sample Preparation

The samples are mixed with 5 μL BOLT®LDS Sample buffer and 2 μL BOLT® Sample Reducing Agent and then heated for 10 min at 70° C. before SDS-PAGE was performed. 30 μg of total protein was used for SDS-PAGE and BOLT™4-12% SDS-PAGE gel, 10 well was employed.

e. SDS Page and Blotting Method

TRANS-BLOT® TURBO™ System Transfer was used. SDS-PAGE was performed applying 200 V for 40 min. Transfer was done using the TRANS-BLOT® TURBO™ Transfer System for 30 minutes.

f. Antibody and Blocking Method

After transfer, the membranes were blocked at RT for 1 h. NET-gelatine was used as blocking reagent. Antibody HPA035364 from atlas antibodies was used for the detection of CCDC39, and antibody ab8227 from abcam for the detection of Actin. Membranes were cut at about 60 kDa before the antibodies were added. The membranes were incubated overnight at 4° C. with the primary antibodies. After three washes (10 min each) with blocking solution at RT, horseradish peroxidase-conjugated secondary antibody, was added at RT for 1 h (diluted 1:20 000). The membranes were washed again three times with blocking solution 10 min each at RT.

g. Chemiluminescent Signal Development

Signals were visualized with a chemiluminescent substrate kit (LUMINATA™ Crescendo, Classico or Forte Western HRP substrate, depending on the intensity of the signal) and the CHEMIDOC™ MP System.

2. Western Blot of Endogenous CCDC39 in Differentiated ALI Culture a. Cell Lysis 250 µL ALI lysis buffer (for details of the composition cf. Table 17) was added per insert and incubated on ice for 15 min. Before, during (every 5 min) and at the end of incubation, ALI lysis buffer was pipetted back and forth. After transfer into EPPENDORF® tubes and rinsing of each insert with 150 µL ALI lysis buffer, samples were vortexed thoroughly. At this step, samples could optionally be stored at −20° C. until further processing.

TABLE 17

| Substance | Stock | Final | For 10 ml |
|---|---|---|---|
| TRITON ® X-100 | 10% | 1% | 1 ml |
| NaCl | 1.5M | 150 mM | 1 ml |
| SDS | 1% | 0.1% | 1 ml |
| Tris | 250 mM | 50 mM | 2 ml |
| Protease inhibitor cOmplete | 25× | 1× | 0.4 ml |
| WFI | | | 4.5 ml |

b. Separation of Axonemal Lysate from Whole Cell Lysate

Samples were added to Lysing Matrix A Tubes (tubes were washed before with 70% EthOH and garnet is removed). The tubes were fastened and frozen in liquid nitrogen for 20 seconds while moving the tube. Tubes were quickly inserted into MP FASTPREP-24™ (HOM-1), settings: 6.5 m/s, 3×1 min. Subsequently, tubes were left to condense on ice for 15 minutes before transferring the liquid to fresh EPPENDORF® tubes and spinning at 1100 rpm, 4° C., for 20 minutes. The supernatant was transferred to new EPPENDORF® tubes and pellet and supernatant were stored at −20° C. until further processing.

c. Preparation of Axonemal Extract Lysate: High-Salt Extraction of Ciliary Axonemal Protein Each pellet was resuspended in 50 µl MMRB+0.1% TRITON® X-100 (for details of the composition of MMRB+0.1% TRITON® X-100 see Table 18) and incubated on ice for 30 minutes (with occasional gentle vortexing). After spinning at 14,000 rpm at 4° C. for 10 minutes, the supernatant was transferred to new EPPENDORF® tubes and stored at −20° C. until further processing.

TABLE 18

| Substance | Stock | Final | Volume for 1 ml |
|---|---|---|---|
| HMEN (cf. Table 19) | 1× | — | 982 µl |
| DTT (e.g. Sigma 646563) | 1M | 2 mM | 2 µl |
| β-Mercaptoethanol (e.g. Sigma M3148) | 100% | 70 mM | 5 µl |
| TRITON ® X-100 | 10% | 0.1% | 10 µl |
| Protease inhibitor cOmplete (Roche/Sigma 11873580001) | 25× | 1× | 40 µl |

TABLE 19

| Substance | Final |
|---|---|
| HEPES, pH 7.4 | 30 mM |
| MgSO4 | 5 mM |
| EDTA | 0.1 mM |
| NaCl | 625 mM |

d. Preparation of Lysates for Western Blot

Samples were thawed on ice and 30 µl of sample were transferred to new EPPENDORF® tubes. 12 µL LDS sample buffer and 5 µl 10× Reducing Agent were added before heating the samples at 70° C., 350 rpm for 10 minutes. 5, 10 and 30 µl were applied per well to a BOLT™ 4-12% SDS-PAGE gel, 10 well.

e. SDS Page and Blotting Method: Cf. IV 1 e f. Antibody and Blocking Method: Cf. IV 1 f g. Chemiluminescent Signal Development: Cf. IV 1 g II. Results CCDC40 expression was determined in HEK293 cells after 6 h, 24 h, 48 h, 72 h and 144 h post-transfection. In particular, $2/1.4/0.3/0.2/0.05\times10^6$ cells were seeded in 6-well plates and cells were transfected 24 h after seeding with different CCDC40 constructs (2.5 µg/9.5 $cm^2$) using LIPOFECTAMINE™2000. The CCDC40 mRNA constructs used in this experiment were T06 to T10 (SEQ ID NO: 1, and SEQ ID NO: 5 to SEQ ID NO: 8). Cell lysis was performed 6, 24, 48, 72 and 144 h after transfection and 50 µg of total protein lysate were analyzed with SDS-PAGE and Western Blot.

As it can be seen in FIG. 1, a peak translation efficiency was detectable 6 h post-transfection of CCDC40 mRNAs in HEK cells.

The next experiment was performed as described above except that in this case, $2\times10^6$ HEK293, $7.5\times10^5$ BEAS-2B and $5\times10^5$ RPMI 2650 cells were seeded in 6-well plates and protein lysates analyzed with SDS-PAGE and Western Blot (HEK293: 50 µg, RPMI 2650:20 µg, BEAS-2B: 30 µg of total lysate). CCDC40 was detected using Anti-CCDC40 Antibody (HPA022974) from Atlas Antibodies (1:2000).

Here, it could be observed that T09 (CYBA; SEQ ID NO: 1) and T10 (human CMV IE9 and 3' UTR from human Growth hormone SEQ ID NO: 8) UTRs led to the highest translation efficiency 6 h post-transfection in BEAS-2B, RPMI2650 and HEK293 cells (FIG. 2).

Two experiments were then performed to investigate restoration of cilia motility in patient derived ALI cultures. In particular, in the first experiment a non-differentiated ALI culture (data not shown) was used (ciliary cells had a deletion of exon 1 and 2 resulting in very short and less motile cilia), whereas in the second experiment a differentiated ALI culture was used. In both cases, the ALI culture was transfected with 3 μg LF92/CCDC40 (ETH031T09; SEQ ID NO: 1) every other day for 1 month for a total of 16 transfections. As readout a high speed video microscopy (HSVM) was performed every 24 h and immune fluorescence immunocytochemistry (IF-ICC). Prior transfection and every 24 h after transfection, videos (20 per insert) were taken and CFB (ciliary beat frequency) was calculated using the SAVA Software. Allover 16 transfections (1 month) were performed. Measurement was done at 37° C. using the 40× magnification. Calculated are the mean values of the cilia beat frequency (CBF).

Repeated transfection of LF92/CCDC40 was well tolerated in patient derived fully differentiated ALI cultures. The CCDC40 protein could be detected in naturally occurring subcellular region, i.e. cilia, of airway epithelial cells after 22 d by IF-ICC and cilia motility increased after LF92/CCDC40 transfection until day 18 to ~50% of normal cilia beat frequency as it can be seen in FIG. 3 for the experiment with the differentiated ALI culture.

As described in the Material and Methods section, an undifferentiated ALI culture was obtained using Medium G and transfections (TF) started 18 days post air-lift. Transfections (TFs) of CCDC40 patient ALI culture with CCDC40 mRNA/LF92 were performed once a week for 4 weeks (=4×TF). Mucociliary clearance (MCC) was measured using 0.5 μm fluorescent beads at 20× magnification. 30 s videos of different areas are taken and analyzed with the Polargraph software from NIKON®one week after the last TF.

Importantly, restoration of cilia beating in CCDC40 patient ALI after four weekly CCDC40 mRNA/LF92 transfections could be detected. Moreover, cilia beating was synchronized, which allowed a directed particle transport as it can be seen in FIG. 4. For comparison, particle transport is shown in FIG. 5 in case of a control, i.e. fourfold tdTomato mRNA/LF111 transfection, and a healthy control.

Thus, successful CCDC40 mRNA/LF92 TF of patient ALI culture with LF92, as indicated by a comparison with the tdTomato control, during the differentiation phase of the ciliary cells resulted in successful cilia growth, successful cilia beating, successful directed particle transport, and successful protein detection (CCDC39 as binding partner of CCDC40+GAS8/DNALI1 as part of the DRC complex). Moreover, tdTomato control inserts did not show any of the above mentioned effects.

FIG. 6 demonstrates successful incorporation of GAS8 protein within the axonemes after repeated patient ALI treatment with CCDC40 mRNA as in healthy controls which is absent in control (tdTomato mRNA) treated patient ALIs. FIG. 7 demonstrates successful incorporation of DNALI-1 protein within the axonemes after repeated patient ALI treatment with CCDC40 mRNA as in healthy controls which is absent in control (tdTomato mRNA) treated patient ALIs. FIG. 8 demonstrates successful incorporation of CCDC39 protein within the axonemes after repeated patient ALI treatment with CCDC40 mRNA as in healthy controls which is absent in control (tdTomato mRNA) treated patient ALIs.

To summarize, cilia motility could not be restored to a significant level when using the differentiated ALI culture, but partially restored when using the differentiated ALI culture.

Figure 11:
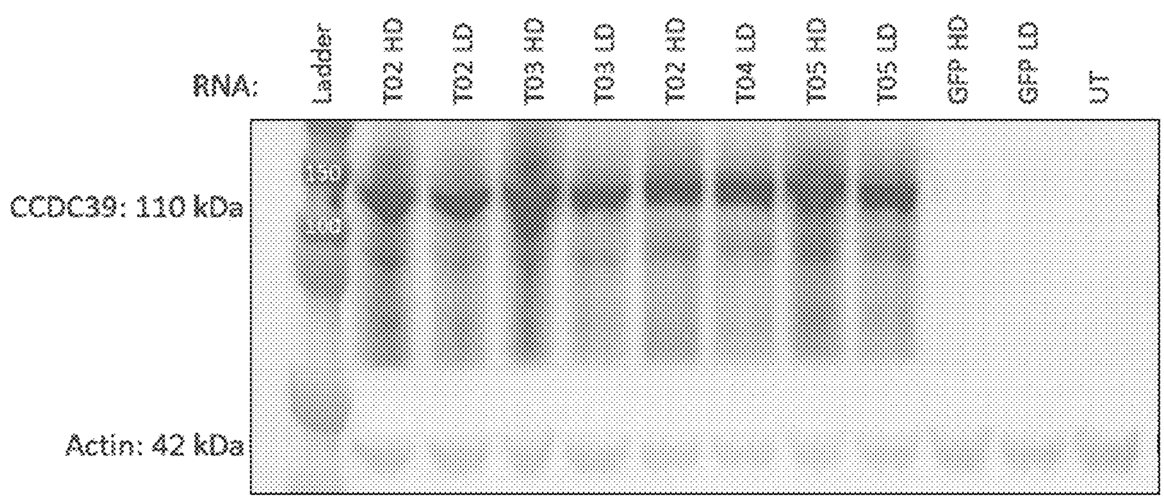

With respect to the CCDC39 experiments, CCDC39 proteins could be detected by Western Blot analyses 6 h and 24 h after transfection in HEK-293 and BEAS-2B cells as it can be seen in FIG. 9. As shown in FIG. 11, CCDC39 (ETH047T03; SEQ ID NO: 13) expression could be detected after 6 h in 16HBE14o- using Proteasome Inhibitor. The same experiment was also performed for ETH047T02 (SEQ ID NO: 12), ETH047T04 (SEQ ID NO: 2), and ETH047T05 (SEQ ID NO: 14) with comparable results. As shown in FIG. 12, CCDC39 (ETH047T03; SEQ ID NO: 13) expression could also be detected after 24 h in 16HBE14o- using Proteasome Inhibitor.

Exemplary sequences described in the application are provided below. The disclosure provides, in some embodiments, polyribonucleotides comprising, for example, the UTR sequences set forth in SEQ ID NO: 1 or 2, or a sequence at least 95%, 96%, 97%, 98%, or 99% identical to such sequences, or a polyribonucleotide sequence, such as an mRNA, corresponding to or encoded by any of the foregoing. In certain embodiments of any of the foregoing, the polynucleotide or polyribonucleotide is modified (e.g., comprises nucleotide analogues, as described herein).

CCDC40 sequence with CYBA 5' and 3' UTR (ETH031T09):

*Part of the T7 promoter*, Ethris' minimal 5' UTR, *CYBA 5' UTR*, *Kozak element*, start codon (AUG), codon optimized sequence encoding a functional version of a human CCDC40 protein, stop codon (UGA), CYBA *3' UTR*, part of restriction site for BstBl, polyA: tail of "A" produced via post polyadenylation of mRNA

SEQ ID NO: 1

*GGGAGA*C*CGCGCCUAGCAGUGUCCCAGCCGGGUUCGUGUCGCC**GCCACC*AUGGCUGAAC

CUGGCGGAGCCGCCGGAAGAUCCCACCCUGAAGAUGGCUCUGCCAGCGAGG

GCGAGAAAGAGGGCAACAACGAGAGCCACAUGGUGUCCCCCCCAGAGAAGGA

CGACGGCCAGAAAGGCGAAGAGGCCGUGGGCUCUACCGAGCACCCUGAGGA

AGUGACCACACAGGCCGAGGCCGCCAUUGAAGAGGGCGAGGUGGAAACAGAG

GGCGAAGCCGCUGUGGAAGGCGAAGAGGAAGCCGUGUCUUACGGCGACGCC

GAGAGCGAGGAAGAGUACUACUACACCGAGACAAGCAGCCCCGAGGGCCAGA

UCUCUGCCGCCGAUACCACCUACCCCUACUUCAGCCCCCCUCAGGAACUGCC

UGGGGAAGAGGCCUACGAUAGCGUGUCCGGCGAAGCUGGCCUGCAGGGCUU

-continued

UCAGCAGGAAGCCACAGGCCCUCCCGAGAGCCGGGAAAGAAGAGUGACAAGC

CCCGAGCCUAGCCACGGCGUGCUGGGACCAUCUGAGCAGAUGGGCCAAGUG

ACCUCUGGCCCUGCUGUGGGCAGACUGACAGGCAGCACAGAGGAACCUCAG

GGCCAGGUGCUGCCUAUGGGAGUGCAGCACCGGUUCAGACUGAGCCACGGC

AGCGACAUCGAGAGCAGCGACCUGGAAGAGUUCGUCAGCCAGGAACCCGUGA

UCCCUCCUGGCGUGCCAGAUGCCCAUCCCAGGGAAGGCGAUCUGCCCGUGU

UCCAGGACCAGAUCCAGCAGCCCUCUACCGAAGAGGGGGCUAUGGCCGAGAG

AGUGGAAAGCGAGGGCUCCGACGAAGAAGCCGAGGACGAGGGAUCUCAGCU

GGUGGUGCUGGACCCCGACCACCCUCUGAUGGUGCGGUUUCAGGCCGCCCU

GAAGAACUACCUGAACCGGCAGAUCGAGAAGCUGAAACUGGACCUGCAGGAA

CUGGUGGUGGCCACAAAGCAGAGCAGAGCCCAGAGACAGGAACUGGGCGUG

AACCUGUACGAGGUGCAGCAGCAUCUGGUGCAUCUGCAGAAGCUGCUGGAAA

AGAGCCACGACCGGCACGCCAUGGCCAGCUCUGAGCGCAGACAGAAAGAGGA

AGAACUGCAGGCCGCCAGAGCCCUGUACACCAAGACAUGCGCCGCUGCCAAC

GAGGAACGGAAGAAGCUGGCUGCCCUGCAGACCGAGAUGGAAAACCUGGCUC

UGCACCUGUUCUACAUGCAGAAUAUCGACCAGGACAUGCGGGACGACAUCAG

AGUGAUGACCCAGGUCGUGAAGAAGGCCGAGACAGAGAGAAUCCGGGCCGAG

AUUGAGAAGAAAAAGCAGGACCUGUACGUGGACCAGCUGACCACCAGGGCCC

AGCAGCUGGAAGAGGAUAUCGCCCUGUUCGAGGCCCAGUACCUGGCCCAGG

CCGAAGAUACCCGGAUCCUGAGAAAGGCCGUGUCCGAGGCCUGCACCGAGAU

CGAUGCCAUCAGCGUGGAAAAGCGGCGGAUCAUGCAGCAGUGGGCCAGCAG

CCUCGUGGGCAUGAAGCACAGAGAUGAGGCCCACCGGGCCGUGCUGGAAGC

UCUGAGAGGCUGUCAGCACCAGGCCAAGAGCACCGACGGCGAGAUCGAGGC

CUACAAGAAAUCCAUCAUGAAGGAAGAGGAAAAGAACGAGAAACUGGCCAGCA

UCCUGAACAGAACCGAAACCGAGGCCACCCUGCUGCAGAAACUGACCACCCA

GUGCCUGACCAAACAGGUGGCCCUGCAGUCCCAGUUCAACACCUACAGACUG

ACCCUGCAGGACACCGAGGACGCCCUGAGUCAGGAUCAGCUGGAACAGAUGA

UUCUGACCGAGGAACUGCAGGCUAUCCGGCAGGCCAUUCAGGGGGAGCUGG

AACUGCGGAGAAAGACCGACGCCGCCAUCAGAGAGAAGCUGCAGGAACACAU

GACCAGCAACAAGACCACCAAGUACUUCAACCAGCUGAUUCUGCGCCUGCAG

AAAGAAAAGACCAACAUGAUGACACACCUGAGCAAGAUCAACGGCGACAUUGC

CCAGACCACCCUGGACAUCACCCACACCAGCAGCAGACUGGACGCCCACCAG

AAAACCCUGGUGGAACUGGACCAGGAUGUGAAGAAAGUGAACGAGCUGAUCA

CCAACAGCCAGAGCGAGAUCAGCCGGCGGACCAUCCUGAUCGAGAGAAAGCA

GGGCCUGAUCAACUUCCUGAACAAACAGCUGGAAAGAAUGGUGUCCGAGCUG

GGCGGCGAGGAAGUGGGACCUCUGGAACUGGAAAUCAAGCGGCUGAGCAAG

CUGAUCGACGAGCACGACGGCAAGGCCGUGCAGGCUCAAGUGACAUGGCUG

CGGCUGCAGCAGGAAAUGGUCAAAGUGACCCAGGAACAGGAAGAACAGCUGG

CCUCCCUGGACGCCAGCAAGAAAGAACUGCACAUCAUGGAACAGAAAAAGCU

GCGGGUGGAAAGCAAGAUCGAGCAGGAAAAAAAAGAACAGAAAGAAAUCGAGC

-continued

ACCACAUGAAGGACCUGGACAACGACCUGAAGAAACUGAAUAUGCUGAUGAAC

AAGAACCGCUGCUCCAGCGAAGAACUGGAACAGAACAACAGAGUGACCGAGA

ACGAGUUCGUGCGGAGCCUGAAGGCCAGCGAGCGGGAAACCAUCAAGAUGCA

GGACAAGCUGAACCAGCUGUCCGAGGAAAAAGCCACACUGCUGAACCAGCUG

GUGGAAGCCGAGCACCAGAUCAUGCUGUGGGAGAAGAAGAUCCAGCUGGCCA

AAGAAAUGCGGAGCAGCGUGGACAGCGAGAUCGGCCAGACCGAAAUCAGAGC

CAUGAAGGGCGAGAUCCACCGGAUGAAAGUGCGGCUGGGACAGCUGCUGAAA

CAGCAGGAAAAGAUGAUCCGGGCCAUGGAACUGGCCGUGGCCAGACGGGAAA

CCGUGACAACCCAGGCUGAGGGCCAGCGGAAGAUGGACAGAAAGGCCCUGAC

CCGGACCGACUUCCACCACAAGCAGCUGGAACUGAGGCGGAAGAUCCGGGAC

GUGCGGAAGGCCACCGAUGAGUGCACAAAGACAGUGCUGGAACUGGAAGAGA

CACAGCGGAACGUGUCCUCCAGCCUGCUGGAAAAACAGGAAAAGCUGAGCGU

GAUCCAGGCCGACUUCGACACCCUGGAAGCUGACCUGACAAGACUGGGAGCC

CUGAAAAGACAGAACCUGUCCGAGAUCGUGGCACUGCAGACCCGGCUGAAAC

AUCUGCAGGCUGUGAAAGAGGGACGCUACGUGUUCCUGUUCAGAUCCAAGCA

GUCUCUGGUGCUGGAAAGACAGCGGCUGGACAAGCGGCUGGCACUGAUUGC

CACCAUCCUGGAUAGAGUGCGCGACGAGUACCCACAGUUCCAGGAAGCACUG

CACAAGGUGUCCCAGAUGAUCGCCAACAAGCUGGAAUCCCCUGGCCCCAGCU

GACCUCGCCCCGGACCUGCCCUCCCGCCAGGUGCACCCACCUGCAAUAAAUGCAGCGAAGCC

GGGAUUCG-polyA

CCDC39 sequence with CYBA UTRs (ETH047T04):

*Part of the T7 promoter*, Ethris' minimal 5′ UTR, CYBA *5′ UTR*, *Kozak element*, start codon (AUG), codon optimized sequence encoding a functional version of a human CCDC39 protein, stop codon (UGA), CYBA *3′ UTR*, part of restriction site for BstBl, *poly(A) tail*

SEQ ID NO: 2

GGGAGACCGCGCCUAGCAGUGUCCCAGCCGGGUUCGUGUCGCCGCCACCAUGAGCAGCG

AGUUUCUGGCCGAACUGCACUGGGAGGACGGCUUCGCUAUUCCCGUGGCCA

ACGAGGAAAACAAGCUGCUGGAAGAUCAGCUGAGCAAGCUGAAGGACGAGAG

AGCCUCUCUGCAGGACGAGCUGAGAGAGUACGAGGAACGGAUCAACAGCAUG

ACCAGCCACUUCAAGAACGUGAAGCAAGAGCUGAGCAUCACCCAGAGCCUGU

GCAAGGCCAGAGAGAGAGAGAAACCGAGAGCGAGGAACACUUCAAGGCUAUCGC

CCAGCGCGAGCUGGGAAGAGUGAAGGAUGAGAUCCAGCGGCUGGAAAACGA

GAUGGCCAGCAUCCUGGAAAAGAAGUCCGACAAAGAGAACGGCAUCUUCAAG

GCCACACAGAAGCUGGACGGCCUGAAGUGCCAGAUGAACUGGGAUCAGCAGG

CCCUGGAAGCCUGGCUGGAAGAGUCUGCCCACAAGGAUUCUGACGCCCUGAC

ACUGCAGAAGUACGCCCAGCAGGACGACAACAAGAUCCGGGCUCUGACCCUG

CAGCUGGAAAGACUGACCCUGGAAUGCAACCAGAAGCGGAAGAUCCUGGACA

ACGAGCUGACCGAGACAAUCAGCGCCCAGCUGGAACUGGAUAAGGCCGCUCA

GGACUUCAGAAAGAUCCACAACGAGCGGCAAGAACUGAUCAAGCAGUGGGAG

AACACCAUCGAGCAGAUGCAGAAACGCGACGGCGACAUCGACAACUGCGCCC

-continued

UGGAACUCGCCCGGAUCAAGCAAGAGACACGCGAGAAAGAGAACCUGGUCAA

AGAGAAGAUCAAGUUCCUCGAGUCCGAGAUCGGCAACAACACCGAGUUCGAG

AAGCGGAUCAGCGUGGCCGACAGAAAGCUGCUGAAGUGCAGAACCGCCUACC

AGGACCACGAGACAAGCCGGAUUCAGCUCAAGGGCGAGCUGGAUUCUCUGAA

GGCCACCGUGAACAGAACCAGCAGCGAUCUGGAAGCCCUGCGGAAGAACAUC

AGCAAGAUCAAGAAGGACAUCCACGAGGAAACCGCCAGGCUGCAGAAAACAAA

GAACCACAAUGAGAUCAUCCAGACCAAGCUGAAAGAGAUCACCGAAAAGACCA

UGAGCGUGGAAGAGAAGGCCACAAACCUGGAAGAUAUGCUCAAAGAGGAAGA

GAAAGACGUCAAAGAGGUGGACGUUCAACUGAACCUGAUUAAGGGCGUGCUG

UUCAAGAAGGCCCAAGAGCUGCAGACCGAAACCAUGAAGGAAAAGGCCGUCC

UGUCUGAGAUCGAGGGCACCAGAUCUAGCCUGAAGCACCUGAACCAUCAGCU

GCAGAAGCUCGACUUCGAGACACUGAAGCAGCAAGAGAUCAUGUACAGCCAG

GAUUUCCACAUCCAGCAGGUCGAGCGGCGGAUGUCUAGACUGAAGGGCGAG

AUCAACUCCGAGGAAAAACAGGCCCUCGAGGCCAAGAUCGUGGAACUGAGAA

AGAGCCUCGAAGAGAAGAAGUCUACCUGCGGCCUGCUGGAAACCCAGAUUAA

GAAGCUGCACAACGACCUGUACUUCAUCAAGAAAGCCCACAGCAAGAACAGCG

ACGAGAAGCAGAGCCUGAUGACCAAGAUCAAUGAGCUGAACCUGUUCAUCGA

UCGGAGCGAAAAAGAGCUGGACAAGGCCAAGGGCUUCAAGCAGGACCUGAUG

AUCGAGGACAACCUGCUGAAGCUGGAAGUGAAGCGGACCAGAGAGAUGCUGC

ACAGCAAGGCCGAGGAAGUGCUGUCUCUGGAAAAGCGGAAGCAGCAGCUGUA

CACCGCCAUGGAAGAGAGAACCGAAGAGAUCAAGGUGCACAAGACCAUGCUG

GCUUCCCAGAUCAGAUACGUGGACCAAGAGCGCGAGAACAUCUCCACCGAGU

UUAGAGAGAGACUGUCCAAGAUCGAGAAGCUGAAGAACCGCUACGAGAUCCU

GACCGUCGUGAUGCUGCCUCCUGAGGGCGAAGAGGAAAAGACCCAGGCCUAC

UACGUGAUCAAGGCAGCCCAAGAAAAAGAGGAACUCCAGAGAGAAGGCGACU

GCCUGGACGCCAAGAUUAACAAGGCCGAAAAAGAAAUCUACGCCCUCGAGAA

CACCCUGCAGGUCCUGAACAGCUGCAACAACAACUACAAGCAGAGCUUCAAGA

AAGUCACCCCUAGCUCCGACGAGUACGAGCUGAAGAUUCAGCUGGAAGAACA

GAAAAGAGCCGUGGACGAGAAGUACAGAUACAAGCAGCGGCAGAUCAGAGAG

CUGCAAGAGGAUAUCCAGAGCAUGGAAAACACCCUGGACGUGAUCGAGCACC

UGGCCAACAACGUGAAAGAGAAGCUGUCCGAGAAACAGGCCUACAGCUUUCA

GCUGUCCAAAGAGACAGAGGAACAGAAGCCCAAACUGGAACGCGUGACCAAG

CAGUGCGCCAAGCUGACAAAAGAGAUCCGGCUGCUGAAAGACACCAAGGACG

AAACCAUGGAAGAACAAGACAUCAAGCUGCGCGAGAUGAAGCAGUUCCACAAA

GUGAUCGACGAGAUGCUGGUGGACAUCAUUGAAGAGAACACAGAGAUCCGCA

UCAUCCUGCAGACCUAUUUUCAGCAGAGCGGCCUGGAACUGCCUACCGCCUC

UACAAAGGGCAGCAGACAGAGCAGCAGAUCCCCUAGCCACACAAGCCUGAGC

GCCAGAAGCUCUAGAAGCACCAGCACCUCUACCAGCCAGUCCAGCAUUAAGG

UGCUGGAACUCAAGUUCCCCGCCAGCUCUAGCCUCGUGGGAAGCCCUUCUAG

ACCUAGCAGCGCCUCUAGCAGCUCCAGCAACGUGAAGUCCAAGAAAAGCUCC

-continued

AAGUGACCUCGCCCCGGACCUGCCCUCCCGCCAGGUGCACCCACCUGCAAUAAAUGCAGCG

AAGCCGGGAUUCGAAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAAAAA tdTomato:

*Part of the T7 promoter*, Ethris' minimal 5′ UTR, *vector backbone sequence (pVAX Vektor: Life Technologies)*, *Kozak element*, *start codon (AUG)*, codon optimized sequence encoding a functional version of a tdTomato protein, *stop codon (UAG)*, part of restriction site for NotI, *part of the vector backbone sequence (pVAX Vektor: Life Technologies)*

SEQ ID NO: 3

GGGAGACCCAAGCUGGCUAGCGUUUAAACUUAAGCUUGGUACCGCGGCCCGGGAUCCACCGGUCGCCACCAU

GGUGAGCAAGGGCGAGGAGGUCAUCAAAGAGUUCAUGCGCUUCAAGGUGCG

CAUGGAGGGCUCCAUGAACGGCCACGAGUUCGAGAUCGAGGGCGAGGGCGA

GGGCCGCCCCUACGAGGGCACCCAGACCGCCAAGCUGAAGGUGACCAAGGG

CGGCCCCCUGCCCUUCGCCUGGGACAUCCUGUCCCCCCAGUUCAUGUACGG

CUCCAAGGCGUACGUGAAGCACCCCGCCGACAUCCCCGAUUACAAGAAGCUG

UCCUUCCCCGAGGGCUUCAAGUGGGAGCGCGUGAUGAACUUCGAGGACGGC

GGUCUGGUGACCGUGACCCAGGACUCCUCCCUGCAGGACGGCACGCUGAUC

UACAAGGUGAAGAUGCGCGGCACCAACUUCCCCCCCGACGGCCCCGUAAUGC

AGAAGAAGACCAUGGGCUGGGAGGCCUCCACCGAGCGCCUGUACCCCCGCG

ACGGCGUGCUGAAGGGCGAGAUCCACCAGGCCCUGAAGCUGAAGGACGGCG

GCCACUACCUGGUGGAGUUCAAGACCAUCUACAUGGCCAAGAAGCCCGUGCA

ACUGCCCGGCUACUACUACGUGGACACCAAGCUGGACAUCACCUCCCACAAC

GAGGACUACACCAUCGUGGAACAGUACGAGCGCUCCGAGGGCCGCCACCACC

UGUUCCUGGGGCAUGGCACCGGCAGCACCGGCAGCGGCAGCUCCGGCACCG

CCUCCUCCGAGGACAACAACAUGGCCGUCAUCAAAGAGUUCAUGCGCUUCAA

GGUGCGCAUGGAGGGCUCCAUGAACGGCCACGAGUUCGAGAUCGAGGGCGA

GGGCGAGGGCCGCCCCUACGAGGGCACCCAGACCGCCAAGCUGAAGGUGAC

CAAGGGCGGCCCCCUGCCCUUCGCCUGGGACAUCCUGUCCCCCCAGUUCAU

GUACGGCUCCAAGGCGUACGUGAAGCACCCCGCCGACAUCCCCGAUUACAAG

AAGCUGUCCUUCCCCGAGGGCUUCAAGUGGGAGCGCGUGAUGAACUUCGAG

GACGGCGGUCUGGUGACCGUGACCCAGGACUCCUCCCUGCAGGACGGCACG

CUGAUCUACAAGGUGAAGAUGCGCGGCACCAACUUCCCCCCCGACGGCCCCG

UAAUGCAGAAGAAGACCAUGGGCUGGGAGGCCUCCACCGAGCGCCUGUACCC

CCGCGACGGCGUGCUGAAGGGCGAGAUCCACCAGGCCCUGAAGCUGAAGGA

CGGCGGCCACUACCUGGUGGAGUUCAAGACCAUCUACAUGGCCAAGAAGCCC

GUGCAACUGCCCGGCUACUACUACGUGGACACCAAGCUGGACAUCACCUCCC

ACAACGAGGACUACACCAUCGUGGAACAGUACGAGCGCUCCGAGGGCCGCCA

CCACCUGUUCCUGUACGGCAUGGACGAGCUGUACAAGUAGGCGGCCAAUUCUGCAGAA

AAAAAAAAAAAAAAAAAAAAAAAAAAAAAAAAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAGCGGCC

-continued

MCIDAS sequence with Ethris' minimal 5' UTR and optional 3' UTR:

*Part of the T7 promoter*, Ethris' minimal 5′ UTR, *Kozak element*, start codon (AUG), codon optimized sequence encoding a functional version of a human MCIDAS protein, stop codon (UGA), *optional 3′ UTR* (also functions as reverse primer binding site for PCR based template production), restriction site for NheI, *poly(A) tail*

SEQ ID NO: 4

*GGGAGA*_C_*GCCACC*AUGCAAGCUUGUGGCGGCGGAGCUGCUGGAAGAAGGGCCU

UCGAUAGCAUCUGCCCCAACCGGAUGCUUGCCCUUCCUGGUAGAGCCCUGCU

GUGCAAGCCUGGCAAGCCCGAGAGAAAGUUCGCCCCUCCAAGAAAGUUCUUC

CCCGGCUGUACUGGCGGCAGCCCUGUGUCUGUGUAUGAGGACCCUCCUGAU

GCCGAGCCUACAGCUCUGCCUGCUCUGACCACAAUCGACCUGCAGGAUCUGG

CCGAUUGCAGCUCUCUGCUGGGAUCUGAUGCUCCUCCUGGCGGAGAUCUGG

CUGCCUCUCAGAAUCACAGCCACCAGACAGAGGCCGACUUCAACCUGCAAGA

CUUCCGGGACACCGUGGACGACCUGAUCAGCGAUAGCAGCAGCAUGAUGAGC

CCCACUCUGGCCAGCGGCGAUUUCCCAUUCAGCCCCUGUGACAUCAGCCCUU

UCGGCCCUUGUCUGAGCCCUCCACUGGAUCCUAGAGCACUGCAGAGCCCACC

UCUGAGGCCUCCAGAUGUUCCUCCACCUGAGCAGUACUGGAAAGAGGUGGCC

GACCAGAACCAGAGAGCACUGGGCGACGCUCUGGUGGAAAACAACCAGCUGC

ACGUGACCCUGACACAGAAGCAAGAAGAGAUCGCCAGCCUGAAAGAACGGAA

UGUGCAGCUGAAAGAGCUGGCCUCCAGGACAAGACACCUGGCCAGUGUGCU

GGACAAGCUGAUGAUCACCCAGAGCAGAGAUUGCGGAGCCGCCGCUGAACCU

UUUCUGCUGAAGGCCAAGGCCAAGAGAAGCCUGGAAGAACUGGUGUCUGCCG

CCGGACAGGAUUGCGCUGAAGUGGAUGCCAUCCUGCGCGAGAUCAGCGAGA

GAUGUGAUGAGGCCCUGCAGAGCAGGGACCCCAAAAGACCUAGACUGCUGCC

CGAGCCUGCCAACACCGAUACCAGACCUGGAAAUCUGCACGGCGCCUUCAGA

GGCCUGAGAACCGAUUGCUCUAGAAGCGCCCUGAACCUGAGCCACAGCGAAC

UCGAAGAAGGCGGCAGCUUCAGCACCCGGAUCAGAAGCCACAGCACCAUCAG

AACCCUGGCCUUUCCACAGGGCAACGCCUUCACAAUCAGAACCGCCAACGGC

GGCUACAAGUUCAGAUGGGUGCCAAGCUGAGCUAGC*CACCGGGCAAUACGA*

*GCUCAAGCCAGUCUC**AAAAAAAAAAAAAAAAAAAAAAAAAAAAAAAAAAAAAAAAAAAAAAAAAAAAAAAAAAAAAAAA*

*AAAAAAAAAAAAAAAAAAAAAAAAAAAAAAAAAAAAAAAAAAAAAAAAAAAAAAAA*

Sequence with Ethris' minimal 5' UTR (ETH031T06):

*Part of the T7 promoter*, Ethris' minimal 5′ UTR, *Kozak element*, start codon (AUG), codon optimized sequence encoding a functional version of a human CCDC40 protein, stop codon (UGA), part of restriction site for BstBI, *polyA*: tail of "A" produced via post polyadenylation of mRNA

SEQ ID NO: 5

*GGGAGA*_C_*GCCACC*AUGGCUGAACCUGGCGGAGCCGCCGGAAGAUCCCACCCUG

AAGAUGGCUCUGCCAGCGAGGGCGAGAAAGAGGGCAACAACGAGAGCCACAU

GGUGUCCCCCCCAGAGAAGGACGACGGCCAGAAAGGCGAAGAGGCCGUGGG

CUCUACCGAGCACCCUGAGGAAGUGACCACACAGGCCGAGGCCGCCAUUGAA

GAGGGCGAGGUGGAAACAGAGGGCGAAGCCGCUGUGGAAGGCGAAGAGGAA

GCCGUGUCUUACGGCGACGCCGAGAGCGAGGAAGAGUACUACUACACCGAGA

-continued

CAAGCAGCCCCGAGGGCCAGAUCUCUGCCGCCGAUACCACCUACCCCUACUU

CAGCCCCCCUCAGGAACUGCCUGGGGAAGAGGCCUACGAUAGCGUGUCCGG

CGAAGCUGGCCUGCAGGGCUUUCAGCAGGAAGCCACAGGCCCUCCCGAGAG

CCGGGAAAGAAGAGUGACAAGCCCCGAGCCUAGCCACGGCGUGCUGGGACCA

UCUGAGCAGAUGGGCCAAGUGACCUCUGGCCCUGCUGUGGGCAGACUGACA

GGCAGCACAGAGGAACCUCAGGGCCAGGUGCUGCCUAUGGGAGUGCAGCAC

CGGUUCAGACUGAGCCACGGCAGCGACAUCGAGAGCAGCGACCUGGAAGAGU

UCGUCAGCCAGGAACCCGUGAUCCCUCCUGGCGUGCCAGAUGCCCAUCCCAG

GGAAGGCGAUCUGCCCGUGUUCCAGGACCAGAUCCAGCAGCCCUCUACCGAA

GAGGGGGCUAUGGCCGAGAGAGUGGAAAGCGAGGGCUCCGACGAAGAAGCC

GAGGACGAGGGAUCUCAGCUGGUGGUGCUGGACCCCGACCACCCUCUGAUG

GUGCGGUUUCAGGCCGCCCUGAAGAACUACCUGAACCGGCAGAUCGAGAAGC

UGAAACUGGACCUGCAGGAACUGGUGGUGGCCACAAAGCAGAGCAGAGCCCA

GAGACAGGAACUGGGCGUGAACCUGUACGAGGUGCAGCAGCAUCUGGUGCA

UCUGCAGAAGCUGCUGGAAAAGAGCCACGACCGGCACGCCAUGGCCAGCUCU

GAGCGCAGACAGAAAGAGGAAGAACUGCAGGCCGCCAGAGCCCUGUACACCA

AGACAUGCGCCGCUGCCAACGAGGAACGGAAGAAGCUGGCUGCCCUGCAGAC

CGAGAUGGAAAACCUGGCUCUGCACCUGUUCUACAUGCAGAAUAUCGACCAG

GACAUGCGGGACGACAUCAGAGUGAUGACCCAGGUCGUGAAGAAGGCCGAGA

CAGAGAGAAUCCGGGCCGAGAUUGAGAAGAAAAAGCAGGACCUGUACGUGGA

CCAGCUGACCACCAGGGCCCAGCAGCUGGAAGAGGAUAUCGCCCUGUUCGAG

GCCCAGUACCUGGCCCAGGCCGAAGAUACCCGGAUCCUGAGAAAGGCCGUGU

CCGAGGCCUGCACCGAGAUCGAUGCCAUCAGCGUGGAAAAGCGGCGGAUCAU

GCAGCAGUGGGCCAGCAGCCUCGUGGGCAUGAAGCACAGAGAUGAGGCCCA

CCGGGCCGUGCUGGAAGCUCUGAGAGGCUGUCAGCACCAGGCCAAGAGCAC

CGACGGCGAGAUCGAGGCCUACAAGAAAUCCAUCAUGAAGGAAGAGGAAAAG

AACGAGAAACUGGCCAGCAUCCUGAACAGAACCGAAACCGAGGCCACCCUGC

UGCAGAAACUGACCACCCAGUGCCUGACCAAACAGGUGGCCCUGCAGUCCCA

GUUCAACACCUACAGACUGACCCUGCAGGACACCGAGGACGCCCUGAGUCAG

GAUCAGCUGGAACAGAUGAUUCUGACCGAGGAACUGCAGGCUAUCCGGCAGG

CCAUUCAGGGGGAGCUGGAACUGCGGAGAAAGACCGACGCCGCCAUCAGAGA

GAAGCUGCAGGAACACAUGACCAGCAACAAGACCACCAAGUACUUCAACCAGC

UGAUUCUGCGCCUGCAGAAAGAAAAGACCAACAUGAUGACACACCUGAGCAA

GAUCAACGGCGACAUUGCCCAGACCACCCUGGACAUCACCCACACCAGCAGC

AGACUGGACGCCCACCAGAAAACCCUGGUGGAACUGGACCAGGAUGUGAAGA

AAGUGAACGAGCUGAUCACCAACAGCCAGAGCGAGAUCAGCCGGCGGACCAU

CCUGAUCGAGAGAAAGCAGGGCCUGAUCAACUUCCUGAACAAACAGCUGGAA

AGAAUGGUGUCCGAGCUGGGCGGCGAGGAAGUGGGACCUCUGGAACUGGAA

AUCAAGCGGCUGAGCAAGCUGAUCGACGAGCACGACGGCAAGGCCGUGCAG

GCUCAAGUGACAUGGCUGCGGCUGCAGCAGGAAAUGGUCAAAGUGACCCAGG

-continued

AACAGGAAGAACAGCUGGCCUCCCUGGACGCCAGCAAGAAAGAACUGCACAU

CAUGGAACAGAAAAAGCUGCGGGUGGAAAGCAAGAUCGAGCAGGAAAAAAAA

GAACAGAAAGAAAUCGAGCACCACAUGAAGGACCUGGACAACGACCUGAAGAA

ACUGAAUAUGCUGAUGAACAAGAACCGCUGCUCCAGCGAAGAACUGGAACAG

AACAACAGAGUGACCGAGAACGAGUUCGUGCGGAGCCUGAAGGCCAGCGAGC

GGGAAACCAUCAAGAUGCAGGACAAGCUGAACCAGCUGUCCGAGGAAAAAGC

CACACUGCUGAACCAGCUGGUGGAAGCCGAGCACCAGAUCAUGCUGUGGGAG

AAGAAGAUCCAGCUGGCCAAAGAAAUGCGGAGCAGCGUGGACAGCGAGAUCG

GCCAGACCGAAAUCAGAGCCAUGAAGGGCGAGAUCCACCGGAUGAAAGUGCG

GCUGGGACAGCUGCUGAAACAGCAGGAAAAGAUGAUCCGGGCCAUGGAACUG

GCCGUGGCCAGACGGGAAACCGUGACAACCCAGGCUGAGGGCCAGCGGAAG

AUGGACAGAAAGGCCCUGACCCGGACCGACUUCCACCACAAGCAGCUGGAAC

UGAGGCGGAAGAUCCGGGACGUGCGGAAGGCCACCGAUGAGUGCACAAAGA

CAGUGCUGGAACUGGAAGAGACACAGCGGAACGUGUCCUCCAGCCUGCUGGA

AAAACAGGAAAAGCUGAGCGUGAUCCAGGCCGACUUCGACACCCUGGAAGCU

GACCUGACAAGACUGGGAGCCCUGAAAAGACAGAACCUGUCCGAGAUCGUGG

CACUGCAGACCCGGCUGAAACAUCUGCAGGCUGUGAAAGAGGGACGCUACGU

GUUCCUGUUCAGAUCCAAGCAGUCUCUGGUGCUGGAAAGACAGCGGCUGGA

CAAGCGGCUGGCACUGAUUGCCACCAUCCUGGAUAGAGUGCGCGACGAGUAC

CCACAGUUCCAGGAAGCACUGCACAAGGUGUCCCAGAUGAUCGCCAACAAGC

UGGAAUCCCCUGGCCCCAGCUGAUUCG-*polyA*

Sequence with TISU 5' UTR (ETH031T07):

*Part of the 17 promoter*, Ethris' minimal 5' UTR with additional U nucleotide, *TISU element*, start codon (AUG), codon optimized sequence encoding a functional version of a human CCDC40 protein, stop codon (UGA), part of restriction site for BstBl, *polyA*: tail of "A" produced via post polyadenylation of mRNA

SEQ ID NO: 6

*GGGAGA*CU*GCCAAG*AUGGCUGAACCUGGCGGAGCCGCCGGAAGAUCCCACCCU

GAAGAUGGCUCUGCCAGCGAGGGCGAGAAAGAGGGCAACAACGAGAGCCACA

UGGUGUCCCCCCCAGAGAAGGACGACGGCCAGAAAGGCGAAGAGGCCGUGG

GCUCUACCGAGCACCCUGAGGAAGUGACCACACAGGCCGAGGCCGCCAUUGA

AGAGGGCGAGGUGGAAACAGAGGGCGAAGCCGCUGUGGAAGGCGAAGAGGA

AGCCGUGUCUUACGGCGACGCCGAGAGCGAGGAAGAGUACUACUACACCGAG

ACAAGCAGCCCCGAGGGCCAGAUCUCUGCCGCCGAUACCACCUACCCCUACU

UCAGCCCCCCUCAGGAACUGCCUGGGGAAGAGGCCUACGAUAGCGUGUCCG

GCGAAGCUGGCCUGCAGGGCUUUCAGCAGGAAGCCACAGGCCCUCCCGAGA

GCCGGGAAAGAAGAGUGACAAGCCCCGAGCCUAGCCACGGCGUGCUGGGAC

CAUCUGAGCAGAUGGGCCAAGUGACCUCUGGCCCUGCUGUGGGCAGACUGA

CAGGCAGCACAGAGGAACCUCAGGGCCAGGUGCUGCCUAUGGGAGUGCAGC

ACCGGUUCAGACUGAGCCACGGCAGCGACAUCGAGAGCAGCGACCUGGAAGA

GUUCGUCAGCCAGGAACCCGUGAUCCCUCCUGGCGUGCCAGAUGCCCAUCC

CAGGGAAGGCGAUCUGCCCGUGUUCCAGGACCAGAUCCAGCAGCCCUCUACC

-continued

GAAGAGGGGGCUAUGGCCGAGAGAGUGGAAAGCGAGGGCUCCGACGAAGAA

GCCGAGGACGAGGGAUCUCAGCUGGUGGUGCUGGACCCCGACCACCCUCUG

AUGGUGCGGUUUCAGGCCGCCCUGAAGAACUACCUGAACCGGCAGAUCGAGA

AGCUGAAACUGGACCUGCAGGAACUGGUGGUGGCCACAAAGCAGAGCAGAGC

CCAGAGACAGGAACUGGGCGUGAACCUGUACGAGGUGCAGCAGCAUCUGGU

GCAUCUGCAGAAGCUGCUGGAAAAGAGCCACGACCGGCACGCCAUGGCCAGC

UCUGAGCGCAGACAGAAAGAGGAAGAACUGCAGGCCGCCAGAGCCCUGUACA

CCAAGACAUGCGCCGCUGCCAACGAGGAACGGAAGAAGCUGGCUGCCCUGCA

GACCGAGAUGGAAAACCUGGCUCUGCACCUGUUCUACAUGCAGAAUAUCGAC

CAGGACAUGCGGGACGACAUCAGAGUGAUGACCCAGGUCGUGAAGAAGGCCG

AGACAGAGAGAAUCCGGGCCGAGAUUGAGAAGAAAAAGCAGGACCUGUACGU

GGACCAGCUGACCACCAGGGCCCAGCAGCUGGAAGAGGAUAUCGCCCUGUUC

GAGGCCCAGUACCUGGCCCAGGCCGAAGAUACCCGGAUCCUGAGAAAGGCCG

UGUCCGAGGCCUGCACCGAGAUCGAUGCCAUCAGCGUGGAAAAGCGGCGGA

UCAUGCAGCAGUGGGCCAGCAGCCUCGUGGGCAUGAAGCACAGAGAUGAGG

CCCACCGGGCCGUGCUGGAAGCUCUGAGAGGCUGUCAGCACCAGGCCAAGA

GCACCGACGGCGAGAUCGAGGCCUACAAGAAAUCCAUCAUGAAGGAAGAGGA

AAAGAACGAGAAACUGGCCAGCAUCCUGAACAGAACCGAAACCGAGGCCACCC

UGCUGCAGAAACUGACCACCCAGUGCCUGACCAAACAGGUGGCCCUGCAGUC

CCAGUUCAACACCUACAGACUGACCCUGCAGGACACCGAGGACGCCCUGAGU

CAGGAUCAGCUGGAACAGAUGAUUCUGACCGAGGAACUGCAGGCUAUCCGGC

AGGCCAUUCAGGGGGAGCUGGAACUGCGGAGAAAGACCGACGCCGCCAUCA

GAGAGAAGCUGCAGGAACACAUGACCAGCAACAAGACCACCAAGUACUUCAAC

CAGCUGAUUCUGCGCCUGCAGAAAGAAAAGACCAACAUGAUGACACACCUGA

GCAAGAUCAACGGCGACAUUGCCCAGACCACCCUGGACAUCACCCACACCAG

CAGCAGACUGGACGCCCACCAGAAAACCCUGGUGGAACUGGACCAGGAUGUG

AAGAAAGUGAACGAGCUGAUCACCAACAGCCAGAGCGAGAUCAGCCGGCGGA

CCAUCCUGAUCGAGAGAAAGCAGGGCCUGAUCAACUUCCUGAACAAACAGCU

GGAAAGAAUGGUGUCCGAGCUGGGCGGCGAGGAAGUGGGACCUCUGGAACU

GGAAAUCAAGCGGCUGAGCAAGCUGAUCGACGAGCACGACGGCAAGGCCGUG

CAGGCUCAAGUGACAUGGCUGCGGCUGCAGCAGGAAAUGGUCAAAGUGACCC

AGGAACAGGAAGAACAGCUGGCCUCCCUGGACGCCAGCAAGAAAGAACUGCA

CAUCAUGGAACAGAAAAAGCUGCGGGUGGAAAGCAAGAUCGAGCAGGAAAAA

AAAGAACAGAAAGAAAUCGAGCACCACAUGAAGGACCUGGACAACGACCUGAA

GAAACUGAAUAUGCUGAUGAACAAGAACCGCUGCUCCAGCGAAGAACUGGAA

CAGAACAACAGAGUGACCGAGAACGAGUUCGUGCGGAGCCUGAAGGCCAGCG

AGCGGGAAACCAUCAAGAUGCAGGACAAGCUGAACCAGCUGUCCGAGGAAAA

AGCCACACUGCUGAACCAGCUGGUGGAAGCCGAGCACCAGAUCAUGCUGUGG

GAGAAGAAGAUCCAGCUGGCCAAAGAAAUGCGGAGCAGCGUGGACAGCGAGA

UCGGCCAGACCGAAAUCAGAGCCAUGAAGGGCGAGAUCCACCGGAUGAAAGU

-continued

GCGGCUGGGACAGCUGCUGAAACAGCAGGAAAAGAUGAUCCGGGCCAUGGAA

CUGGCCGUGGCCAGACGGGAAACCGUGACAACCCAGGCUGAGGGCCAGCGG

AAGAUGGACAGAAAGGCCCUGACCCGGACCGACUUCCACCACAAGCAGCUGG

AACUGAGGCGGAAGAUCCGGGACGUGCGGAAGGCCACCGAUGAGUGCACAAA

GACAGUGCUGGAACUGGAAGAGACACAGCGGAACGUGUCCUCCAGCCUGCUG

GAAAAACAGGAAAAGCUGAGCGUGAUCCAGGCCGACUUCGACACCCUGGAAG

CUGACCUGACAAGACUGGGAGCCCUGAAAAGACAGAACCUGUCCGAGAUCGU

GGCACUGCAGACCCGGCUGAAACAUCUGCAGGCUGUGAAAGAGGGACGCUAC

GUGUUCCUGUUCAGAUCCAAGCAGUCUCUGGUGCUGGAAAGACAGCGGCUG

GACAAGCGGCUGGCACUGAUUGCCACCAUCCUGGAUAGAGUGCGCGACGAG

UACCCACAGUUCCAGGAAGCACUGCACAAGGUGUCCCAGAUGAUCGCCAACA

AGCUGGAAUCCCCUGGCCCCAGCUGAUUCG-polyA

Sequence with hAg 5' UTR but without 3' UTR (ETH031T08):

*Part of the T7 promoter*, Ethris' minimal 5' UTR, hAg *5'UTR*, *Kozak element*, start codon (AUG), codon optimized sequence encoding a functional version of a human CCDC40 protein, stop codon (UGA), part of restriction site for BstBl, polyA: tail of "A" produced via post polyadenylation of mRNA

SEQ ID NO: 7

*GGGAGA*CUCUUCUGGUCCCCACAGACUCAGAGAGAAC*GCCACC*AUGGCUGAACC

UGGCGGAGCCGCCGGAAGAUCCCACCCUGAAGAUGGCUCUGCCAGCGAGGG

CGAGAAAGAGGGCAACAACGAGAGCCACAUGGUGUCCCCCCAGAGAAGGAC

GACGGCCAGAAAGGCGAAGAGGCCGUGGGCUCUACCGAGCACCCUGAGGAA

GUGACCACACAGGCCGAGGCCGCCAUUGAAGAGGGCGAGGUGGAAACAGAG

GGCGAAGCCGCUGUGGAAGGCGAAGAGGAAGCCGUGUCUUACGGCGACGCC

GAGAGCGAGGAAGAGUACUACUACACCGAGACAAGCAGCCCCGAGGGCCAGA

UCUCUGCCGCCGAUACCACCUACCCCUACUUCAGCCCCCCUCAGGAACUGCC

UGGGGAAGAGGCCUACGAUAGCGUGUCCGGCGAAGCUGGCCUGCAGGGCUU

UCAGCAGGAAGCCACAGGCCCUCCCGAGAGCCGGGAAAGAAGAGUGACAAGC

CCCGAGCCUAGCCACGGCGUGCUGGGACCAUCUGAGCAGAUGGGCCAAGUG

ACCUCUGGCCCUGCUGUGGGCAGACUGACAGGCAGCACAGAGGAACCUCAG

GGCCAGGUGCUGCCUAUGGGAGUGCAGCACCGGUUCAGACUGAGCCACGGC

AGCGACAUCGAGAGCAGCGACCUGGAAGAGUUCGUCAGCCAGGAACCCGUGA

UCCCUCCUGGCGUGCCAGAUGCCCAUCCCAGGGAAGGCGAUCUGCCCGUGU

UCCAGGACCAGAUCCAGCAGCCCUCUACCGAAGAGGGGGCUAUGGCCGAGAG

AGUGGAAAGCGAGGGCUCCGACGAAGAAGCCGAGGACGAGGGAUCUCAGCU

GGUGGUGCUGGACCCCGACCACCCUCUGAUGGUGCGGUUUCAGGCCGCCCU

GAAGAACUACCUGAACCGGCAGAUCGAGAAGCUGAAACUGGACCUGCAGGAA

CUGGUGGUGGCCACAAAGCAGAGCAGAGCCCAGAGACAGGAACUGGGCGUG

AACCUGUACGAGGUGCAGCAGCAUCUGGUGCAUCUGCAGAAGCUGCUGGAAA

AGAGCCACGACCGGCACGCCAUGGCCAGCUCUGAGCGCAGACAGAAAGAGGA

AGAACUGCAGGCCGCCAGAGCCCUGUACACCAAGACAUGCGCCGCUGCCAAC

GAGGAACGGAAGAAGCUGGCUGCCCUGCAGACCGAGAUGGAAAACCUGGCUC

-continued

UGCACCUGUUCUACAUGCAGAAUAUCGACCAGGACAUGCGGGACGACAUCAG

AGUGAUGACCCAGGUCGUGAAGAAGGCCGAGACAGAGAGAAUCCGGGCCGAG

AUUGAGAAGAAAAAGCAGGACCUGUACGUGGACCAGCUGACCACCAGGGCCC

AGCAGCUGGAAGAGGAUAUCGCCCUGUUCGAGGCCCAGUACCUGGCCCAGG

CCGAAGAUACCCGGAUCCUGAGAAAGGCCGUGUCCGAGGCCUGCACCGAGAU

CGAUGCCAUCAGCGUGGAAAAGCGGCGGAUCAUGCAGCAGUGGGCCAGCAG

CCUCGUGGGCAUGAAGCACAGAGAUGAGGCCCACCGGGCCGUGCUGGAAGC

UCUGAGAGGCUGUCAGCACCAGGCCAAGAGCACCGACGGCGAGAUCGAGGC

CUACAAGAAAUCCAUCAUGAAGGAAGAGGAAAAGAACGAGAAACUGGCCAGCA

UCCUGAACAGAACCGAAACCGAGGCCACCCUGCUGCAGAAACUGACCACCCA

GUGCCUGACCAAACAGGUGGCCCUGCAGUCCCAGUUCAACACCUACAGACUG

ACCCUGCAGGACACCGAGGACGCCCUGAGUCAGGAUCAGCUGGAACAGAUGA

UUCUGACCGAGGAACUGCAGGCUAUCCGGCAGGCCAUUCAGGGGGAGCUGG

AACUGCGGAGAAAGACCGACGCCGCCAUCAGAGAGAAGCUGCAGGAACACAU

GACCAGCAACAAGACCACCAAGUACUUCAACCAGCUGAUUCUGCGCCUGCAG

AAAGAAAAGACCAACAUGAUGACACACCUGAGCAAGAUCAACGGCGACAUUGC

CCAGACCACCCUGGACAUCACCCACACCAGCAGCAGACUGGACGCCCACCAG

AAAACCCUGGUGGAACUGGACCAGGAUGUGAAGAAAGUGAACGAGCUGAUCA

CCAACAGCCAGAGCGAGAUCAGCCGGCGGACCAUCCUGAUCGAGAGAAAGCA

GGGCCUGAUCAACUUCCUGAACAAACAGCUGGAAAGAAUGGUGUCCGAGCUG

GGCGGCGAGGAAGUGGGACCUCUGGAACUGGAAAUCAAGCGGCUGAGCAAG

CUGAUCGACGAGCACGACGGCAAGGCCGUGCAGGCUCAAGUGACAUGGCUG

CGGCUGCAGCAGGAAAUGGUCAAAGUGACCCAGGAACAGGAAGAACAGCUGG

CCUCCCUGGACGCCAGCAAGAAAGAACUGCACAUCAUGGAACAGAAAAAGCU

GCGGGUGGAAAGCAAGAUCGAGCAGGAAAAAAAAGAACAGAAAGAAAUCGAGC

ACCACAUGAAGGACCUGGACAACGACCUGAAGAAACUGAAUAUGCUGAUGAAC

AAGAACCGCUGCUCCAGCGAAGAACUGGAACAGAACAACAGAGUGACCGAGA

ACGAGUUCGUGCGGAGCCUGAAGGCCAGCGAGCGGGAAACCAUCAAGAUGCA

GGACAAGCUGAACCAGCUGUCCGAGGAAAAAGCCACACUGCUGAACCAGCUG

GUGGAAGCCGAGCACCAGAUCAUGCUGUGGGAGAAGAAGAUCCAGCUGGCCA

AAGAAAUGCGGAGCAGCGUGGACAGCGAGAUCGGCCAGACCGAAAUCAGAGC

CAUGAAGGGCGAGAUCCACCGGAUGAAAGUGCGGCUGGGACAGCUGCUGAAA

CAGCAGGAAAAGAUGAUCCGGGCCAUGGAACUGGCCGUGGCCAGACGGGAAA

CCGUGACAACCCAGGCUGAGGGCCAGCGGAAGAUGGACAGAAAGGCCCUGAC

CCGGACCGACUUCCACCACAAGCAGCUGGAACUGAGGCGGAAGAUCCGGGAC

GUGCGGAAGGCCACCGAUGAGUGCACAAAGACAGUGCUGGAACUGGAAGAGA

CACAGCGGAACGUGUCCUCCAGCCUGCUGGAAAAACAGGAAAAGCUGAGCGU

GAUCCAGGCCGACUUCGACACCCUGGAAGCUGACCUGACAAGACUGGGAGCC

CUGAAAAGACAGAACCUGUCCGAGAUCGUGGCACUGCAGACCCGGCUGAAAC

AUCUGCAGGCUGUGAAAGAGGGACGCUACGUGUUCCUGUUCAGAUCCAAGCA

-continued

GUCUCUGGUGCUGGAAAGACAGCGGCUGGACAAGCGGCUGGCACUGAUUGC

CACCAUCCUGGAUAGAGUGCGCGACGAGUACCCACAGUUCCAGGAAGCACUG

CACAAGGUGUCCCAGAUGAUCGCCAACAAGCUGGAAUCCCCUGGCCCCAGCU

GAUUCG-polyA

Sequence with human CMV IE9 5' UTR and human Growth hormone 3' UTR (ETH031T10):

*Part of the T7 promoter*, Ethris' minimal 5′ UTR, human CMV IE9 *5′ UTR*, *Kozak element*, start codon (AUG), codon optimized sequence encoding a functional version of a human CCDC40 protein, stop codon (UGA), human Growth hormone *3′ UTR*, part of restriction site for BstBl, polyA: tail of "A" produced via post polyadenylation of mRNA

SEQ ID NO: 8

*GGGAGA*C*CAGAUCGCCUGGAGACGCCAUCCACGCUGUUUUGACCUCCAUAGAAG*

*ACACCGGGACCGAUCCAGCCUCCGCGGCCGGGAACGGUGCAUUGGAACGCG*

*GAUUCCCCGUGCCAAGAGUGACUCACCGUCCUUGACACG**GCCACC*AUGGCUG

AACCUGGCGGAGCCGCCGGAAGAUCCCACCCUGAAGAUGGCUCUGCCAGCGA

GGGCGAGAAAGAGGGCAACAACGAGAGCCACAUGGUGUCCCCCCAGAGAAG

GACGACGGCCAGAAAGGCGAAGAGGCCGUGGGCUCUACCGAGCACCCUGAG

GAAGUGACCACACAGGCCGAGGCCGCCAUUGAAGAGGGCGAGGUGGAAACAG

AGGGCGAAGCCGCUGUGGAAGGCGAAGAGGAAGCCGUGUCUUACGGCGACG

CCGAGAGCGAGGAAGAGUACUACUACACCGAGACAAGCAGCCCCGAGGGCCA

GAUCUCUGCCGCCGAUACCACCUACCCCUACUUCAGCCCCCCUCAGGAACUG

CCUGGGGAAGAGGCCUACGAUAGCGUGUCCGGCGAAGCUGGCCUGCAGGGC

UUUCAGCAGGAAGCCACAGGCCCUCCCGAGAGCCGGGAAAGAAGAGUGACAA

GCCCCGAGCCUAGCCACGGCGUGCUGGGACCAUCUGAGCAGAUGGGCCAAG

UGACCUCUGGCCCUGCUGUGGGCAGACUGACAGGCAGCACAGAGGAACCUCA

GGGCCAGGUGCUGCCUAUGGGAGUGCAGCACCGGUUCAGACUGAGCCACGG

CAGCGACAUCGAGAGCAGCGACCUGGAAGAGUUCGUCAGCCAGGAACCCGUG

AUCCCUCCUGGCGUGCCAGAUGCCCAUCCCAGGGAAGGCGAUCUGCCCGUG

UUCCAGGACCAGAUCCAGCAGCCCUCUACCGAAGAGGGGGCUAUGGCCGAGA

GAGUGGAAAGCGAGGGCUCCGACGAAGAAGCCGAGGACGAGGGAUCUCAGC

UGGUGGUGCUGGACCCCGACCACCCUCUGAUGGUGCGGUUUCAGGCCGCCC

UGAAGAACUACCUGAACCGGCAGAUCGAGAAGCUGAAACUGGACCUGCAGGA

ACUGGUGGUGGCCACAAAGCAGAGCAGAGCCCAGAGACAGGAACUGGGCGU

GAACCUGUACGAGGUGCAGCAGCAUCUGGUGCAUCUGCAGAAGCUGCUGGAA

AAGAGCCACGACCGGCACGCCAUGGCCAGCUCUGAGCGCAGACAGAAAGAGG

AAGAACUGCAGGCCGCCAGAGCCCUGUACACCAAGACAUGCGCCGCUGCCAA

CGAGGAACGGAAGAAGCUGGCUGCCCUGCAGACCGAGAUGGAAAACCUGGCU

CUGCACCUGUUCUACAUGCAGAAUAUCGACCAGGACAUGCGGGACGACAUCA

GAGUGAUGACCCAGGUCGUGAAGAAGGCCGAGACAGAGAGAAUCCGGGCCGA

GAUUGAGAAGAAAAAGCAGGACCUGUACGUGGACCAGCUGACCACCAGGGCC

CAGCAGCUGGAAGAGGAUAUCGCCCUGUUCGAGGCCCAGUACCUGGCCCAG

GCCGAAGAUACCCGGAUCCUGAGAAAGGCCGUGUCCGAGGCCUGCACCGAGA

-continued

UCGAUGCCAUCAGCGUGGAAAAGCGGCGGAUCAUGCAGCAGUGGGCCAGCA

GCCUCGUGGGCAUGAAGCACAGAGAUGAGGCCCACCGGGCCGUGCUGGAAG

CUCUGAGAGGCUGUCAGCACCAGGCCAAGAGCACCGACGGCGAGAUCGAGG

CCUACAAGAAAUCCAUCAUGAAGGAAGAGGAAAAGAACGAGAAACUGGCCAGC

AUCCUGAACAGAACCGAAACCGAGGCCACCCUGCUGCAGAAACUGACCACCC

AGUGCCUGACCAAACAGGUGGCCCUGCAGUCCCAGUUCAACACCUACAGACU

GACCCUGCAGGACACCGAGGACGCCCUGAGUCAGGAUCAGCUGGAACAGAUG

AUUCUGACCGAGGAACUGCAGGCUAUCCGGCAGGCCAUUCAGGGGGAGCUG

GAACUGCGGAGAAAGACCGACGCCGCCAUCAGAGAGAAGCUGCAGGAACACA

UGACCAGCAACAAGACCACCAAGUACUUCAACCAGCUGAUUCUGCGCCUGCA

GAAAGAAAAGACCAACAUGAUGACACACCUGAGCAAGAUCAACGGCGACAUUG

CCCAGACCACCCUGGACAUCACCCACACCAGCAGCAGACUGGACGCCCACCA

GAAAACCCUGGUGGAACUGGACCAGGAUGUGAAGAAAGUGAACGAGCUGAUC

ACCAACAGCCAGAGCGAGAUCAGCCGGCGGACCAUCCUGAUCGAGAGAAAGC

AGGGCCUGAUCAACUUCCUGAACAAACAGCUGGAAAGAAUGGUGUCCGAGCU

GGGCGGCGAGGAAGUGGGACCUCUGGAACUGGAAAUCAAGCGGCUGAGCAA

GCUGAUCGACGAGCACGACGGCAAGGCCGUGCAGGCUCAAGUGACAUGGCU

GCGGCUGCAGCAGGAAAUGGUCAAAGUGACCCAGGAACAGGAAGAACAGCUG

GCCUCCCUGGACGCCAGCAAGAAAGAACUGCACAUCAUGGAACAGAAAAAGC

UGCGGGUGGAAAGCAAGAUCGAGCAGGAAAAAAAAGAACAGAAAGAAAUCGAG

CACCACAUGAAGGACCUGGACAACGACCUGAAGAAACUGAAUAUGCUGAUGAA

CAAGAACCGCUGCUCCAGCGAAGAACUGGAACAGAACAACAGAGUGACCGAG

AACGAGUUCGUGCGGAGCCUGAAGGCCAGCGAGCGGGAAACCAUCAAGAUGC

AGGACAAGCUGAACCAGCUGUCCGAGGAAAAAGCCACACUGCUGAACCAGCU

GGUGGAAGCCGAGCACCAGAUCAUGCUGUGGGAGAAGAAGAUCCAGCUGGC

CAAAGAAAUGCGGAGCAGCGUGGACAGCGAGAUCGGCCAGACCGAAAUCAGA

GCCAUGAAGGGCGAGAUCCACCGGAUGAAAGUGCGGCUGGGACAGCUGCUG

AAACAGCAGGAAAAGAUGAUCCGGGCCAUGGAACUGGCCGUGGCCAGACGGG

AAACCGUGACAACCCAGGCUGAGGGCCAGCGGAAGAUGGACAGAAAGGCCCU

GACCCGGACCGACUUCCACCACAAGCAGCUGGAACUGAGGCGGAAGAUCCGG

GACGUGCGGAAGGCCACCGAUGAGUGCACAAAGACAGUGCUGGAACUGGAAG

AGACACAGCGGAACGUGUCCUCCAGCCUGCUGGAAAAACAGGAAAAGCUGAG

CGUGAUCCAGGCCGACUUCGACACCCUGGAAGCUGACCUGACAAGACUGGGA

GCCCUGAAAAGACAGAACCUGUCCGAGAUCGUGGCACUGCAGACCCGGCUGA

AACAUCUGCAGGCUGUGAAAGAGGGACGCUACGUGUUCCUGUUCAGAUCCAA

GCAGUCUCUGGUGCUGGAAAGACAGCGGCUGGACAAGCGGCUGGCACUGAU

UGCCACCAUCCUGGAUAGAGUGCGCGACGAGUACCCACAGUUCCAGGAAGCA

CUGCACAAGGUGUCCCAGAUGAUCGCCAACAAGCUGGAAUCCCCUGGCCCCA

GCUGA*CGGGUGGCAUCCCUGUGACCCCUCCCCAGUGCCUCUCCUGGCCCUG*

-continued

*GAAGUUGCCACUCCAGUGCCCACCAGCCUUGUCCUAAUAAAAUUAAGUUGC*

*AUC*UUCG-polyA

ETH031T28: N terminal EGFP tag-CCDC40

*Part of the T7 promoter*, Ethris' minimal 5′ UTR, *Kozak element*, start codon (AUG), sequence encoding an *EGFP* protein, *G4S spacer*, codon optimized sequence encoding a functional version of a human CCDC40 protein, stop codon (UGA), part of restriction site for BstBl, *poly(A) tail*

SEQ ID NO: 9

*GGGAGA* *CGCCACC* AUG*GUGAGCAAGGGCGAGGAGCUGUUCACCGGGGUGGUGC*

*CCAUCCUGGUCGAGCUGGACGGCGACGUAAACGGCCACAAGUUCAGCGUGU*

*CCGGCGAGGGCGAGGGCGAUGCCACCUACGGCAAGCUGACCCUGAAGUUCA*

*UCUGCACCACCGGCAAGCUGCCCGUGCCCUGGCCCACCCUCGUGACCACCCU*

*GACCUACGGCGUGCAGUGCUUCAGCCGCUACCCCGACCACAUGAAGCAGCAC*

*GACUUCUUCAAGUCCGCCAUGCCCGAAGGCUACGUCCAGGAGCGCACCAUCU*

*UCUUCAAGGACGACGGCAACUACAAGACCCGCGCCGAGGUGAAGUUCGAGGG*

*CGACACCCUGGUGAACCGCAUCGAGCUGAAGGGCAUCGACUUCAAGGAGGAC*

*GGCAACAUCCUGGGGCACAAGCUGGAGUACAACUACAACAGCCACAACGUCU*

*AUAUCAUGGCCGACAAGCAGAAGAACGGCAUCAAGGUGAACUUCAAGAUCCG*

*CCACAACAUCGAGGACGGCAGCGUGCAGCUCGCCGACCACUACCAGCAGAAC*

*ACCCCCAUCGGCGACGGCCCCGUGCUGCUGCCCGACAACCACUACCUGAGCA*

*CCCAGUCCGCCCUGAGCAAAGACCCCAACGAGAAGCGCGAUCACAUGGUCCU*

*GCUGGAGUUCGUGACCGCCGCCGGGAUCACUCUCGGCAUGGACGAGCUGUA*

*CAAG* *GGCGGAGGGGGCAGC* GCUGAACCUGGCGGAGCCGCCGGAAGAUCCCACCCUG

AAGAUGGCUCUGCCAGCGAGGGCGAGAAAGAGGGCAACAACGAGAGCCACAU

GGUGUCCCCCCCAGAGAAGGACGACGGCCAGAAAGGCGAAGAGGCCGUGGG

CUCUACCGAGCACCCUGAGGAAGUGACCACACAGGCCGAGGCCGCCAUUGAA

GAGGGCGAGGUGGAAACAGAGGGCGAAGCCGCUGUGGAAGGCGAAGAGGAA

GCCGUGUCUUACGGCGACGCCGAGAGCGAGGAAGAGUACUACUACACCGAGA

CAAGCAGCCCCGAGGGCCAGAUCUCUGCCGCCGAUACCACCUACCCCUACUU

CAGCCCCCCUCAGGAACUGCCUGGGGAAGAGGCCUACGAUAGCGUGUCCGG

CGAAGCUGGCCUGCAGGGCUUUCAGCAGGAAGCCACAGGCCCUCCCGAGAG

CCGGGAAAGAAGAGUGACAAGCCCCGAGCCUAGCCACGGCGUGCUGGGACCA

UCUGAGCAGAUGGGCCAAGUGACCUCUGGCCCUGCUGUGGGCAGACUGACA

GGCAGCACAGAGGAACCUCAGGGCCAGGUGCUGCCUAUGGGAGUGCAGCAC

CGGUUCAGACUGAGCCACGGCAGCGACAUCGAGAGCAGCGACCUGGAAGAGU

-continued

UCGUCAGCCAGGAACCCGUGAUCCCUCCUGGCGUGCCAGAUGCCCAUCCCAG

GGAAGGCGAUCUGCCCGUGUUCCAGGACCAGAUCCAGCAGCCCUCUACCGAA

GAGGGGGCUAUGGCCGAGAGAGUGGAAAGCGAGGGCUCCGACGAAGAAGCC

GAGGACGAGGGAUCUCAGCUGGUGGUGCUGGACCCCGACCACCCUCUGAUG

GUGCGGUUUCAGGCCGCCCUGAAGAACUACCUGAACCGGCAGAUCGAGAAGC

UGAAACUGGACCUGCAGGAACUGGUGGUGGCCACAAAGCAGAGCAGAGCCCA

GAGACAGGAACUGGGCGUGAACCUGUACGAGGUGCAGCAGCAUCUGGUGCA

UCUGCAGAAGCUGCUGGAAAAGAGCCACGACCGGCACGCCAUGGCCAGCUCU

GAGCGCAGACAGAAAGAGGAAGAACUGCAGGCCGCCAGAGCCCUGUACACCA

AGACAUGCGCCGCUGCCAACGAGGAACGGAAGAAGCUGGCUGCCCUGCAGAC

CGAGAUGGAAAACCUGGCUCUGCACCUGUUCUACAUGCAGAAUAUCGACCAG

GACAUGCGGGACGACAUCAGAGUGAUGACCCAGGUCGUGAAGAAGGCCGAGA

CAGAGAGAAUCCGGGCCGAGAUUGAGAAGAAAAAGCAGGACCUGUACGUGGA

CCAGCUGACCACCAGGGCCCAGCAGCUGGAAGAGGAUAUCGCCCUGUUCGAG

GCCCAGUACCUGGCCCAGGCCGAAGAUACCCGGAUCCUGAGAAAGGCCGUGU

CCGAGGCCUGCACCGAGAUCGAUGCCAUCAGCGUGGAAAAGCGGCGGAUCAU

GCAGCAGUGGGCCAGCAGCCUCGUGGGCAUGAAGCACAGAGAUGAGGCCCA

CCGGGCCGUGCUGGAAGCUCUGAGAGGCUGUCAGCACCAGGCCAAGAGCAC

CGACGGCGAGAUCGAGGCCUACAAGAAAUCCAUCAUGAAGGAAGAGGAAAAG

AACGAGAAACUGGCCAGCAUCCUGAACAGAACCGAAACCGAGGCCACCCUGC

UGCAGAAACUGACCACCCAGUGCCUGACCAAACAGGUGGCCCUGCAGUCCCA

GUUCAACACCUACAGACUGACCCUGCAGGACACCGAGGACGCCCUGAGUCAG

GAUCAGCUGGAACAGAUGAUUCUGACCGAGGAACUGCAGGCUAUCCGGCAGG

CCAUUCAGGGGGAGCUGGAACUGCGGAGAAAGACCGACGCCGCCAUCAGAGA

GAAGCUGCAGGAACACAUGACCAGCAACAAGACCACCAAGUACUUCAACCAGC

UGAUUCUGCGCCUGCAGAAAGAAAAGACCAACAUGAUGACACACCUGAGCAA

GAUCAACGGCGACAUUGCCCAGACCACCCUGGACAUCACCCACACCAGCAGC

AGACUGGACGCCCACCAGAAAACCCUGGUGGAACUGGACCAGGAUGUGAAGA

AAGUGAACGAGCUGAUCACCAACAGCCAGAGCGAGAUCAGCCGGCGGACCAU

CCUGAUCGAGAGAAAGCAGGGCCUGAUCAACUUCCUGAACAAACAGCUGGAA

AGAAUGGUGUCCGAGCUGGGCGGCGAGGAAGUGGGACCUCUGGAACUGGAA

AUCAAGCGGCUGAGCAAGCUGAUCGACGAGCACGACGGCAAGGCCGUGCAG

GCUCAAGUGACAUGGCUGCGGCUGCAGCAGGAAAUGGUCAAAGUGACCCAGG

AACAGGAAGAACAGCUGGCCUCCCUGGACGCCAGCAAGAAAGAACUGCACAU

CAUGGAACAGAAAAAGCUGCGGGUGGAAAGCAAGAUCGAGCAGGAAAAAAAA

GAACAGAAAGAAAUCGAGCACCACAUGAAGGACCUGGACAACGACCUGAAGAA

ACUGAAUAUGCUGAUGAACAAGAACCGCUGCUCCAGCGAAGAACUGGAACAG

AACAACAGAGUGACCGAGAACGAGUUCGUGCGGAGCCUGAAGGCCAGCGAGC

GGGAAACCAUCAAGAUGCAGGACAAGCUGAACCAGCUGUCCGAGGAAAAAGC

CACACUGCUGAACCAGCUGGUGGAAGCCGAGCACCAGAUCAUGCUGUGGGAG

AAGAAGAUCCAGCUGGCCAAAGAAAUGCGGAGCAGCGUGGACAGCGAGAUCG

-continued

GCCAGACCGAAAUCAGAGCCAUGAAGGGCGAGAUCCACCGGAUGAAAGUGCG

GCUGGGACAGCUGCUGAAACAGCAGGAAAAGAUGAUCCGGGCCAUGGAACUG

GCCGUGGCCAGACGGGAAACCGUGACAACCCAGGCUGAGGGCCAGCGGAAG

AUGGACAGAAAGGCCCUGACCCGGACCGACUUCCACCACAAGCAGCUGGAAC

UGAGGCGGAAGAUCCGGGACGUGCGGAAGGCCACCGAUGAGUGCACAAAGA

CAGUGCUGGAACUGGAAGAGACACAGCGGAACGUGUCCUCCAGCCUGCUGGA

AAAACAGGAAAAGCUGAGCGUGAUCCAGGCCGACUUCGACACCCUGGAAGCU

GACCUGACAAGACUGGGAGCCCUGAAAAGACAGAACCUGUCCGAGAUCGUGG

CACUGCAGACCCGGCUGAAACAUCUGCAGGCUGUGAAAGAGGGACGCUACGU

GUUCCUGUUCAGAUCCAAGCAGUCUCUGGUGCUGGAAAGACAGCGGCUGGA

CAAGCGGCUGGCACUGAUUGCCACCAUCCUGGAUAGAGUGCGCGACGAGUAC

CCACAGUUCCAGGAAGCACUGCACAAGGUGUCCCAGAUGAUCGCCAACAAGC

UGGAAUCCCCUGGCCCCAGCUGAUUCG*AAAAAAAAAAAAAAAAAAAAAAAAAAAAAAAAAAAAAAAA*

*AAAAAAAAAAAAAAAAAAAAAAAAAAAAAAAAAAAAAAAAAAAAAAAAAAAAAAAAAAAAAAAAAAAAAAAAAAAAAAAA*

ETH031T30: C terminal EGFP tag-CCDC40

*Part of the 17 promoter*, Ethris' minimal 5′ UTR, *Kozak element*, start codon (AUG), codon optimized sequence encoding a functional version of a human CCDC40 protein, *G4S spacer*, sequence encoding an *EGFP* protein, stop codon (UGA), part of restriction site for BstBl, *poly(A) tail*

SEQ ID NO: 10

*GGGAGA* *CGCCACC* AUGGCUGAACCUGGCGGAGCCGCCGGAAGAUCCCACCCUG

AAGAUGGCUCUGCCAGCGAGGGCGAGAAAGAGGGCAACAACGAGAGCCACAU

GGUGUCCCCCCCAGAGAAGGACGACGGCCAGAAAGGCGAAGAGGCCGUGGG

CUCUACCGAGCACCCUGAGGAAGUGACCACACAGGCCGAGGCCGCCAUUGAA

GAGGGCGAGGUGGAAACAGAGGGCGAAGCCGCUGUGGAAGGCGAAGAGGAA

GCCGUGUCUUACGGCGACGCCGAGAGCGAGGAAGAGUACUACUACACCGAGA

CAAGCAGCCCCGAGGGCCAGAUCUCUGCCGCCGAUACCACCUACCCCUACUU

CAGCCCCCCUCAGGAACUGCCUGGGGAAGAGGCCUACGAUAGCGUGUCCGG

CGAAGCUGGCCUGCAGGGCUUUCAGCAGGAAGCCACAGGCCCUCCCGAGAG

CCGGGAAAGAAGAGUGACAAGCCCCGAGCCUAGCCACGGCGUGCUGGGACCA

UCUGAGCAGAUGGGCCAAGUGACCUCUGGCCCUGCUGUGGGCAGACUGACA

GGCAGCACAGAGGAACCUCAGGGCCAGGUGCUGCCUAUGGGAGUGCAGCAC

CGGUUCAGACUGAGCCACGGCAGCGACAUCGAGAGCAGCGACCUGGAAGAGU

UCGUCAGCCAGGAACCCGUGAUCCCUCCUGGCGUGCCAGAUGCCCAUCCCAG

GGAAGGCGAUCUGCCCGUGUUCCAGGACCAGAUCCAGCAGCCCUCUACCGAA

GAGGGGGCUAUGGCCGAGAGAGUGGAAAGCGAGGGCUCCGACGAAGAAGCC

GAGGACGAGGGAUCUCAGCUGGUGGUGCUGGACCCCGACCACCCUCUGAUG

GUGCGGUUUCAGGCCGCCCUGAAGAACUACCUGAACCGGCAGAUCGAGAAGC

UGAAACUGGACCUGCAGGAACUGGUGGUGGCCACAAAGCAGAGCAGAGCCCA

GAGACAGGAACUGGGCGUGAACCUGUACGAGGUGCAGCAGCAUCUGGUGCA

UCUGCAGAAGCUGCUGGAAAAGAGCCACGACCGGCACGCCAUGGCCAGCUCU

-continued

GAGCGCAGACAGAAAGAGGAAGAACUGCAGGCCGCCAGAGCCCUGUACACCA

AGACAUGCGCCGCUGCCAACGAGGAACGGAAGAAGCUGGCUGCCCUGCAGAC

CGAGAUGGAAAACCUGGCUCUGCACCUGUUCUACAUGCAGAAUAUCGACCAG

GACAUGCGGGACGACAUCAGAGUGAUGACCCAGGUCGUGAAGAAGGCCGAGA

CAGAGAGAAUCCGGGCCGAGAUUGAGAAGAAAAAGCAGGACCUGUACGUGGA

CCAGCUGACCACCAGGGCCCAGCAGCUGGAAGAGGAUAUCGCCCUGUUCGAG

GCCCAGUACCUGGCCCAGGCCGAAGAUACCCGGAUCCUGAGAAAGGCCGUGU

CCGAGGCCUGCACCGAGAUCGAUGCCAUCAGCGUGGAAAAGCGGCGGAUCAU

GCAGCAGUGGGCCAGCAGCCUCGUGGGCAUGAAGCACAGAGAUGAGGCCCA

CCGGGCCGUGCUGGAAGCUCUGAGAGGCUGUCAGCACCAGGCCAAGAGCAC

CGACGGCGAGAUCGAGGCCUACAAGAAAUCCAUCAUGAAGGAAGAGGAAAAG

AACGAGAAACUGGCCAGCAUCCUGAACAGAACCGAAACCGAGGCCACCCUGC

UGCAGAAACUGACCACCCAGUGCCUGACCAAACAGGUGGCCCUGCAGUCCCA

GUUCAACACCUACAGACUGACCCUGCAGGACACCGAGGACGCCCUGAGUCAG

GAUCAGCUGGAACAGAUGAUUCUGACCGAGGAACUGCAGGCUAUCCGGCAGG

CCAUUCAGGGGGAGCUGGAACUGCGGAGAAAGACCGACGCCGCCAUCAGAGA

GAAGCUGCAGGAACACAUGACCAGCAACAAGACCACCAAGUACUUCAACCAGC

UGAUUCUGCGCCUGCAGAAAGAAAAGACCAACAUGAUGACACACCUGAGCAA

GAUCAACGGCGACAUUGCCCAGACCACCCUGGACAUCACCCACACCAGCAGC

AGACUGGACGCCCACCAGAAAACCCUGGUGGAACUGGACCAGGAUGUGAAGA

AAGUGAACGAGCUGAUCACCAACAGCCAGAGCGAGAUCAGCCGGCGGACCAU

CCUGAUCGAGAGAAAGCAGGGCCUGAUCAACUUCCUGAACAAACAGCUGGAA

AGAAUGGUGUCCGAGCUGGGCGGCGAGGAAGUGGGACCUCUGGAACUGGAA

AUCAAGCGGCUGAGCAAGCUGAUCGACGAGCACGACGGCAAGGCCGUGCAG

GCUCAAGUGACAUGGCUGCGGCUGCAGCAGGAAAUGGUCAAAGUGACCCAGG

AACAGGAAGAACAGCUGGCCUCCCUGGACGCCAGCAAGAAAGAACUGCACAU

CAUGGAACAGAAAAAGCUGCGGGUGGAAAGCAAGAUCGAGCAGGAAAAAAAA

GAACAGAAAGAAAUCGAGCACCACAUGAAGGACCUGGACAACGACCUGAAGAA

ACUGAAUAUGCUGAUGAACAAGAACCGCUGCUCCAGCGAAGAACUGGAACAG

AACAACAGAGUGACCGAGAACGAGUUCGUGCGGAGCCUGAAGGCCAGCGAGC

GGGAAACCAUCAAGAUGCAGGACAAGCUGAACCAGCUGUCCGAGGAAAAAGC

CACACUGCUGAACCAGCUGGUGGAAGCCGAGCACCAGAUCAUGCUGUGGGAG

AAGAAGAUCCAGCUGGCCAAAGAAAUGCGGAGCAGCGUGGACAGCGAGAUCG

GCCAGACCGAAAUCAGAGCCAUGAAGGGCGAGAUCCACCGGAUGAAAGUGCG

GCUGGGACAGCUGCUGAAACAGCAGGAAAAGAUGAUCCGGGCCAUGGAACUG

GCCGUGGCCAGACGGGAAACCGUGACAACCCAGGCUGAGGGCCAGCGGAAG

AUGGACAGAAAGGCCCUGACCCGGACCGACUUCCACCACAAGCAGCUGGAAC

UGAGGCGGAAGAUCCGGGACGUGCGGAAGGCCACCGAUGAGUGCACAAAGA

CAGUGCUGGAACUGGAAGAGACACAGCGGAACGUGUCCUCCAGCCUGCUGGA

AAAACAGGAAAAGCUGAGCGUGAUCCAGGCCGACUUCGACACCCUGGAAGCU

GACCUGACAAGACUGGGAGCCCUGAAAAGACAGAACCUGUCCGAGAUCGUGG

-continued

CACUGCAGACCCGGCUGAAACAUCUGCAGGCUGUGAAAGAGGGACGCUACGU

GUUCCUGUUCAGAUCCAAGCAGUCUCUGGUGCUGGAAAGACAGCGGCUGGA

CAAGCGGCUGGCACUGAUUGCCACCAUCCUGGAUAGAGUGCGCGACGAGUAC

CCACAGUUCCAGGAAGCACUGCACAAGGUGUCCCAGAUGAUCGCCAACAAGC

UGGAAUCCCCUGGCCCCAGCGGCGGAGGGGGCAGCGUGAGCAAGGGCGAGGAGCUG

UUCACCGGGGUGGUGCCCAUCCUGGUCGAGCUGGACGGCGACGUAAACGGC

CACAAGUUCAGCGUGUCCGGCGAGGGCGAGGGCGAUGCCACCUACGGCAAG

CUGACCCUGAAGUUCAUCUGCACCACCGGCAAGCUGCCCGUGCCCUGGCCCA

CCCUCGUGACCACCCUGACCUACGGCGUGCAGUGCUUCAGCCGCUACCCCGA

CCACAUGAAGCAGCACGACUUCUUCAAGUCCGCCAUGCCCGAAGGCUACGUC

CAGGAGCGCACCAUCUUCUUCAAGGACGACGGCAACUACAAGACCCGCGCCG

AGGUGAAGUUCGAGGGCGACACCCUGGUGAACCGCAUCGAGCUGAAGGGCA

UCGACUUCAAGGAGGACGGCAACAUCCUGGGGCACAAGCUGGAGUACAACUA

CAACAGCCACAACGUCUAUAUCAUGGCCGACAAGCAGAAGAACGGCAUCAAG

GUGAACUUCAAGAUCCGCCACAACAUCGAGGACGGCAGCGUGCAGCUCGCCG

ACCACUACCAGCAGAACACCCCCAUCGGCGACGGCCCCGUGCUGCUGCCCGA

CAACCACUACCUGAGCACCCAGUCCGCCCUGAGCAAAGACCCCAACGAGAAG

CGCGAUCACAUGGUCCUGCUGGAGUUCGUGACCGCCGCCGGGAUCACUCUC

GGCAUGGACGAGCUGUACAAGUGAUUCGAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAAAAAAAAAAAAAAAAAAAAAAAAAAAAAAAA

ETH031T26: N terminal HA Tag-CCDC40-T2A peptide-tdTomato with 5' and 3' CYBA UTRs Part of the T7 promoter, Ethris' minimal 5' UTR, CYBA 5' UTR, *Kozak element*, start codon (AUG), HA Tag, G4S spacer, codon optimized sequence encoding a functional version of a human CCDC40 protein,, *T2A peptide*, tdTomato, stop codon (UGA), CYBA *3' UTR*, part of restriction site for BstBl, poly(A) tail

SEQ ID NO: 11

GGGAGACCGCGCCUAGCAGUGUCCCAGCCGGGUUCGUGUCGCCGCCACCAUGUA

CCCCUACGACGUGCCCGACUACGCCGGCGGAGGGGGCAGCGCUGAACCUGGCGGAGCCGCCGGA

AGAUCCCACCCUGAAGAUGGCUCUGCCAGCGAGGGCGAGAAAGAGGGCAACA

ACGAGAGCCACAUGGUGUCCCCCCCAGAGAAGGACGACGGCCAGAAAGGCGA

AGAGGCCGUGGGCUCUACCGAGCACCCUGAGGAAGUGACCACACAGGCCGA

GGCCGCCAUUGAAGAGGGCGAGGUGGAAACAGAGGGCGAAGCCGCUGUGGA

AGGCGAAGAGGAAGCCGUGUCUUACGGCGACGCCGAGAGCGAGGAAGAGUA

CUACUACACCGAGACAAGCAGCCCCGAGGGCCAGAUCUCUGCCGCCGAUACC

-continued
ACCUACCCCUACUUCAGCCCCCCUCAGGAACUGCCUGGGGAAGAGGCCUACG
AUAGCGUGUCCGGCGAAGCUGGCCUGCAGGGCUUUCAGCAGGAAGCCACAG
GCCCUCCCGAGAGCCGGGAAAGAAGAGUGACAAGCCCCGAGCCUAGCCACGG
CGUGCUGGGACCAUCUGAGCAGAUGGGCCAAGUGACCUCUGGCCCUGCUGU
GGGCAGACUGACAGGCAGCACAGAGGAACCUCAGGGCCAGGUGCUGCCUAU
GGGAGUGCAGCACCGGUUCAGACUGAGCCACGGCAGCGACAUCGAGAGCAG
CGACCUGGAAGAGUUCGUCAGCCAGGAACCCGUGAUCCCUCCUGGCGUGCC
AGAUGCCCAUCCCAGGGAAGGCGAUCUGCCCGUGUUCCAGGACCAGAUCCAG
CAGCCCUCUACCGAAGAGGGGGCUAUGGCCGAGAGAGUGGAAAGCGAGGGC
UCCGACGAAGAAGCCGAGGACGAGGGAUCUCAGCUGGUGGUGCUGGACCCC
GACCACCCUCUGAUGGUGCGGUUUCAGGCCGCCCUGAAGAACUACCUGAACC
GGCAGAUCGAGAAGCUGAAACUGGACCUGCAGGAACUGGUGGUGGCCACAAA
GCAGAGCAGAGCCCAGAGACAGGAACUGGGCGUGAACCUGUACGAGGUGCA
GCAGCAUCUGGUGCAUCUGCAGAAGCUGCUGGAAAAGAGCCACGACCGGCAC
GCCAUGGCCAGCUCUGAGCGCAGACAGAAAGAGGAAGAACUGCAGGCCGCCA
GAGCCCUGUACACCAAGACAUGCGCCGCUGCCAACGAGGAACGGAAGAAGCU
GGCUGCCCUGCAGACCGAGAUGGAAAACCUGGCUCUGCACCUGUUCUACAUG
CAGAAUAUCGACCAGGACAUGCGGGACGACAUCAGAGUGAUGACCCAGGUCG
UGAAGAAGGCCGAGACAGAGAGAAUCCGGGCCGAGAUUGAGAAGAAAAAGCA
GGACCUGUACGUGGACCAGCUGACCACCAGGGCCCAGCAGCUGGAAGAGGA
UAUCGCCCUGUUCGAGGCCCAGUACCUGGCCCAGGCCGAAGAUACCCGGAUC
CUGAGAAAGGCCGUGUCCGAGGCCUGCACCGAGAUCGAUGCCAUCAGCGUG
GAAAAGCGGCGGAUCAUGCAGCAGUGGGCCAGCAGCCUCGUGGGCAUGAAG
CACAGAGAUGAGGCCCACCGGGCCGUGCUGGAAGCUCUGAGAGGCUGUCAG
CACCAGGCCAAGAGCACCGACGGCGAGAUCGAGGCCUACAAGAAAUCCAUCA
UGAAGGAAGAGGAAAAGAACGAGAAACUGGCCAGCAUCCUGAACAGAACCGAA
ACCGAGGCCACCCUGCUGCAGAAACUGACCACCCAGUGCCUGACCAAACAGG
UGGCCCUGCAGUCCCAGUUCAACACCUACAGACUGACCCUGCAGGACACCGA
GGACGCCCUGAGUCAGGAUCAGCUGGAACAGAUGAUUCUGACCGAGGAACUG
CAGGCUAUCCGGCAGGCCAUUCAGGGGGAGCUGGAACUGCGGAGAAAGACC
GACGCCGCCAUCAGAGAGAAGCUGCAGGAACACAUGACCAGCAACAAGACCA
CCAAGUACUUCAACCAGCUGAUUCUGCGCCUGCAGAAAGAAAAGACCAACAUG
AUGACACACCUGAGCAAGAUCAACGGCGACAUUGCCCAGACCACCCUGGACA
UCACCCACACCAGCAGCAGACUGGACGCCCACCAGAAAACCCUGGUGGAACU
GGACCAGGAUGUGAAGAAAGUGAACGAGCUGAUCACCAACAGCCAGAGCGAG
AUCAGCCGGCGGACCAUCCUGAUCGAGAGAAAGCAGGGCCUGAUCAACUUCC
UGAACAAACAGCUGGAAAGAAUGGUGUCCGAGCUGGGCGGCGAGGAAGUGG
GACCUCUGGAACUGGAAAUCAAGCGGCUGAGCAAGCUGAUCGACGAGCACGA
CGGCAAGGCCGUGCAGGCUCAAGUGACAUGGCUGCGGCUGCAGCAGGAAAU
GGUCAAAGUGACCCAGGAACAGGAAGAACAGCUGGCCUCCCUGGACGCCAGC
AAGAAAGAACUGCACAUCAUGGAACAGAAAAAGCUGCGGGUGGAAAGCAAGAU -continued

CGAGCAGGAAAAAAAAGAACAGAAAGAAAUCGAGCACCACAUGAAGGACCUGG

ACAACGACCUGAAGAAACUGAAUAUGCUGAUGAACAAGAACCGCUGCUCCAGC

GAAGAACUGGAACAGAACAACAGAGUGACCGAGAACGAGUUCGUGCGGAGCC

UGAAGGCCAGCGAGCGGGAAACCAUCAAGAUGCAGGACAAGCUGAACCAGCU

GUCCGAGGAAAAAGCCACACUGCUGAACCAGCUGGUGGAAGCCGAGCACCAG

AUCAUGCUGUGGGAGAAGAAGAUCCAGCUGGCCAAAGAAAUGCGGAGCAGCG

UGGACAGCGAGAUCGGCCAGACCGAAAUCAGAGCCAUGAAGGGCGAGAUCCA

CCGGAUGAAAGUGCGGCUGGGACAGCUGCUGAAACAGCAGGAAAAGAUGAUC

CGGGCCAUGGAACUGGCCGUGGCCAGACGGGAAACCGUGACAACCCAGGCU

GAGGGCCAGCGGAAGAUGGACAGAAAGGCCCUGACCCGGACCGACUUCCACC

ACAAGCAGCUGGAACUGAGGCGGAAGAUCCGGGACGUGCGGAAGGCCACCG

AUGAGUGCACAAAGACAGUGCUGGAACUGGAAGAGACACAGCGGAACGUGUC

CUCCAGCCUGCUGGAAAAACAGGAAAAGCUGAGCGUGAUCCAGGCCGACUUC

GACACCCUGGAAGCUGACCUGACAAGACUGGGAGCCCUGAAAAGACAGAACC

UGUCCGAGAUCGUGGCACUGCAGACCCGGCUGAAACAUCUGCAGGCUGUGAA

AGAGGGACGCUACGUGUUCCUGUUCAGAUCCAAGCAGUCUCUGGUGCUGGA

AAGACAGCGGCUGGACAAGCGGCUGGCACUGAUUGCCACCAUCCUGGAUAGA

GUGCGCGACGAGUACCCACAGUUCCAGGAAGCACUGCACAAGGUGUCCCAGA

UGAUCGCCAACAAGCUGGAAUCCCCUGGCCCCAGCGGCAGCGGCGAGGGCAGAGG

CAGCCUGCUGACCUGCGGCGACGUGGAGGAGAACCCCGGCCCCAUGGUGAGCAAGGGCGAGGAGG

*UCAUCAAAGAGUUCAUGCGCUUCAAGGUGCGCAUGGAGGGCUCCAUGAACGG*

*CCACGAGUUCGAGAUCGAGGGCGAGGGCGAGGGCCGCCCCUACGAGGGCAC*

*CCAGACCGCCAAGCUGAAGGUGACCAAGGGCGGCCCCCUGCCCUUCGCCUG*

*GGACAUCCUGUCCCCCCAGUUCAUGUACGGCUCCAAGGCGUACGUGAAGCAC*

*CCCGCCGACAUCCCCGAUUACAAGAAGCUGUCCUUCCCCGAGGGCUUCAAGU*

*GGGAGCGCGUGAUGAACUUCGAGGACGGCGGUCUGGUGACCGUGACCCAGG*

*ACUCCUCCCUGCAGGACGGCACGCUGAUCUACAAGGUGAAGAUGCGCGGCAC*

*CAACUUCCCCCCCGACGGCCCCGUAAUGCAGAAGAAGACCAUGGGCUGGGAG*

*GCCUCCACCGAGCGCCUGUACCCCCGCGACGGCGUGCUGAAGGGCGAGAUC*

*CACCAGGCCCUGAAGCUGAAGGACGGCGGCCACUACCUGGUGGAGUUCAAGA*

*CCAUCUACAUGGCCAAGAAGCCCGUGCAACUGCCCGGCUACUACUACGUGGA*

*CACCAAGCUGGACAUCACCUCCCACAACGAGGACUACACCAUCGUGGAACAG*

*UACGAGCGCUCCGAGGGCCGCCACCACCUGUUCCUGGGGCAUGGCACCGGC*

-continued

*AGCACCGGCAGCGGCAGCUCCGGCACCGCCUCCUCCGAGGACAACAACAUGG*

*CCGUCAUCAAAGAGUUCAUGCGCUUCAAGGUGCGCAUGGAGGGCUCCAUGAA*

*CGGCCACGAGUUCGAGAUCGAGGGCGAGGGCGAGGGCCGCCCCUACGAGGG*

*CACCCAGACCGCCAAGCUGAAGGUGACCAAGGGCGGCCCCCUGCCCUUCGCC*

*UGGGACAUCCUGUCCCCCCAGUUCAUGUACGGCUCCAAGGCGUACGUGAAGC*

*ACCCCGCCGACAUCCCCGAUUACAAGAAGCUGUCCUUCCCCGAGGGCUUCAA*

*GUGGGAGCGCGUGAUGAACUUCGAGGACGGCGGUCUGGUGACCGUGACCCA*

*GGACUCCUCCCUGCAGGACGGCACGCUGAUCUACAAGGUGAAGAUGCGCGG*

*CACCAACUUCCCCCCCGACGGCCCCGUAAUGCAGAAGAAGACCAUGGGCUGG*

*GAGGCCUCCACCGAGCGCCUGUACCCCCGCGACGGCGUGCUGAAGGGCGAG*

*AUCCACCAGGCCCUGAAGCUGAAGGACGGCGGCCACUACCUGGUGGAGUUCA*

*AGACCAUCUACAUGGCCAAGAAGCCCGUGCAACUGCCCGGCUACUACUACGU*

*GGACACCAAGCUGGACAUCACCUCCCACAACGAGGACUACACCAUCGUGGAA*

*CAGUACGAGCGCUCCGAGGGCCGCCACCACCUGUUCCUGUACGGCAUGGAC*

*GAGCUGUACAAG*UGA*CCUCGCCCCGGACCUGCCCUCCCGCCGGUGCACCC*

*ACCUGCAAUAAAUGCAGCGAAGCCGGGA*UUCG*AAAAAAAAAAAAAAAAAAAAAAAAAAAAAAA*

*AAAAAAAAAAAAAAAAAAAAAAAAAAAAAAAAAAAAAAAAAAAAAAAAAAAAAAAAAAAAAAAAAAAAAAAAAAAAAAAA*

*AAAA*

ETH047T02 (CCDC39 with Ethris' minimal UTR):

*Part of the 17 promoter*, Ethris' minimal 5′ UTR, *Kozak element*, start codon (AUG), codon optimized sequence encoding a functional version of a human CCDC39 protein, stop codon (UGA), part of restriction site for BstBl, *poly(A) tail*

SEQ ID NO: 12

*GGGAGA**CGCCACC*AUGAGCAGCGAGUUUCUGGCCGAACUGCACUGGGAGGACG

GCUUCGCUAUUCCCGUGGCCAACGAGGAAAACAAGCUGCUGGAAGAUCAGCU

GAGCAAGCUGAAGGACGAGAGAGCCUCUCUGCAGGACGAGCUGAGAGAGUAC

GAGGAACGGAUCAACAGCAUGACCAGCCACUUCAAGAACGUGAAGCAAGAGC

UGAGCAUCACCCAGAGCCUGUGCAAGGCCAGAGAGAGAGAAACCGAGAGCGA

GGAACACUUCAAGGCUAUCGCCCAGCGCGAGCUGGGAAGAGUGAAGGAUGAG

AUCCAGCGGCUGGAAAACGAGAUGGCCAGCAUCCUGGAAAAGAAGUCCGACA

AAGAGAACGGCAUCUUCAAGGCCACACAGAAGCUGGACGGCCUGAAGUGCCA

GAUGAACUGGGAUCAGCAGGCCCUGGAAGCCUGGCUGGAAGAGUCUGCCCA

CAAGGAUUCUGACGCCCUGACACUGCAGAAGUACGCCCAGCAGGACGACAAC

AAGAUCCGGGCUCUGACCCUGCAGCUGGAAAGACUGACCCUGGAAUGCAACC

AGAAGCGGAAGAUCCUGGACAACGAGCUGACCGAGACAAUCAGCGCCCAGCU

-continued

GGAACUGGAUAAGGCCGCUCAGGACUUCAGAAAGAUCCACAACGAGCGGCAA

GAACUGAUCAAGCAGUGGGAGAACACCAUCGAGCAGAUGCAGAAACGCGACG

GCGACAUCGACAACUGCGCCCUGGAACUCGCCCGGAUCAAGCAAGAGACACG

CGAGAAAGAGAACCUGGUCAAAGAGAAGAUCAAGUUCCUCGAGUCCGAGAUC

GGCAACAACACCGAGUUCGAGAAGCGGAUCAGCGUGGCCGACAGAAAGCUGC

UGAAGUGCAGAACCGCCUACCAGGACCACGAGACAAGCCGGAUUCAGCUCAA

GGGCGAGCUGGAUUCUCUGAAGGCCACCGUGAACAGAACCAGCAGCGAUCUG

GAAGCCCUGCGGAAGAACAUCAGCAAGAUCAAGAAGGACAUCCACGAGGAAA

CCGCCAGGCUGCAGAAAACAAAGAACCACAAUGAGAUCAUCCAGACCAAGCUG

AAAGAGAUCACCGAAAAGACCAUGAGCGUGGAAGAGAAGGCCACAAACCUGG

AAGAUAUGCUCAAAGAGGAAGAGAAAGACGUCAAAGAGGUGGACGUUCAACU

GAACCUGAUUAAGGGCGUGCUGUUCAAGAAGGCCCAAGAGCUGCAGACCGAA

ACCAUGAAGGAAAAGGCCGUCCUGUCUGAGAUCGAGGGCACCAGAUCUAGCC

UGAAGCACCUGAACCAUCAGCUGCAGAAGCUCGACUUCGAGACACUGAAGCA

GCAAGAGAUCAUGUACAGCCAGGAUUUCCACAUCCAGCAGGUCGAGCGGCGG

AUGUCUAGACUGAAGGGCGAGAUCAACUCCGAGGAAAAACAGGCCCUCGAGG

CCAAGAUCGUGGAACUGAGAAAGAGCCUCGAAGAGAAGAAGUCUACCUGCGG

CCUGCUGGAAACCCAGAUUAAGAAGCUGCACAACGACCUGUACUUCAUCAAG

AAAGCCCACAGCAAGAACAGCGACGAGAAGCAGAGCCUGAUGACCAAGAUCAA

UGAGCUGAACCUGUUCAUCGAUCGGAGCGAAAAAGAGCUGGACAAGGCCAAG

GGCUUCAAGCAGGACCUGAUGAUCGAGGACAACCUGCUGAAGCUGGAAGUGA

AGCGGACCAGAGAGAUGCUGCACAGCAAGGCCGAGGAAGUGCUGUCUCUGG

AAAAGCGGAAGCAGCAGCUGUACACCGCCAUGGAAGAGAGAACCGAAGAGAU

CAAGGUGCACAAGACCAUGCUGGCUUCCCAGAUCAGAUACGUGGACCAAGAG

CGCGAGAACAUCUCCACCGAGUUUAGAGAGAGACUGUCCAAGAUCGAGAAGC

UGAAGAACCGCUACGAGAUCCUGACCGUCGUGAUGCUGCCUCCUGAGGGCG

AAGAGGAAAAGACCCAGGCCUACUACGUGAUCAAGGCAGCCCAAGAAAAAGAG

GAACUCCAGAGAGAAGGCGACUGCCUGGACGCCAAGAUUAACAAGGCCGAAA

AAGAAAUCUACGCCCUCGAGAACACCCUGCAGGUCCUGAACAGCUGCAACAA

CAACUACAAGCAGAGCUUCAAGAAAGUCACCCCUAGCUCCGACGAGUACGAG

CUGAAGAUUCAGCUGGAAGAACAGAAAAGAGCCGUGGACGAGAAGUACAGAU

ACAAGCAGCGGCAGAUCAGAGAGCUGCAAGAGGAUAUCCAGAGCAUGGAAAA

CACCCUGGACGUGAUCGAGCACCUGGCCAACAACGUGAAAGAGAAGCUGUCC

GAGAAACAGGCCUACAGCUUUCAGCUGUCCAAAGAGACAGAGGAACAGAAGC

CCAAACUGGAACGCGUGACCAAGCAGUGCGCCAAGCUGACAAAAGAGAUCCG

GCUGCUGAAAGACACCAAGGACGAAACCAUGGAAGAACAAGACAUCAAGCUGC

GCGAGAUGAAGCAGUUCCACAAAGUGAUCGACGAGAUGCUGGUGGACAUCAU

UGAAGAGAACACAGAGAUCCGCAUCAUCCUGCAGACCUAUUUUCAGCAGAGC

GGCCUGGAACUGCCUACCGCCUCUACAAAGGGCAGCAGACAGAGCAGCAGAU

CCCCUAGCCACACAAGCCUGAGCGCCAGAAGCUCUAGAAGCACCAGCACCUC

UACCAGCCAGUCCAGCAUUAAGGUGCUGGAACUCAAGUUCCCCGCCAGCUCU

-continued

AGCCUCGUGGGAAGCCCUUCUAGACCUAGCAGCGCCUCUAGCAGCUCCAGCA

ACGUGAAGUCCAAGAAAAGCUCCAAGUGAUUCGAAAAAAAAAAAAAAAAAAAAAAAAAAAAAA

*AAAAAAAAAAAAAAAAAAAAAAAAAAAAAAAAAAAAAAAAAAAAAAAAAAAAAAAAAAAAAAAAAAAAAAAAAAAAAAAAAAAAAAA*

*AAA*

RNA encoding for human CCDC39 sequence and contains TISU element as 5′ UTR (ETH047T03)

*Part of the T7 promoter*, Ethris' minimal 5′ UTR with additional U nucleotide, *TISU element*, start codon (AUG), codon optimized sequence encoding a functional version of a human CCDC39 protein, stop codon (UGA), part of restriction site for BstBl, *poly(A) tail*

SEQ ID NO: 13

*GGGAGA*__CU__*GCCAAG*AUGAGCAGCGAGUUUCUGGCCGAACUGCACUGGGAGGAC

GGCUUCGCUAUUCCCGUGGCCAACGAGGAAAACAAGCUGCUGGAAGAUCAGC

UGAGCAAGCUGAAGGACGAGAGAGCCUCUCUGCAGGACGAGCUGAGAGAGUA

CGAGGAACGGAUCAACAGCAUGACCAGCCACUUCAAGAACGUGAAGCAAGAG

CUGAGCAUCACCCAGAGCCUGUGCAAGGCCAGAGAGAGAGAAACCGAGAGCG

AGGAACACUUCAAGGCUAUCGCCCAGCGCGAGCUGGGAAGAGUGAAGGAUGA

GAUCCAGCGGCUGGAAAACGAGAUGGCCAGCAUCCUGGAAAAGAAGUCCGAC

AAAGAGAACGGCAUCUUCAAGGCCACACAGAAGCUGGACGGCCUGAAGUGCC

AGAUGAACUGGGAUCAGCAGGCCCUGGAAGCCUGGCUGGAAGAGUCUGCCC

ACAAGGAUUCUGACGCCCUGACACUGCAGAAGUACGCCCAGCAGGACGACAA

CAAGAUCCGGGCUCUGACCCUGCAGCUGGAAAGACUGACCCUGGAAUGCAAC

CAGAAGCGGAAGAUCCUGGACAACGAGCUGACCGAGACAAUCAGCGCCCAGC

UGGAACUGGAUAAGGCCGCUCAGGACUUCAGAAAGAUCCACAACGAGCGGCA

AGAACUGAUCAAGCAGUGGGAGAACACCAUCGAGCAGAUGCAGAAACGCGAC

GGCGACAUCGACAACUGCGCCCUGGAACUCGCCCGGAUCAAGCAAGAGACAC

GCGAGAAAGAGAACCUGGUCAAAGAGAAGAUCAAGUUCCUCGAGUCCGAGAU

CGGCAACAACACCGAGUUCGAGAAGCGGAUCAGCGUGGCCGACAGAAAGCUG

CUGAAGUGCAGAACCGCCUACCAGGACCACGAGACAAGCCGGAUUCAGCUCA

AGGGCGAGCUGGAUUCUCUGAAGGCCACCGUGAACAGAACCAGCAGCGAUCU

GGAAGCCCUGCGGAAGAACAUCAGCAAGAUCAAGAAGGACAUCCACGAGGAA

ACCGCCAGGCUGCAGAAAACAAAGAACCACAAUGAGAUCAUCCAGACCAAGCU

GAAAGAGAUCACCGAAAAGACCAUGAGCGUGGAAGAGAAGGCCACAAACCUG

GAAGAUAUGCUCAAAGAGGAAGAGAAAGACGUCAAAGAGGUGGACGUUCAAC

UGAACCUGAUUAAGGGCGUGCUGUUCAAGAAGGCCCAAGAGCUGCAGACCGA

AACCAUGAAGGAAAAGGCCGUCCUGUCUGAGAUCGAGGGCACCAGAUCUAGC

CUGAAGCACCUGAACCAUCAGCUGCAGAAGCUCGACUUCGAGACACUGAAGC

AGCAAGAGAUCAUGUACAGCCAGGAUUUCCACAUCCAGCAGGUCGAGCGGCG

GAUGUCUAGACUGAAGGGCGAGAUCAACUCCGAGGAAAAACAGGCCCUCGAG

GCCAAGAUCGUGGAACUGAGAAAGAGCCUCGAAGAGAAGAAGUCUACCUGCG

GCCUGCUGGAAACCCAGAUUAAGAAGCUGCACAACGACCUGUACUUCAUCAA

-continued

GAAAGCCCACAGCAAGAACAGCGACGAGAAGCAGAGCCUGAUGACCAAGAUC

AAUGAGCUGAACCUGUUCAUCGAUCGGAGCGAAAAAGAGCUGGACAAGGCCA

AGGGCUUCAAGCAGGACCUGAUGAUCGAGGACAACCUGCUGAAGCUGGAAGU

GAAGCGGACCAGAGAGAUGCUGCACAGCAAGGCCGAGGAAGUGCUGUCUCU

GGAAAAGCGGAAGCAGCAGCUGUACACCGCCAUGGAAGAGAGAACCGAAGAG

AUCAAGGUGCACAAGACCAUGCUGGCUUCCCAGAUCAGAUACGUGGACCAAG

AGCGCGAGAACAUCUCCACCGAGUUUAGAGAGAGACUGUCCAAGAUCGAGAA

GCUGAAGAACCGCUACGAGAUCCUGACCGUCGUGAUGCUGCCUCCUGAGGG

CGAAGAGGAAAAGACCCAGGCCUACUACGUGAUCAAGGCAGCCCAAGAAAAA

GAGGAACUCCAGAGAGAAGGCGACUGCCUGGACGCCAAGAUUAACAAGGCCG

AAAAAGAAAUCUACGCCCUCGAGAACACCCUGCAGGUCCUGAACAGCUGCAAC

AACAACUACAAGCAGAGCUUCAAGAAAGUCACCCCUAGCUCCGACGAGUACGA

GCUGAAGAUUCAGCUGGAAGAACAGAAAAGAGCCGUGGACGAGAAGUACAGA

UACAAGCAGCGGCAGAUCAGAGAGCUGCAAGAGGAUAUCCAGAGCAUGGAAA

ACACCCUGGACGUGAUCGAGCACCUGGCCAACAACGUGAAAGAGAAGCUGUC

CGAGAAACAGGCCUACAGCUUUCAGCUGUCCAAAGAGACAGAGGAACAGAAG

CCCAAACUGGAACGCGUGACCAAGCAGUGCGCCAAGCUGACAAAAGAGAUCC

GGCUGCUGAAAGACACCAAGGACGAAACCAUGGAAGAACAAGACAUCAAGCU

GCGCGAGAUGAAGCAGUUCCACAAAGUGAUCGACGAGAUGCUGGUGGACAUC

AUUGAAGAGAACACAGAGAUCCGCAUCAUCCUGCAGACCUAUUUUCAGCAGA

GCGGCCUGGAACUGCCUACCGCCUCUACAAAGGGCAGCAGACAGAGCAGCAG

AUCCCCUAGCCACACAAGCCUGAGCGCCAGAAGCUCUAGAAGCACCAGCACC

UCUACCAGCCAGUCCAGCAUUAAGGUGCUGGAACUCAAGUUCCCCGCCAGCU

CUAGCCUCGUGGGAAGCCCUUCUAGACCUAGCAGCGCCUCUAGCAGCUCCAG

CAACGUGAAGUCCAAGAAAAGCUCCAAGUGAUUCGAAAAAAAAAAAAAAAAAAAAAAAAAAAA

*AAAAAAAAAAAAAAAAAAAAAAAAAAAAAAAAAAAAAAAAAAAAAAAAAAAAAAAAAAAAAAAAAAAAAAAAAAAAAAAAAAAAA*

*AAAAAAA*

ETH047T05: SP30; RNA encoding for human CCDC39 and containing *random sequence of 30 nucleotides* (*SP30*) which was used as 5′ UTR

*Part of the T7 promoter*, **Ethris' minimal 5′ UTR, *SP30 as 5′ UTR*, *Kozak element***, start codon (AUG), codon optimized sequence encoding a functional version of a human CCDC39 protein, stop codon (UGA), part of restriction site for BstBl, *poly(A) tail*

SEQ ID NO: 14

*GGGAGA*C*AUUGAAAUUUAUCUCUUGUGUUGUGGUCGC**GCCACC*AUGAGCAGCGAGUUU

CUGGCCGAACUGCACUGGGAGGACGGCUUCGCUAUUCCCGUGGCCAACGAG

GAAAACAAGCUGCUGGAAGAUCAGCUGAGCAAGCUGAAGGACGAGAGAGCCU

CUCUGCAGGACGAGCUGAGAGAGUACGAGGAACGGAUCAACAGCAUGACCAG

CCACUUCAAGAACGUGAAGCAAGAGCUGAGCAUCACCCAGAGCCUGUGCAAG

GCCAGAGAGAGAGAAACCGAGAGCGAGGAACACUUCAAGGCUAUCGCCCAGC

GCGAGCUGGGAAGAGUGAAGGAUGAGAUCCAGCGGCUGGAAAACGAGAUGG

CCAGCAUCCUGGAAAAGAAGUCCGACAAAGAGAACGGCAUCUUCAAGGCCAC

-continued

ACAGAAGCUGGACGGCCUGAAGUGCCAGAUGAACUGGGAUCAGCAGGCCCUG

GAAGCCUGGCUGGAAGAGUCUGCCCACAAGGAUUCUGACGCCCUGACACUGC

AGAAGUACGCCCAGCAGGACGACAACAAGAUCCGGGCUCUGACCCUGCAGCU

GGAAAGACUGACCCUGGAAUGCAACCAGAAGCGGAAGAUCCUGGACAACGAG

CUGACCGAGACAAUCAGCGCCCAGCUGGAACUGGAUAAGGCCGCUCAGGACU

UCAGAAAGAUCCACAACGAGCGGCAAGAACUGAUCAAGCAGUGGGAGAACAC

CAUCGAGCAGAUGCAGAAACGCGACGGCGACAUCGACAACUGCGCCCUGGAA

CUCGCCCGGAUCAAGCAAGAGACACGCGAGAAAGAGAACCUGGUCAAAGAGA

AGAUCAAGUUCCUCGAGUCCGAGAUCGGCAACAACACCGAGUUCGAGAAGCG

GAUCAGCGUGGCCGACAGAAAGCUGCUGAAGUGCAGAACCGCCUACCAGGAC

CACGAGACAAGCCGGAUUCAGCUCAAGGGCGAGCUGGAUUCUCUGAAGGCCA

CCGUGAACAGAACCAGCAGCGAUCUGGAAGCCCUGCGGAAGAACAUCAGCAA

GAUCAAGAAGGACAUCCACGAGGAAACCGCCAGGCUGCAGAAAACAAAGAACC

ACAAUGAGAUCAUCCAGACCAAGCUGAAAGAGAUCACCGAAAAGACCAUGAGC

GUGGAAGAGAAGGCCACAAACCUGGAAGAUAUGCUCAAAGAGGAAGAGAAAG

ACGUCAAAGAGGUGGACGUUCAACUGAACCUGAUUAAGGGCGUGCUGUUCAA

GAAGGCCCAAGAGCUGCAGACCGAAACCAUGAAGGAAAAGGCCGUCCUGUCU

GAGAUCGAGGGCACCAGAUCUAGCCUGAAGCACCUGAACCAUCAGCUGCAGA

AGCUCGACUUCGAGACACUGAAGCAGCAAGAGAUCAUGUACAGCCAGGAUUU

CCACAUCCAGCAGGUCGAGCGGCGGAUGUCUAGACUGAAGGGCGAGAUCAAC

UCCGAGGAAAAACAGGCCCUCGAGGCCAAGAUCGUGGAACUGAGAAAGAGCC

UCGAAGAGAAGAAGUCUACCUGCGGCCUGCUGGAAACCCAGAUUAAGAAGCU

GCACAACGACCUGUACUUCAUCAAGAAAGCCCACAGCAAGAACAGCGACGAGA

AGCAGAGCCUGAUGACCAAGAUCAAUGAGCUGAACCUGUUCAUCGAUCGGAG

CGAAAAAGAGCUGGACAAGGCCAAGGGCUUCAAGCAGGACCUGAUGAUCGAG

GACAACCUGCUGAAGCUGGAAGUGAAGCGGACCAGAGAGAUGCUGCACAGCA

AGGCCGAGGAAGUGCUGUCUCUGGAAAAGCGGAAGCAGCAGCUGUACACCGC

CAUGGAAGAGAGAACCGAAGAGAUCAAGGUGCACAAGACCAUGCUGGCUUCC

CAGAUCAGAUACGUGGACCAAGAGCGCGAGAACAUCUCCACCGAGUUUAGAG

AGAGACUGUCCAAGAUCGAGAAGCUGAAGAACCGCUACGAGAUCCUGACCGU

CGUGAUGCUGCCUCCUGAGGGCGAAGAGGAAAAGACCCAGGCCUACUACGUG

AUCAAGGCAGCCCAAGAAAAAGAGGAACUCCAGAGAGAAGGCGACUGCCUGG

ACGCCAAGAUUAACAAGGCCGAAAAAGAAAUCUACGCCCUCGAGAACACCCUG

CAGGUCCUGAACAGCUGCAACAACAACUACAAGCAGAGCUUCAAGAAAGUCAC

CCCUAGCUCCGACGAGUACGAGCUGAAGAUUCAGCUGGAAGAACAGAAAAGA

GCCGUGGACGAGAAGUACAGAUACAAGCAGCGGCAGAUCAGAGAGCUGCAAG

AGGAUAUCCAGAGCAUGGAAAACACCCUGGACGUGAUCGAGCACCUGGCCAA

CAACGUGAAAGAGAAGCUGUCCGAGAAACAGGCCUACAGCUUUCAGCUGUCC

AAAGAGACAGAGGAACAGAAGCCCAAACUGGAACGCGUGACCAAGCAGUGCG

CCAAGCUGACAAAAGAGAUCCGGCUGCUGAAAGACACCAAGGACGAAACCAU

GGAAGAACAAGACAUCAAGCUGCGCGAGAUGAAGCAGUUCCACAAAGUGAUC

-continued

GACGAGAUGCUGGUGGACAUCAUUGAAGAGAACACAGAGAUCCGCAUCAUCC

UGCAGACCUAUUUUCAGCAGAGCGGCCUGGAACUGCCUACCGCCUCUACAAA

GGGCAGCAGACAGAGCAGCAGAUCCCCUAGCCACACAAGCCUGAGCGCCAGA

AGCUCUAGAAGCACCAGCACCUCUACCAGCCAGUCCAGCAUUAAGGUGCUGG

AACUCAAGUUCCCCGCCAGCUCUAGCCUCGUGGGAAGCCCUUCUAGACCUAG

CAGCGCCUCUAGCAGCUCCAGCAACGUGAAGUCCAAGAAAAGCUCCAAGUGA

UUCGAAAAAAAAAAAAAAAAAAAAAAAAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAA

The invention claimed is:

1. A method of treating a ciliopathy in a subject in need thereof, comprising:

administering to the respiratory system of the subject a pharmaceutical composition comprising a polyribonucleotide, wherein the polyribonucleotide is an mRNA that can be translated into a functional version of a protein coiled-coil domain containing 39 (CCDC39) and/or a protein coiled-coil domain containing 40 (CCDC40) and a lipidoid, wherein a defect in the protein CCDC39 and/or the protein CCDC40 is associated with said ciliopathy, wherein CCDC39 protein and/or CCDC40 protein are produced in the respiratory system of the subject in an amount effective for improving ciliary motility, and wherein:

a) the composition comprises a lipidoid, wherein the lipidoid is the R-isomer of C12-(2-3-2) and has the structure shown in formula (VI):

Formula (VI)

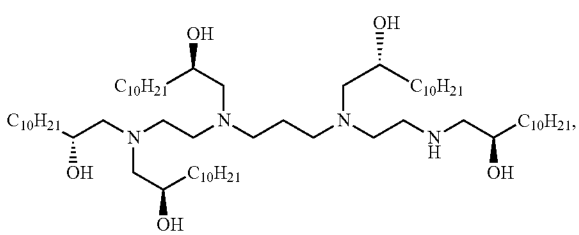

and/or b) the composition comprises a lipidoid having the structure shown in formula (VII):

formula (VII)

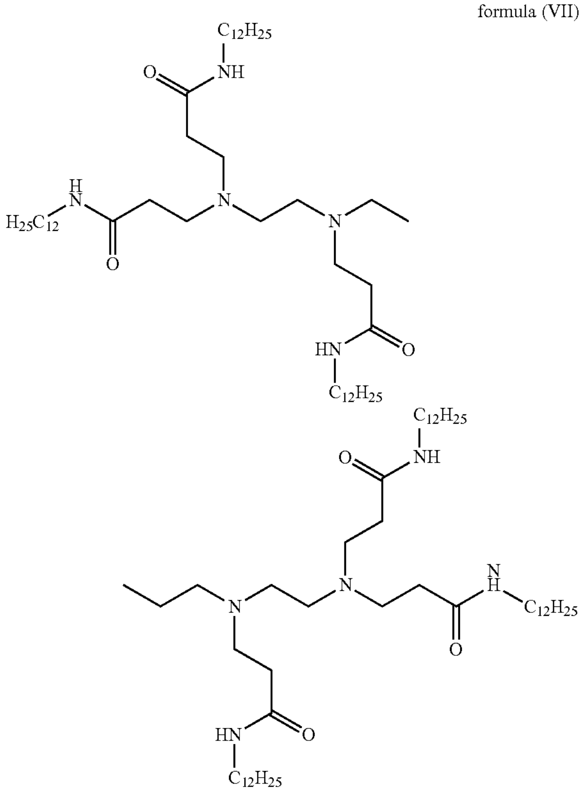

wherein said polyribonucleotide encoding human CCDC40 comprises a sequence that is at least 85% identical to one or more of SEQ ID NO: 1 or 5 to 11; and/or said polyribonucleotide encoding human CCDC39 comprises a sequence that is at least 85% identical to one or more of SEQ ID NO: 2 or 12 to 14, thereby improving ciliary motility and treating the ciliopathy in the subject.

2. The method of treating a ciliopathy according to claim 1, wherein administration of the pharmaceutical composition comprises:

(a) administration using a nasal spray, a nebulizer, and/or by inhalation; and/or (b) administration via a spray or droplets.

3. The method of treating a ciliopathy according to claim 2, wherein administration of the pharmaceutical composition comprises administration via nasal spray or nasal droplets.

4. The method of treating a ciliopathy according to claim 1, wherein the pharmaceutical composition is administered at least once a week and/or for at least two weeks, for at least 3 weeks, or for at least 4 weeks.

5. The method of treating a ciliopathy according to claim 1, wherein the pharmaceutical composition is administered twice a week for at least 1 week, for at least 2 weeks, for at least 3 weeks or for at least 4 weeks.

6. The method of treating a ciliopathy according to claim 1, wherein the pharmaceutical composition further comprises N-acetylcysteine (NAC) and/or a hypertonic solution comprising sodium chloride.

7. The method of treating a ciliopathy according to claim 6, wherein the concentration of NAC in the composition is between 3% and 20% (weight/weight).

8. The method of treating a ciliopathy according to claim 1, wherein a) the pharmaceutical composition further comprises one or more additional polyribonucleotides, and wherein a) said one or more additional polyribonucleotides are separate and encode a multiciliate differentiation and DNA synthesis associated cell cycle (MCIDAS) protein, GEMC1, FOXJ1, or E2F4VP16; and/or b) said one or more polyribonucleotides are multicistronic and encode MCIDAS protein, GEMC1, FOXJ1, or E2F4VP16.

9. The method of treating a ciliopathy according to claim 1, wherein said pharmaceutical composition further comprises a reagent selected from the group consisting of a lipid, a liposome, a micelle, a polymer, a dendrimer, a liposomal transfection reagent, a lipid transfection enhancer, and a liposomal transfection enhancer.

10. The method of treating a ciliopathy according to claim 9, wherein said lipid or lipidoid is a cationic lipid or cationic lipidoid, respectively.

11. The method of treating a ciliopathy according to claim 1, wherein said polyribonucleotide encoding human CCDC40 comprises a sequence set forth as one or more of SEQ ID NO: 1 or 5 to 11; and/or said polyribonucleotide encoding human CCDC39 comprises a sequence set forth as one or more of SEQ ID NO: 2 or 12 to 14.

12. The method of treating a ciliopathy according to claim 1, wherein the subject has been subjected prior to treatment to any of the following:

a) inhalation of an appropriate solution or to washing their nasal cavities and/or sinus with a solution, and/or b) an assay in order to determine whether the subject suffers from an inflammation, and wherein the subject has been positively determined to have an inflammation.

13. The method of treating a ciliopathy according to claim 12, wherein the solution comprises a mucolytic agent, a hypertonic saline or N-acetylcysteine (NAC).

14. The method of treating a ciliopathy according to claim 1, further comprising administering to the subject a second pharmaceutical composition comprising one or more additional polyribonucleotides, wherein the one or more additional polyribonucleotides encode a multiciliate differentiation and DNA synthesis associated cell cycle (MCIDAS)-protein, GEMC1, FOXJ1, or E2F4VP16.

15. The method of treating a ciliopathy according to claim 1, wherein the polyribonucleotide comprises unmodified and modified nucleotides.

16. The method of treating a ciliopathy according to claim 1, wherein the composition comprises the lipidoid which is the R-isomer of C12-(2-3-2) having the structure shown in formula (VI), and wherein the lipidoid is formulated with DPPC, cholesterol, and PEG-lipid DMG-PEG2000.

17. The method of treating a ciliopathy according to claim 16, wherein lipidoid, DPPC, cholesterol, and PEG-lipid DMG-PEG2000 are formulated at the molar ratios 8:5.29:4.41:0.88, respectively.

18. The method of treating a ciliopathy according to claim 1, wherein the composition comprises the lipidoid having the structure shown in formula (VII), and wherein the lipidoid is formulated with DPPC, cholesterol, and PEG-lipid DMG-PEG2000.

19. The method of treating a ciliopathy according to claim 18, wherein lipidoid, DPPC, cholesterol, and PEG-lipid DMG-PEG2000 are formulated at the molar ratios 8:5.29:4.41:0.88, respectively.

20. The method of treating a ciliopathy according to claim 1, wherein the composition further comprises N-acetylcysteine (NAC), a hypertonic solution comprising sodium chloride, and/or wherein the lipidoid is formulated with the lipids DPPC, cholesterol, and PEG-lipid DMG-PEG2000.

21. The method of treating a ciliopathy according to claim 1, further comprising: selecting the subject, wherein said ciliopathy is primary ciliary dyskinesia (PCD), wherein the subject has acute inflammation of the respiratory system, and wherein the acute inflammation is characterized by; i) locally increased blood flow, ii) increased capillary permeability, and/or iii) increased numbers of neutrophils, macrophages, and/or lymphocytes.

* * * * *